US011899014B2

(12) United States Patent
Cornish et al.

(10) Patent No.: US 11,899,014 B2
(45) Date of Patent: Feb. 13, 2024

(54) DETECTION OF ANALYTES USING LIVE CELLS

(71) Applicant: THE TRUSTEES OF COLUMBIA UNIVERSITY IN THE CITY OF NEW YORK, New York, NY (US)

(72) Inventors: Virginia Wood Cornish, New York, NY (US); Nili Ostrov, Brookline, MA (US); Miguel Jimenez, Winthrop, MA (US); Sonja Billerbeck, Groningen (NL)

(73) Assignee: THE TRUSTEES OF COLUMBIA UNIVERSITY IN THE CITY OF NEW YORK, New York, NY (US)

(*) Notice: Subject to any disclaimer, the term of this patent is extended or adjusted under 35 U.S.C. 154(b) by 21 days.

(21) Appl. No.: 16/906,669

(22) Filed: Jun. 19, 2020

(65) Prior Publication Data

US 2020/0319180 A1 Oct. 8, 2020

Related U.S. Application Data

(60) Division of application No. 15/596,837, filed on May 16, 2017, now Pat. No. 10,725,036, which is a (Continued)

(51) Int. Cl.
*G01N 33/566* (2006.01)
*C12Q 1/02* (2006.01)

(Continued)

(52) U.S. Cl.
CPC .......... *G01N 33/566* (2013.01); *C12Q 1/005* (2013.01); *C12Q 1/02* (2013.01); *C12Q 1/025* (2013.01);

(Continued)

(58) Field of Classification Search
CPC .......... G01N 33/566; G01N 33/56961; G01N 33/5695; G01N 33/56916;

(Continued)

(56) References Cited

U.S. PATENT DOCUMENTS 6,406,856 B1 6/2002 Glover et al.
6,692,696 B1 * 2/2004 Alberte ............... G01N 33/566 422/50

(Continued)

FOREIGN PATENT DOCUMENTS

WO WO-8910967 A * 11/1989 .......... C07K 14/005
WO WO 2005/042695 A2 5/2005
WO WO 2010/127111 A1 11/2010

OTHER PUBLICATIONS

U.S. Appl. No. 15/596,837 (U.S. Pat. No. 10,725,036), filed May 16, 2017 (Jul. 28, 2020).

(Continued)

*Primary Examiner* — Ruixiang Li
(74) *Attorney, Agent, or Firm* — Baker Botts L.L.P.

(57) ABSTRACT

The present invention provides sensor cells comprising a receptor that binds to an analyte indicative of the presence of an agent, where binding of the analyte to the receptor triggers a detection event that is indicative of the presence of the agent. In certain embodiments, the detection event is appearance of a reporter detectable by the naked eye. The present invention also provides uses of such sensor cells for detecting the presence of an agent in a sample.

Figure 1A:
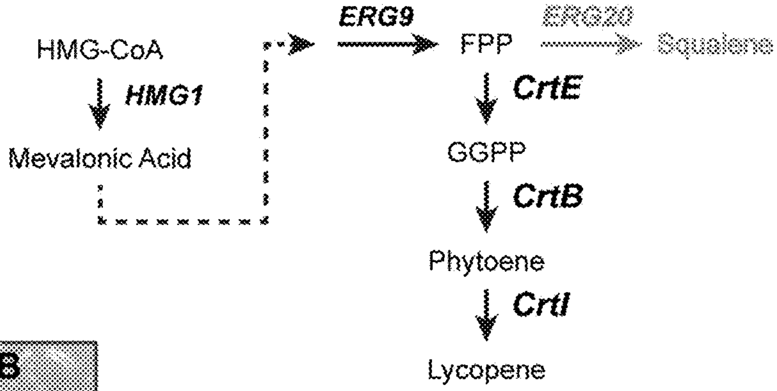

27 Claims, 23 Drawing Sheets
(19 of 23 Drawing Sheet(s) Filed in Color)
Specification includes a Sequence Listing.

Related U.S. Application Data continuation-in-part of application No. PCT/US2015/061373, filed on Nov. 18, 2015.

(60) Provisional application No. 62/081,441, filed on Nov. 18, 2014.

(51) Int. Cl.
*G01N 33/74* (2006.01)
*G01N 33/50* (2006.01)
*C12Q 1/00* (2006.01)
*C12Q 1/06* (2006.01)
*G01N 33/569* (2006.01)

(52) U.S. Cl.
CPC .......... *C12Q 1/06* (2013.01); *G01N 33/5023* (2013.01); *G01N 33/5038* (2013.01); *G01N 33/569* (2013.01); *G01N 33/5695* (2013.01); *G01N 33/56911* (2013.01); *G01N 33/56916* (2013.01); *G01N 33/56961* (2013.01); *G01N 33/74* (2013.01); *G01N 2333/726* (2013.01)

(58) Field of Classification Search
CPC .......... G01N 33/56911; G01N 33/569; G01N 33/5038; G01N 2333/726; C12Q 1/025; C12Q 1/02; C12Q 1/06; C12Q 1/005
See application file for complete search history.

(56) References Cited

U.S. PATENT DOCUMENTS

| | | | |
|---|---|---|---|
| 7,223,550 | B2 | 5/2007 | Dhanasekaran et al. |
| 9,809,862 | B2 | 11/2017 | Peralta-yahya et al. |
| 2003/0008331 | A1 | 1/2003 | Lerner |
| 2010/0221817 | A1 | 9/2010 | Ostermann et al. |
| 2012/0135497 | A1 | 5/2012 | Schofield et al. |
| 2017/0205401 | A1 | 7/2017 | Tyo et al. |

OTHER PUBLICATIONS

U.S. Appl. No. 15/596,837, filed Jun. 19, 2020 Issue Fee Payment.
U.S. Appl. No. 15/596,837, filed Mar. 27, 2020 Notice of Allowance.
U.S. Appl. No. 15/596,837, filed Mar. 9, 2020 Amendment and Request for Continued Examination (RCE).
U.S. Appl. No. 15/596,837, filed Dec. 9, 2019 Final Office Action.
U.S. Appl. No. 15/596,837, filed Nov. 8, 2019 Response to Non-Final Office Action.
U.S. Appl. No. 15/596,837, filed May 9, 2019 Non-Final Office Action.
U.S. Appl. No. 15/596,837, filed Mar. 14, 2019 Response to Restriction Requirement.
U.S. Appl. No. 15/596,837, filed Dec. 14, 2018 Restriction Requirement.
Abramoff et al., "Image processing with ImageJ," Biophotonics International 11:36-42 (2004).
Ali et al., "Expression of plant cyclic nucleotide-gated cation channels in yeast," J. Exp. Botany 57:125-138 (2006).
Alper et al., "Identifying gene targets for the metabolic engineering of lycopene biosynthesis in *Escherichia coli*," Metab Eng 7:155-164 (2005).
Anderson et al., "Unique Phenotype of Opaque Cells in the White-Opaque Transition of Candida albicans," J. Bacterial. 169(12):5579-5588 (1987).
Andreatta et al., "Simultaneous alignment and clustering of peptide data using a Gibbs sampling approach," Bioinformatics 29(1):8-14 (2013).
Armbruster et al., "Evolving the lock to fit the key to create a family of G protein-coupled receptors potently activated by an inert ligand," PNAS USA 104(12):5163-5168 (2007).
Armstrong, "Genetics of eubacterial carotenoid biosynthesis: a Colorful Tale," Annu Rev Microbiol 51:629-659 (1997).
Ault et al., "Creation of GPCR-based chemical sensors by directed evolution in yeast," Protein Eng Des Sel 19(1):1-8 (2006).
Bashor et al., "Using Engineered Scaffold Interactions to Reshape MAP Kinase Pathway Signaling Dynamics," Science 319:1539-1543 (2008).
Belkin et al., "Oxidative Stress Detection with *Escherichia coli* Harboring a katG' ::lux Fusion," Appl Environ Microbiol 62(7):2252-2256 (1996).
Bellin et al., "Integrated circuit-based electrochemical sensor for spatially resolved detection of redox-active metabolites in biofilms," Nat. Commun. 5:3256 (2014).
Berman et al., "Candida Albicans: a molecular revolution built on lessons from budding yeast," Nat Rev Genet 3:918-932 (2002).
Blignaut et al., "Ca3 Fingerprinting of Candida albicans Isolates from Human Immunodeficiency Virus-Positive and Healthy Individuals Reveals a New Clade in South Africa," J. Clin. Microbial. 40(3):826-836 (2002).
Bourbonnais et al., "Secretion of Somatostatin by *Saccharomyces cerevisiae* Correct Proteolytic Processing of pro-α-Factor-Somatostatin Hybrids Requires the Products of the KEX2 and STE13 Genes," J. Biol. Chem. 263(30):15342-15347 (1988).
Brown et al., "Hidden Killers: Human Fungal Infections," Sci Transl Med 4:165rv13 (2012).
Cairns et al., "Order of action of components in the yeast pheromone response pathway revealed with a dominant allele of the STE11 kinase and the multiple phosphorylation of the STE7 kinase," Genes Dev 6:1305-1318 (1992).
Celic et al., "Sequences in the Intracellular Loops of the Yeast Pheromone Receptor Ste2p Required for G Protein Activation," Biochemistry 42:3004-3017 (2003).
Chemler et al., "Biosynthesis of isoprenoids, polyunsaturated fatty acids and flavonoids in *Saccharomyces cerevisiae*," Microbiol Cell Fact 5:20 (2006).
Cloak et al., "Quorum Sensing and Production of Autoinducer-2 in *Campylobacter* spp., *Escherichia coli* O157:H7, and *Salmonella enterica* Serovar Typhimurium in Foods," Appl Environ Microbiol 68(9):4666-4671 (2002).
Conklin et al., "Engineering GPCR signaling pathways with RASSLs," Nat Methods 5(8):673-678 (2008).
De Nobel et al., "An Assay of Relative Cell Wall Porosity in *Saccharomyces cerevisiae*, *Kluyveromyces lactis* and *Schizosaccharomyces pombe*," Yeast 6:483-490 (1990).
De Nobel et al., "Passage of Molecules Through Yeast Cell Walls: a Brief Essay-Review," Yeast 7:313-323 (1991).
Dong et al., "Directed molecular evolution of DREADDs: a generic approach to creating next-generation RASSLs," Nat Protocols 5(3):561-573 (2010).
Dumitru et al., "In Vivo and in Vitro Anaerobic Mating in Candida albicans," Eukaryotic Cell 6(3):465-472 (2007).
Ebert et al., "Identification of Gastric Cancer Patients by Serum Protein Profiling," J Proteome Res 3:1261-1266 (2004).
Eilam et al., "Nystatin Effects on Cellular Calcium in *Saccharomyces-cerevisiae*," Biochim. Biophys. Acta 692:238-243 (1982).
Erickson et al., "Edg-2/Vzg-1 Couples to the Yeast Pheromone Response Pathway Selectively in Response to Lysophosphatidic Acid," J Biol Chem 273(3):1506-1510 (1998).
Erlenbach et al., "Functional expression of M(1), M(3) and M(5) muscarinic acetylcholine receptors in yeast," J Neurochem 77:1327-1337 (2001).
Extended European Search Report dated Apr. 30, 2018 in Application No. EP 15861179.
Felipe et al., "Functional genome of the human pathogenic fungus *Paracoccidioides brasiliensis*," FEMS Immunol. Med. Microbiol. 45:369-381 (2005).
Findlay et al., "Yeast-Based Biosensors and Their Incorporation of Mammalian Protein Receptors for High-Throughput Screening," Handbook of Biosensors and Biochips, Chapter 13 (2007).
Fukuda et al., "Amplification of agonist stimulation of human G-protein-coupled receptor signaling in yeast," Anal Biochem 417:182-187 (2011).

(56) References Cited

OTHER PUBLICATIONS

Garjonyte et al., "Amperometric biosensors for lactic acid based on baker's and wine yeast," Microchim Acta 164:177-183 (2009).
Gomes-Rezende et al., "Functionality of the Paracoccidioides Mating α-Pheromone-Receptor System," PLoS ONE 7(10):e47033 (2012).
Goughenour et al., "Quantitative Microplate-Based Growth Assay for Determination of Antifungal Susceptibility of Histoplasma capsulatum Yeasts," J. Clin. Microbiol. 53(10):3286-3295 (2015).
Gu et al., "Some observations in freeze-drying of recombinant bioluminescent *Escherichia coli* for toxicity monitoring," J Biotechnol 88:95-105 (2001).
Gujraty et al., "Functional Characterization of Peptide-Based Anthrax Toxin Inhibitors," Mol. Pharm 2(5):367-372 (2005).
Hagen et al., "Pheromone Response Elements are Necessary and Sufficient for Basal and Pheromone-Induced Transcription of the FUS1 Gene of *Saccharomyces cerevisiae*," Mol Cell Biol. 11(6):2952-2961 (1991).
Han et al., "Optimization of bio-indigo production by recombinant *E. coli* harboring fmo gene," Enzyme and Microbial Technology 42:617-623 (2008).
Hansen et al., "Versatile biosensor vectors for detection and quantification of mercury," FEMS Microbial Lett 193:123-127 (2000).
Harris et al., "Field evaluation of Crystal VC Rapid Dipstick test for cholera during a cholera outbreak in Guinea-Bissau," Trop Med Int Health 14(9):1117-1121 (2009).
Hauser et al., "The First Extracellular Loop of the *Saccharomyces cerevisiae* G Protein-coupled Receptor Ste2p Undergoes a Conformational Change upon Ligand Binding," J Biol Chem 282(14):10387-10397 (2007).
Higashijima et al., "Physiological activities of peptides are correlated with the conformations of membrane-bound molecules: α-Mating factor from *Saccharomyces cerevisiae* and analog peptides," FEBS Letters 159(1,2):229-232 (1983).
Higgins et al., "The major Vibrio cholerae autoinducer and its role in virulence factor production," Nature 450:883-886 (2007).
Hingorani et al., "Preinvasive and invasive ductal pancreatic cancer and its early detection in the mouse," Cancer Cell 4:437-450 (2003).
Hollis et al., "Design and Application of a Biosensor for Monitoring Toxicity of Compounds to Eukaryotes," Appl. Environ. Microbiol. 66(4):1676-1679 (2000).
Hotez et al., "The Neglected Tropical Diseases of Latin America and the Caribbean: a Review of Disease Burden and Distribution and a Roadmap for Control and Elimination," PLoS Negl. Trop. Dis. 2(9):e300 (2008).
Huang et al., "N-Acetylglucosamine Induces White to Opaque Switching, a Mating Prerequisite in Candida albicans," PLoS Pathog 6(3):e1000806 (2010).
Huat et al., "Entamoeba histolytica acetyl-CoA synthetase: biomarker of acute amoebic liver abscess," Asian Pac J Trop Biomed 4(6):446-450 (2014).
Hull et al., "Evidence for Mating of the 'Asexual' Yeast *Candida albicans* in a Mammalian Host," Science 289:307-310 (2000).
Huzarewich et al., "Application of "omics" to Prion Biomarker Discovery," J. Biomed Biotechnol, Article ID 613504 (2010).
Ignatovica et al., "Identification and analysis of functionally important amino acids in human purinergic 12 receptor using a *Saccharomyces cerevisiae* expression system," FEBS J 279:180-191 (2012).
International Search Report dated Apr. 1, 2016 in International Application No. PCT/US15/61373.
Janbon et al., "Monosomy of a specific chromosome determines L-sorbose utilization: a novel regulatory mechanism in Candida albicans," PNAS USA 95:5150-5155 (1998).
Janiak et al., "Functional expression of the Candida albicans α-factor receptor in *Saccharomyces cerevisiae*," Fungal Genetics and Biology 42:328-338 (2005).
King et al., "Control of Yeast Mating Signal Transduction by a Mammalian β2-Adrenergic Receptor and Gs α Subunit," Science 250:121-123 (1990).
Krogh et al., "Predicting Transmembrane Protein Topology with a Hidden Markov Model: Application to Complete Genomes," J. of Mol. Biol. 305:567-580 (2001).
Kyte et al., "A Simple Method for Displaying the Hydropathic Character of a Protein," J. Mol. Biol. 157:105-132 (1982).
Lachke et al., "Skin Facilitates Candida albicans Mating," Infect. Immun. 71(9):4970-4976 (2003).
LaRocque et al., "Proteomic Analysis of Vibrio cholerae in Human Stool," Infect. Immun. 76(9):4145-4151 (2008).
Leavitt et al., "Dominant negative mutations in the α-factor receptor, a G protein-coupled receptor encoded by the STE2 gene of the yeast *Saccharomyces cerevisiae*," Mol Gen Genet 261:917-932 (1999).
Lee et al., "Expression-level optimization of a multi-enzyme pathway in the absence of a high-throughput assay," Nucleic Acids Research 41(22):10668-10678 (2013).
Lequin, "Enzyme Immunoassay (EIA)/Enzyme-Linked Immunosorbent Assay (ELISA)," Clinical Chemistry 51(12):2415-2418 (2005).
Levskaya et al., "Engineering *Escherichia coli* to see light," Nature 438:441-442 (2005).
Lin et al., "Aromatic Residues at the Extracellular Ends of Transmembrane Domains 5 and 6 Promote Ligand Activation of the G Protein-Coupled α-Factor Receptor," Biochemistry 42:293-301 (2003).
Lin et al., "DJ-1 isoforms in whole blood as potential biomarkers of Parkinson disease," Sci Rep 2:954 (2012).
Ma et al., "A cyclic peptide-polymer probe for the detection of Clostridium botulinum neurotoxin serotype A," Toxicon 47:901-908 (2006).
MacKay et al., "Gene Expression Analyzed by High-resolution State Array Analysis and Quantitative Proteomics: Response of Yeast to Mating Pheromone," Mol Cell Proteomics 3:478-489 (2004).
Magee et al., "Induction of Mating in Candida albicans by Construction of MTLa and MTLα Strains," Science 289:310-313 (2000).
Martin et al., "Causes and Consequences of Variability in Peptide Mating Pheromones of Ascomycete Fungi," Molecular Biology and Evolution 28(7):1987-2003 (2011).
Martin et al., "Mate-recognition and species boundaries in the ascomycetes," Fungal Diversity 58:1-12 (2013).
Martin et al., "Mutagenic Mapping of Helical Structures in the Transmembrane Segments of the Yeast α-Factor Receptor," J. Mol. Biol. 317:765-788 (2002).
Mathew et al., "Differential Interactions of Fluorescent Agonists and Antagonists with the Yeast G Protein Coupled Receptor Ste2p," J. Mol. Biol. 409(4):513-528 (2011).
Mavrodi et al., "Functional Analysis of Genes for Biosynthesis of Pyocyanin and Phenazine-1-Carboxamide from Pseudomonas aeruginosa PAO1," J. Bacteriology 183(21):6454-6465 (2001).
Mayrhofer et al., "Functional Characterization of an α-Factor-Like Sordaria macrospora Peptide Pheromone and Analysis of Its Interaction with Its Cognate Receptor in *Saccharomyces cerevisiae*," Eukaryot Cell 4(4):661-672 (2005).
Minic et al., "Functional expression of olfactory receptors in yeast and development of a bioassay for odorant screening," FEBS J 272:524-537 (2005).
Miret et al., "Functional Expression of Heteromeric Calcitonin Gene-related Peptide and Adrenomedullin Receptors in Yeast," J. Biol. Chem. 277(9):6881-6887 (2002).
Mischak et al., "Capillary Electrophoresis-Mass Spectrometry As a Powerful Tool in Biomarker Discovery and Clinical Diagnosis: an Update of Recent Developments," Mass Spectrom Rev 28:703-724 (2009).
Miyajima et al., "Secretion of mature mouse interleukin-2 by *Saccharomyces cerevisiae*: use of a general secretion vector containing promoter and leader sequences of the mating pheromone α-factor," Gene 37:155-161 (1985).
Myers et al., "Improving accuracy of cell and chromophore concentration measurements using optical density," BMC Biophys. 6:4 (2013).
Naider et al., "The α-factor mating pheromone of *Saccharomyces cerevisiae*: a model for studying the interaction of peptide hormones and G protein-coupled receptors," Peptides 25:1441-1463 (2004).

(56) References Cited

OTHER PUBLICATIONS

Niwa, "Biomarker discovery for kidney diseases by mass spectrometry," J. Chromatogr. B 870:148-153 (2008).
Olivo et al., "Detection and Quantitation of Human Respiratory Syncytial Virus (RDV) Using Minigenome cDNA and a Sindbis Virus Replicon: a Prototype Assay for Negative-Strand RNA Viruses," Virology 251:198-205 (1998).
Pausch, "G-protein-coupled receptors in *Saccharomyces cerevisiae*: high-throughput screening assays for drug discovery," Trends Biotechnol 15:487-494 (1997).
Pei et al., "Engineered GPCRs as Tools to Modulate Signal Transduction," Physiology 23:313-321 (2008).
Pfaller et al., "Epidemiology of Invasive Candidiasis: a Persistent Public Health Problem," Clin. Microbiol. Rev. 20:133-163 (2007).
Pi et al., "Transcriptional Activation upon Pheromone Stimulation Mediated by a Small Domain of *Saccharomyces cervisiae* Ste12p," Molecular and Cellular Biology 17(11):6410-6418 (1997).
Pierce et al., "Seven-Transmembrane Receptors," Nat Rev Mol. Cell Biol. 3:639-650 (2002).
Pisa et al., "Different Brain Regions are Infected with Fungi in Alzheimer's Disease," Sci Rep 5:15015 (2015).
Price et al., "Functional Coupling of a Mammalian Somatostatin Receptor to the Yeast Pheromone Response Pathway," Mol. Cell Biol. 15(11):6188-6195 (1995).
Price et al., "Pharmacological Characterization of the Rat A2a Adenosine Receptor Functionally Coupled to the Yeast Pheromone Response Pathway," Mol. Pharmacol 50:829-837 (1996).
Ptitsyn et al., "A Biosensor for Environmental Genotoxin Screening Based on an Sos lux Assay in Recombinant *Escherichia coli* Cells," Appl Environ Microbiol 63(11):4377-4384 (1997).
Radhika et al., "Chemical sensing of DNT by engineered olfactory yeast strain," Nat Chem Biol 3(6):325-330 (2007).
Rafati et al., "Amastin Peptide-Binding Antibodies as Biomarkers of Active Human Visceral Leishmaniasis," Clin Vaccine Immunol 13(10):1104-1110 (2006).
Ramirez-Zavala et al., "Environmental Induction of White-Opaque Switching in Candida albicans," PLoS Pathog 4(6):e1000089 (2008).
Ramirez-Zavaleta et al., "Subtelomeric Silencing of the MTL3 Locus of Candida glabrata Requires yKu70, yKu80, and Rif1 Proteins," Eukaryotic Cell 9(10):1602-1611 (2010).
Restrepo et al., "Growth of *Paracoccidioides brasiliensis* Yeast Phase in a Chemically Defined Culture Medium," J. Clin. Microbiol. 12(2):279-281 (1980).
Rider et al., "A B Cell-Based Sensor for Rapid Identification of Pathogens," Science 301:213-215 (2003).
Ro et al., "Production of the antimalarial drug precursor artemisinic acid in engineered yeast," Nature 440:940-943 (2006).
Sanchez et al., "Reevaluation of the Violacein Biosynthetic Pathway and its Relationship to Indolocarbazole Biosynthesis," ChemBioChem 7:1231-1240 (2006).
Sander et al., "Heterologous expression of the human D2S dopamine receptor in protease-deficient *Saccharomyces cerevisiae* strains," Eur. J. Biochem 226:697-705 (1994).
Santos et al., "Melanin-Based High-Throughput Screen for L-Tyrosine Production in *Escherichia coli*," Appl. Environ. Microbiol. 74(4):1190-1197 (2008).
Sauer et al., "Mass spectrometry tools for the classification and identification of bacteria," Nat Rev Microbiol 8:74-82 (2010).
Schofield et al., "Development of a yeast biosensor—biocatalyst for the detection and biodegradation of the organophosphate paraoxon," Applied Microbiology and Biotechnology 76:1383-1394 (2007).
Sherwood et al., "Mutations in GSF1 and GSF2 Alter Glucose Signaling in *Saccharomyces cerevisiae*," Genetics 147:557-566 (1997).
Shin et al., "Freeze-dried recombinant bacteria for on-site detection of phenolic compounds by color change," J Biotechnol 119:36-43 (2005).
Sievers et al., "Fast, scalable generation of high-quality protein multiple sequence alignments using Clustal Omega," Molecular Systems Biology 7:539-539 (2011).
Son et al., "Identification of Ligand Binding Regions of the *Saccharomyces cerevisiae* α-Factor Pheromone Receptor by Photoaffinity Cross-Linking," Biochemistry 43:13193-13203 (2004).
Spira et al., "Multi-electrode array technologies for neuroscience and cardiology," Nat. Nanotechnol. 8:83-94 (2013).
Stocker et al., "Development of a Set of Simple Bacterial Biosensors for Quantitative and Rapid Measurements of Arsenite and Arsenate in Potable Water," Environ. Sci. Technol. 37:4743-4750 (2003).
Struss et al., "Chapter 14: Biosensing Systems Based on Genetically Engineered Whole Cells," in Recognition Receptors in Biosensors (ed. M. Zourob) pp. 565-598 (Springer New York, 2010).
Su et al., "Microbial biosensors: A review," Biosens. Bioelectron. 26:1788-1799 (2011).
Takahashi et al., "Membrane localization of scaffold proteins promotes graded signaling in the yeast MAP kinase cascade," Curr Biol 18(16):1184-1191 (2008).
Toine et al., "A new highly specific and robust yeast androgen bioassay for the detection of agonists and antagonists," Analytical and Bioanalytical Chemistry 389:1549-1558 (2007).
Torres et al., "Presence and expression of the mating type locus in Paracoccidioides brasiliensis isolates," Fungal Genet. Biol. 47:373-380 (2010).
Tracewell et al., "Directed enzyme evolution: climbing fitness peaks one amino acid at a time," Curr Opin Chem Biol 13:3-9 (2009).
Umanah et al., "Changes in Conformation at the Cytoplasmic Ends of the Fifth and Sixth Transmembrane Helices of a Yeast G Protein-Coupled Receptor in Response to Ligand Binding," Biochemistry 50:6841-6854 (2011).
Umanah et al., "Identification of Residue-to-residue Contact between a Peptide Ligand and its G Protein-coupled Receptor Using Periodate-mediated Dihydroxyphenylalanine Cross-linking and Mass Spectrometry," J Biol Chem 285(50):39425-39436 (2010).
Van der Meer et al., "Where microbiology meets microengineering: design and applications of reporter bacteria," Nat Rev Microbiol 8:511-522 (2010).
Van Dyk et al., "Rapid and Sensitive Pollutant Detection by Induction of Heat Shock Gene-Bioluminescence Gene Fusions," Appl Environ Microbiol 60(5):1414-1420 (1994).
Van Everbroeck et al., "Cerebrospinal fluid biomarkers in Creutzfeldt-Jakob disease," Clin Neural Neurosurg 107:355-360 (2005).
Van Holten et al., "Circulating Biomarkers for Predicting Cardiovascular Disease Risk; a Systematic Review and Comprehensive Overview of Meta-Analyses," PLoS ONE 8(4):e62080 (2013).
Verwaal et al., "High-Level Production of Beta-Carotene in *Saccharomyces cerevisiae* by Successive Transformation with Carotenogenic Genes from Xanthophyllomyces dendrorhous," Appl Environ Microbiol 73(13):4342-4350 (2007).
Villanueva et al., "Differential exoprotease activities confer tumor-specific serum peptidome patterns," J Clin Invest 116:271-284 (2006).
Villanueva et al., "Serum Peptide Profiling by Magnetic Particle-Assisted, Automated Sample Processing and MALDI-TOF Mass Spectrometry," Anal. Chem. 76:1560-1570 (2004).
Wang et al., "Pheromone Signaling Mechanisms in Yeast: a Prototypical Sex Machine," Science 306:1508-1509 (2004).
Wang et al., "Pheromone-regulated Sumoylation of Transcription Factors That Mediate the Invasive to Mating Developmental Switch in Yeast," J Biol Chem 281(4):1964-1969 (2006).
Wendland et al., "Characterization of α-factor pheromone and pheromone receptor genes of Ashbya gossypii," FEMS Yeast Res 11:418-429 (2011).
Werlen et al., "Measurement of Biologically Available Naphthalene in Gas and Aqueous Phases by Use of a Pseudomonas putida Biosensor," Appl Environ Microbiol 70:43-51 (2004).
Wingler et al., "Reiterative Recombination for the in vivo assembly of libraries of multigene pathways," PNAS 108(37):15135-15140 (2011).
Worsham et al., "Quantitative plating of Histoplasma capsulatum without addition of conditioned medium or siderophores," J. Med. Vet. Mycol. 26:137-143 (1988).
Xu et al., "Yeast That Smell," J Biochem Tech 1(1):06-08 (2008).

(56) References Cited

OTHER PUBLICATIONS

Yagi, "Applications of whole-cell bacterial sensors in biotechnology and environmental science," Appl Microbial Biotechnol 73:1251-1258 (2007).

Yang et al., "Prognostic Polypeptide Blood Plasma Biomarkers of Alzheimer's Disease Progression," J Alzheimer's Dis 40:659-666 (2014).

* cited by examiner

Induction of lycopene biosynthesis by the natural yeast peptide, α-factor.

Improvement of lycopene readout speed in optimal laboratory conditions.

FIG. 9A
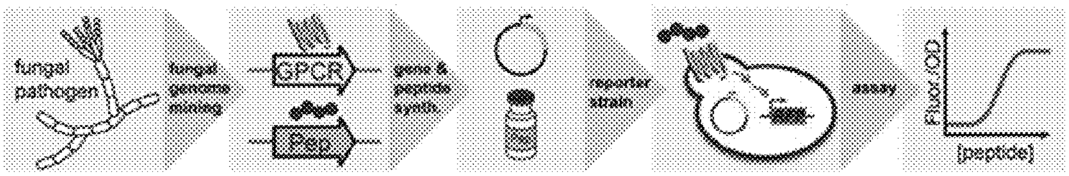
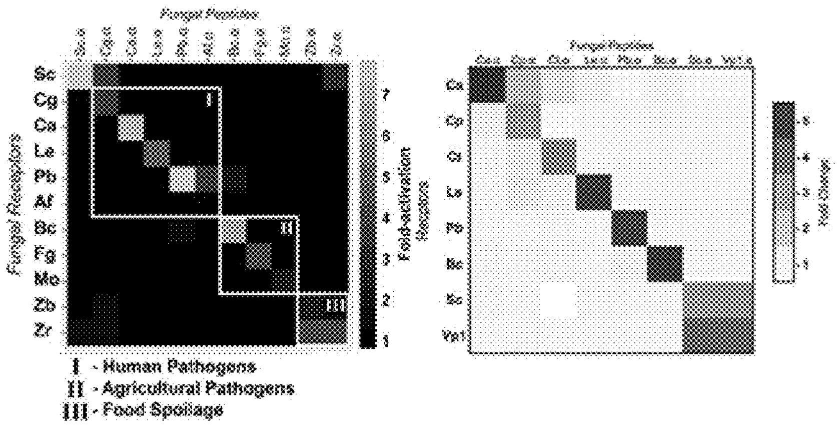
FIG. 9B
| Fungal Pathogen | $EC_{50}$ (nM) |
|---|---|
| *S. cerevisiae* (Sc) | 190 |
| *C. glabrata* (Cg) | 3600 |
| *C. albicans* (Ca) | 4.1 |
| *L. elongisporous* (Le) | 51 |
| *P. brasiliensis* (Pb) | 34 |
| *A. fumigatus* (Af) | NA |
| *B. cinerea* (Bc) | 4.8 |
| *F. graminearum* (Fg) | 1300 |
| *M. oryzae* (Mo) | 5000 |
| *Z. bailii* (Zb) | 20 |
| *Z. rouxii* (Zr) | 35 |
FIG. 9C FIG. 11A
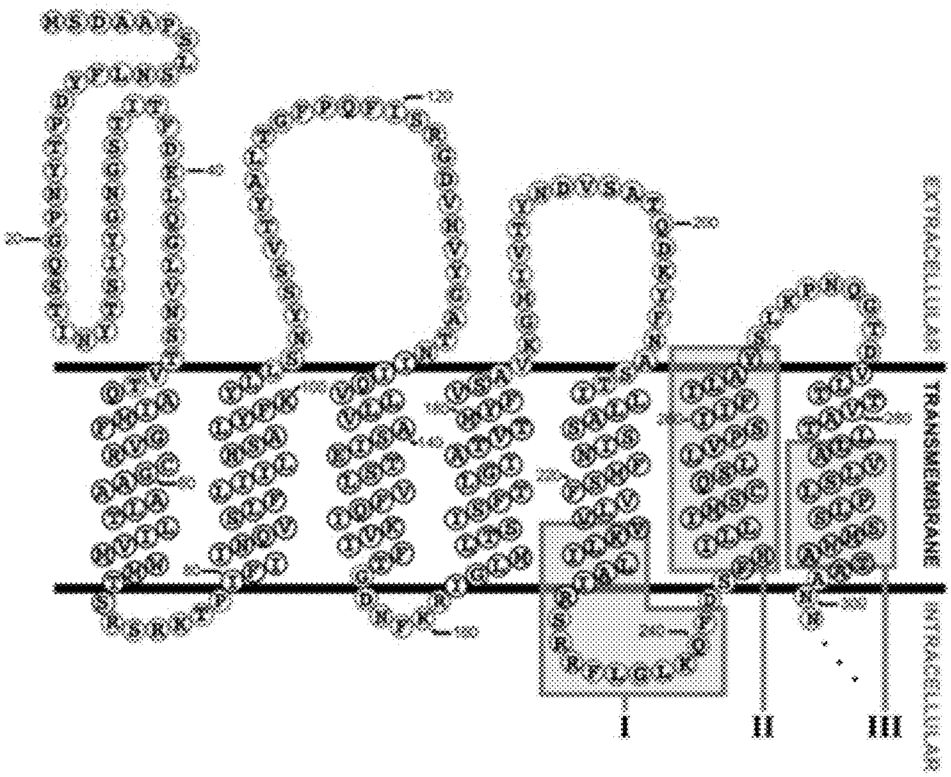
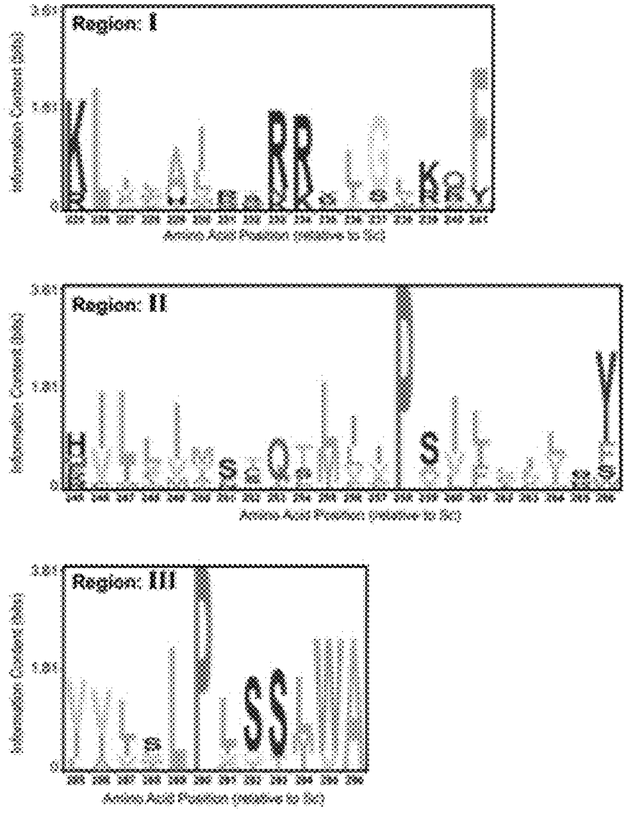
FIG. 11B
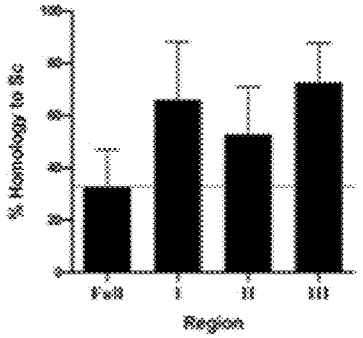
FIG. 11C

| sequence | GRAUY |
|---|---|
| Cluster 1 | |
| ————nWHWLRLDPGQPLY– | −0.964 |
| ————WHWLQLKPGQPMY– | −0.869 |
| ————WHWLRLRYGEPIY– | −0.768 |
| ————gdwgWFWYVPRPGDPAM– | −0.635 |
| ————WHWVRLRKGQGLF– | −0.585 |
| ————WSWITLRPGQPIF– | 0.054 |
| ————WHWLELDNGQPIY– | 0.7 |
| Cluster 2 | |
| ————KPHWTTYGYYEPQ– | −1.838 |
| ————kfKFRLTRYGWFSPN– | −0.92 |
| ————kkNSRFLTYWFFQPIm | −0.375 |
| ————GFRLTNFGYFEPG– | −0.315 |
| Cluster 3 | |
| tyedflrvykNWWSFQNPDRPDL– | −1.265 |
| vsdrvkqmlsHWWNFRNPDTANL– | −0.883 |
| tyadflrayqSWNTFVNPDRPNL– | −0.778 |

FIG. 14A
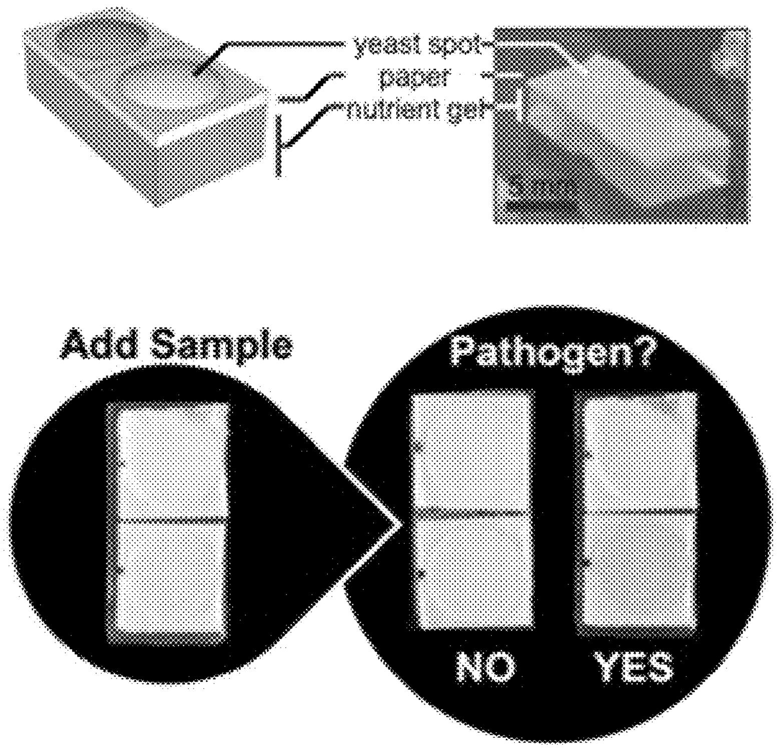
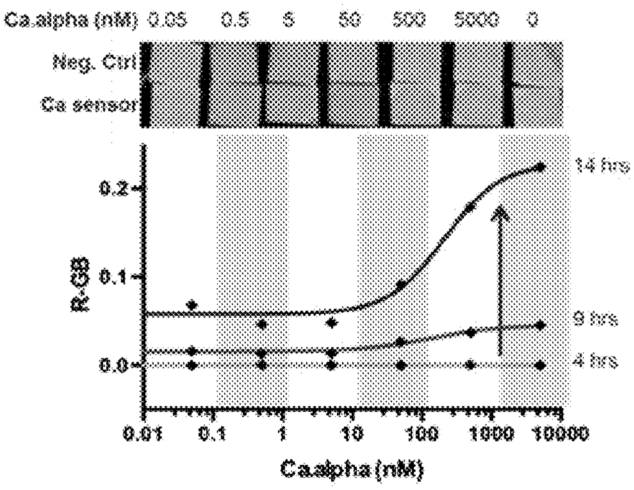
FIG. 14B
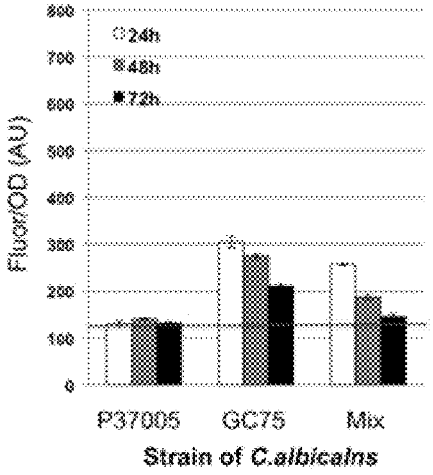
FIG. 14C

FIG. 17A
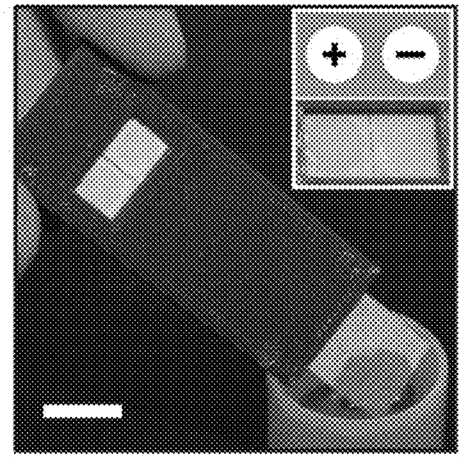
FIG. 17B
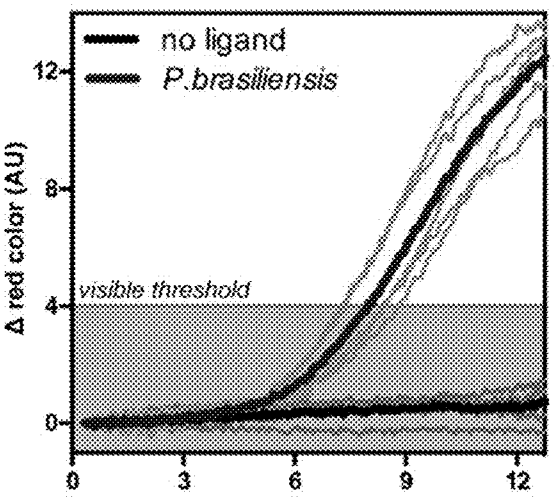
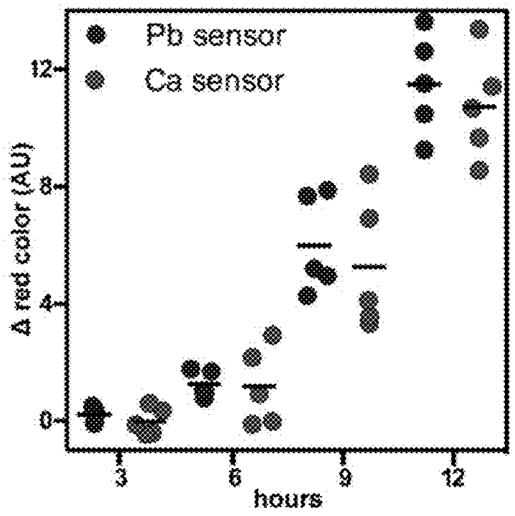
FIG. 17C
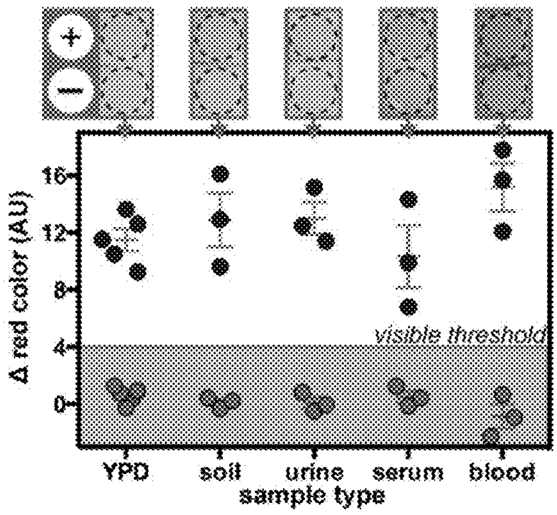
FIG. 17D

FIG. 19A
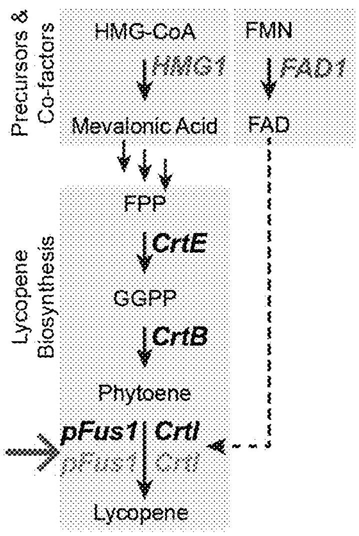
FIG. 19B
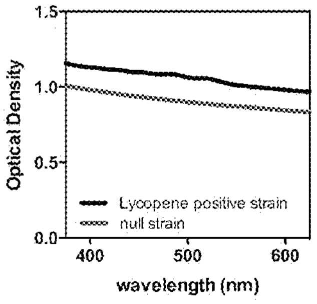
FIG. 19C
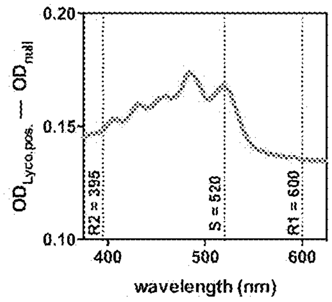
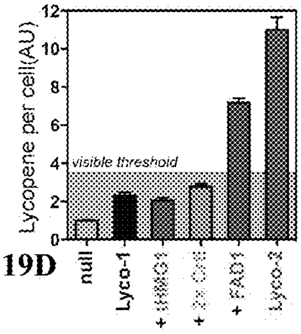
FIG. 19D
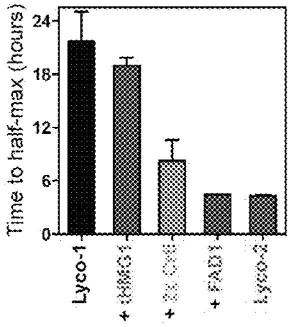
FIG. 19E
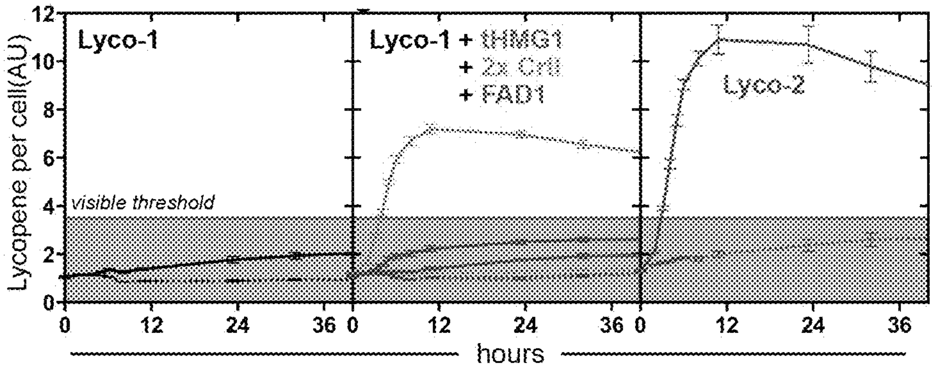
FIG. 19F FIG. 19G FIG. 19H FIG. 20A
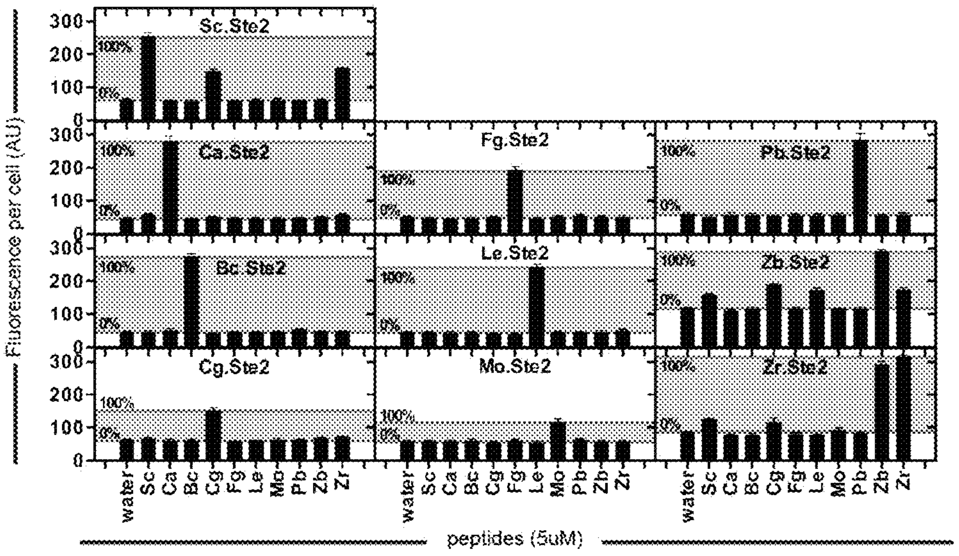
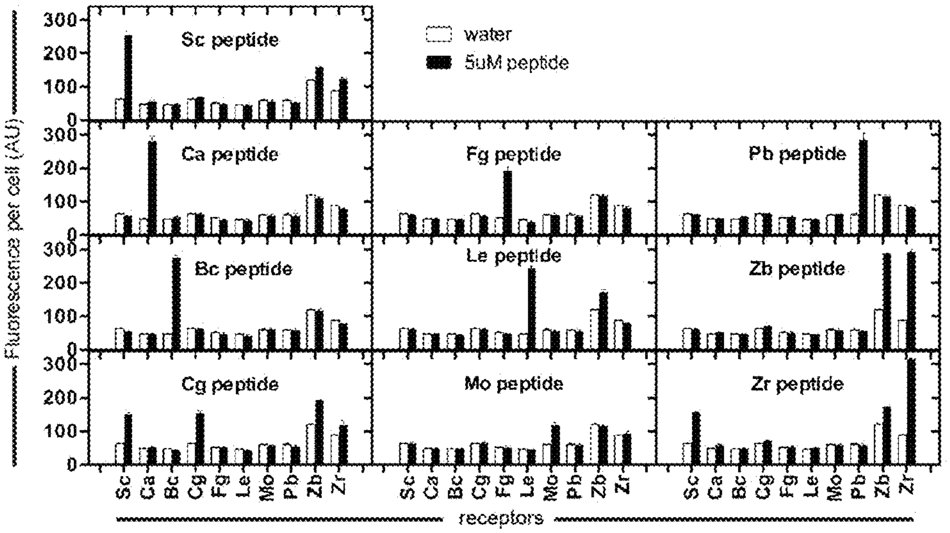
FIG. 20B

FIG. 22A

FIG. 22B

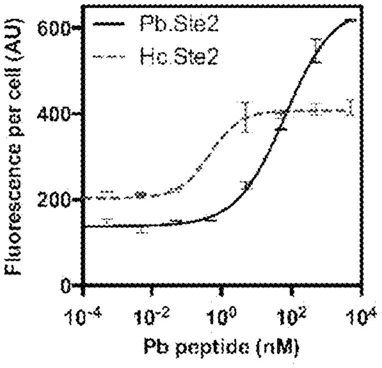

FIG. 22C

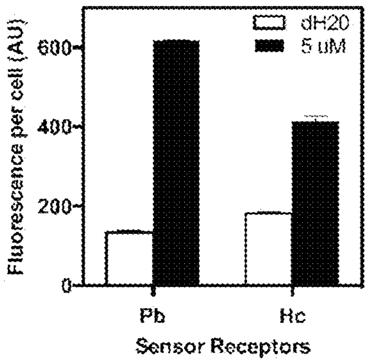

FIG. 22D

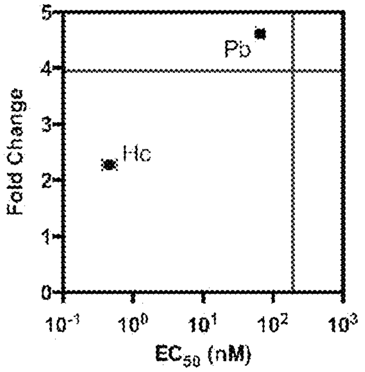

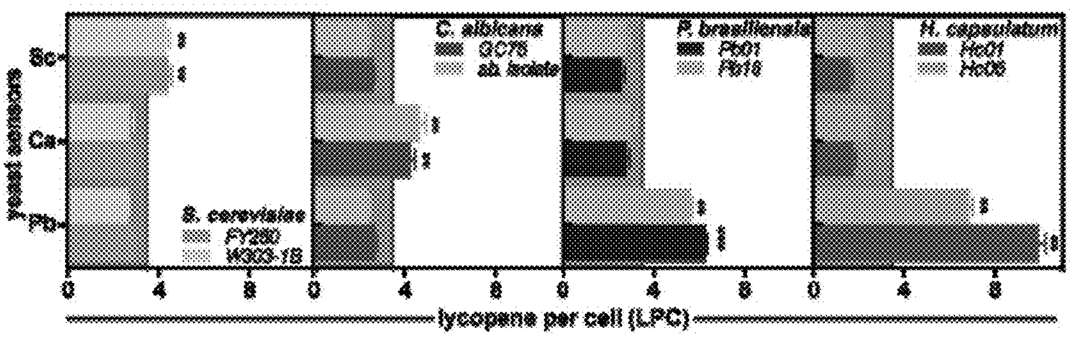

FIG. 22E

```
Pb - M  SFDPF  Q  VVFHKADGTPFNVSIH LD FVQY   VCINY   QLGA VIA  MLA L  60
Hc - M  SFDPF  Q  VVFHKADGTPFNVSIH LD FVQY   VCINY   QLGA VIA  MLA L  60

Pb - T  S KRR PVFFLNT AL MNFARLLCMTIYFTTGFN  YA F  DYS VPGSAYA S L  120
Hc - T  S KRR PVFFLNT AL MNFARLLCMTIYFTTGFN  YA F  DYS VPGSAYA S L  120

Pb - G  F T LVI MEMSL IQT VVC TL IQR LL  VS  I L AIGFR GLMVENCIA   180
Hc - G  F T LVI MEMSL IQT VVC TL IQR LL  VS  I L AIGFR GLMVENCIA   180

Pb - I  ASNF PFIWLQSASNI ITISTCFFSAVFVTKL YALVTR RLG TRFGAMQVMFI   240
Hc - I  ASNF PFIWLQSASNI ITISTCFFSAVFVTKL YALVTR RLG TRFGAMQVMFI   240

Pb - S QTMVIPAIFSI QYP P YEMNSN FTLVAIFLPLSSLWA AT  SFET  SG HQY   300
Hc - S QTMVIPAIFSI QYP P YEMNSN FTLVAIFLPLSSLWA AT  SFET  SG HQY   300

Pb - LW SE SN  T S  QS  QN  T RSGGSVAT LSPD LD  Y    V AC KA       356
Hc - LW SE SN  T S  QCS CQN  T RSGGSVAT LSPD LD  Y      AC KA       357
```

DETECTION OF ANALYTES USING LIVE CELLS

CROSS-REFERENCE TO RELATED APPLICATIONS

This application is a divisional of U.S. patent application Ser. No. 15/596,837, filed May 16, 2017, which is a continuation-in-part of International Patent Application No. PCT/US2015/061373, filed Nov. 18, 2015, which claims priority to U.S. Provisional Patent Application Ser. No. 62/081,441, filed Nov. 18, 2014, priority to all of which are claimed, and the contents of all of which are incorporated by reference in their entireties herein. International Patent Application No. PCT/US2015/061373 includes a Sequence Listing which is incorporated by reference herein.

GRANT INFORMATION

This invention was made with government support under grant AI110794 awarded by the National Institutes of Health, grant HR0011-15-2-0032 awarded by the Department of Defense/Defense Advanced Research Projects Agency, and grant 1144155 awarded by the National Science Foundation. The government has certain rights in the invention.

SEQUENCE LISTING

A Sequence Listing conforming to the rules of WIPO Standard ST.25 is hereby incorporated by reference. Said Sequence Listing has been filed as an electronic document via PatentCenter in ASCII formatted text. The electronic document, created on Sep. 1, 2023, is entitled "070050_6405_ST25.txt", and is 281,368 bytes in size.

1. INTRODUCTION

The present invention relates to methods and compositions for detecting the presence of an agent in a test sample using a whole cell reporter. In certain embodiments, detection can be performed without the aid of instrumentation, for example outside of a laboratory setting, permitting home and field tests for interrogating the status of biological systems. The present invention may be used, for example, to identify pathogens and thereby limit the dissemination of disease.

2. BACKGROUND

2.1. Whole-Cell Biosensors

Microbial whole-cell bio-reporters present unique advantages for environmental sensing, such as the probing of complex biochemical processes, compatibility with aqueous media, self-renewal by replication, portability by freeze-drying, availability of numerous natural sensing pathways, and ease of engineering new functions (e.g., by directed evolution).[1,2] Bacterial whole cell sensors have previously been demonstrated for detection of DNA damage,[3] heat shock,[4] oxidative stress,[5] heavy metals,[6-8] viruses,[9] and light.[10] Yeast and mammalian whole cell sensors have also been reported. For yeast whole cell sensors, see Hollis (2000) and Radhika (2007). For mammalian whole cell sensors, see Rider, (2003).

2.2. Peptides as Analytes

While natural receptors can be utilized for detection of a broad range of analytes, proteins and their peptide epitopes present a ubiquitous pool of natural biomarkers which are highly characteristic of the organisms that produce them. Peptides can thus be used as targets for detection of pathogenic organisms, food born toxins, immunogens and bioterrorism agents. For example, see the recent development of mass spectrometry of proteolized samples as a diagnostic tool for various diseases.[11,12]

2.3. Using GPCRs for Detection

G-protein coupled receptors (GPCR) constitute a large family of seven-transmembrane receptors for hormones, neurotransmitters, chemokines, calcium, odorants, taste molecules and even light.[19] GPCR signaling pathways are highly conserved among diverse species. Furthermore, GPCR-activation of the Mitogen-activated protein kinase (MAPK) phosphorylation cascade is conserved from yeast to mammals,[19] with different MAPK families activated by multiple different GPCRs.

It was shown that yeast pheromone receptors can be functionally replaced by expressing mammalian GPCRs that couple to the endogenous MAPK signaling pathway, so that the corresponding mammalian agonist activates the yeast pheromone response using different reporter genes[21-23] beta-galactosidase[24-26] or auxotrophic markers.[27-29]

G-protein coupled receptors (GPCRs) have previously been implemented in yeast to develop high-throughput drug discovery assays based around mammalian receptors by using a growth based reporter.[13,14] Additionally, yeast has also been used to functionally express native fungal receptors to study the biology of the respective fungi.[15-18] These previous studies coupled the GPCRs to the endogenous pheromone response pathway by using laboratory assays requiring instrumentation.

3. SUMMARY OF THE INVENTION

The present invention relates to methods and compositions for detecting the presence of an agent, for example, but not limited to, a human disease agent (e.g., a pathogenic agent), an agricultural agent, an industrial and model organism agent, a bioterrorism agent, or a heavy metal contaminant, by detecting the presence of an analyte indicative of the presence of the agent in a test sample. In certain embodiments, the analyte is the agent itself, a portion of the agent (e.g., a portion generated by proteolysis), or a product of the agent. The methods utilize a sensor cell bearing a receptor that is specific for the analyte, where binding of the receptor to the analyte triggers a detection event that is indicative of the presence of the agent. The reporter can be coupled to the receptor. In certain embodiments, the sensor cell is a microbe that is easy and quick to propagate, for example a yeast cell, and the reporter gene product is detectable to the naked eye, for example a pigmented compound such as (red) lycopene. In certain non-limiting embodiments, the present disclosure provides an engineered baker's yeast that uses G-protein coupled receptors (GPCRs) to detect a range of peptide ligands associated with specific target agents and uses the red plant pigment lycopene as a fast, non-technical, visual readout. In certain non-limiting embodiments, the present disclosure provides methods of engineering peptide-activated GPCRs to detect non-cognate agent-specific peptides and to improve performance (e.g., sensitivity and/or specificity) against peptide ligands, using directed evolution.

The present invention provides methods of detecting the presence of an agent of interest in a sample. In certain embodiments, the method comprises: contacting the sample with a sensor cell comprising a non-native G-protein coupled receptor (GPCR) that binds to an analyte indicative of the presence of the agent, wherein binding of the analyte to the receptor triggers appearance of a reporter detectable by the naked eye, wherein the increased expression is indicative of the presence of the agent. The agent can be selected from the group consisting of human disease agents, agricultural agents, industrial and model organism agents, bioterrorism agents, and heavy metal contaminants. In certain embodiments, the non-native GPCR receptor is engineered to bind to the analyte. In certain embodiments, the non-native GPCR receptor is engineered by directed evolution. In certain embodiments, the non-native GPCR receptor is a fungal pheromone GPCR. In certain embodiments, the non-native GPCR receptor is selected from the group consisting of the GPCRs listed in Tables 2 and 6.

In certain embodiments, the sensor cell is a microbe. In certain embodiments, the sensor cell is a fungal cell. In certain embodiments, the sensor cell is a yeast cell. In certain embodiments, the sensor cell is *S. cerevisiae*. In certain embodiments, the sensor cell comprises a nucleic acid encoding the receptor. In certain embodiments, the nucleic acid is linked to a promoter.

In certain embodiments, the analyte is a cognate ligand for the non-native GPCR receptor. In certain embodiments, the analyte is a non-cognate ligand for the non-native GPCR receptor.

In certain embodiments, the analyte is a peptide. In certain embodiments, the peptide is a fungal mating pheromone. The fungal mating pheromone can be selected from the group consisting of human fungal mating pheromones (meaning mating pheromones of fungi that can colonize or infect humans), non-human animal fungal mating pheromones (meaning mating pheromones of fungi that colonize or infect a non-human animal), plant fungal mating pheromones (meaning mating pheromones of fungi that colonize or infect a plant), food fungal mating pheromones (meaning mating pheromones of fungi that colonize or infect human or non-human animal food items), and industrial/model fungal mating pheromone. In non-limiting examples, the human fungal mating pheromone can be selected form the group consisting of the mating pheromones of *C. albicans, C. glabrata, P. brasiliensis, L. elongisporous, P. rubens, C. guillermondi, C. tropicalis, C. parapsilosis, C. lusitaniae, S. scheckii*, and *Candida krusei*. An example of a non-human animal fungal mating pheromone is the mating pheromone of *P. destructans*. In non-limiting examples, the plant fungal mating pheromone can be selected from the group consisting of the mating pheromones of *F. graminearum, M. oryzea, B. cinerea, G. candidum*, and *C. purpurea*. In non-limiting examples, the food fungal mating pheromone can be selected from the group consisting of the mating pheromones of *Zygosaccharomyces bailii, Zygosaccharomyces rouxii*, and *N. fischeri*. In non-limiting examples, the industrial/model fungal mating pheromone can be selected from the group consisting of the mating pheromones of *S. cerevisiae, K. lactis, S. pombe, V. polyspora* (receptor 1), *V. polyspora* (receptor 2), *S. stipitis, S. japonicas, S. castellii*, and *S. octosporus, A. oryzae, T melanosporum, D. haptotyla, C. tenuis, Y. lipolytica, T. delbrueckii, B. bassiana, K. pastoris, A. nidulans, N. crassa*, and *H. jecorina.*

In non-limiting examples, the peptide can be selected from the group consisting of the peptides listed in Table 5. In certain embodiments, the peptide has a length of about 5-25 residues. In certain embodiments, the peptide has a length of about 9-23 residues.

In certain embodiments, the peptide is associated with a bacterial infection. In certain embodiments, the peptide is associated with *Vibrio cholera*. In non-limiting examples, the peptide associated with *Vibrio cholerae* can be selected from the group consisting of a peptide having an amino acid sequence set forth in VEVPGSQHIDSQKKA (SEQ ID NO: 26), a peptide having an amino acid sequence that is at least 80%, at least 90% or at least 95% about homologous to SEQ ID NO: 26, a peptide having an amino acid sequence set forth in VPGSQHIDS (SEQ ID NO: 27), and a peptide having an amino acid sequence that is at least about 80%, at least 90% or at least 95% homologous to SEQ ID NO: 27. In certain embodiments, the peptide is derived from cholera toxin. The peptide derived from cholera toxin can be selected from the group consisting of the peptides listed in Table 7.

In certain embodiments, the non-native GPCR receptor is coupled to the reporter. In certain embodiments, the method further comprises culturing the sensor cell for an effective period of time; and determining expression of the reporter gene. In certain embodiments, determining expression of the reporter gene does not comprise instrumentation. In certain embodiments, the reporter is a biosynthesized visible-light pigment. In certain embodiments, the reporter is lycopene. In certain embodiments, the sensor cell is engineered to express the receptor.

In certain embodiments, the sample is selected from the group consisting of water samples and body fluid samples. The water sample can be selected from the group consisting of fresh water, sea water, and sewage samples. The body fluid sample can be selected from the group consisting of intestinal fluids, diarrhea, mucus, blood, cerebrospinal fluid, lymph, pus, saliva, vomit, urine, bile, and sweat.

Additionally, the present invention provides a sensor cell comprising a non-GPCR receptor that binds to an analyte indicative of the presence of the agent, wherein binding of the analyte to the receptor triggers appearance of a reporter detectable by the naked eye, wherein the increased expression is indicative of the presence of the agent.

Furthermore, the present invention provides a kit for detecting the presence of an agent of interest, comprising a sensor cell as described above. In certain embodiments, the kit further comprises a negative control. In certain embodiments, the kit further comprises a substrate that comprises the sensor cell. In certain embodiments, the substrate is comprised in a dipstick. In certain embodiments, the kit further comprises a nutrient source.

4. BRIEF DESCRIPTION OF THE FIGURES

The patent or application file contains at least one drawing executed in color. Copies of this patent or patent application publication with color drawing(s) will be provided by the Office upon request and payment of the necessary fee.

Figure 1B:
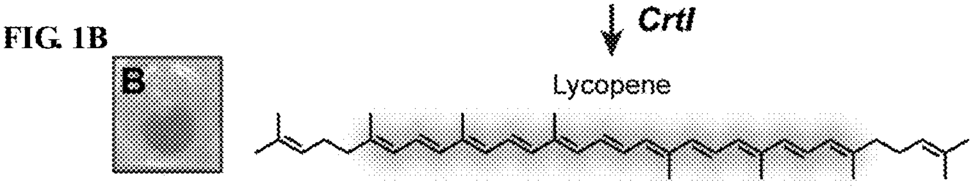

FIGS. 1A and 1B depict biosynthesis of lycopene. (A) Introduction of *E. herbicola* carotenoid enzymes (CrtEBI) result in biosynthesis of lycopene from endogenous yeast farnesyl pyrophosphate. (B) A lycopene-producing yeast strain becomes visibly colored.

Figure 2:
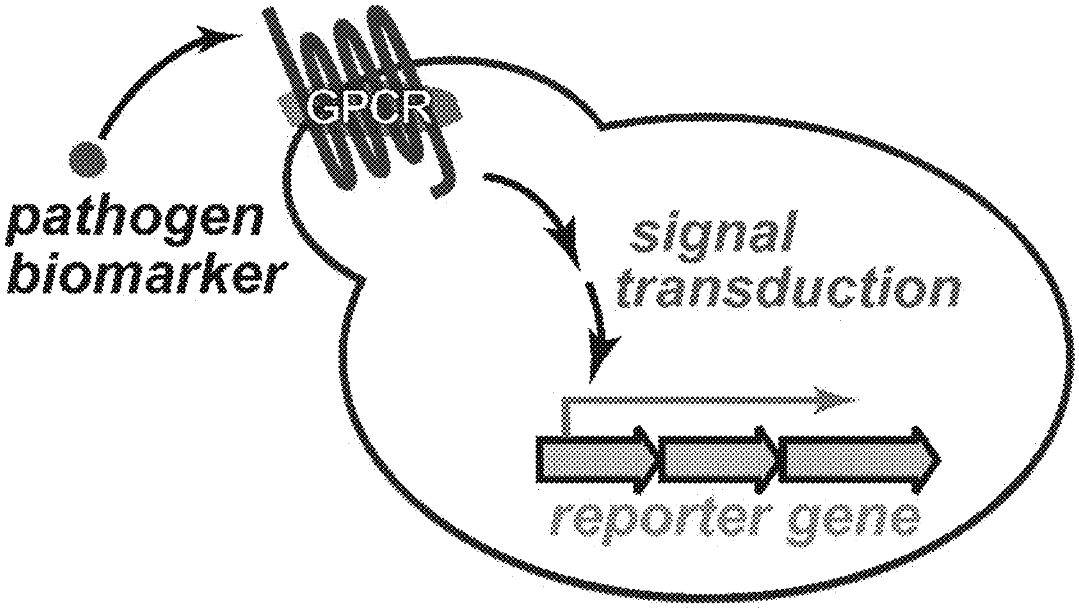

FIG. 2 depicts eukaryotic biosensor design. Binding of one or more agent-specific analyte (e.g., a peptide) to a receptor triggers a signal transduction cascade, resulting in induction of CrtI (or other Crt) gene responsible for a reporter (e.g., lycopene) biosynthesis or other reporter genes. The G-protein coupled receptor operates via the mating signaling pathway in yeast.

Figure 3:
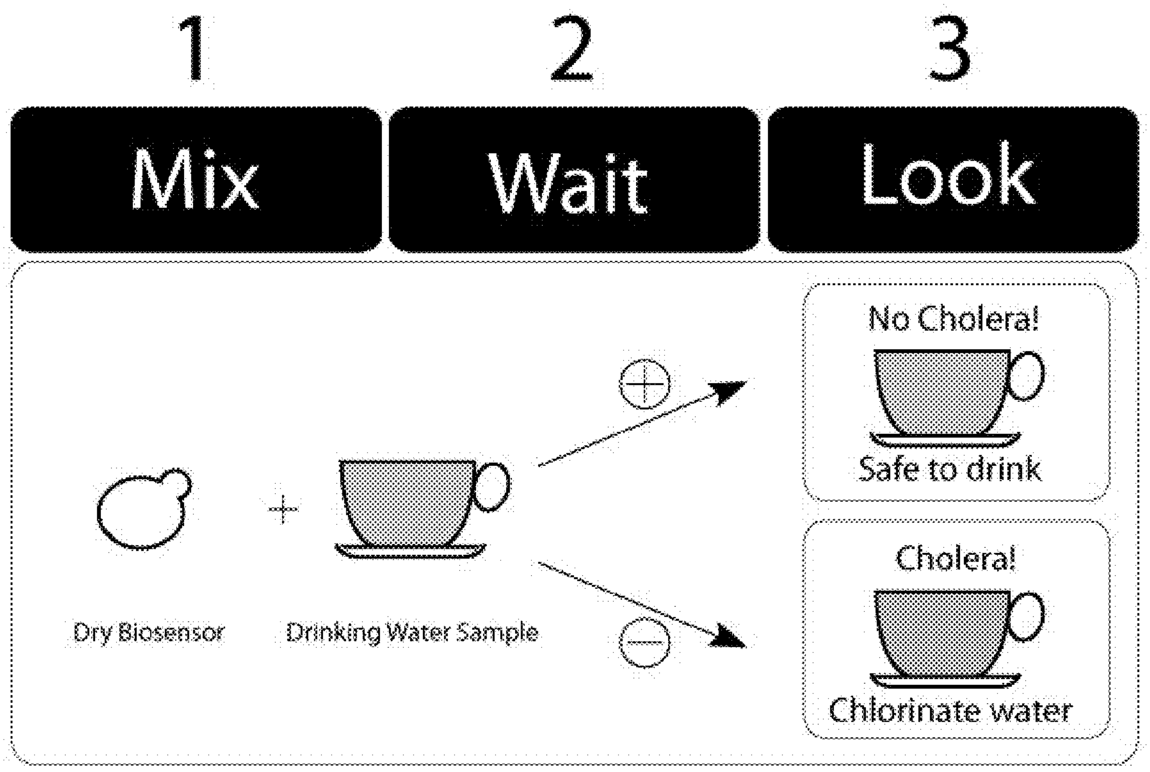

FIG. 3 depicts one embodiment of cell-based detection of cholera pathogen in drinking water. Engineered sensor is added to cholera-contaminated water or a clinical sample.

Binding of the cholera pathogen-specific peptide induces a signal cascade in the sensor cell, resulting in amplification of a color reporter gene colorimetric signal.

Figure 4A:
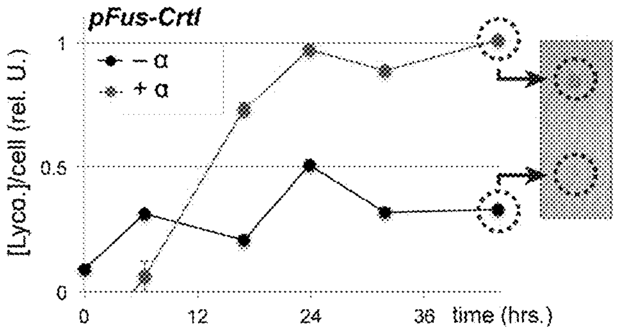
Figure 4B:
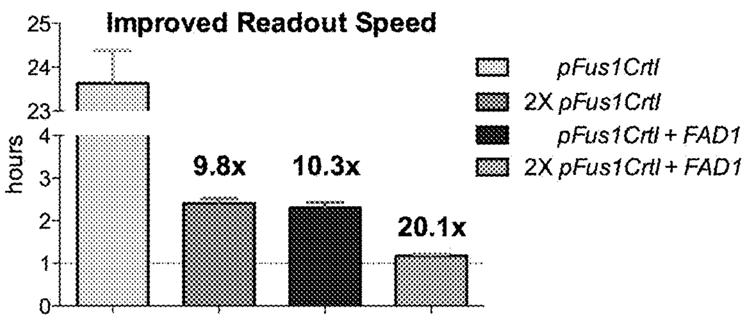

FIGS. 4A and 4B depict experimental results with yeast strains that produced lycopene in response to activation of the endogenous GPCR Ste2. FIG. 4A shows induction of lycopene biosynthesis by the natural yeast peptide, α-factor. FIG. 4B shows improvement of lycopene readout speed with modification of the yeast strain, in laboratory conditions.

Figure 5:
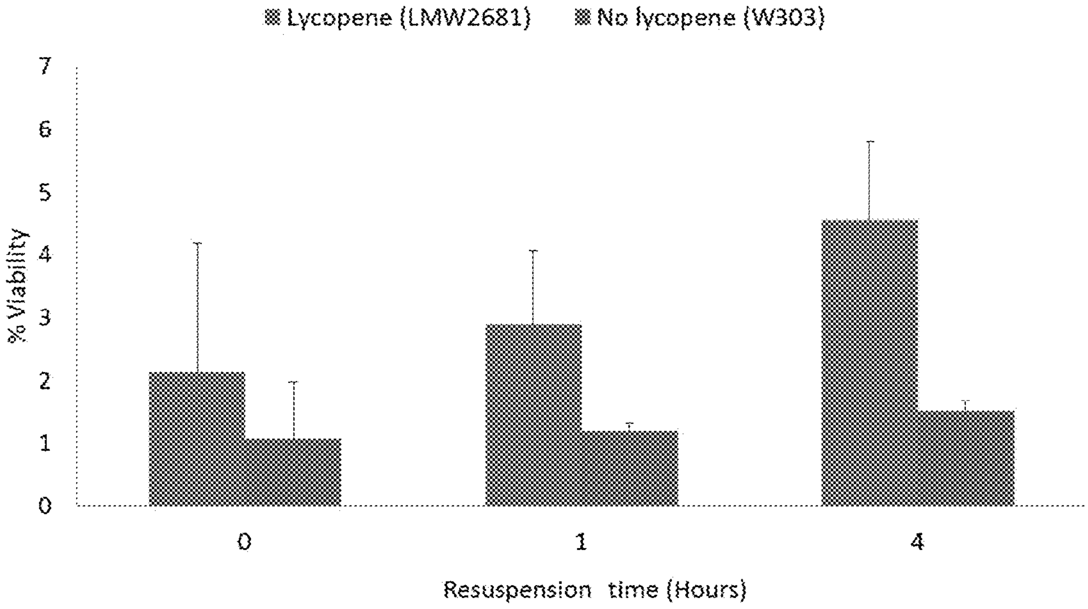

FIG. 5 depicts viability of yeast after freeze-drying. $10^8$ cells were freeze dried and resuspended in YPD. Cell was then plated to quantify survival after 0, 1 or 4 hours in YPD media.

Figure 6:
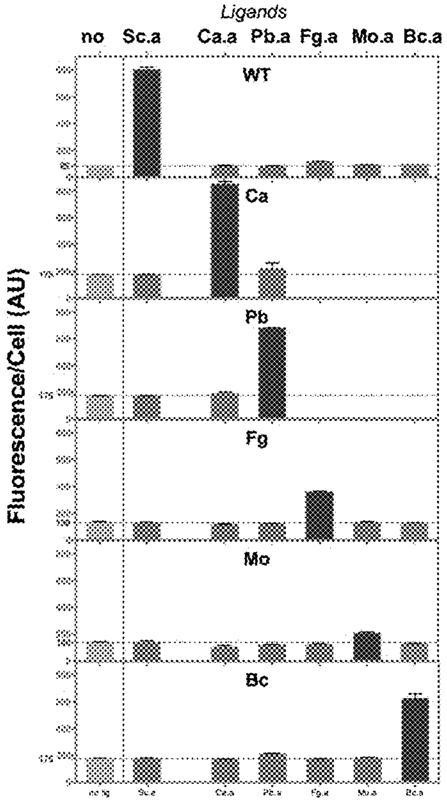

FIG. 6 depicts functional and specific response of fungal GPCRs measured by fluorescence. "Xx.a" denotes peptide pheromones derived from species Xx. Species abbreviations: Sc, *S. cerevisiea*; Ca, *C. albicans*; Pb, *P. brasiliensis*; Fg, *F. graminearum*; Mo, *M. oryzea*; Bc, *B. cinerea*.

Figure 7:
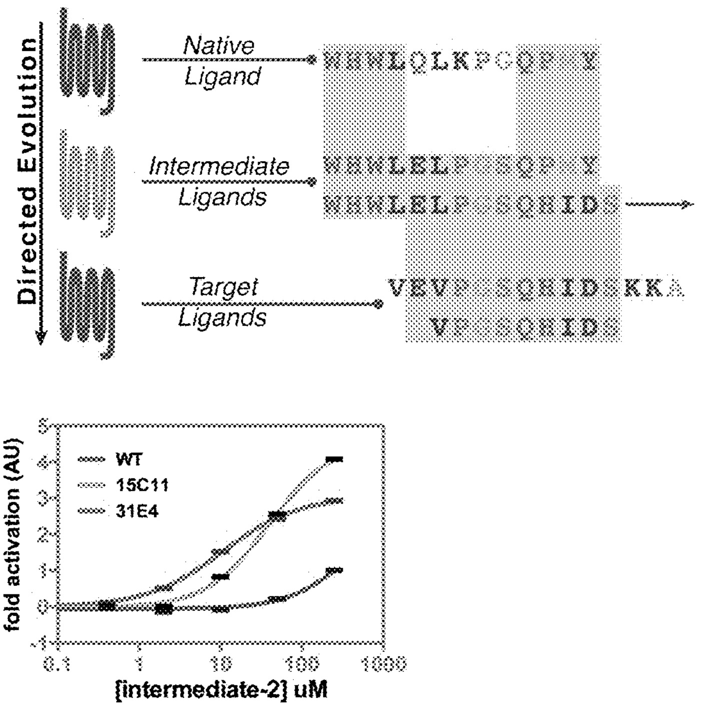

FIG. 7 depicts a peptide-centric directed evolution (DE) approach. The peptide-centric DE approach permitted direct use of hybrid peptides that march from αF to the target peptide analytes. After rounds of DE, mutant engineered receptors gained activity to an intermediate peptide and then further increased EC50.

Figure 8:
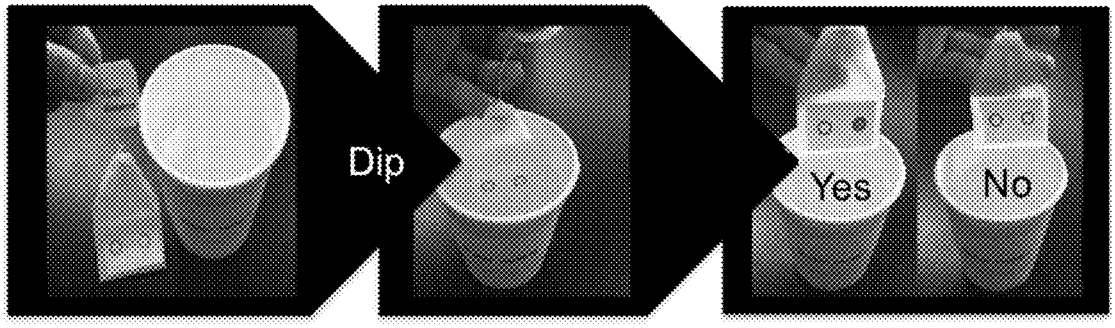

FIG. 8 depicts one embodiment of cell-based detection of an agent of interest. A yeast-based biosensor constructed around engineered baker's yeast is extremely cheap to produce, portable as a freeze-dried product, and simple to use. A non-technical user simply adds a sample and waits for a color change signaling the presence of the agent.

FIGS. 9A-9C depict specific detection of fungal peptides. (A) Mining of fungal receptor-pheromone pairs. Fungal receptor gene was cloned into *S. cerevisiae* sensor strain, and tested using a synthetic fungal peptide pheromone, using a fluorescent readout. (B) Orthogonality matrices of fungal receptors, measured in biosensor strain using fungal GPCR-peptide pairs. (C) EC50 values for fungal receptors.

Figure 10:
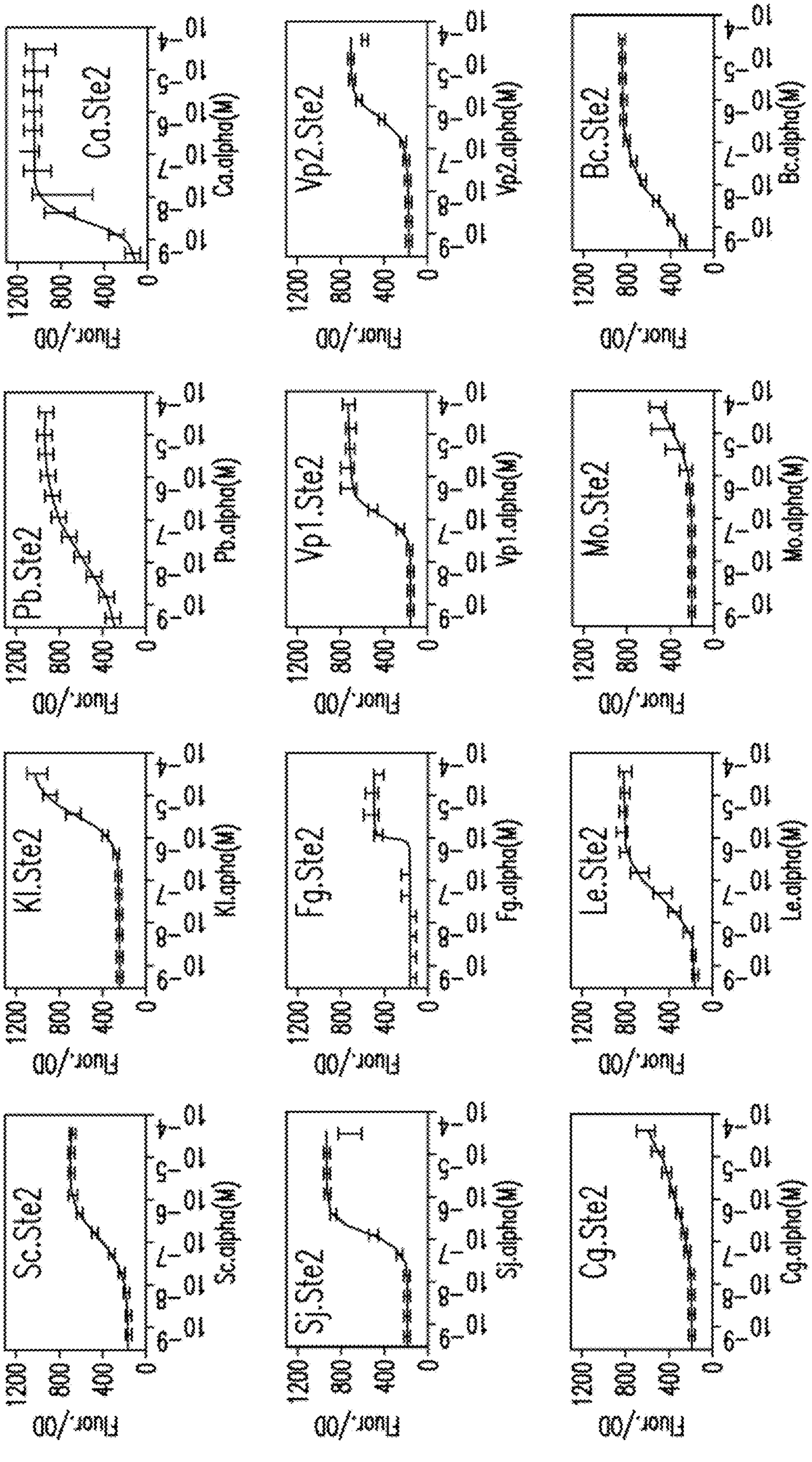
Figure 10:
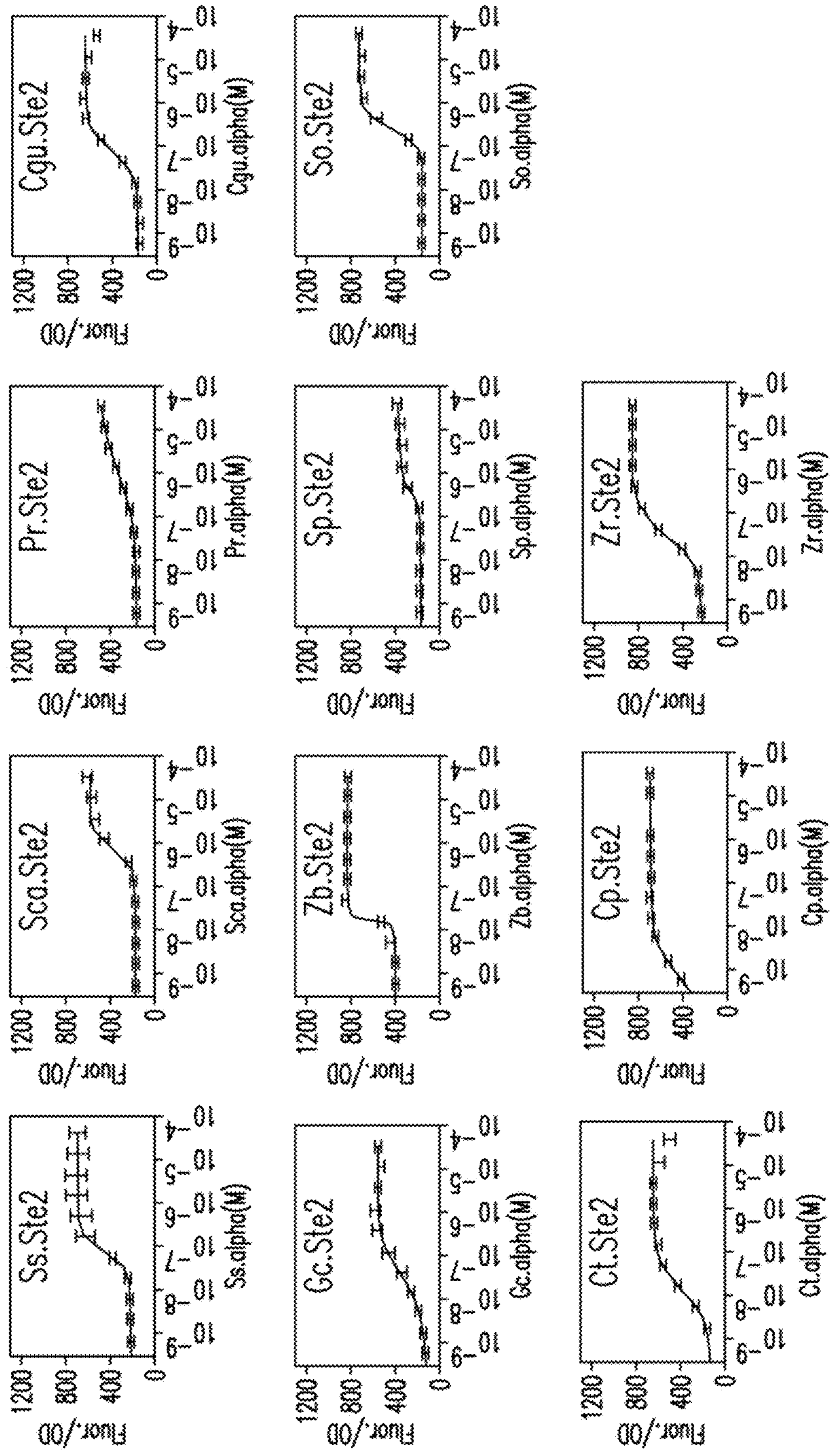

FIG. 10 depicts functional characterization of fungal GPCR-peptide pairs. GPCR was engineered into *S. cerevisiae* sensor cell, and induced using its native fungal peptide (synthetic peptide). Induction of fluorescent marker was monitored in culture.

FIGS. 11A-11C depict common topology of fungal GPCRs. (A) Topological model of the *S. cerevisiae* Ste receptor was predicted by TMHMM v2.0. All the GPCRs characterized have similar topological profile which includes three key regions of higher homology to *S. cerevisiae* Ste2 (gray boxes). Region I corresponds to the third intracellular loop and shows two positively charged residues with high conservation at positions 233 and 234 relative to the *S. cerevisiae* Ste2. Region II corresponds to the sixth transmembrane helix and contains an essential proline that is conserved across all the receptors at position 258 relative to the *S. cerevisiae* Ste2. Region III shows the highest level of conservation and also includes an essential proline conserved across all the receptors at position 290 relative to the *S. cerevisiae* Ste2. (B) Sequence logo results after alignment of the 23 characterized receptors. These three key regions have higher density of conserved residues with some residues conserved across all receptors. (C) Percent homology of different regions the 23 receptors when compared to the corresponding region of the *S. cerevisiae* Ste2.

Figure 12A:
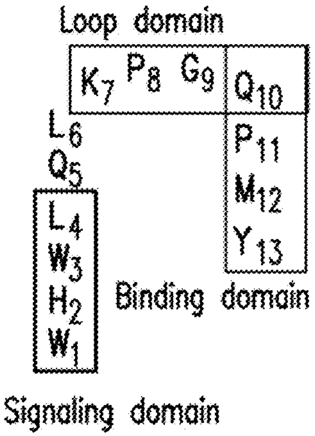
Figure 12B:
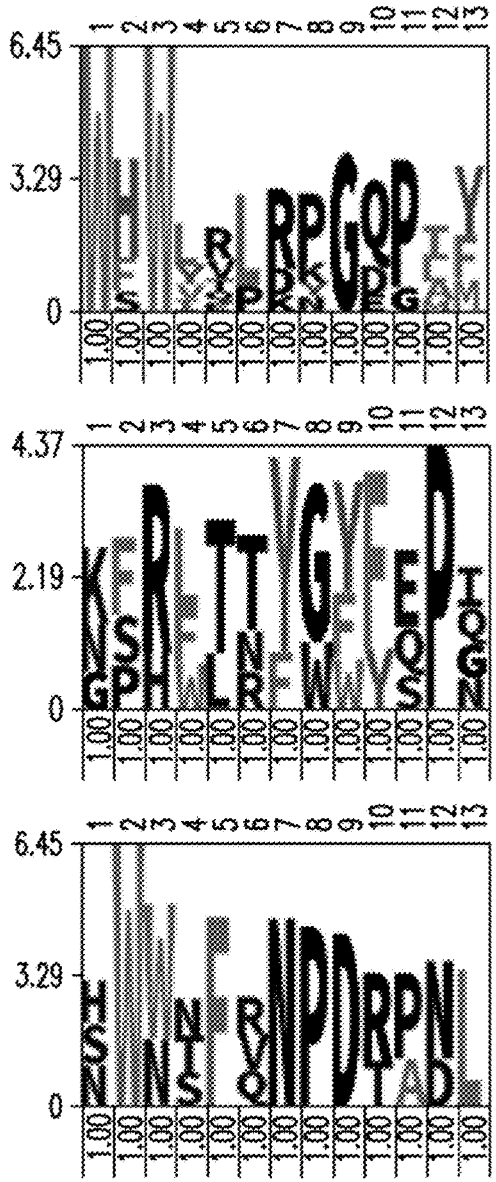
Figure 13C:
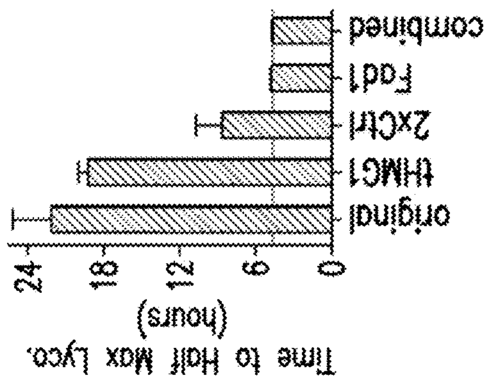
Figure 13B:
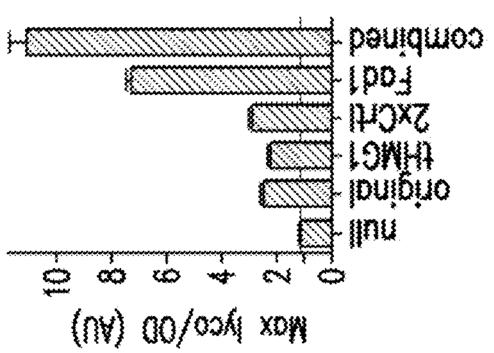
Figure 13D:
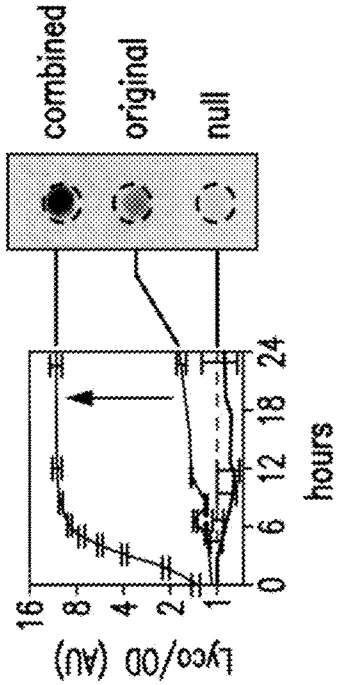
Figure 13A:
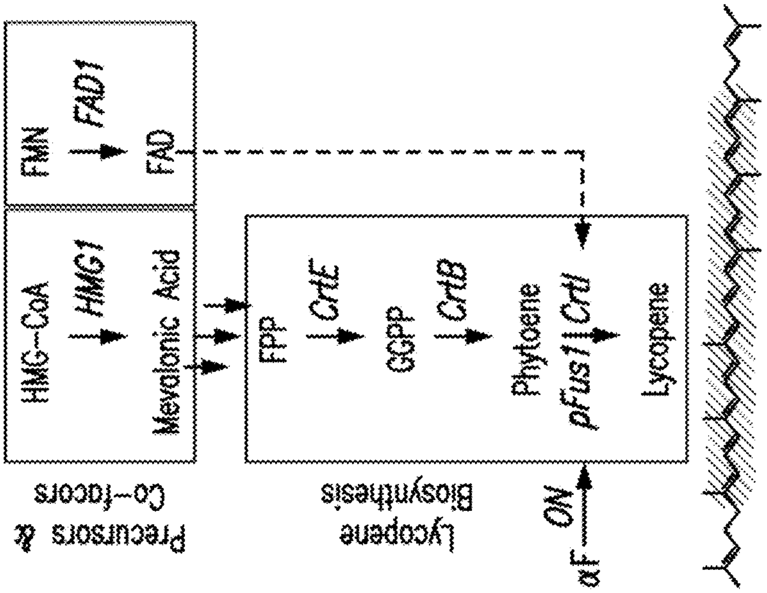

FIGS. 12A and 12B depict characteristics of peptide ligands. (A) Functional domains within *S. cerevisiae* alpha factor. Residues in blue were shown to have a strong impact on binding when changed to alanine, while residues in purple were shown to be involved in signaling. [Naider et al. (2004)]. These findings led to the simplified designation of the N-terminus of alpha factor as the signaling domain and the C-terminus as the binding domain, with internal residues $L_6$ and $G_9$ strongly contributing to peptide binding. (B) Functional peptide ligands were aligned and clustered according to [Andreatta et al. (2013)]. Positive and negative charges (red and green, respectively) were indicated in colored bolt. Sequences within each of the clusters were shown along with the resulting sequence logos. Logos only highlight the identified 13-residue motifs.

FIGS. 13A-13D depict enhancement of lycopene output. (A) Detailed lycopene pathway w/ co-factors and improved yield lycopene yield & time of visible detection. (B and C) Lycopene yield (B) and response time (C) were optimized using the natural *S. cerevisiae* alpha factor response. Overexpression of genes tHMG1, CrtI and Fad1 showed gradual increase in lycopene yield allowing faster visible response. (D) Characterization of lycopene output in response to alpha factor peptide of pathogenic fungi *C. Albicans*.

FIGS. 14A-14C depict detection of pheromone-producing *C. albicans* strain via biosensor strain. (A) Design of "Yeast Block" product and functional demonstration of integrated biosensor. (B) Dose-response curve of lycopene-producing biosensor using synthetic *C. albians* alpha pheromone. (C) Biosensor response to different pheromone-producing *C. albicans* strains, as measured using fluorescence output. Each of the *C. albicans* were grown first on Phloxine B stained agar and opaque colonies were selected. These opaques colonies were cultured and their supernatants were assayed.

Figure 15:
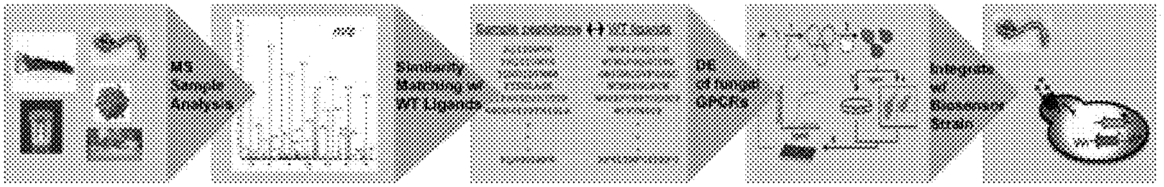

FIG. 15 depicts a process from biomarker identification to a novel biosensor. Workflow starts with identification of potential peptide biomarkers by mass spectrometry, leading to identification of parent GPCR used for directed evolution. The resulting GPCR which binds the selected biomarker is incorporated into the biosensor cell.

Figure 16:
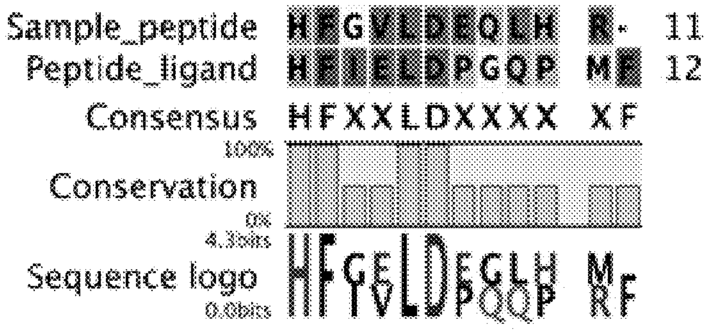
Figures 18A, 18B, 18C, 18D, 18E:
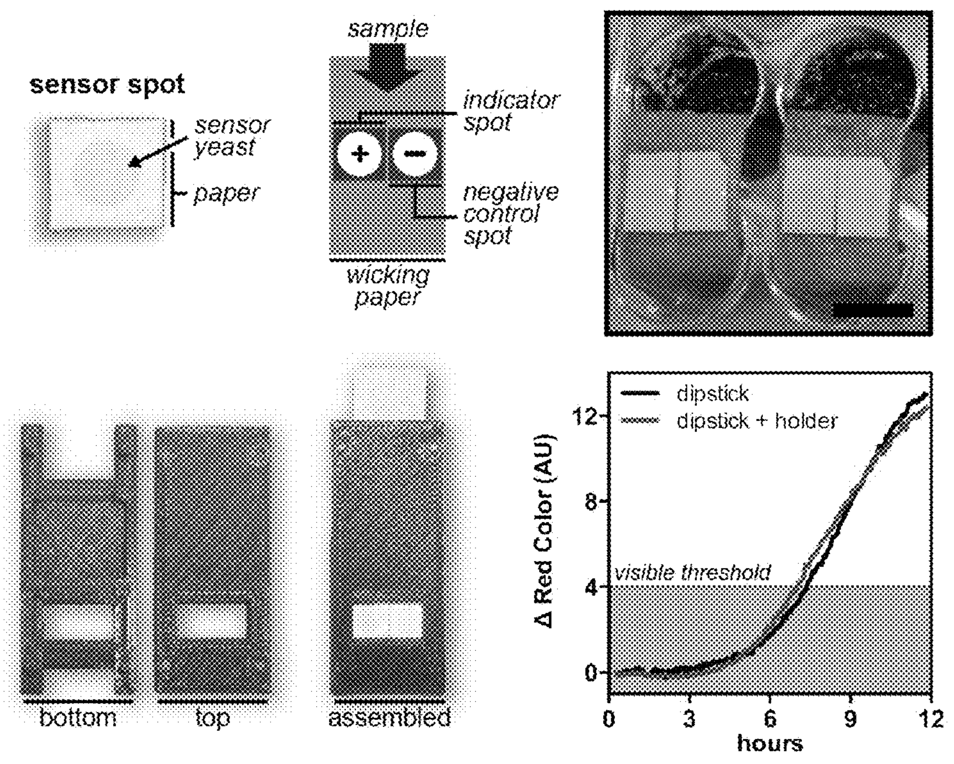
Figures 21A, 21B, 21C, 21D:
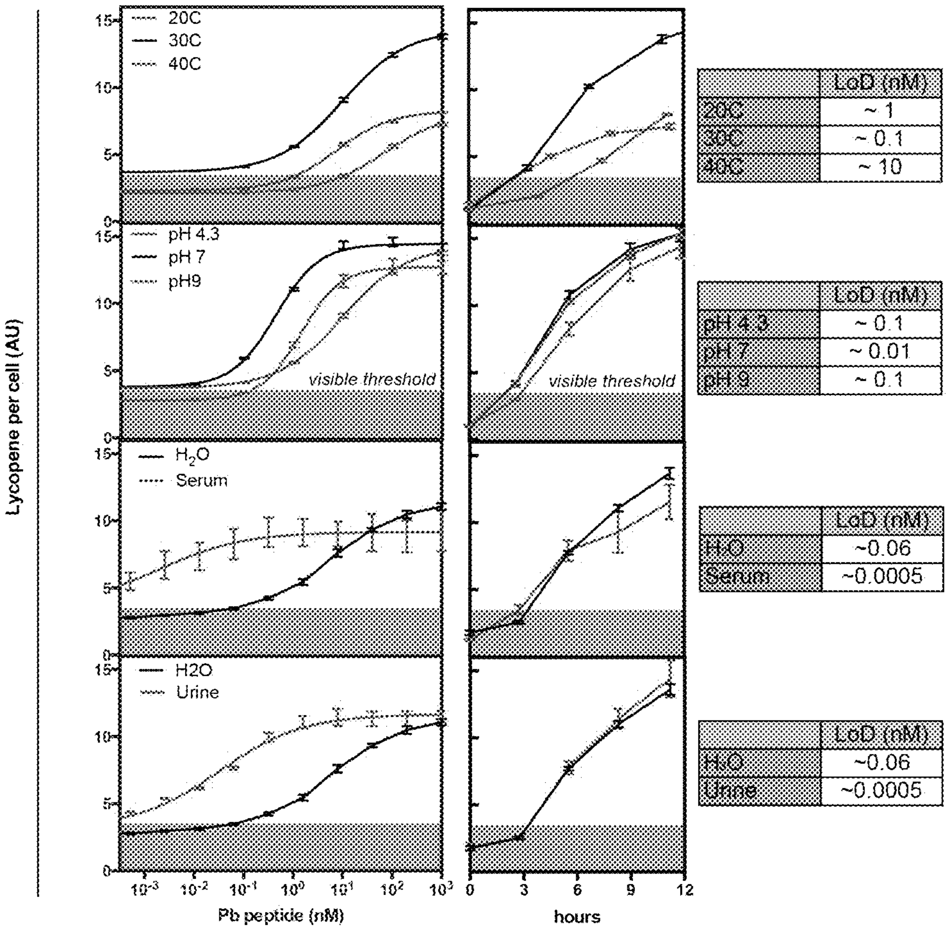

FIG. 16 depicts best matching fungal library member/peptidome member pair. The sample peptide HFGVLDEQLHR (SEQ ID NO:132) is similar in length and sequence (36% identity) to the natural mating pheromone activating the mating GPCR of *Zygosaccharomyces rouxii*.

FIGS. 17A-17D. (A) Dipstick device. Inset: positive readout, "+" biosensor strain. "–" negative control cells. (B) Quantitative analysis of lycopene production using dipstick assay, as scored by time-lapse photography for detection of 1 μM synthetic *P. brasiliensis* mating peptide. Individual runs shown in light color, average response shown in dark color. Shading indicates visible threshold. (C) *P. brasiliensis* and *C. albicans* mating peptides were reproducibly detected using the dipstick assay. Maximal response was achieved by 12 hours after exposure to the respective peptides (1 μM). (D) Detection of *P. brasiliensis* mating peptide in complex samples. Liquid samples were supplemented with synthetic *P. brasiliensis* mating peptide (blue) or water (grey), and scored as in B. YPD—media only, Soil—standard potting soil, Urine—50% pooled human urine Serum—50% human serum, Blood—2% whole blood. All experiments were performed using 1 μM peptide and supplemented with YPD media.

FIGS. 18A-18E. Paper-based dipstick assay. (A) Engineered *S. cerevisiae* biosensor cells spotted on paper are the only active component required for the dipstick assay. Spot diameter—5 mm. (B) Dipstick assay includes two spots, indicator biosensor strain and control strain, placed on top of a strip of paper towel that acts as wicking paper. The indicator biosensor spot detects the target ligand and the negative control spot contains a strain with an off-target receptor. This design enables easy visual interpretation of the results as well as quantification by calculating the difference in the pixel color values between the two spots (see Supplementary Methods). (C) Representative photograph of the dipstick for detection of the fungal pathogen *P. brasiliensis* in soil. Left—no mating peptide in soil. Right—mating peptide added to soil. Scale bar—1 cm. (D) A simple plastic holder was designed to enable easy use of the dipstick assay. Thin black bars—2 cm. (E) Dipstick holder does not affect biosensor performance as shown by time course measurement of the *P. brasiliensis* dipstick test response using 1 μM cognate peptide.

FIGS. 19A-19H. Optimization of peptide-induced lycopene production. (A) Lycopene biosynthetic pathway. Lycopene production is induced (red arrow) by mating-signal dependent activation of the FUS1 promoter. Biosynthetic enzymes shown in bold. Genes targeted for optimization shown in colors. HMG-CoA: 3-hydroxy-3-methylglutaryl-coenzyme A, FMN: flavin mononucleotide, FAD: flavin adenine dinucleotide, FPP: farnesyl pyrophosphate, GGPP: geranylgeranyl pyrophosphate. (B) Optical density spectrum of constitutive lycopene producing and lycopene null strains. (C) The spectrum of lycopene in yeast cells calculated from B. This spectrum allows selection of wavelengths for spectroscopic measurement of lycopene per cell (see Supplementary Methods). (D) Maximal lycopene yield per cell calculated from time course data in F-H. "Null" (grey)—parental strain (no lycopene genes); "Lyco-1" (black)—parental strain with single copy CrtE, CrtB and CrtI; "tHMG1" (green)—Lyco-1 with plasmid-borne truncated copy of Hmg1; "2×CrtI" (orange)—Lyco-1 with plasmid-borne copy of CrtI; "Fad1" (blue)—Lyco-1 with plasmid-borne copy of Fad1; "Lyco-2" (red)—Lyco-1 with additional genes genomically integrated. (E) The time to half-maximal lycopene yield was used to compare readout speed. Strains as in D. (F-H), Time course of lycopene strains induced with 10 μM of *S. cerevisiae* peptide (solid line) or water (dotted line). Strains as in D.

FIGS. 20A-20B. Specificity of fungal mating receptors. (A) Heterologous receptors ('species.Ste2') were induced with 5 μM of the indicated fungal mating peptide. mCherry fluorescence was measured after 9 hours. Basal (0%) and maximal (100%) fluorescence used indicated in grey. (B) Data as in A. Activation of heterologous mating receptors shown here grouped by mating peptide.

FIGS. 21A-21D. *P. brasiliensis* biosensor characterization in liquid culture. Dose-response and time-course data shown for *S. cerevisiae* strain carrying *P. brasiliensis* Ste2 receptor (Ca.Ste2) under different conditions: (A)—temperatures, (B)—pH, (C)—50% human serum and (D)—50% human urine. Lycopene yield was determined by absorbance after 9 hours. All experiments were performed using 1 μM synthetic peptide. The limit of detection (LoD, lowest peptide concentration producing significant signal over background, ** $P \leq 0.01$) is shown for each sample conditions. N=3.

FIGS. 22A-22E. Comparison of mating receptors from human pathogens *P. brasiliensis* and *H. capsulatum*. (A) Protein sequence comparison of the *P. brasiliensis* (Pb.Ste2) (SEQ ID NO: 12) and *H. capsulatum* (Hc.Ste2) (SEQ ID NO: 222) receptors. Positions that differ highlighted in grey. (B) Dose response curve using Pb.Ste2 and Hc.Ste2 receptors cloned in *S. cerevisiae* and induced with the common cognate ligand (see Table 9, below). Measurement was taken after 12 hours. All measurements were performed in duplicate. (C) Comparison of basal (dH2O) and maximum (5 μM) activation level for Pb and Hc mating receptor using the same synthetic ligand, as shown in B. (D) Comparison of Pb.Ste2 and Hc.Ste2 receptors fold-activation and EC50 values calculated from panel B. Grey cross lines mark the equivalent values for *S. cerevisiae* wild type mating receptor Ste2 activated by its own cognate peptide. While Hc.Ste2 exhibited higher sensitivity to the common mating peptide than Pb.Ste2, it also had higher basal level and lower maximal activation making it less effective for detection using the visible lycopene readout. (E) Lycopene production induced by culture supernatant from clinically isolated fungal pathogens. Lycopene per cell measured by spectroscopy at 9 hours  $P \leq 0.01$, * $P \leq 0.001$, N=3.

5. DETAILED DESCRIPTION OF THE INVENTION

The present invention relates to methods and compositions for detecting the presence of an agent of interest in a test sample.

For clarity and not by way of limitation, the detailed description is divided into the following subsections:

(i) Agents of Interest
(ii) Sensor cells;
(iii) Receptors and coupling systems;
(iv) Detection events;
(v) Analytes;
(vi) Methods of use; and
(vii) Kits

5.1. Agents of Interest

Presently disclosed sensor calls can be used to detect the presence of a variety of agents. Non-limiting examples of suitable agents include human disease agents (human pathogenic agents), agricultural agents, industrial and model organism agents, bioterrorism agents, and heavy metal contaminants.

Human disease agents include, but are not limited to infectious disease agents, oncological disease agents, neurodegenerative disease agents, kidney disease agents, cardiovascular disease agents, clinical chemistry assay agents, and allergen and toxin agents.

Infectious disease agents include, but are not limited to, fungal pathogens, bacterial pathogens, viral pathogens, and protozoan pathogens, as well as toxins produced by same. Non-limiting examples of fungal pathogens include *C. albicans, C. glabrata, P. brasiliensis, L. elongisporous, P. rubens, C. guillermondi, C. tropicalis, C. parapsilosis, C. lusitaniae, S. scheckii*, and *Candida krusei*.

Non-limiting examples of bacterial pathogens include *Vibrio cholerae, Staphylococcus aureus* and Methicillin-resistant *Staphylococcus aureus* (MRSA) strains, *Bacillus subtilis, Streptococcus pneumonia*, Group B *Streptococcus, Salmonella* sp., *Listeria monocytogenes, Chlamydia trachomatis, Neisseria gonorrhoeae, Clostridium difficile, Yersinia enterocolitica, Legionella* sp., *Mycobacterium tuberculosis, Klebsiella pneumoniae, Klebsiella oxytoca, Serratia marcescens, Neisseria meningitis, Streptococcus pneumoniae, Pseudomonas aeruginosa, Streptococcus pyogenes*, botulinum toxin of *Clostridium botulinum, Shigella*/Enteroinvasive *E. coli*, Shiga toxin from the Shiga toxin-producing *Escherichia coli* (STEC), and Verotoxin derived from *Shigella dysenteriae*. Analytes that are indicative of the presence of bacterial pathogens include, but are not limited to, quorum sensing small molecules such as the *Vibrio cholera* CAI-1,[69] inter-species bacterial quorum sensing AL-2,[70] or components of the bacterial LPS.

Non-limiting examples of viral pathogens include Ebola virus, HPV, HIV, influenza, Hepatitis C Virus, Hepatitis B Virus. Cytomegalovirus (CMV), Epstein-Barr virus (EBV), Respiratory syncytial virus (RSV), Norovirus, Sapovirus, and measles virus. Analytes that are indicative of the presence of viral pathogens include, but are not limited to, capsid protein or peptides, and other viral particles.

Non-limiting examples of protozoan pathogens include *Trichomonas vaginalis, Cryptosporidium, Cyclospora cayetanensis, Giardia lamblia*, and biomarkers for Amoebiasis derived from *Entamoeba histolytica* such as *E. histolytica* ADP-forming acetyl-CoA synthetase (EhACS) or related peptides [Huat (2014)], Leishmaniasis biomarkers such as the amastin signature peptide [Rafati (2006)].

Oncological disease agents include, but are not limited to, lung, breast, colorectum, prostate, stomach, liver, kidney or cervix cancer, leukemia, Kaposi sarcoma, Testis, Ovary, thyroid, and other cancer peptide biomarkers unique for certain cancer types, which can be identified by mass spectrometry.[60-63]

Neurodegenerative disease agents include, but are not limited to, peptide biomarkers indicated in Alzheimer's,[64] [notably fungal biomarker for Alzheimer's were recently suggested in Pisa (2015)], the protein DJ-1 or peptides thereof as biomarkers for Parkinson disease,[65] and biomarkers for prion disease such as proteins or peptides of the 14-3-3 family in cerebrospinal fluid for detection of Creutzfeldt-Jakob disease [Van Everbroeck (2005) and Huzarewich (2010)].

Clinical chemistry assay (for general health diagnostics) agents include, but are not limited to, peptide hormones. Peptide hormones include, but are not limited to, neurohypophysial hormones (e.g., oxytocin and vasopressin) and pancreatic hormones (e.g., glucagon, insulin and somatostatin).

Allergen and toxin agents include, but are not limited to, peptide derived from immunogenic wheat peptide (e.g., gluten), and carcinogen aflatoxin B1 derived from the fungi *A. flavus*.

Kidney disease agents include, but are not limited to, proteins and peptides identified as urinary biomarkers for kidney disease, such as β2-microglobulin, and differential patterns of peptides in type 2 diabetis[66].

Cardiovascular disease agents include, but are not limited to, proteins and peptides indicative for atherothrombosis or risk markers for stroke. Markers for primary cardiovascular events include peptides derived from C-reactive protein, fibrinogen, cholesterol, apolipoprotein B, high density lipoprotein, and small molecules like vitamin D. Markers for secondary cardiovascular events include peptides derived from cardiac troponins I and T, C-reactive protein, serum creatinine, and cystatin C. Risk markers for primary stroke, include peptides derived from fibrinogen and serum uric acid [Van Holten et al. (2013)]

Agricultural agents include, but are not limited to, fungal pathogens of animals and plants, and fungal agents causing food spoilage. Fungal pathogens of animals and plants include, but are not limited, to animal fungal pathogens and plant fungal pathogens. Animal fungal pathogens include, but is not limited to, *P. destructans*. Non-limiting examples of plant fungal pathogens include *F. graminearum, M. oryzea, B. cinerea, G. candidum*, and *C. purpurea*. Non-limiting examples of fungal agents causing food spoilage include *Z. bailii, Z. rouxii*, and *N. fischeri*.

Industrial and model organism agents include, but are not limited to, fungal agents used for genetic studies and industrial applications such as food production, pharmaceutical production, fine chemical production, bioremediation, including, but not limited to, *S. cerevisiae, K lactis, S. pombe, V. polyspora* (receptor 1), *V. polyspora* (receptor 2), *S. stipitis, S. japonicus, S. castellii*, and *S. octosporus*.

Bioterrorism agents include, but are not limited to, peptide biomarkers for *Bacillus anthracis* (causative agent of anthrax—e.g., one of three polypeptides that comprise the anthrax toxin secreted by the pathogen: protective antigen (PA), lethal factor (LF) and edema factor (EF)),[67] *Clostridium botulinum* (causative agent of botulism—e.g., Botulinum neurotoxin peptides such as the cyclic peptide C11-019),[68] viral agents such as smallpox (Variola virus) and Viral encephalitis, Ebola virus.

Heavy metal contaminant include, but are not limited to, cadmium, mercury, lead or arsenic, as bound to biological receptors.

In certain embodiments, the agent is the same as the analyte, as disclosed herein. In certain embodiments, the agent is different from the analyte.

5.2. Sensor Cells

The sensor cell can be engineered to comprise one or more component of the assay system disclosed herein. As used herein, the term "engineered" means that one or more component is introduced into a sensor cell or its parent cell by a method selected from the group consisting of recombinant DNA techniques (e.g., Reiterative Recombination and CRISPR), natural genetic events, conjugation, and a combination thereof. Sensor cells can be prokaryotic cells or eukaryotic cells. In certain embodiments, a presently disclosed sensor cell is a microbe, including, but not limited to, bacteria, fungi, and slime molds. In certain embodiments, the sensor cell is a fungal cell. In certain embodiments, the fungal cell is a yeast cell. Non-limiting examples of yeast cells include *Saccharomyces cerevisiae, Pichia pastoris* and *Schizosaccharomyces pombe*. In one non-limiting embodiment, the sensor cell is *Saccharomyces cerevisiae*. Additional non-limiting examples of fungal cells include *Candida albicans, Paracoccidioides brasiliensis, Fusarium graminearum, Magnaporthe oryzae*, and *Botrytis cinerea*. In certain embodiments, the sensor cell is a bacterial cell. Non-limiting examples of bacterial cells include *Escherichia coli, Bacillus subtilis*, and *Lactobacillus acidophilus*.

5.3 Receptors and Coupling Systems

The present invention provides for receptors and coupling systems wherein a sensor cell comprises (e.g., bears) a receptor that binds to an analyte, where binding of the analyte triggers a detection event that is indicative of the presence of the agent (e.g., expression of a detectable reporter gene, including increased or decreased expression), release of a therapeutic molecule that directly remediates the agent, production of a redox active molecule, or a change in the membrane potential of the sensor cell). In certain embodiments, the sensor cell is engineered to bind to the analyte.

As used herein, the term "receptor" means a molecule (e.g., a ligand) that binds to a presently disclosed analyte that is indicative of the presence of an agent of interest. A presently disclosed receptor is positioned, either inherently or by association with a membrane protein, at the cell surface exposed to the extracellular environment. In certain embodiments, the receptor is a protein. In certain embodiment, the receptor is a naturally occurring (native) protein or a portion thereof. In certain embodiments, the receptor is a portion of a naturally occurring protein comprised in a fusion protein with one or more heterologous proteins. In certain embodiments, the receptor is a mutated version of a naturally occurring protein. In certain embodiments, the receptor is a synthetic protein. In certain embodiments, the receptor is a partly-synthetic protein. In certain embodiments, the receptor comprises one or more non-protein element.

In certain embodiments, the receptor is a non-protein molecule. In one non-limiting embodiment, the receptor is an aptamer or a riboswitch. The receptor may be comprised of a single element or may be comprised of a plurality of elements/subunits.

In certain non-limiting embodiments, the sensor cell comprises a receptor that binds to an analyte, wherein the receptor is coupled to a detectable reporter gene such that when the analyte binds to the receptor, expression of the reporter gene is increased or induced. In certain embodiments, the receptor is coupled to a detectable reporter gene such that when an analyte binds to the receptor, expression of the reporter gene is inhibited (for example, by binding of a transcriptional repressor). In certain embodiments, the analyte is a peptide, e.g., an agent-specific peptide.

As used herein, the term "coupled to" means that binding of an analyte to a receptor is causally linked, directly or indirectly, to and triggers a detection event that is indicative of the presence of the agent (e.g., expression of a detectable reporter gene (induced or inhibited expression), release of a therapeutic molecule that directly remediates the agent, production of a redox active molecule, or a change in the membrane potential of the sensor cell). In certain embodiments, the detection event is expression of a detectable reporter gene. In certain embodiments, the detection event is induced expression of a detectable reporter gene. The receptor may be linked to expression level of the reporter gene through, for example, a pathway of interacting molecules. This pathway may be host-endogenous or engineered.

In certain embodiments, the sensor cell is engineered to express the receptor, for example, by the introduction of a nucleic acid encoding the receptor. In certain embodiments, the nucleic acid is operably linked to a promoter element. In certain embodiments, the promoter element is constitutively active. In certain embodiments, the promoter element is inducibly active. In certain embodiments, the receptor is expressed on the surface of the sensor cell. In certain embodiments, the receptor is expressed on internal membranes of the sensor cell. In certain embodiments, the receptor is expressed in the cytoplasm of the sensor cell.

In certain embodiments, the analyte is a natural (cognate) ligand of the receptor; the coupled analyte-receptor system utilizes a receptor and its natural (cognate) ligand as the analyte. In certain embodiments, the coupled analyte-receptor system is a receptor engineered to bind a different non-cognate ligand as analyte, by way of directed evolution detailed below.

In certain non-limiting embodiments, the sensor cell expresses a single species of analyte receptor. In certain non-limiting embodiments, the sensor cell expresses a plurality of species of analyte receptor.

In certain non-limiting embodiments, the sensor cell comprises an analyte-specific receptor which is coupled to a detectable reporter gene by a G-protein signaling pathway. Hence, in certain embodiments, the receptor is a G-protein coupled receptor (GPCR) polypeptide or protein. In certain embodiments, the receptor is a non-native GPCR receptor.

In certain non-limiting embodiments, a yeast pheromone sensing system is used for analyte detection. The yeast pheromone signaling pathway is well studied structurally and is functionally similar to hormone and neurotransmitter signaling pathways in mammals.[20] In certain non-limiting embodiments, the receptor is a variant of the yeast Ste2 receptor or Ste3 receptor, wherein the receptor is modified so that it binds to the analyte rather than yeast pheromone. In certain embodiments, the receptor or portion thereof is a polypeptide that is at least about 40%, at least about 50%, at least about 60%, at least about 70%, at least about 80%, at least about 90%, at least about 95%, at least about 98% homologous, or at least about 99% homologous to the native yeast Ste2 or yeast Ste3 receptor. "Homologous" or "homology" can mean sequence (nucleotide sequence or amino acid sequence) homology or structural homology. In certain embodiments, "homology" or "homologous" refers to sequence (nucleotide sequence or amino acid sequence) homology. The sequence homology can be determined by standard software such as BLAST or FASTA. The receptor binds specifically to the analyte (e.g., agent-specific peptide) under assay conditions or under natural conditions (for example, but not limited to, at room temperature (e.g., 20-25° C., at or around body temperature (e.g., 30-40° C.), field temperature (e.g., 5-40° C.) or between about 20-40° C.). In certain non-limiting embodiments, the receptor is a chimeric protein comprising one or more fragment originating from other receptor proteins, or evolved from non-homologous receptor protein to bind to the analyte (e.g., agent-specific peptide) and interface with a signaling pathway. In certain non-limiting embodiments the receptor is a yeast GPCR polypeptide other than a pheromone binding receptor, such as Gpr1 putative sugar binding receptor and the cognate Gα protein Gpa2.

The present invention also provides a nucleic acid encoding the receptor and a host cell comprising said nucleic acid. The nucleic acid can be used to produce a presently disclosed sensor cell. The nucleic acid can be introduced into the host cell such that it is operably linked to an inducible or constitutively active promoter element. In certain embodiments, the sensor cell is a yeast cell, and a nucleic acid encoding a receptor is introduced into the yeast cell either as a construct or a plasmid in which it is operably linked to a promoter active in the yeast cell or such that it is inserted into the yeast cell genome at a location where it is operably linked to a suitable promoter. Non-limiting examples of suitable yeast promoters include, but are not limited to, constitutive promoters pTef1, pPgk1, pCyc1, pAdh1, pKex1, pTdh3, pTpi1, pPyk1, and pHxt7 and inducible promoters pGal1, pCup1, pMet15, and pFus1.

In certain non-limiting embodiments, receptor activation induces reporter gene expression under a FUS1 promoter, which allows for a convenient screen using reporter gene activation. In one non-limiting example, a GPCR polypeptide is expressed in a yeast cell and is coupled to the yeast pheromone mating system such that GPCR binding activates the yeast Fus1 promoter to express a downstream reporter gene.[27] The GPCR DNA sequence can then be varied, and this library of altered receptors may be screened for binding of an analyte (e.g., an agent-specific peptide) using production of reporter gene as an indicator of binding.[13,26]

In certain non-limiting embodiments, where the pathway includes the yeast pheromone sensing pathway, a nucleic acid encoding the reporter is operably linked to at least a transcription controlling portion of the Fus1 promoter, for example, but not limited to, an activating sequence located in the region (−300) to (+400) of the Fus1 gene (Gene ID: 850330). In certain non-limiting embodiments, where the pathway includes the yeast pheromone sensing pathway, a nucleic acid encoding the reporter is operably linked to a Ste12-binding element [(A/T)GAAACA], such that binding of Ste12 acts as a transactivator of the expression of the reporter. In certain non-limiting embodiments, where the pathway includes the yeast pheromone sensing pathway, a nucleic acid encoding the reporter is alternatively linked to one or more inducible promoter other than pFus1, e.g., pFus2, pFig2, and/or pAga1. In certain embodiments, receptor-activation is linked to an engineered pheromone-responsive transcription factor, which binds a synthetic transcription controlling element distinct from the Ste12-binding element. The transcription factor Ste12 is composed of a DNA-binding domain, a pheromone responsive domain and an activation domain. The feasibility of engineering Ste12 to bind to non-natural control elements but remain to activate transcription in a pheromone-responsive manner has been shown [Pi et al (1997)].

In certain embodiments, a GPCR is engineered by directed evolution (DE) to alter its stability, specificity, and/or sensitivity. Hence, a receptor that is activated by a desired analyte can be generated by mutagenesis and selection in the laboratory. Several research groups have established DE in yeast as tool for changing mammalian GPCR ligand specificity.[13,14,30-32] Non-limiting examples of such engineered GPCRs include mammalian tachykinin receptors, secretin receptors, opioid receptors, and calcitonin receptors. Non-limiting examples of DE to develop a stable reporter strain are provided in the Examples section.

In certain embodiments, the GPCR is a fungal GPCR. In certian embodiments, the GPCR is a fungal phermone GPCR. In certain non-limiting embodiments, a fungal Ste2-type or Ste3-type GPCR derived from one or more fungus is engineered into *S. cerevisiae* or other yeast cells to serve as a receptor for detecting an agent of interest. While any peptide-sensing GPCR can be repurposed as a detection element in a yeast cell, fungal pheromone GPCRs have several key advantages for biosensor engineering. First, this type of GPCRs (GPCRs homologous to the *S cerevisiae* Ste2) couple robustly to the host/native pheromone pathway (see FIGS. 9 and 10), and several have been expressly validated in *S. cerevisiae* with little to no further modifications.[15-18]. Second, fungal pheromone GPCRs from related fungi recognize different peptides based on the natural evolution of this class of GPCR.[33] For example, as shown in FIG. 12 and Table 1, these fungal GPCRs recognize a diverse set of peptide ligands. Third, fungal pheromone GPCRs are highly specific for their respective peptides (see FIG. 9), since they must mediate the species-specific mating reaction while preventing interspecies breeding.[34] Furthermore, though there is no crystal structure of these GPCRs, extensive biochemical characterization and mutagenesis data indicates that the *S. cerevisiae* GPCR has a large binding interface across the seven transmembrane helices and the extracellular loops modulating ligand binding.[35-40]

Based on these characteristics, fungal pheromone GPCRs offer a highly viable platform for DE towards binding of novel peptide ligands (e.g., non-cognate peptide ligands) through mutagenesis of specific portions of the receptor, the peptide or both.

In certain embodiments, the receptors are identified by searching protein and genomic databases (e.g., NCBI, UniProt) for proteins and/or genes with homology (structural or sequence homology) to *S. cerevisiae* Ste2 receptor. In certain embodiments, the receptor has an average amino acid sequence homology of 33% to *S. cerevisiae* Ste2, ranging from 66% to 15% as calculated with Clustal Omega [Sievers (2014)].

In certain embodiments, the receptors have seven transmembrane helices, an extracellular N-terminus, an intracellular C-terminus, three extracellular loops and three intracellular loops when analyzed by TMHMM v2.0 [Krogh et al. (2001)]. As shown in FIG. 11, there are three key regions that have higher density of conserved residues with some residues conserved across all receptors: Region I, Region II, and Region III. Region I corresponds to the third intracellular loop and shows two positively charged residues with high conservation at positions 233 and 234 relative to the *S. cerevisiae* Ste2. Region II corresponds to the sixth transmembrane helix and contains an essential proline that is conserved across all the receptors at position 258 relative to the *S. cerevisiae* Ste2. Region III shows the highest level of conservation and also includes an essential proline conserved across all the receptors at position 290 relative to the *S. cerevisiae* Ste2. Based on previous mutational studies of the *S. cerevisiae* Ste2 receptor, these three regions are important in mediating signal transduction and interactions with the downstream G-protein. [Ćelić et al. (2003); Martin et al. (2002)]. In certain embodiments, the receptor has at least about >30%, at least about 40%, at least about 50%, at least about 60%, at least about 70%, at least about 80%, at least about 85%, at least about 90%, at least about 95%, at least about 99%, or least about 100% homologous to Region 1 and/or Region 2 and/or Region 3. The receptor functions in a *S. cerevisiae* biosensor.

In certain embodiments, when coupled to a lycopene reporter system, as described below, a fungal-derived GPCR, optionally further modified by directed evolution, generates lycopene in the sensor cell in response to the peptide pheromones produced by an agent of interest. Pheromone GPCRs from related fungi can naturally recognize different peptide pheromones based on the highly specific characteristics of this class of GPCRs, which mediate the species-specific mating reaction while preventing interspecies breeding. As described in the Example section, putative GPCRs can be cloned and screened against their putative cognate peptide pheromones using a detector gene, e.g., a fluorescent reporter gene.

The present invention provides a sensor cell (e.g., a yeast cell) comprising a receptor, which is a fungal receptor modified to bind to a bacterial pathogen-specific analyte, such as one from *V. cholerae*. In certain embodiments, this modification is achieved via directed evolution. The natural yeast pheromone mating receptors Ste2 or Ste3, evolved to bind to a peptide pheromone ligand, are not necessarily likely to adjust to bacterial pathogen-specific analyte and therefore can be deleted from the strain to prevent false activation of reporter gene. A mammalian or hybrid G-protein can be used to enhance GPCR signal transduction in a yeast cell. The remaining genes in the pathway may be endogenous to the yeast sensor cell, or may be engineered for improved performance.

One or more rounds of DE can be performed to generate a GPCR responsive to the natural cholera analytes and peptides. In certain embodiments, cholera-specific peptides can be generated by adding sequence-specific proteases (e.g., trypsin, chymotrypsin, LysN, or GluC) to a given sample. Also, using available computational methods, a peptide database of in-silico proteolized proteomes from bacterial pathogens (e.g., *Vibrio cholerae, Staphylococcus aureus, Bacillus subtilis, Streptococcus pneumonia, Salmonella* sp., *Listeria monocytogenes*), fungal pathogens (e.g., *Aspergillus niger, Candida albicans, Cryptococcus neoformans, Cryptococcus gattii, Histoplasma capsulatum, Pneumocystis jirovecii* and *Stachybotrys*) viral pathogens (e.g., Ebola virus, HPV, HIV, influenza viruses), or proteolysis pattern of any single protein of interst e.g. produced during an industrial process, can be generated. This peptide database can be searched using peptide motifs derived from analysis of the natural diversity of fungal pheromones.

A computational approach can also be used to discover target peptide analytes that are amenable to detection by an engineered fungal GPCR. This computational method generates a pool of high priority targets that can be highly amenable to a DE approach. Engineered receptors such as 15C11 and 31E4, that show increased ligand promiscuity as starting points to generate engineered GPCRs, can be used to detect these new target peptide ligands from a diverse set of bacterial pathogens. Additionally, some of the natural peptide pheromones produced by bacterial pathogens can be targeted.

DE can be implemented to optimize any engineered GPCR for improved signal levels, enhanced EC50 and/or signal transduction kinetics. Of the six GPCR families, the secretin and fungal pheromone receptor families naturally sense peptides. Moreover, the rhodopsin receptor family also contains members with peptide ligands. Representative members of each of these families have been heterologously expressed in yeast and functionally coupled to the pheromone response pathway: neurotensin NT1 (rhodopsin-like), growth-hormone-releasing-hormone receptor (secretin-like), *Sordaria macrospora* pheromone receptor (fungal pheromone-like). These GPCRs can be engineered into a yeast cell as a method for detecting their cognate peptide ligands, e.g., growth hormone or neurotensin, for monitoring or quantification.

Fungal Ste2-type or Ste3-type GPCRs as well as other peptide-specific GPCRs mentioned above can be used as a platform for developing engineered peptide-activated GPCRs to generically detect agent-specific analytes. In certain embodiments, the present disclosure provides a step-wise Directed Evolution (DE) strategy based on intermediate hybrid peptides to change the ligand specificity of the parent GPCRs to bind the target peptides.

In certain embodiments, the engineered GPCR is an engineered receptor for the detection of *Vibrio cholerae*. The receptor can detect a peptide derived from the Cholera toxin (CTx). Additionally, there is a reservoir of biochemical and mutational data of the yeast Ste2 and Ste3 receptor in the literature.[35-37,39,40,43] The same strategy can be used for detection of other fungal, viral or bacterial analytes described below.

GPCRs constitute a large class of cell-surface receptors that can be activated by a variety of other ligands, e.g., full proteins, small molecules (e.g., nucleotides and lipids), or light. A variety of these non-peptide sensing receptors have been functionally expressed in yeast.[44] These receptors can be employed and engineered into the biosensor to sense analytes other than peptides, e.g., small molecules, proteins or heavy metals.

Non-limiting examples of DNA encoding certain GPCRs of the invention are set forth in Tables 2 and 6 below; the invention further provides for proteins encoded by said DNA sequences.

5.4. Detection Events

Being of the analyte to the receptor triggers a detection event that is indicative of the presence of the agent. The detection events include, but are not limited to, appearance of a reporter (including expression (increased or decreased expression) of a detectable reporter gene), release of a therapeutic molecule that directly remediates the agent, production of a redox active molecule, and a change in the membrane potential of the sensor cell.

In certain embodiments, the detection event is appearance of a reporter. The reporter can be a result of expression of a reporter gene. A reporter can include an enzyme that can produce chromogenic product on a substrate. In certain embodiments, the detection event is increased expression of a reporter gene.

In certain embodiments, the reporter is a laboratory reporter. A "laboratory reporter" means a reporter that cannot be detected by the naked eye (e.g., the change or appearance of the color cannot be detected by the naked eye), and/or a reporter whose detection requires instrumentation. Suitable laboratory reporters include, but are not limited to, bioluminescent, fluorescent, and certain chromogenic reporters. Bioluminescent reporters include, but are not limited to, luciferase. Fluorescent reporters include, but are not limited to, various fluorescent proteins (e.g., a green fluorescent protein, a red fluorescent protein, a yellow fluorescent protein, a blue fluorescent protein). Non-laboratory chromogenic reporters include, but are not limited to, beta-galactosidase, beta-glucoronidase, and horse-radish peroxidase. In certain embodiments, the reporter is a fluorescent protein.

In certain embodiments, the reporter does not comprise a laboratory reporter. In certain embodiments, the reporter is a non-laboratory reporter. A "non-laboratory reporter" means a reporter that can be detected by the naked eye (e.g., the change or appearance of the color can be detected by the naked eye), and/or whose detection does not require instrumentation (e.g., reporters that are not conventionally used as research tools). Non-laboratory reporters include, but are not limited to, enzymes in the biosynthetic pathways of pigments (biosynthesized pigments that absorb in the visible light spectrum, also referred to as "biosynthesized visible-light pigments"), electrochemical, and reporters which constitute release of one or more therapeutic molecule. Certain chromogenic reporters are non-laboratory reporters, e.g., lycopene.

Biosynthesized visible-light pigments include, but are not limited to, terpenoids, carotenoids, lycopene, violacein and its precursors, melanin, and indigo. In certain embodiments, the reporter is a terpenoid. In certain embodiments, the reporter is a carotenoid. In certain embodiments, the reporter is lycopene. In certain embodiments, the receptor does not comprise a fluorescent protein.

Binding of analyte can induce or alternatively repress reporter gene expression. In the absence of an analyte, there may be essentially no reporter gene expression, reporter gene expression may occur at an undetectable level (e.g., undetectable by the naked eye), or reporter gene expression may occur at a baseline level that detectably increases upon analyte binding.

Violacein and deoxyviolacein are blue pigments isolated from several bacteria. [Sánchez (2006)]. Heterologous expression of the involved genes vioABCDE and optimization of production yields has been shown in *E. coli* and *S. cerevisiae*. [Lee (2013)].

Melanin is a black diffusible macromolecule whose overproduction has been achieved from L-tyrosine as precursor by heterologous co-expression of a tyrosinase in *E. coli* [Santos (2008)].

Production of the blue pigment bio-indigo from tryptophan as a precursor using a bacterial flavin-containing monooxygenase from the methylotrophic bacteria *Methylophaga aminisulfidivorans* has been achieved and optimized in *E. coli* [Hwan Han (2008)].

Carotenoids are a class of terpenoids composed of 8 isoprene units totaling 40 carbon atoms. Lycopene is a specific naturally produced carotenoid pigment whose heterologous expression in *E. coli* using the genes CrtE, CrtB and CrtI has been extensively studied.[45] If lycopene is used as a reporter, a presently disclosed sensor cell can be engineered to contain the genes required for synthesis and at least one of said genes can be the detectable reporter gene coupled to activation by peptide receptor binding (e.g., at least a portion of the Fus1 promoter). As a non-limiting example, the gene coupled may be CrtI, CrtE or CrtB.

Lycopene can be visualized by the naked eye, is widely validated in yeast metabolic engineering, and is non-toxic. Lycopene is the first intermediate in carotenoid biosynthesis that has a sufficiently conjugated π-system to absorb in the visible region.[46] Thus, unlike standard laboratory reporters like lacZ that require exogenously added caged dyes (X-gal) or fluorescent proteins that require specialized equipment (fluorimeter), lycopene can be directly observed by a non-technical person. Additionally, the biosynthesis of lycopene from endogenous yeast farnesyl pyrophosphate is well established in yeast, requiring only three heterologous genes (FIG. 1).[47]

Use of a biosynthesized visible-light pigment as a simple visual readout has a number of advantages. Use of a biosynthesized visible-light pigment readout requires no complex equipment since it can be seen by the naked eye and requires no expensive externally added reagent, since it can be biosynthesized from endogenous substrates. In contrast, most whole-cell biosensors reported in the literature use laboratory readouts such as fluorescent proteins, lacZ, or luciferase, which require the use of expensive equipment, externally added chromogenic reagents or both.[48-51]

In certain embodiments, lycopene is modified to achieve better response times, signal-to-noise and robustness. For example, in certain embodiments, one or more alternate pheromone-responsive promoter is used.[52] In certain embodiments, one or more synthetic Fus1-like promoter is used.[53] In certain embodiments, one or more variant of the transcription factor Ste12 is used.[54] In certain embodiments, one or more enhancement to the pheromone response pathway is made.[55-58] In certain embodiments, one or more variant of the Crt genes including homologues is used.[59] In certain embodiments, one or more codon optimized version and engineered version with enhanced activity or activation modality is used.

Additional biosynthesized visible-light pigments include mutants of CrtI disclosed in Schmidt-Dannert, C., Umeno, D. & Arnold, F. H. Molecular breeding of carotenoid biosynthetic pathways. Nat Biotech 18, 750-753 (2000), biosynthetic enzymes that generate alternate carotenoid pigments disclosed in Umeno, D. & Arnold, F. H. Evolution of a Pathway to Novel Long-Chain Carotenoids. J. Bacteriol. 186, 1531-1536 (2004), and lycopene enzymes from alternate organism disclosed in Verwaal, R. et al. High-Level Production of Beta-Carotene in *Saccharomyces cerevisiae* by Successive Transformation with Carotenogenic Genes from *Xanthophyllomyces dendrorhous*. Appl. Environ. Microbiol. 73, 4342-4350 (2007).

A presently disclosed sensor cell may also report in a non-measurable, non-visible way by releasing a therapeutic molecule that directly remediates the detected agent. In general, microbial cells have been used to produce therapeutic molecules such as peptides, proteins and other bioactive small-molecules. [Bourbonnais (1988); Miyajima (1985); Ro (2006)]. Similar to the generation of lycopene, a presently disclosed sensor cell can be coupled to the biosynthesis and secretion of such therapeutic molecule.

In certain embodiments, the detection event is release of a therapeutically relevant molecule, which can be reported through an electronic device. Interfacing to an electronic device can allow reporting to occur much more rapidly and produce a quantitative result. Additionally or alternatively, the release of a therapeutic molecule can be used to directly remediate the agent detected by a presently disclosed sensor cell.

In certain embodiments, the detection event is production of a redox active molecule. Others have in general coupled whole cells electrochemically to electrodes. This is usually done by mixing the cells with a redox-active molecule (a mediator) that couples a redox-active enzymatic process within the cell to a redox reaction on the electrode surface. [Su (2011); Eilam (1982); Garjonyte (2009)].

In certain embodiments, the production or release of a redox active molecule is detected by a redox reaction on an electrode. The redox active molecule can be biosynthesized in an analogous way as lycopene, e.g., by introducing the relevant biosynthetic enzymes into a presently disclosed sensor cell. Similarly, the production of this redox active molecule can be triggered by coupling one of the relevant biosynthetic enzymes to the pheromone signaling pathway. In certain embodiments, the redox active molecule is phenazine. The relevant biosynthetic enzymes are known [Mavrodi (2001)], and their secretion from a bacteria has been measured through the use of an electronic device [Bellin (2014)].

In certain embodiments, the detection event is a change in the membrane potential of the sensor cell. Electronic device that can measure changes in the membrane potential of cells are very common in neuroscience (e.g., multi electrode arrays). [Spira (2013)]. Such a device can be used to measure changes in membrane potential in our biosensor. In certain embodiments, the, a change in the membrane potential of the sensor cell is expression of a cAMP-activated ion channel in the sensor cell (e.g., a yeast cell). This type of channel has been shown to be functional in yeast. [Ali (2006)]

Signal Amplification:

In order to improve the robustness of the reporter signal, quorum sensing signal amplification strategy can be used. Specifically, binding of analyte not only induces expression of visible reporter gene but also induces the expression of enzymes responsible for synthesis of quorum sensing molecules in yeast, or alternative GPCR ligands such as a-factor or alpha-factor. Thus, enhanced sensitivity can be achieved by signal amplification using a positive feedback loop. Signal amplification in this form naturally exists in *S. cerevisiae* and other fungi using the same GPCRs described below such as Ste2

5.5. Analytes

Suitable analytes can be any ligand which is capable of binding to a receptor, where such binding triggers a detection event that is indicative of the presence of the agent, including triggering a cellular response by the sensor receptor. Suitable analytes include, but are not limited to, proteins, polypeptides (including amino acid polymers), and peptides. "Protein" generally refers to molecules having a particular defined 3-dimensional (3D) structure, whereas "polypeptide" refers to any polymers of amino acids, regardless of length, sequence, structure, and function. "Peptide" is generally reserved for a short oligomer that often but not necessarily lacks a stable conformation. [Creighton Proteins: Structures and Molecular Properties 2$^{nd}$ Edition, ISBN-10: 071677030X]. Proteins can be longer than 50 amino acid residues and peptides can be between 3 and 50 amino acid residues or longer.

In certain embodiments, an analyte is a peptide epitope. As used herein, the term a "peptide epitope" refers to a sub-region of amino acids within a larger polypeptide or protein. A peptide epitope can be composed of about 3-50 residues that are either continuous within the larger polypeptide or protein, or can also be a group of 3-50 residues that are discontinuous in the primary sequence of the larger polypeptide or protein but that are spatially near in three-dimensional space. The recognized peptide epitope can stretch over the complete length of the polypeptide or protein, the peptide epitope can be part of a peptide, the peptide epitope can be part of a full protein and can be released from that protein by proteolytic treatment or can remain part of the protein molecule.

Some sensor cells (e.g., yeast cells, e.g. *S. cerevisiae* or *Candida albicans*) are surrounded by a thick cell wall, which can cause a permeability barrier to large molecules. The permeability of the *S. cerevisiae* cell wall was shown to be strongly growth phase-dependent, being most porous and plastic during exponential phase. [Nobel et al. (1991)]. The cell wall was shown to be permeable to molecules of a hydrodynamic radius of 5.8 nm, corresponding to a globular protein of 400 kDa. [Nobel (1990)]. Similar sized proteins are functionally secreted from yeast cells like *S. cerevisiae, C. albicans, C. glabrata* by passaging the cell wall [Nobel (1991)]. Therefore, polypeptides or proteins of up to at least 400 kDa may be accessible to the cell surface receptor as analytes. However, proteins or polypeptides beyond this range can also be detected. In certain embodiments, proteolysis are used to fragment the polypeptide or protein to release smaller polypeptides that can serve as the analyte and be accessible to the cell surface receptors.

The analytes can be natural, engineered or synthetic analytes. Virtually any peptide and modified peptide can be assayed using the composition and methods of this invention, including secreted peptides or fragments of proteins which may be released from the protein by a protease. Proteolysis can be induced by one or more host-specific proteases and/or by addition to a given sample of sequence-specific proteases such as trypsin, chymotrypsin, Gluc, and LysN. Modifications of peptides include but are not limited to post-translational farnesylation, glycosylation, deamination, and proteolytic processing.

In certain embodiments, the peptide is a fungal mating pheromone, e.g., a peptide specific to a fungal pathogen. Non-limiting examples of fungal mating pheromones include human fungal mating pheromones (meaning mating pheromones of fungi that can colonize or infect humans), non-human fungal mating pheromones (meaning mating pheromones of fungi that colonize or infect a non-human animal), plant fungal mating pheromones (meaning mating pheromones of fungi that colonize or infect a plant), food fungal mating pheromones (e.g., food safety/spoilage) (meaning mating pheromones of fungi that colonize or infect human or non-human animal food items), and industrial/model fungal mating pheromones. In certain embodiments, the industrial/model fungal mating pheromones are fungi species that are used for making food (e.g., fermentation of alcohol). In certain embodiments, the industrial/model fungal mating pheromones are fungi species that are used for industrial microbiology, e.g., production of drugs, or pesticides in agriculture. In certain embodiments, the industrial/model fungal mating pheromones are fungi species that are used for academic research.

Non-limiting examples of human fungal mating pheromones include the mating pheromones of *C. albicans, C. glabrata, P. brasiliensis, L. elongisporous, P. rubens, C. guillermondi, C. tropicalis, C. parapsilosis, C. lusitaniae, S. scheckii*. and *Candida krusei*.

Non-limiting examples of non-human animal fungal mating pheromones include the mating pheromone of *P. destructans*.

Non-limiting examples of plant fungal mating pheromones include the mating pheromones of *F. graminearum, M. oryzea, B. cinerea, G. candidum*, and *C. purpurea*.

Non-limiting examples of food fungal mating pheromones include the mating pheromones of *Zygosaccharomyces bailii, Zygosaccharomyces rouxii*, and *N. fischeri*.

Non-limiting examples of industrial/model fungal mating pheromones include the mating pheromones of *S. cerevisiae, K lactis, S. pombe, V. polyspora* (receptor 1), *V. polyspora* (receptor 2), *S. stipitis, S. japonicas, S. castellii*, and *S. octosporus, A. oryzae, T. melanosporum, D. haptotyla, C. tenuis, Y. lipolytica, T. delbrueckii, B. bassiana, K. pastoris, A. nidulans, N. crassa*, and *H. jecorina*.

In certain embodiments, the peptide is a peptide disclosed in Table 5.

In certain embodiments, the physicochemical properties, e.g., peptide length, overall charge, charge distribution and hydrophobicity/hydrophilicity, of a peptide are determined by using the program ProtParam on the Expasy server [Walker (2005) ISBN 978-1-59259-890-8]. In certain embodiments, the peptide has a length of 3 residues or more, a length of 4 residues or more, a length of 5 residues or more, 6 residues or more, 7, residues or more, 8 residues or more, 9 residues or more, 10 residues or more, 11 residues or more, 12 residues or more, 13 residues or more, 14 residues or more, 15 residues or more, 16 residues or more, 17 residues or more, 18 residues or more, 19 residues or more, 20 residues or more, 21 residues or more, 22 residues or more, 23 residues or more, 24 residues or more, 25 residues or more, 26 residues or more, 27 residues or more, 28 residues or more, 29 residues or more, 30 residues or more, 31 residues or more, 32 residues or more, 33 residues or more, 34 residues or more, 35 residues or more, 36 residues or more, 37 residues or more, 38 residues or more, 39 residues or more, 40 residues or more, 41 residues or more, 42 residues or more, 43 residues or more, 44 residues or more, 45 residues or more, 46 residues or more, 47 residues or more, 48 residues or more, 49 residues or more, or 50 residues or more. In certain embodiments, the peptide has a length of 3-50 residues, 5-50 residues, 3-45 residues, 5-45 residues, 3-40 residues, 5-40 residues, 3-35 residues, 5-35 residues, 3-30 residues, 5-30 residues, 3-25 residues, 5-25 residues, 3-20 residues, 5-20 residues, 3-15 residues, 5-15 residues, 3-10 residues, 3-10 residues, 5-10 residues, 10-15 residues, 15-20 residues, 20-25 residues, 25-30 residues, 30-35 residues, 35-40 residues, 40-45 residues, or 45-50 residues. In certain embodiments, the peptide has a length of 9-25 residues. In certain embodiments, the peptide has a length of 9-23 residues. In one non-limiting embodiments, the peptide has a length of 9 residues. In one non-limiting embodiments, the peptide has a length of 10 residues. In one non-limiting embodiments, the peptide has a length of 11 residues. In one non-limiting embodiments, the peptide has a length of 12 residues. In one non-limiting embodiments, the peptide has a length of 13 residues. In one non-limiting embodiments, the peptide has a length of 14 residues. In one non-limiting embodiments, the peptide has a length of 15 residues. In one non-limiting embodiments, the peptide has a length of 16 residues. In one non-limiting embodiments, the peptide has a length of 17 residues. In one non-limiting embodiments, the peptide has a length of 18 residues. In one non-limiting embodiments, the peptide has a length of 19 residues. In one non-limiting embodiments, the peptide has a length of 20 residues. In one non-limiting embodiments, the peptide has a length of 21 residues. In one non-limiting embodiments, the peptide has a length of 22 residues. In one non-limiting embodiments, the peptide has a length of 23 residues.

In certain embodiments, the peptide is hydrophobic. In certain embodiments, the peptide is mildly hydrophilic.

In certain embodiments, the peptide is a *S. cerevisiae* pheromone alpha-factor. The C-terminus of the *S. cerevisiae* pheromone alpha-factor is involved in binding to the receptor. The N-terminus of the *S. cerevisiae* pheromone alpha-factor contributes to signaling due to receptor activation.

Non-limiting examples of classes of peptide analytes include the following.

5.5.1. Peptides as Analytes in Diseases 5.5.1.1. Peptides in Fungal Infections

Suitable analyte peptides associated with fungal infections include, but are not limited to, a peptide from *Aspergillus* (e.g., *Aspergillus niger*), *Candida* (e.g., *C. albicans* or *C. glabrata*), *Cryptococcus* (e.g., *Cryptococcus neoformans* or *Cryptococcus gattii*), *Histoplasma* (e.g., *Histoplasma capsulatum*), *Pneumocystis* (e.g., *Pneumocystis jirovecii*), or *Stachybotrys* (e.g., *Stachybotrys chartarum*).

In certain embodiments, the agent-specific peptide is a peptide pheromone produced by a pathogenic fungus or a proteolytic product from a pathogenic fungus.

5.5.1.2. Peptides in Bacterial Infections

Suitable analyte peptides associated with bacterial infections include, but are not limited to, a peptide from *V. cholera* (e.g., Cholera toxin), *Staphylococcus aureus* (e.g., staphylococcal auto-inducing peptide or portion of beta toxin), and *Salmonella* spec. (e.g., *Salmonella* Exotoxins). In certain embodiments, an agent-specific analyte is a peptide derived from the cholera toxin or a proteolytic product from cholera. The proteolytic product from cholera can be generated by a host-specific protease and/or by an exogenous protease. In certain embodiments, an agent-specific analyte is a small molecule secreted or derived from *Vibrio cholera*. In certain embodiments, an agent-specific peptide is *Vibrio cholerae* specific or at least specific to a small group of bacteria including *Vibrio cholerae* (for example a group of up to 10 known species or up to 5 known species).

In certain embodiments, the peptide derived from the cholera toxin is selected from the group consisting of the peptides disclosed in Table 7.

In certain embodiments, the peptide associated with *V. cholera* is selected from the group consisting of a peptide having an amino acid sequence set forth in VEVPGSQHIDSQKKA (SEQ ID NO: 26), a peptide having an amino acid sequence that is at least about 80% (e.g., at least about 85%, at least about 90%, at least about 95%, at least about 98%, or at least about 99%) homologous to SEQ ID NO: 26, a peptide having an amino acid sequence set forth in VPGSQHIDS (SEQ ID NO: 27), and a peptide having an amino acid sequence that is at least 80% (e.g., at least about 85%, at least about 90%, at least about 95%, at least about 98%, or at least about 99%) homologous to SEQ ID NO: 27.

5.5.1.3. Peptides in Viral Infections

Suitable analyte peptides associated with viral infections include, but are not limited to, a peptide from Ebola virus (e.g., secreted glycoprotein), Influenza virus (e.g., Hemagglutinin), or HIV (e.g., HIV glycoprotein)

5.5.1.4. Peptides in Non-Infectious Disease

Patterns of peptide biomarkers unique for certain cancer types have been identified by mass spectrometry.[60-63] Suitable analyte peptides associated with cancer include, but are not limited to, protein portions released from human endogenous proteins by tumor-specific exopeptidases or antibody-derived peptide biomarkers for well characterized disease states.

Peptide or protein biomarkers have been identified in other diseases, e.g., Alzheimers,[64] Parkinson,[65] or different kidney diseases.[66] Such peptides and proteins may also function as analytes.

5.5.2. Peptides as Analytes in Food Safety 5.5.2.1. Toxins

Suitable analyte peptides associated with food toxins include, but are not limited to, a peptide from *Clostridium botulinum* (e.g., Botulinum toxin), Shiga toxin-producing *Escherichia coli* (STEC) (e.g., Shiga toxin), and *Shigella dysenteriae* (e.g., Verotoxin).

5.5.2.2. Immunogens and Allergens

Suitable analyte peptides associated with food immunogens and allergens include, but are not limited to, immunogenic wheat peptide (e.g., gluten).

5.5.3. Peptides in Plant & Crop Infections

Suitable analyte peptides associated with plant and crop infections include, but are not limited to, a peptide of *Fusarium graminearum, Botrytis cinerea, Magnaporthe oryzae*, and *Geotrichum candidum.*

5.5.4. Peptides in Bioterrorism

Suitable analyte peptides associated with bioterrorism include, but are not limited to, peptides of *Bacillus anthracis* (anthrax), e.g., one of three polypeptides that comprise the anthrax toxin secreted by the pathogen: protective antigen (PA), lethal factor (LF) and edema factor (EF),[67] or *Clostridium botulinum* (botulism), e.g., Botulinum neurotoxin peptides such as the cyclic peptide C11-019.[68]

5.5.5. Other Analytes

Non-peptide analytes can include, but are not limited to, quorum sensing small molecules such as the *Vibrio Cholera* CAI-1,[69] inter-species bacterial quorum sensing AL-2,[70] aflatoxin B1 produced by *Aspergillus flavus*, components of the bacterial LPS, or heavy metals contaminants such as cadmium, mercury, lead or arsenic.

5.6. Methods of Use

The present invention provides for a method of detecting the presence of an agent of interest in a sample using the sensor cell disclosed herein. In certain embodiments, the method comprises contacting the sample with a sensor cell (e.g., a yeast sensor cell) comprising (e.g., bearing) a receptor (e.g., a non-native GPCR receptor) that binds to an analyte indicative of the presence of the agent, wherein binding of the analyte to the receptor triggers a detection event that is indicative of the presence of the agent (e.g., increased expression of a reporter gene).

In certain embodiments, the receptor is coupled to the reporter gene. The method further comprises culturing the sensor cell for an effective period of time; and determining expression of the reporter gene. In certain embodiments, determining whether expression of the reporter gene comprises detecting the expression of the reporter gene by the naked eye and does not require instrumentation. In certain non-limiting embodiments, the reporter is lycopene.

In certain embodiments, the detection event is release of a therapeutic molecule that directly remediates the agent.

In certain embodiments, the detection event is production of a redox active molecule. The method further comprises measuring the production of the redox active molecule. In certain embodiments, measuring the production of the redox active molecule comprises an electronic device. The redox active molecule can be phenazine.

In certain embodiments, the detection event is a change in the membrane potential of the sensor cell. The change in the membrane potential of the sensor cell comprises expression of a cAMP-activated ion channel in the sensor cell.

The particulars of the receptor, coupling, and reporter gene are described in the sections above.

The method for determining whether the reporter gene is or has been expressed depends upon the particular reporting gene used. If the reporter gene produces a visibly detectable product, such as lycopene, it can be detected with the naked eye or colorimetrically. Means of detection of reporter genes known in the art can be used.

In certain non-limiting embodiments, the receptor is a G-protein coupled receptor (GPCR) engineered to bind to the analyte.

By way of non-limiting example, a method of detecting the presence of *Vibrio cholerae* in a water sample can include detecting the presence of a peptide associated with *Vibrio cholerae* in the water sample by a method comprising:

contacting the water sample with a sensor yeast cell bearing a GPCR polypeptide that binds to the analyte coupled to a CrtI gene such that when the peptide binds to the receptor, expression of the CrtI gene is induced and lycopene is produced;

culturing the sensor yeast cell for an effective period of time; and determining whether lycopene has been produced.

The analyte associated with *Vibrio cholerae* can be a peptide having at least about 80%, at least about 85%, at least about 90%, at least about 95%, at least about 98%, or at least about 99% homologous to VEVPGSQHIDSQKKA (SEQ ID NO: 26) or VPGSQHIDS (SEQ ID NO: 27). The effective period of time can be hours (e.g., about 24 hours, about 18 hours, about 12 hours, about 8 hours, about 6 hours, about 4 hours, about 3 hours, or about 2 hours) or minutes (e.g., about 90 minutes, about 60 minutes, about 45 minutes, about 30 minutes, about 20 minutes, about 15 minutes, about 10 minutes, about 5 minutes, about 3 minutes, about 2 minutes, or about 1 minute).

In certain non-limiting embodiments, the present invention provides for a method of detecting the presence of a fungus or a fungal pathogen, comprising detecting the presence of an analyte associated with said fungus or a fungal pathogen in a sample by a method comprising:

contacting the sample with a sensor cell comprising (e.g., bearing) a receptor that binds to the analyte coupled to a reporter gene such that when the analyte binds to the receptor, expression of a detectable reporter gene is induced;

culturing the sensor cell for an effective period of time; and determining whether the reporter gene is expressed. In certain non-limiting embodiments, the receptor is a G-protein coupled yeast receptor engineered to bind to the analyte. In certain non-limiting embodiments, the reporter gene expression is detected by the naked eye and does not require instrumentation. In certain non-limiting embodiments, the reporter gene product is lycopene.

In certain embodiments, the sensor cell is a freeze-dried or other dried cell, e.g., a freeze-dried yeast cell. The cell can be activated for use by addition of a food source, e.g., sugar or agar.

Non-limiting examples of samples can include a water sample and a sample of body fluid. Non-limiting examples of water samples include fresh water, sea water, and sewage samples. Non-limiting examples of body fluid samples include intestinal fluids, diarrhea or other feces, mucus (e.g., sputum), blood, cerebrospinal fluid, lymph, pus, saliva, vomit, urine, bile, and sweat. In certain embodiments, the agent to be detected is a plant fungal pathogen. A plant can be shaken in water to provide a water sample containing the fungal pathogen, or a soil sample can be mixed with water and tested for the fungal pathogen, or a portion of plant material (e.g., a fluid obtained from the plant) can be used as a sample.

5.7. Kits

The present invention provides kits for detecting the presence of an agent of interest, for example but not limited to a chemical or a pathogen, as described above. Kits can include one or more sensor cells, as described above, and can be used to perform methods of detecting the presence of an agent, as described above. Kits can further include one or more controls. Kits can include both a positive and a negative control. Kits can include a substrate that comprises the sensor cells and on which or in which detection can occur, e.g., a dish, cup, bowl, plate, paper, chip, gel, bag, stick, syringe, jar, or bottle. Kits can include a food or nutrient source, e.g., sugar or agar. Kits can include components to improve cell viability, including one or more carbon sources, one or more nitrogen sources, one or more trace nutrient sources, and one or more additional nutrient sources to improve response speed. Kits can include additional assay components, including proteases to release target peptides, dyes, filters, and/or cryo-protectants. Kits can be produced by combining all required assay components (e.g., nutrients, sensor cells, and proteases) and freeze-drying, air-drying, or binding this component mix to a substrate. In certain embodiments, the kit comprises a protease (e.g., a protease from prokaryote sources or a protease from eukaryote sources) for digestion of the agent into smaller detectable peptides.

FIG. 14A represents a kit ("Yeast Block") in accordance with one non-limiting embodiments. As shown in FIG. 14A, the kit comprises a yeast cell, a piece of paper, a negative control, and a nutrient source.

5.7.1 Dipstick Embodiments

In particular non-limiting embodiments, the invention provides for a kit comprising biosensor cells on a solid support comprised in a dipstick configuration. The solid support may be any natural and/or synthetic material, including but not limited to glass fiber, cellulose, quartz fiber, cellulose fiber, polytetrafluoroethylene, cotton, rayon, viscose, etc. In non-limiting examples, the support material may be configured such that the biosensor cells may be applied by filtration; for example, biosensor cells may be applied, by filtration, to a filter paper or disk, and then at least a portion of that paper or disk (e.g. a section of the filter paper or disk) may be incorporated into a dipstick configuration. Alternatively, the biosensor cells may be applied by direct application, for example, applying a volume of liquid culture. The solid support may be affixed, prior to or after (or concurrently with) application of biosensor cells, to a support strip to create a dipstick having a proximal end that may be directly or indirectly held by the user and a distal end bearing the solid support and biosensor cells, permitting dipping the biosensor into a sample to be tested. In certain embodiments, the support strip has liquid wicking activity (e.g., absorbent paper or other material). The proximal end of the dipstick may optionally fit into a holder (to form a dipstick device) that facilitates gripping the dipstick device. In certain non-limiting embodiments, the dipstick comprises a solid support having at least a portion of its surface bearing an amount of biosensor cells sufficient to generate detectable signal after contacting an analyte of interest, and optionally a portion bearing an amount of a negative control (e.g. cells that would not generate detectable signal after contact with the analyte of interest). In certain non-limiting embodiments, the dipstick comprises a solid support having at least several portions of its surface (e.g., an array) each bearing distinct biosensor cells with each type of biosensor cells present in an amount sufficient to generate detectable signal after contacting its corresponding analyte or analytes of interest. In certain non-limiting embodiments, the amount of biosensor is at least between about $1\times10^6$ and $5\times10^8$ cells, or between about $1\times10^7$ and $1\times10^8$ cells. Cells may be applied to the support, for example, by vacuum filtration. After application of biosensor to solid support, the composition may optionally be allowed to dry for at least about 20 minutes. The present invention provides for a kit comprising one or more dipstick, and optionally comprising one or more holder; in a particular embodiment, the kit comprises 1-3 holders, or one holder, and at least 3 or at least 5 or at least 10 dipsticks for testing for the same or different analytes. In certain non-limiting embodiments, a method is provided in which the dipstick described above may be used to detect an analyte of interest or an array of analytes of interest by dipping its distal end, bearing the biosensor cells and/or the negative control cells and/or the array of distinct biosensor cell types, into a sample such that the biosensor cells and/or the negative control cells and/or the array of distinct biosensor cell types contact the sample, and then incubating the dipstick at a temperature that is at least about 20° C., preferably greater than 20° C., and preferably greater than 25° C., for a period of time that allows signal to develop, for example, but not limited to, at least about 1 hour, at least about 3 hours, at least about 5 hours, at least about 7 hours, at least about 10 hours, at least about 12 hours or at least 15 hours. In certain situations, it may be desirable to add liquid (e.g. water, saline, or a medium that allows or promotes growth of biosensor cells) to a sample prior to testing; for example, where the biosensor is a yeast, a sample may be diluted with yeast growth medium. In certain exemplary non-limiting embodiments, urine or serum may be diluted 1:1 with yeast growth medium, and blood may be diluted about 2:98 with yeast growth medium. A solid sample, such as soil or stool, may be suspended in yeast growth medium prior to testing. In certain non-limiting embodiments, a kit is provided comprising at least one dipstick as described above, optionally a dipstick holder, and either liquid nutrient medium or powdered medium that can be reconstituted, by addition of water or other liquid, to form a liquid nutrient medium for growth of biosensor cells. In certain non-limiting embodiments, a kit is provided comprising at least one dipstick as described above, optionally a dipstick holder, and either liquid yeast nutrient medium or powdered medium that can be reconstituted, by addition of water or other liquid, to form a liquid yeast nutrient medium for growth of yeast biosensor cells, as described above.

6. EXAMPLES

6.1. Example 1: Yeast Strains that Produce Lycopene in Response to Activation of the Endogenous GPCR Ste2

A yeast strain producing lycopene in response to the activation of the endogenous GPCR, Ste2 was generated by the natural *S. cerevisiae* peptide pheromone, α-Factor (αF). A parental reporter strain was made by deleting the cyclin-dependent kinase inhibitor Far1 to prevent cell-cycle arrest and deleted the G-protein activating protein Sst2 to prevent signal attenuation. For general procedures, see Pausch, M. H. G-protein-coupled receptors in *Saccharomyces cerevisiae*: high-throughput screening assays for drug discovery. Trends Biotechnol. 15, 487-494 (1997). Then, the carotenoid genes derived from *E. herbicola*, CrtE, and CrtB were placed under the control of the constitutive promoters pTef1 and pPgk1, respectively. The final biosynthetic gene CrtI was placed under control of the Fus1 promoter, a downstream target of the pheromone response pathway. See Bardwell, L. A walk-through of the yeast mating pheromone response pathway. Peptides 26, 339-350 (2005). This lycopene reporter cassette was introduced into the parental reporter strain through Reiterative Recombination. See Wingler, L. M. & Cornish, V. W. Reiterative Recombination for the in vivo assembly of libraries of multigene pathways. Proc Natl Acad Sci USA 108, 15135-15140 (2011). This v1.0 reporter strain became visibly orange 36 hours after exposure to αF, as shown in FIG. 4A.

Through modification of the v1.0 strain, a lycopene response time of 2 hours under optimal culture conditions and less than 6 hours in a stringent product prototype assay was observed. To do so, the CrtI amount was increased with an additional chromosomal copy of the pFus1-CrtI construct. This led to a 9.8-fold improvement in response time. The catalytic activity of CrtI was improved by increasing FAD content in the cell through the overexpression of the FAD synthetase FAD1. See Schaub, P. et al. On the Structure and Function of the Phytoene Desaturase CRTI from *Pantoea ananatis*, a Membrane-Peripheral and FAD-Dependent Oxidase/Isomerase. PLoS ONE 7, e39550 (2012); Wu, M., Repetto, B., Glerum, D. M. & Tzagoloff, A. Cloning and characterization of FAD1, the structural gene for flavin adenine dinucleotide synthetase of *Saccharomyces cerevisiae*. Mol. Cell. Biol. 15, 264-271 (1995). This modification independently led to a 10.3-fold improvement in the response time, and to a 21.1-fold improvement when combined with the increased CrtI copy number. These results are shown in FIG. 4B.

TABLE 1

Key genes and sequences.

| Key Genes | Nucleotide Sequence |
|---|---|
| *E. herbicola* CrtI | ATGAAGAAAACCGTAGTGATTGGTGCAGGTTTTGGTG<br>GTTTAGCTTTGGCTATACGTCTACAAGCTGCAGGTAT<br>TCCTACAGTGCTATTGGAGCAAAGAGACAAACCAGGA<br>GGAAGAGCTTATGTTTGGCACGATCAAGGCTTTACCT<br>TTGATGCTGGTCCTACAGTCATCACTGATCCTACTGC<br>ATTGGAAGCTTTGTTCACCTTAGCTGGTAGAAGAATG<br>GAAGATTATGTCCGTCTATTGCCTGTCAAGCCGTTTT<br>ACAGATTGTGTTGGGAATCTGGTAAAACCCTAGATTA<br>CGCCAATGACAGTGCTGAACTAGAAGCTCAGATTACG<br>CAGTTTAATCCCAGAGATGTCGAAGGTTACAGGAGAT<br>TCCTTGCCTATTCCCAAGCTGTTTTCCAAGAGGGTTA<br>TCTTCGTTTGGGTTCAGTTCCATTCCTGTCCTTTAGG<br>GATATGCTTAGAGCAGGTCCTCAGTTGTTGAAGCTAC<br>AAGCATGGCAAAGTGTGTATCAGTCTGTTTCGAGATT<br>TATCGAGGATGAACATCTGAGACAAGCATTCTCATTC<br>CACAGTCTTCTAGTTGGAGGTAATCCCTTTACCACAT<br>CGAGCATATATACGTTGATTCACGCTTTGGAAAGAGA<br>ATGGGGAGTTTGGTTTCCTGAAGGTGGAACAGGTGCT<br>TTGGTTAATGGTATGGTGAAGCTATTCACGGATTTGG<br>GTGGAGAAATAGAGCTGAATGCAAGAGTGGAAGAACT<br>TGTTGTAGCAGACAACAGAGTCTCACAAGTTAGACTT<br>GCTGATGGTAGGATCTTCGATACAGATGCTGTAGCTT<br>CAAACGCAGATGTAGTGAACACTTATAAAAAGTTGTT<br>GGGACATCATCCTGTTGGACAAAAGAGAGCAGCTGCT<br>TTGGAGAGGAAATCTATGAGCAACTCGTTGTTTGTCC<br>TTTACTTTGGGCTGAATCAACCACACTCACAACTAGC<br>TCATCACACAATCTGCTTTGGTCCTAGATACAGAGAG<br>CTGATAGATGAAATTTTCACTGGATCTGCTTTAGCAG<br>ACGATTTTTCCCTGTACTTGCATTCACCATGTGTTAC |

TABLE 1-continued

| Key genes and sequences. | |
|---|---|
| Key Genes | Nucleotide Sequence |
| | TGATCCCTCTTTAGCACCACCTGGTTGTGCTAGCTTC<br>TATGTACTAGCACCTGTACCACATTTGGGTAATGCTC<br>CATTAGATTGGGCACAAGAAGGACCGAAATTGAGGGA<br>TAGGATCTTCGACTATTTGGAAGAACGTTACATGCCA<br>GGTTTGAGATCTCAGTTGGTTACACAGAGGATATTCA<br>CACCAGCTGATTTTCATGATACTCTAGATGCGCATTT<br>AGGTAGCGCTTTTTCCATTGAGCCACTTTTGACGCAA<br>AGTGCTTGGTTTAGACCACACAACAGAGATTCTGACA<br>TTGCCAATCTGTACCTAGTAGGTGCAGGAACTCATCC<br>AGGAGCTGGTATTCCTGGAGTTGTAGCTTCTGCTAAA<br>GCTACTGCTAGTCTGATGATCGAGGATTTGCAGTAA<br>(SEQ ID NO: 1) |
| *E. herbicola* CrtE | ATGGTTTCTGGTTCGAAAGCAGGAGTATCACCTCATA<br>GGGAAATCGAAGTCATGAGACAGTCCATTGATGACCA<br>CTTAGCAGGATTGTTGCCAGAAACAGATTCCCAGGAT<br>ATCGTTAGCCTTGCTATGAGAGAAGGTGTTATGGCAC<br>CTGGTAAACGTATCAGACCTTTGCTGATGTTACTTGC<br>TGCAAGAGACCTGAGATATCAGGGTTCTATGCCTACA<br>CTACTGGATCTAGCTTGTGCTGTTGAACTGACACATA<br>CTGCTTCCTTGATGCTGGATGACATGCCTTGTATGGA<br>CAATGCGGAACTTAGAAGAGGTCAACCAACAACCCAC<br>AAGAAATTCGGAGAATCTGTTGCCATTTTGGCTTCTG<br>TAGGTCTGTTGTCGAAAGCTTTTGGCTTGATTGCTGC<br>AACTGGTGATCTTCCAGGTGAAAGGAGAGCACAAGCT<br>GTAAACGAGCTATCTACTGCAGTTGGTGTTCAAGGTC<br>TAGTCTTAGGACAGTTCAGAGATTTGAATGACGCAGC<br>TTTGGACAGAACTCCTGATGCTATCCTGTCTACGAAC<br>CATCTGAAGACTGGCATCTTGTTCTCAGCTATGTTGC<br>AAATCGTAGCCATTGCTTCTGCTTCTTCACCATCTAC<br>TAGGGAAACGTTACACGCATTCGCATTGGACTTTGGT<br>CAAGCCTTTCAACTGCTAGACGATTTGAGGGATGATC<br>ATCCAGAGACAGGTAAAGACCGTAACAAAGACGCTGG<br>TAAAAGCACTCTAGTCAACAGATTGGGTGCTGATGCA<br>GCTAGACAGAAACTGAGAGAGCACATTGACTCTGCTG<br>ACAAACACCTGACATTTGCATGTCCACAAGGAGGTGC<br>TATAAGGCAGTTTATGCACCTATGGTTTGGACACCAT<br>CTTGCTGATTGGTCTCCAGTGATGAAGATCGCCTAA<br>(SEQ ID NO: 2) |
| *E. herbicola* CrtB | ATGAGTCAACCACCTTTGTTGGATCATGCTACTCAAA<br>CGATGGCTAATGGTTCCAAGTCCTTTGCTACAGCAGC<br>TAAACTGTTTGACCCAGCTACTAGAAGATCAGTGCTT<br>ATGCTGTACACTTGGTGTAGACACTGTGATGACGTTA<br>TAGATGACCAGACACATGGTTTCGCATCTGAAGCTGC<br>TGCAGAAGAAGAGGCTACTCAGAGATTGGCTAGATTG<br>AGAACGCTTACACTTGCAGCTTTTGAAGGTGCTGAGA<br>TGCAAGATCCTGCTTTTGCTGCATTCCAAGAAGTTGC<br>ACTAACACACGGTATTACGCCAAGAATGGCACTTGAT<br>CACTTGGATGGTTTCGCAATGGATGTTGCTCAAACTC<br>GTTACGTGACCTTTGAAGACACCTTGAGATACTGCTA<br>CCATGTTGCTGGAGTAGTTGGTTTGATGATGGCAAGA<br>GTAATGGGTGTAAGAGACGAAAGGGTTTTGGACAGAG<br>CTTGTGATCTAGGTTTGGCTTTTCAGCTGACAAACAT<br>CGCGAGAGATATTATCGACGATGCAGCTATTGACAGA<br>TGCTATCTACCTGCTGAATGGTTGCAAGATGCTGGTC<br>TAACTCCTGAGAATTACGCTGCAAGAGAGAACAGAGC<br>TGCATTAGCAAGAGTTGCTGAAAGGCTGATAGACGCT<br>GCTGAACCCTATTACATCTCAAGTCAAGCTGGATTGC<br>ATGATCTACCACCTAGATGTGCTTGGGCTATAGCTAC<br>TGCAAGATCTGTCTACAGAGAGATTGGCATCAAGGTA<br>AAAGCTGCAGGTGGTTCTGCTTGGGATAGACGTCAAC<br>ACACTAGCAAAGGAGAGAAGATTGCGATGCTTATGGC<br>TGCACCAGGACAAGTCATTCGTGCCAAAACAACCAGA<br>GTTACACCAAGACCTGCTGGTTTATGGCAAAGACCTG<br>TCTAA (SEQ ID NO: 3) |
| *S. cerevisiae* Fad1 | ATGCAGTTGAGCAAGGCTGCTGAGATGTGTTATGAGA<br>TAACAAACTCTTACTTACACATAGACCAGAAATCTCA<br>GATAATAGCAAGTACACAAGAAGCGATACGGTTGACA<br>AGAAAATACTTACTAAGTGAAATTTTTGTACGTTGGA<br>GTCCACTGAATGGGGAAATATCATTCTCGTACAACGG<br>AGGAAAAGATTGCCAGGTATTACTACTGTTATATCTG<br>AGTTGCTTATGGGAATATTTCTTCATTAAGGCTCAAA<br>ATTCCCAATTCGATTTCGAGTTTCAAAGCTTCCCCAT |

TABLE 1-continued

| Key genes and sequences. | |
|---|---|
| Key Genes | Nucleotide Sequence |
| | GCAAAGACTTCCAACTGTTTTCATTGATCAAGAAGAA<br>ACTTTCCCTACATTAGAGAATTTTGTACTGGAAACCT<br>CAGAGCGATATTGCCTTTCCTTATACGAATCACAAAG<br>GCAATCTGGTGCATCGGTCAATATGGCAGACGCATTT<br>AGAGATTTTATAAAGATATACCCTGAGACCGAAGCTA<br>TAGTGATAGGTATTAGACACACAGACCCATTTGGTGA<br>AGCATTAAAGCCTATTCAAAGAACAGATTCTAACTGG<br>CCTGATTTTATGAGGTTGCAACCTCTCTTACACTGGG<br>ACTTAACCAATATATGGAGTTTCTTACTGTATTCTAA<br>TGAGCCAATTTGTGGACTATATGGTAAAGGTTTCACA<br>TCAATCGGCGGAATTAACAACTCATTGCCTAACCCAC<br>ACTTGAGAAAGGACTCCAATAATCCAGCCTTGCATTT<br>TGAATGGGAAATCATTCATGCATTTGGCAAGGACGCA<br>GAAGGCGAACGTAGTTCCGCTATAAACACGTCACCTA<br>TTTCCGTGGTGGATAAGGAAAGATTCAGCAAATACCA<br>TGACAATTACTATCCTGGCTGGTATTTGGTTGATGAC<br>ACTTTAGAGAGAGCAGGCAGGATCAAGAATTAA<br>(SEQ ID NO: 4) |

6.2. Example 2: Cloning and Screening of Putative GPCRs Against Putative Cognate Fungal Peptide Hormones Several putative GPCRs were screened against their putative cognate peptide pheromones using a fluorescent reporter gene.[33] Recognition of pheromones from the following pathogenic fungi was shown in *S. cerevisiae:*

Human Pathogens:

- *Candida albicans* (functional expression in yeast previously shown)[17]
- *Paracoccidioides brasiliensis* (functional expression in yeast previously shown)[16]
- *Candida glabrata*

Plant Pathogens:

- *Fusarium graminearum* (grain disease)
- *Magnaporthe* oryzea (Rice blast)
- *Botrytis cinerea* (Grey mould)

As shown in FIG. 6, these receptors were orthogonal to the endogenous *S. cerevisiae* pheromone receptor and demonstrated a high level of specificity. Their EC50 values were as follows: *C. albicans,* 51 nM; *P. brasiliensis,* 9 nM; *F. graminearum,* 230 nM; *M. oryzea,* 5 uM; *B. cinerea,* <1 nM. Additionally, the GPCR from *B. cinerea* showed activity against the putative pheromone from *Aspergillus flavus* and therefore may provide a useful diagnostic against this human pathogen. The results also demonstrated that these receptors succesfully generate lycopene in the disclosed reporter strain.

TABLE 2

| Pathogens and associated sequences | | | |
|---|---|---|---|
| Pathogen | Amino acid sequence of peptide analyte used | Amino acid sequence of GPCRs used | DNA coding sequence of corresponding GPCRs that sense peptide analyte |
| *Candida albicans* | GFRLTNFG<br>YFEPG<br>(SEQ ID<br>NO: 5) | MNINSTFIPDKPGDII<br>ISYSIPGLDQPIQIPFH<br>SLDSFQTDQAKIALV<br>MGITIGSCSMTLIFLI<br>SIMYKTNKLTNLKL<br>KLKLKYILQWINQKI<br>FTKKRNDNKQQQQ<br>QQQQQIESSSYNNTT<br>TTLGGYKLFLFYLNS<br>LILLIGIIRSGCYLNY<br>NLGPLNSLSFVFTG<br>WYDGSSFISSDVTN<br>GFKCILYALVEISLG<br>FQVYVMFKTSNLKI<br>WGIMASLLSIGLGLI<br>VVAFQINLTILSHIRF<br>SRAISTNRSEEESSSS<br>LSSDSVGYVINSIWM<br>DLPTILFSISINIMTIL<br>LIGKLIIAIRTRRYLG<br>LKQFDSFHILLIGFSQ<br>TLIIPSIILVVHYFYLS<br>QNKDSLLQQISLLLII<br>LMLPLSSLWAQTAN<br>NTHNINSSPSLSFISR<br>HHLSDSSRSGGSNTI<br>VSNGGSNGGGGGG<br>GNFPVSGIDAQLPPD<br>IEKILHEDNNYKLLN<br>SNNESVNDGDIIIND<br>EGMITKQITIKRV<br>(SEQ ID NO: 6) | ATGAATATCAATTCAACTTTCATACCTGAT<br>AAACCAGGCGATATAATTATTAGTTATTCA<br>ATTCCAGGATTAGATCAACCAATTCAAATT<br>CCTTTCCATTCATTAGATTCATTTCAAACC<br>GATCAAGCTAAAATAGCTTTAGTCATGGG<br>GATAACTATTGGGAGTTGTTCAATGACATT<br>AATTTTTTTGATTTCTATAATGTATAAAACT<br>AATAAATTAACAAATTTAAAATTAAAATTA<br>AAATTAAAATATATCTTGCAATGGATAAAT<br>CAAAAAATCTTCACCAAAAAAAGGAATGA<br>CAACAAACAACAACAACAACAACAACAAC<br>AACAAATTGAATCATCATCATATAACAATA<br>CTACTACTACGCTGGGGGTTATAAATTAT<br>TTTTATTTTATCTTAATTCATTGATTTTATT<br>AATTGGTATTATTCGATCAGGTTGTTATTT<br>AAATTATAATTTAGGTCCATTAAATTCACT<br>TAGTTTTGTATTTACTGGTTGGTATGATGG<br>ATCATCATTTATATCATCCGATGTAACTAA<br>TGGATTTAAATGTATTTTATATGCTTTAGT<br>GGAAATTTCATTAGGTTTCCAAGTTTATGT<br>GATGTTCAAAACTTCAAATTTAAAAATTTG<br>GGGGATAATGGCATCATTATTATCAATTGG<br>TTTAGGATTGATTGTTGTTGCCTTTCAAATC<br>AATTTAACAATTTTATCTCATATTCGATTTT<br>CCCGGGCTATATCAACTAACAGAAGTGAA<br>GAAGAATCATCATCATCATTATCATCTGAT<br>TCGGTTGGGTATGTGATTAATTCAATATGG<br>ATGGATTTACCAACAATATTATTTTCCATT<br>AGTATTAATATAATGACAATATTATTGATT<br>GGTAAACTTATAATTGCTATTAGAACAAGA<br>CGTTATTTAGGATTGAAACAATTTGATAGT<br>TTCCATATTTTATTAATTGGTTTCAGTCAAA<br>CATTAATTATTCCTTCAATTATTTTGGTGGT<br>TCATTATTTTTATTTATCACAAAATAAAGA<br>TTCTTTATTACAACAAATTAGTCTTTTATTG<br>ATTATTTTAATGTTACCATTAAGTTCTTTAT<br>GGGCTCAAACTGCTAATAATACTCATAATA<br>TTAATTCATCTCCAAGTTTATCATTCATATC<br>TCGTCATCATCTGTCTGATAGTAGTCGTAG<br>TGGTGGTTCCAATACAATTGTTAGTAATGG<br>TGGTAGTAATGGTGGTGGTGGTGGTGGTG<br>GGAATTTCCCTGTTTCAGGTATTGATGCAC<br>AATTACCACCTGATATTGAAAAAATCTTAC<br>ATGAAGATAATAATTATAAATTACTTAATA<br>GTAATAATGAAAGTGTAAATGATGGAGAT<br>ATTATCATTAATGATGAAGGTATGATTACT<br>AAACAAATCACCATCAAAAGAGTGTAG<br>(SEQ ID NO: 7) |
| *Candida glabrata* | WHWVRL<br>RKGQGLF<br>(SEQ ID<br>NO: 8) | MEMGYDPRMYNPR<br>NEYLNFTSVYDVND<br>TIRFSTLDAIVKGLL<br>RIAIVHGVRLGAIFM<br>TLIIMFISSNTWKKPI<br>FIINMVSLMLVMIHS<br>ALSFHYLLSNYSSIS<br>YILTGFPQLITSNNK<br>RIQDAASIVQVLLVA<br>AIEASLVFQIHVMFT<br>IENIKLIREIVLSISIA<br>MGLATVATYLAAAI<br>KLIRGLHDEVMPQT<br>HLIFNLSIILLASSINF<br>MTFILVIKLFFAIRSR<br>RYLGLRQFDAFHILL<br>IMFCQSLLIPSVLYII<br>VYAVDSRSNQDYLI<br>PIANLFVVLSLPLSSI<br>WANTSNNSSRSPKY<br>WKNSQTNKSNGSFV | ATGGAGATGGGCTACGATCCAAGAATGTA<br>TAATCCAAGAAATGAATACTTGAATTTCAC<br>GTCGGTATATGATGTAAATGACACAATCA<br>GATTTTCGACTCTGGACGCCATTGTAAAAG<br>GATTGCTTAGAATTGCCATTGTTCATGGAG<br>TTAGATTGGGAGCAATATTCATGACGTTAA<br>TAATAATGTTTATCTCATCAAATACATGGA<br>AAAAACCCATATTTATAATTAACATGGTGT<br>CGTTGATGTTAGTTATGATTCATTCCGCAC<br>TTAGCTTCCATTACCTTTTATCGAATTATTC<br>TTCAATTTCTTATATACTGACAGGGTTTCCT<br>CAGTTGATTACAAGCAATAATAAACGAAT<br>TCAAGATGCAGCGAGTATAGTCCAAGTTTT<br>ATTGGTTGCTGCGATAGAAGCATCATTGGT<br>ATTTCAGATTCATGTTATGTTTACGATTGA<br>AAACATTAAGCTTATTAGAGAAATAGTACT<br>CTCTATATCGATAGCAATGGGATTGGCAAC<br>AGTGGCTACATATCTTGCTGCAGCAATAAA<br>GCTGATAAGAGGACTGCATGATGAGGTAA<br>TGCCACAAACACATCTTATTTTCAATTTAT<br>CTATAATATTGCTTGCATCCTCCATAAATT |

TABLE 2-continued

Pathogens and associated sequences

| Pathogen | Amino acid sequence of peptide analyte used | Amino acid sequence of GPCRs used | DNA coding sequence of corresponding GPCRs that sense peptide analyte |
|---|---|---|---|
| | | SSISVNSDSQNPLYK<br>KIVRFTSKGDTTRSI<br>VSDSTLAEVGKYSM<br>QDVSNSNFECRDLD<br>FEKVKHTCENFGRIS<br>ETYSELSTLDTTALN<br>ETRLFWKQQSQCDK<br>(SEQ ID NO: 9) | TTATGACATTTATATTGGTCATTAAACTTTT<br>CTTCGCTATTAGATCTAGAAGATATCTCGG<br>TCTTCGTCAATTCGATGCTTTTCATATTTTA<br>TTAATCATGTTCTGCCAGTCATTATTGATA<br>CCCTCAGTATTATATATTATAGTTTACGCG<br>GTTGATAGCAGATCTAATCAGGATTATCTG<br>ATTCCAATTGCCAATTTATTTGTTGTTTTAT<br>CTTTGCCATTATCCTCTATCTGGGCTAACA<br>CATCAAATAACTCATCCAGATCTCCAAAAT<br>ATTGGAAAAACTCTCAAACGAATAAGAGC<br>AATGGGTCTTTTGTCTCTTCAATATCTGTCA<br>ATAGTGACTCACAAAACCCTTTGTACAAAA<br>AGATTGTACGTTTTACATCAAAAGGCGACA<br>CTACCCGTAGTATTGTAAGTGATTCAACAT<br>TAGCAGAGGTGGGAAAATACTCTATGCAA<br>GACGTTAGCAATTCAAACTTTGAATGTCGA<br>GACCTTGATTTTGAGAAGGTAAAACATACT<br>TGCGAAAATTTTGGCAGAATATCTGAAAC<br>ATATAGTGAGTTAAGTACTTTAGATACCAC<br>TGCCCTCAATGAGACTCGGTTGTTTTGGAA<br>ACAACAAAGTCAGTGTGACAAATAG<br>(SEQ ID NO: 10) |
| *Paracoccidioides brasiliensis* | WCTRPGQ<br>GC<br>(SEQ ID<br>NO: 11) | MAPSFDPFNQSVVF<br>HKADGTPFNVSIHEL<br>DDFVQYNTKVCINY<br>SSQLGASVIAGLML<br>AMLTHSEKRRLPVF<br>FLNTFALAMNFARL<br>LCMTIYFTTGFNKSY<br>AYFGQDYSQVPGSA<br>YAASVLGVVFTTLL<br>VISMEMSLLIQTRVV<br>CTTLPDIQRYLLMA<br>VSSAISLMAIGFRLG<br>LMVENCIAIVQASNF<br>APFIWLQSASNITITI<br>STCFFSAVFVTKLAY<br>ALVTRIRLGLTRFGA<br>MQVMFIMSCQTMVI<br>PAIFSILQYPLPKYE<br>MNSNLFTLVAIFLPL<br>SSLWASVATRSSFET<br>SSSGRHQYLWPSEQ<br>SNNVTNSEIKYQVSF<br>SQNHTTLRSGGSVA<br>TTLSPDRLDPVYCEV<br>EAGTKA<br>(SEQ ID<br>NO: 12) | ATGGCACCCTCATTCGACCCCTTCAACCAA<br>AGCGTGGTCTTCCACAAGGCCGACGGAAC<br>TCCATTCAACGTCTCAATCCATGAACTAGA<br>CGACTTCGTGCAGTACAACACCAAAGTCTG<br>CATCAACTACTCTTCCCAGCTCGGAGCATC<br>TGTCATTGCAGGACTCATGCTTGCCATGCT<br>GACACACTCAGAAAAGCGTCGTCTGCCAG<br>TTTTCTTCCTAAACACATTCGCACTGGCCA<br>TGAACTTTGCCCGCCTGCTCTGCATGACCA<br>TCTACTTCACCACGGGCTTCAACAAGTCCT<br>ATGCCTACTTTGGTCAGGATTACTCCCAGG<br>TGCCTGGGAGCGCCTACGCAGCCTCTGTCT<br>TGGGCGTTGTCTTCACCACTCTCCTGGTAA<br>TCAGCATGGAAATGTCCCTCCTGATCCAAA<br>CAAGGGTTGTCTGCACGACCCTTCCGGATA<br>TCCAACGTTATCTACTCATGGCAGTTTCCT<br>CCGCGATTTCCCTGATGGCCATCGGGTTCC<br>GCCTTGGCTTAATGGTTGAGAACTGCATTG<br>CCATTGTGCAGGCGTCGAATTTCGCCCCTT<br>TTATCTGGCTTCAAAGCGCCTCGAACATCA<br>CCATTACGATCAGCACATGTTTCTTCAGTG<br>CCGTCTTTGTTACGAAATTGGCATATGCAC<br>TCGTCACTCGTATACGACTAGGCTTGACGA<br>GGTTTGGTGCTATGCAGGTTATGTTCATCA<br>TGTCCTGCCAGACTATGGTGATTCCAGCCA<br>TCTTCTCAATTCTCCAATACCCACTCCCCA<br>AGTACGAAATGAACTCCAACCTCTTTACGC<br>TGGTGGCCATTTTCCTCCCTCTTTCCTCGCT<br>ATGGGCTTCAGTTGCTACGAGATCCAGTTT<br>CGAGACGTCTTCTTCCGGCCGCCATCAGTA<br>TCTTTGGCCAAGCGAACAGAGCAATAACG<br>TCACCAATTCGGAAATTAAGTATCAGGTCA<br>GCTTCTCTCAGAACCACACTACGTTGCGGT<br>CTGGAGGGTCTGTGGCCACGACACTCTCCC<br>CGGACCGGCTCGACCCGGTTTATTGTGAAG<br>TTGAAGCTGGCACAAAGGCCTAG<br>(SEQ ID NO: 13) |
| *Fusarium graminearum* | WCWWKG<br>QPCW<br>(SEQ ID<br>NO: 14) | MSKEVFDPFTQNVT<br>FFAPDGKTEISIPVA<br>AIDQVRRMMVNTTI<br>NYATQLGACLIMLV<br>VLLVMVPKEKFRRP<br>FMILQITSLVISCCR<br>MLLLSIFHSSQFLDF<br>YVFWGDDHSRIPRS<br>AYAPSVAGNTMSLC | ATGTCTAAGGAAGTTTTCGACCCATTCACT<br>CAAAACGTTACTTTCTTCGCTCCAGACGGT<br>AAGACTGAAATCTCTATCCCAGTTGCTGCT<br>ATCGACCAAGTTAGAAGAATGATGGTTAA<br>CACTACTATCAACTACGCTACTCAATTGGG<br>TGCTTGTTTGATCATGTTGGTTGTTTTGTTG<br>GTTATGGTTCCAAAGGAAAAGTTCAGAAG<br>ACCATTCATGATCTTGCAAATCACTTCTTT<br>GGTTATCTCTTGTTGTAGAATGTTGTTGTTG |

TABLE 2-continued

| Pathogens and associated sequences | | | |
|---|---|---|---|
| Pathogen | Amino acid sequence of peptide analyte used | Amino acid sequence of GPCRs used | DNA coding sequence of corresponding GPCRs that sense peptide analyte |
| | | LVISVETMLMSQAW<br>TMVRLWPNVWKYII<br>AGVSLIVSIMAISVR<br>LAYTIIQNNAVLKLE<br>PAFHMFWLIKWTVI<br>MNVASISWWCAIFN<br>IKLVWHLISNRGILP<br>SYKTFTPMEVLIMT<br>NGILMIIPVIFASLEW<br>AHFVNFESASLTLTS<br>VAVILPLGTLAAQRI<br>ASSAPSSANSTGASS<br>GIRYGVSGPSSFTGF<br>KAPSFSTGTTDRPHV<br>SIYARCEAGTSSREH<br>INPQGVELAKLDPET<br>DHHVRVDRAFLQRE<br>ERIRAPL<br>(SEQ ID<br>NO: 15) | TCTATCTTCCACTCTTCTCAATTCTTGGACT<br>TCTACGTTTTCTGGGGTGACGACCACTCTA<br>GAATCCCAAGATCTGCTTACGCTCCATCTG<br>TTGCTGGTAACACTATGTCTTTGTGTTTGGT<br>TATCTCTGTTGAAACTATGTTGATGTCTCA<br>AGCTTGGACTATGGTTAGATTGTGGCCAAA<br>CGTTTGGAAGTACATCATCGCTGGTGTTTC<br>TTTGATCGTTTCTATCATGGCTATCTCTGTT<br>AGATTGGCTTACACTATCATCCAAAACAAC<br>GCTGTTTTGAAGTTGGAACCAGCTTTCCAC<br>ATGTTCTGGTTGATCAAGTGGACTGTTATC<br>ATGAACGTTGCTTCTATCTCTTGGTGGTGT<br>GCTATCTTCAACATCAAGTTGGTTTGGCAC<br>TTGATCTCTAACAGAGGTATCTTGCCATCT<br>TACAAGACTTTCACTCCAATGGAAGTTTTG<br>ATCATGACTAACGGTATCTTGATGATCATC<br>CCAGTTATCTTCGCTTCTTTGGAATGGGCT<br>CACTTCGTTAACTTCGAATCTGCTTCTTTGA<br>CTTTGACTTCTGTTGCTGTTATCTTGCCATT<br>GGGTACTTTGGCTGCTCAAAGAATCGCTTC<br>TTCTGCTCCATCTTCTGCTAACTCTACTGGT<br>GCTTCTTCTGGTATCAGATACGGTGTTTCT<br>GGTCCATCTTCTTTCACTGGTTTCAAGGCT<br>CCATCTTTCTCTACTGGTACTACTGACAGA<br>CCACACGTTTCTATCTACGCTAGATGTGAA<br>GCTGGTACTTCTTCTAGAGAACACATCAAC<br>CCACAAGGTGTTGAATTGGCTAAGTTGGAC<br>CCAGAAACTGACCACCACGTTAGAGTTGA<br>CAGAGCTTTCTTGCAAAGAGAAGAAAGAA<br>TCAGAGCTCCATTGTAG<br>(SEQ ID NO: 16) |
| *Magnaporthe oryzea* | QWCPRRG<br>QPCW<br>(SEQ ID<br>NO: 17) | MDQTLSATGTATSP<br>PGPALTVDPRFQTIT<br>MLTPALMGQGFEEV<br>QTTPAEINDVYFLAF<br>NTAIGYSTQIGACFI<br>MLLVLLTMTAKARF<br>ARIPTIINTAALVVSII<br>RCTLLVIFFTSTMME<br>FYTIFSDDFSFVHPN<br>DIRRSVAATVFAPLQ<br>LALVEAALMVQAW<br>AMVELWPRAWKVS<br>GIAFSLILATVTVAF<br>KCASAAVTVKSALE<br>PLDPRPYLWIRQTDL<br>AFTTAMVTWFCFLF<br>NVRLIMHMWQNRSI<br>LPTVKGLSPMEVLV<br>MANGLLMVFPVLFA<br>GLYYGNFGQFESAS<br>LTITSVVLVLPLGTL<br>VAQRLAVNNTVAGS<br>SANTDMDDKLAFLG<br>NATTVTSSAAGFAG<br>SSASATRSRLASPRQ<br>NSQLSTSVSAGKPR<br>ADPIDLELQRIDDED<br>DDFSRSGSAGGVRV<br>ERSIERREERL<br>(SEQ ID<br>NO: 18) | ATGGACCAAACTTTGTCTGCTACTGGTACT<br>GCTACTTCTCCACCAGGTCCAGCTTTGACT<br>GTTGACCCAAGATTCCAAACTATCACTATG<br>TTGACTCCAGCTTTGATGGGTCAAGGTTTC<br>GAAGAAGTTCAAACTACTCCAGCTGAAAT<br>CAACGACGTTTACTTCTTGGCTTTCAACAC<br>TGCTATCGGTTACTCTACTCAAATCGGTGC<br>TTGTTTCATCATGTTGTTGGTTTTGTTGACT<br>ATGACTGCTAAGGCTAGATTCGCTAGAATC<br>CCAACTATCATCAACACTGCTGCTTTGGTT<br>GTTTCTATCATCAGATGTACTTTGTTGGTTA<br>TCTTCTTCACTTCTACTATGATGGAATTCTA<br>CACTATCTTCTCTGACGACTTCTCTTTCGTT<br>CACCCAAACGACATCAGAAGATCTGTTGCT<br>GCTACTGTTTTCGCTCCATTGCAATTGGCTT<br>TGGTTGAAGCTGCTTTGATGGTTCAAGCTT<br>GGGCTATGGTTGAATTGTGGCCAAGAGCTT<br>GGAAGGTTTCTGGTATCGCTTTCTCTTTGA<br>TCTTGGCTACTGTTACTGTTGCTTTCAAGTG<br>TGCTTCTGCTGCTGTTACTGTTAAGTCTGCT<br>TTGGAACCATTGGACCCAAGACCATACTTG<br>TGGATCAGACAAACTGACTTGGCTTTCACT<br>ACTGCTATGGTTACTTGGTTCTGTTTCTTGT<br>TCAACGTTAGATTGATCATGCACATGTGGC<br>AAAACAGATCTATCTTGCCAACTGTTAAGG<br>GTTTGTCTCCAATGGAAGTTTTGGTTATGG<br>CTAACGGTTTGTTGATGGTTTTCCCAGTTTT<br>GTTCGCTGGTTTGTACTACGGTAACTTCGG<br>TCAATTCGAATCTGCTTCTTTGACTATCACT<br>TCTGTTGTTTTGGTTTTGCCATTGGGTACTT<br>TGGTTGCTCAAAGATTGGCTGTTAACAACA<br>CTGTTGCTGGTTCTTCTGCTAACACTGACA<br>TGGACGACAAGTTGGCTTTCTTGGGTAACG<br>CTACTACTGTTACTTCTTCTGCTGCTGGTTT<br>CGCTGGTTCTTCTGCTTCTGCTACTAGATCT<br>AGATTGGCTTCTCCAAGACAAAACTCTCAA<br>TTGTCTACTTCTGTTTCTGCTGGTAAGCCA<br>AGAGCTGACCCAATCGACTTGGAATTGCA |

TABLE 2-continued

Pathogens and associated sequences

| Pathogen | Amino acid sequence of peptide analyte used | Amino acid sequence of GPCRs used | DNA coding sequence of corresponding GPCRs that sense peptide analyte |
|---|---|---|---|
| | | | AAGAATCGACGACGAAGACGACGACTTCTCTAGATCTGGTTCTGCTGGTGGTGTTAGAGTTGAAAGATCTATCGAAAGAAGAGAAGAAAGATTGTAG (SEQ ID NO: 19) |
| *Botryhs cinerea* | WCGRPGQPC (SEQ ID NO: 20) | MASNSSNFDPLTQSITILMADGITTVSFTPLDIDFFYYYNVACCINYGAQAGACLLMFFVVVVLTKAVKRKTLLFVLNVLSLIFGFLRAMLYAIYFLQGFNDFYAAFTFDFSRVPRSSYASSVAGSVIPLCMTITVNMSLYLQAYTVCKNLDDIKRIILTTLSAIVALLAIGFRFAATVVNSVAILATSASSVPMQWLVKGTLVTETISIWFFSLIFTGKLVWTLYNRRRNGWRQWSAVRILAAMGGCTMVIPSIFAILEYVTPVSFPEAGSIALTSVALLLPISSLWAGMVTDEETSAIDVSNLTGSRTMLGSQSGNFSRKTHASDITAQSSHLDFSSRKGSNATMMRKGSNAMDQVTTIDCVVEDNQANRGLRDSTEMDLEAMGVRVNKSYGVQKA (SEQ ID NO: 21) | ATGGCTTCTAACTCTTCTAACTTCGACCCATTGACTCAATCTATCACTATCTTGATGGCTGACGGTATCACTACTGTTTCTTTCACTCCATTGGACATCGACTTCTTCTACTACTACAACGTTGCTTGTTGTATCAACTACGGTGCTCAAGCTGGTGCTTGTTTGTTGATGTTCTTCGTTGTTGTTGTTTTGACTAAGGCTGTTAAGAGAAAGACTTTGTTGTTCGTTTTGAACGTTTTGTCTTTGATCTTCGGTTTCTTGAGAGCTATGTTGTACGCTATCTACTTCTTGCAAGGTTTCAACGACTTCTACGCTGCTTTCACTTTCGACTTCTCTAGAGTTCCAAGATCTTCTTACGCTTCTTCTGTTGCTGGTTCTGTTATCCCATTGTGTATGACTATCACTGTTAACATGTCTTTGTACTTGCAAGCTTACACTGTTTGTAAGAACTTGGACGACATCAAGAGAATCATCTTGACTACTTTGTCTGCTATCGTTGCTTTGTTGGCTATCGGTTTCAGATTCGCTGCTACTGTTGTTAACTCTGTTGCTATCTTGGCTACTTCTGCTTCTTCTGTTCCAATGCAATGGTTGGTTAAGGGTACTTTGGTTACTGAAACTATCTCTATCTGGTTCTTCTCTTTGATCTTCACTGGTAAGTTGGTTTGGACTTTGTACAACAGAAGAAGAAACGGTTGGAGACAATGGTCTGCTGTTAGAATCTTGGCTGCTATGGGTGGTTGTACTATGGTTATCCCATCTATCTTCGCTATCTTGGAATACGTTACTCCAGTTTCTTTCCCAGAAGCTGGTTCTATCGCTTTGACTTCTGTTGCTTTGTTGTTGCCAATCTCTTCTTTGTGGGCTGGTATGGTTACTGACGAAGAAACTTCTGCTATCGACGTTTCTAACTTGACTGGTTCTAGAACTATGTTGGGTTCTCAATCTGGTAACTTCTCTAGAAAGACTCACGCTTCTGACATCACTGCTCAATCTTCTCACTTGGACTTCTCTTCTAGAAAGGGTTCTAACGCTACTATGATGAGAAAGGGTTCTAACGCTATGGACCAAGTTACTACTATCGACTGTGTTGTTGAAGACAACCAAGCTAACAGAGGTTTGAGAGACTCTACTGAAATGGACTTGGAAGCTATGGGTGTTAGAGTTAACAAGTCTTACGGTGTTCAAAAGGCTTAG (SEQ ID NO: 22) |

6.3. Example 3: Reduction to Practice of Directed Evolution 6.3.1. Directed Evolution of Reporter Strain A stable reporter strain to perform DE on plasmid-borne receptor variants based on previous methods for DE of GPCRs in yeast was established. This strain was analogous to the lycopene reporter with the lycopene biosynthetic genes replaced by the reporters: pFus1-mCherry (fluorescence), pFus1-His3 (growth advantage), pFus2-Ura3 (negative selection). The chromosomal copy of Ste2 was deleted.

6.3.2. Library Generation and Selection Scheme

The endogenous *S. cerevisiae* Ste2 pheromone receptor was mutated by error-prone PCR and selected for active mutants by fluorescence-activated cell sorting (FACS). The enriched libraries were screened in microtiter plates using a growth based assay using pFus1-His3 as previously reported.[30]

6.3.3. Peptide Ligand Design for Step-Wise DE

A stepwise selection framework that has been used to change substrate specificity of proteins and enzymes was used.[72] Peptide targets that allow generation of a wide range of intermediate hybrid ligands that march from the native peptide ligand (e.g. native yeast α-Factor) to the desired target ligand (e.g. peptides derived from Cholera Toxin) were used for directed evolution.

6.3.4. Successful Demonstration of De Strategy

This DE strategy was applied to CTx and two intermediate peptides (as shown in FIG. 7) were designed. An engineered receptor binding a hybrid peptide that is 71% identical to a peptide derived from the Cholera toxin (intermediate-2, "int-2") was successfully generated. Int-2 had the sequence WHWLELPGSQHIDS (SEQ ID NO: 23). The initial mutant receptor, 15C11, shows an EC50 of 31 uM to intermediate-2. Through further rounds of DE, a mutant receptor, 31E4, was generated with an enhanced EC50 of 11 uM for intermediate-2 (see FIG. 7).

TABLE 3

Peptides used in directed evolution and associated sequences

| Name of peptides used in DE | Amino acid sequence |
|---|---|
| α-Factor, wild type *S. cereviseae* | WHWLQLKPGQPMY (SEQ ID NO: 24) |
| intermediate-1 (int-1) | WHWLEVPGSQPMY (SEQ ID NO: 25) |
| intermediate-2 (int-2) | WHWLEVPGSQHIDS (SEQ ID NO: 26) |
| cholera toxin epitope long (CTxL) | VEVPGSQHIDSQKKA (SEQ ID NO: 27) |
| cholera toxin epitope short (CTxS) | VPGSQHIDS (SEQ ID NO: 28) |

TABLE 4

GPCRs and associated sequences

| Name of hit GPCRs | Amino acid sequence of GPCR | Corresponding DNA coding sequence |
|---|---|---|
| Ste2, wild type<br>*S. cereviseae* | MSDAAPSLSNL<br>FYDPTYNPGQS<br>TINYTSIYGNGS<br>TITFDELQGLV<br>NSTVTQAIMFG<br>VRCGAAALTLI<br>VMWMTSRSRK<br>TPIFIINQVSLFL<br>IILHSALYFKYL<br>LSNYSSVTYAL<br>TGFPQFISRGDV<br>HVYGATNIIQV<br>LLVASIETSLVF<br>QIKVIFTGDNFK<br>RIGLMLTSISFT<br>LGIATVTMYFV<br>SAVKGMIVTYN<br>DVSATQDKYF<br>NASTILLASSIN<br>FMSFVLVVKLI<br>LAIRSRRFLGLK<br>QFDSFHILLIMS<br>CQSLLVPSIIFIL<br>AYSLKPNQGTD<br>VLTTVATLLAV<br>LSLPLSSMWAT<br>AANNASKTNTI<br>TSDFTTSTDRF<br>YPGTLSSFQTD<br>SINNDAKSSLRS<br>RLYDLYPRRKE<br>TTSDKHSERTF<br>VSETADDIEKN<br>QFYQLPTPTSS<br>KNTRIGPFADA<br>SYKEGEVEPVD<br>MYTPDTAADE<br>EARKFWTEDN<br>NNL<br>(SEQ ID NO: 29) | ATGTCTGATGCGGCTCCTTCATTGAGCAATCTATTTTATG<br>ATCCAACGTATAATCCTGGTCAAAGCACCATTAACTACAC<br>TTCCATATATGGGAATGGATCTACCATCACTTTCGATGAG<br>TTGCAAGGTTTAGTTAACAGTACTGTTACTCAGGCCATTA<br>TGTTTGGTGTCAGATGTGGTGCAGCTGCTTTGACTTTGAT<br>TGTCATGTGGATGACATCGAGAAGCAGAAAAACGCCGAT<br>TTTCATTATCAACCAAGTTTCATTGTTTTTAATCATTTTGC<br>ATTCTGCACTCTATTTTAAATATTTACTGTCTAATTACTCT<br>TCAGTGACTTACGCTCTCACCGGATTTCCTCAGTTCATCA<br>GTAGAGGTGACGTTCATGTTTATGGTGCTACAAATATAAT<br>TCAAGTCCTTCTTGTGGCTTCTATTGAGACTTCACTGGTGT<br>TTCAGATAAAAGTTATTTTCACAGGCGACAACTTCAAAA<br>GGATAGGTTTGATGCTGACGTCGATATCTTTCACTTTAGG<br>GATTGCTACAGTTACCATGTATTTTGTAAGCGCTGTTAAA<br>GGTATGATTGTGACTTATAATGATGTTAGTGCCACCCAAG<br>ATAAATACTTCAATGCATCCACAATTTTACTTGCATCCTC<br>AATAAACTTTATGTCATTTGTCCTGGTAGTTAAATTGATT<br>TTAGCTATTAGATCAAGAAGATTCCTTGGTCTCAAGCAGT<br>TCGATAGTTTCCATATTTTACTCATAATGTCATGTCAATCT<br>TTGTTGGTTCCATCGATAATATTCATCCTCGCATACAGTTT<br>GAAACCAAACCAGGGAACAGATGTCTTGACTACTGTTGC<br>AACATTACTTGCTGTATTGTCTTTACCATTATCATCAATGT<br>GGGCCACGGCTGCTAATAATGCATCCAAAACAAACACAA<br>TTACTTCAGACTTTACAACATCCACAGATAGGTTTTATCC<br>AGGCACGCTGTCTAGCTTTCAAACTGATAGTATCAACAAC<br>GATGCTAAAAGCAGTCTCAGAAGTAGATTATATGACCTA<br>TATCCTAGAAGGAAGGAAACAACATCGGATAAACATTCG<br>GAAAGAACTTTTGTTTCTGAGACTGCAGATGATATAGAG<br>AAAAATCAGTTTTATCAGTTGCCCACACCTACGAGTTCAA<br>AAAATACTAGGATAGGACCGTTTGCTGATGCAAGTTACA<br>AAGAGGGAGAAGTTGAACCCGTCGACATGTACACTCCCG<br>ATACGGCAGCTGATGAGGAAGCCAGAAAGTTCTGGACTG<br>AAGATAATAATAATTTA (SEQ ID NO: 30) |
| MClone:<br>15C11 | same as Ste2<br>with mutation:<br>V276A | ATGTCTGATGCGGCTCCTTCATTGAGCAATCTATTTTATG<br>ATCCAACGTATAATCCTGGTCAAAGCACCATTAACTACAC<br>TTCCATATATGGGAATGGATCTACCATCACTTTCGATGAG<br>TTGCAAGGTTTAGTTAACAGTACTGTTACTCAGGCCATTA<br>TGTTTGGTGTCAGATGTGGTGCAGCTGCTTTGACTTTGAT<br>TGTCATGTGGATGACATCGAGAAGCAGAAAAACGCCGAT<br>TTTCATTATCAACCAAGTTTCATTGTTTTTAATCATTTTGC<br>ATTCTGCACTCTATTTTAAATATTTACTGTCTAATTACTCT<br>TCAGTGACTTACGCTCTCACCGGATTTCCTCAGTTCATCA |

TABLE 4-continued

GPCRs and associated sequences

| Name of hit GPCRs | Amino acid sequence of GPCR | Corresponding DNA coding sequence |
|---|---|---|
| | | GTAGAGGTGACGTTCATGTTTATGGTGCTACAAATATAAT TCAAGTCCTTCTTGTGGCTTCTATTGAGACTTCACTGGTGT TTCAGATAAAAGTTATTTTCACAGGCGACAACTTCAAAA GGATAGGTTTGATGCTGACGTCGATATCTTTCACTTTAGG GATTGCTACAGTTACCATGTATTTTGTAAGCGCTGTTAAA GGTATGATTGTGACTTATAATGATGTTAGTGCCACCCAAG ATAAATACTTCAATGCATCCACAATTTTACTTGCATCCTC AATAAACTTTATGTCATTTGTCCTGGTAGTTAAATTGATT TTAGCTATTAGATCAAGAAGATTCCTTGGTCTCAAGCAGT TCGATAGTTTCCATATTTTACTCATAATGTCATGTCAATCT TTGTTGGTTCCATCGATAATATTCATCCTCGCATACAGTTT GAAACCAAACCAGGGAACAGATGCCTTGACTACTGTTGC AACATTACTTGCTGTATTGTCTTTACCATTATCATCAATGT GGGCCACGGCTGCTAATAATGCATCCAAAACAAACACAA TTACTTCAGACTTTACAACATCCACAGATAGGTTTTATCC AGGCACGCTGTCTAGCTTTCAAACTGATAGTATCAACAAC GATGCTAAAAGCAGTCTCAGAAGTAGATTATATGACCTA TATCCTAGAAGGAAGGAAACAACATCGGATAAACATTCG GAAAGAACTTTTGTTTCTGAGACTGCAGATGATATAGAG AAAAATCAGTTTTATCAGTTGCCCACACCTACGAGTTCAA AAAATACTAGGATAGGACCGTTTGCTGATGCAAGTTACA AAGAGGGAGAAGTTGAACCCGTCGACATGTACACTCCCG ATACGGCAGCTGATGAGGAAGCCAGAAAGTTCTGGACTG AAGATAATAATAATTTA (SEQ ID NO: 31) |
| MClone: 31E4 | same as Ste2 with mutation: V276A and Y193C | ATGTCTGATGCGGCTCCTTCATTGAGCAATCTATTTTATG ATCCAACGTATAATCCTGGTCAAAGCACCATTAACTACAC TTCCATATATGGGAATGGATCTACCATCACTTTCGATGAG TTGCAAGGTTTAGTTAACAGTACTGTTACTCAGGCCATTA TGTTTGGTGTCAGATGTGGTGCAGCTGCTTTGACTTTGAT TGTCATGTGGATGACATCGAGAAGCAGAAAAACGCCGAT TTTCATTATCAACCAAGTTTCATTGTTTTTAATCATTTTGC ATTCTGCACTCTATTTTAAATATTTACTGTCTAATTACTCT TCAGTGACTTACGCTCTCACCGGATTTCCTCAGTTCATCA GTAGAGGTGACGTTCATGTTTATGGTGCTACAAATATAAT TCAAGTCCTTCTTGTGGCTTCTATTGAGACTTCACTGGTGT TTCAGATAAAAGTTATTTTCACAGGCGACAACTTCAAAA GGATAGGTTTGATGCTGACGTCGATATCTTTCACTTTAGG GATTGCTACAGTTACCATGTATTTTGTAAGCGCTGTTAAA GGTATGATTGTGACTTATAATGATGTTAGTGCCACCCAAG ATAAATACTTCAATGCATCCACAATTCTACTTGCATCCTC AATAAACTTTATGTCATTTGTCCTGGTAGTTAAATTGATT TTAGCTATTAGATCAAGAAGATTCCTTGGTCTCAAGCAGT TCGATAGTTTCCATATTTTACTCATAATGTCATGTCAATCT TTGTTGGTTCCATCGATAATATTCATCCTCGCATACAGTTT GAAACCAAACCAGGGAACAGATGCCTTGACTACTGTTGC AACATTACTTGCTGTATTGTCTTTACCATTATCATCAATGT GGGCCACGGCTGCTAATAATGCATCCAAAACAAACACAA TTACTTCAGACTTTACAACATCCACAGATAGGTTTTATCC AGGCACGCTGTCTAGCTTTCAAACTGATAGTATCAACAAC GATGCTAAAAGCAGTCTCAGAAGTAGATTATATGACCTA TATCCTAGAAGGAAGGAAACAACATCGGATAAACATTCG GAAAGAACTTTTGTTTCTGAGACTGCAGATGATATAGAG AAAAATCAGTTTTATCAGTTGCCCACACCTACGAGTTCAA AAAATACTAGGATAGGACCGTTTGCTGATGCAAGTTACA AAGAGGGAGAAGTTGAACCCGTCGACATGTACACTCCCG ATACGGCAGCTGATGAGGAAGCCAGAAAGTTCTGGACTG AAGATAATAATAATTTA (SEQ ID NO: 32) |

6.3.5. Demonstration of Proteases to Release Target Ligands

A simple proteolytic degradation of commercially purified CTx was performed. CTx was specifically degraded with either Trypsin or a combination of LysN and GluC. The expected target peptide was successfully detected by mass spectrometry showing it to be released from the full protein. The experiment resulted in a list of released peptides of different length and physicochemical properties which can be used as additional target analytes. Analogous degradation of CTx in the gut or the environment may make target peptides available in field samples. Additionally and alternatively, these extremely robust and cheap proteases may be incorporated into a product formulation.

6.4. Example 4—Yeast Cholera Biosensor

The strain is engineered to respond to a cholera specific peptide by generating a color output.

To develop a cholera peptide binding receptor, the GPCR is subjected to mutagenesis and the resulting library is expressed in the same yeast host. All variants are screened against the peptide, which is synthetically synthesized or originates from bacterial cultures, and strains that show reporter gene expression are further investigated and optimized. Enhanced binding may be achieved by more stringent screening conditions such as lower concentration of target molecule or less copies of the receptor expressed on the cell surface. In certain embodiments, color change is rapid—for example 10 grams, 1 gram, 100 mg, 10 mg, or even 1 mg of freeze dried yeast may result in sufficient red color to be readily apparent to the naked eye, and the assay is desirably sensitive enough to detect low levels of peptide. Non-engineered yeast may be used as controls to test biosensor specificity and false-positive rate. Native alpha factor/Ste2 receptor activation can also be used as a control.

6.5. Example 5—Expressing GPCRs in Yeast

GPCRs were cloned into yeast using the Reiterative Recombination DNA assembly system. The desensitization of the receptor, where prolonged stimulation leads to an attenuated response, was eliminated by deletion of SST2, allowing cells to respond to doses of pheromone that are roughly two orders of magnitude lower than those detected by normal cells and prevent recovery from pheromone-induced growth arrest, even if the ligand was removed.[20] Deletion of Far1 also prevented pheromone-induced cell cycle arrest. The endogenous pheromone receptor Ste2 was deleted to avoid cross talk with yeast mating signal.

6.6. Example 6—Freeze-Drying Yeast

Viability of *S. cerevisiae* was determined after different freeze-drying treatments.[73] The results are shown in FIG. 5. Cell viability of ~1-2% was observed, in agreement with previously published literature.

6.7. Example 7: Detection of Pathogenic Fungi Pheromones Using an Integrated Lycopene Biosensor The engineering of *S. cerevisiae* as a specific and sensitive biosensor for the presence of pathogenic fungi that may be easily used outside the laboratory. The sensor may be used by non-experts, and thus consists of non-technical mixing and color change output that is visible to the naked eye.

Baker's yeast, a safe organism broadly used in the food industry for centuries and easily grown in a robust manner was reprogrammed to express the tomato red pigment lycopene in response to binding of natural pathogen-specific peptides by expressing natural fungal binding receptors. This user-friendly and equipment-free signal is compatible with household use at local communities at-risk for fungi infections.

Fungal pathogens have recently been identified as increasing cause of human disease as well as a cause of population decline in animals and crops. The annual number of cases of sepsis caused by fungal organisms in the U.S. increased by 207% between 1979 and 2000 [Pfaller, Diekema, (2007)]. Several factors contribute to the increase in fungal infections, among which are the increasing number of immunocompromised HIV, cancer and transplantation patients, aging population, and increased global mobility which expands the habitats of endemic opportunistic fungal strains [Pfaller, Diekema, (2007)].

*Candida* fungal species are the major cause of opportunistic mycoses worldwide with 72.8 million annual *candida* species infections cases worldwide and a 33.9% case/fatality ratio [Pfaller, Diekema, (2007)]. *Candida* infections are associated with a high crude mortality of 46% to 75% and a long hospital stay which causes tremendous health care burden. Two fungal species, *C. albicans* and C. *Glabrata*, were shown to be the causative agents of 62% and 12% of *Candidasis*, respectively. [Ramirez-Zavaleta (2010)]. *Candida albicans* is a fungi naturally found in human gastrointestinal, genitourinary tracts and skin, but under compromised immunity it could result in kidney, heart or brain infection [Berman, Sudbery (2002)].

It is difficult to diagnose and distinguish fungal infections. While several anti-fungal therapeutics are available, mortality rates of invasive fungal diseases remain extremely high, often exceeding 50%. This is due to a major clinical bottleneck in early treatment, rooted in significant lack of rapid diagnosis [Brown et al. (2012)]. For example, although several methods are currently available for detection of pathogenic fungi in the laboratory, the current gold standard for confirming *candida* infection in patients remains slow methods such as cultures or cost prohibitive methods such as coagulation assays which are often unavailable in high risk areas for fungal infections. In this Example, a non-technical biosensor that could be used outside of the laboratory for detection of pathogenic fungi was developed.

In order to detect fungal pathogens, fungal receptors that are naturally binding the fungal peptide mating pheromone were generated. *Candida albicans* cells are diploid (a/alpha) and both homothallic and heterothallic mating have been observed in clinical samples, making mating peptide a relevant biomarker for fungal detection. *C. albicans* must switch its phenotype from white to opaque before secretion of pheromones can occur to induce mating, a transition triggered by different environmental signals. The opaque "mating" phenotype was found to be stabilized by the presence of CO2 and GlcNAc and observed during passage through mouse intestines, suggesting persistence of mating-compatible, pheromone producing *C. albicans* cells in the host [Ramirez-Zavala (2008); Huang (2010)]. Mating was also observed in systemic infections and colonization of the skin and intestines. [Hull et al. (2000), Lachke et al (2003), Dumitru (2007)]. *C. glabrata* population is mostly clonal, and while distinct mating types have been identified, pheromone genes are not expressed in most isolates and neither mating types responds to pheromone.

6.7.1. Fungal GPCRs as the Detection Element

Natural fungal GPCRs were cloned and tested for functionality with their respective natural ligands in *S. cerevisiae* biosensor strain. The results for GPCR activation experiments in biosensor strain are presented in FIGS. 9 and 10. Sequence analysis of receptor and peptides are presented in FIGS. 11 and 12 and further discussed in Example 6.8 below.

As shown in FIG. 9, fungal receptors were found to be highly specific for their respective peptide pheromones, with very little crosstalk between receptors. This is due to the critical role of pheromone recognition in fungal mating and conservation of species integrity. For example, species cohabitating a common host, *C. Glabrata* and *C. albicans* did not respond to the other species pheromone. However, *S. cerevisiae* native Ste2 receptor responded to *C. glabrata*, but not to *C. albicans* pheromone, reflecting the difference in phylogenetic distance between the three strains. Interestingly, the *P. brasiliensis* receptor seemed more promiscuous, showing moderate activity when induced with *A. fumigatus* or pheromone.

Most receptor-pheromone pairs were found to be highly sensitive to their ligand peptide, with EC50 values of 4 nM, 51 nM and 34 nM for *C. albicans, L. elongisporous*, and *P. brasiliensis*, respectively, notably higher than the natural activation of the *S. cerevisiae* GPCR-pheromone pair (EC50=190 nM). *C. glabrata* was less active EC50=3.6 μM) in biosensor settings (see FIG. 9).

6.7.2. Lycopene as a Simple, Low-Cost Readout

Having established fungal GPCRs as the detection element, the inventors then implemented and optimized a lycopene biosynthetic pathway as a direct, low-cost readout for the biosensor (see FIG. 13). By overexpressing key pathway genes (CrtI, tHMG1, Fad1), there was significant improvement in the maximal yield of lycopene produced after induction with α-factor. These changes also greatly reduced the time required to reach half maximal biosynthesis of lycopene after induction by α-factor (see FIG. 13C).

6.7.3. An Integrated Biosensor

A product profile that satisfies the unique requirements of a live yeast cell sensor as diagnostic device was developed. Specifically, a core product component, the “Yeast Reporter Tab”, maintaining viable, functional yeast cells while enhancing color contrast and ease of use (see FIG. 14) was developed. Importantly, this kit design incorporates a nutrient gel, a white paper to enhance signal contrast, a concentrated yeast spot to enhance apparent color intensity of the produced lycopene and a control yeast spot to eliminate false positives. The design was viable and functioned.

The integrated biosensor properly responded to a synthetic peptide derived from the human pathogen *C. albicans*. Importantly, the biosensor retained a high level of sensitivity and speed while producing a signal visible to the naked eye (see FIG. 14B).

Furthermore, FIG. 14C shows observed dose-response of the biosensor strain (using fluorescent readout) when exposed to culture supernatants from the homozygous *C. albicans* strains P37005, GC75 or a mixture of the two pathogen strain.

6.8. Example 8: Peptide-Activated Receptors and Peptide Ligands

EXAMPLE 8 is an updated study of EXAMPLE 2. Whole-cell diagnostic device enables the use of integral membrane receptors to mediate highly specific and sensitive detection of biologically relevant ligands. Notably, membrane proteins such as GPCRs have not been amenable for in vitro diagnostics as they are notoriously difficult to express outside of their natural membrane environment. A whole-cell provides access to the untapped repertoire of molecular recognition of GPCRs in much the same way ELISAs allowed access to antibody recognition [Lequin (2005)]. The inventors focused on implementing the highly specific fungal peptide-activated GPCRs, such as Ste2 from *S. cerevisiea*, for detection of fungal peptides.

Fungal GPCRs have several key advantages for biosensor engineering. First, GPCRs homologous to the *S. cerevisiae* Ste2 robustly coupled to the host pheromone pathway. (see FIGS. 9 and 10). Second, these fungal GPCRs recognized a diverse set of peptide ligands (see FIG. 12, Table 5). Third, fungal GPCRs showed very highly specificity for their respective peptides (see FIG. 9). Furthermore, these fungal GPCRs offered a highly viable platform for directed evolution towards binding of novel peptide ligands through mutagenesis of either receptor or peptide.

TABLE 5

Physicochemical properties of functionally verified peptide ligands, ordered by peptide length

| Sequence | Length | MW | IP | Charge (-/+) | GRAVY[a] |
|---|---|---|---|---|---|
| WCGRPGQPC (SEQ ID NO: 20) | 9 | 1 | 8.07 | 0/1 | -0.878 |
| WCTRPGQGC (SEQ ID NO: 11) | 9 | 1.007 | 8.07 | 0/1 | -0.778 |
| WCGHIGQGC (SEQ ID NO: 33) | 9 | 0.960 | 6.72 | 0/0 | 0.078 |
| WCWWKGQPCW (SEQ ID NO: 14) | 10 | 1.379 | 8.06 | 0/1 | -0.800 |
| QWCPRRGQPCW (SEQ ID NO: 17) | 11 | 1.416 | 9.02 | 0/2 | -1.491 |
| WMWTRYGRFSPV (SEQ ID NO: 34) | 12 | 1.585 | 10.84 | 0/2 | -0.558 |
| HLVRLSPGAAMF (SEQ ID NO: 35) | 12 | 1.298 | 9.76 | 0/1 | 0.800 |
| HFIELDPGQPMF (SEQ ID NO: 36) | 12 | 1.430 | 4.35 | 2/0 | -0.125 |
| WHWTSYGVFEPG (SEQ ID NO: 37) | 12 | 1.465 | 5.24 | 1/0 | -0.558 |
| WHWLQLKPGQPMY (SEQ ID NO: 38) | 13 | 1.670 | 8.6 | 0/1 | -0.869 |
| GFRLTNFGYFEPG (SEQ ID NO: 5) | 13 | 1.500 | 6 | 1/2 | -0.315 |
| WHWVRLRKGQGLF (SEQ ID NO: 8) | 13 | 1.682 | 12.1 | 0/3 | -0.585 |
| WSWITLRPGQPIF (SEQ ID NO: 39) | 13 | 1.600 | 9.75 | 0/1 | 0.054 |
| WHWLELDNGQPIY (SEQ ID NO: 40) | 13 | 1.670 | 4.35 | 2/0 | 0.785 |
| WHWLRLRYGEPIY (SEQ ID NO: 41) | 13 | 1.789 | 8.6 | 1/2 | -0.769 |
| KPHWTTYGYYEPQ (SEQ ID NO: 42) | 13 | 1.669 | 6.75 | 1/1 | -1.838 |
| NWHWLRLDPGQPLY (SEQ ID NO: 43) | 14 | 1.795 | 6.74 | 1/1 | -0.964 |
| KFKFRLTRYGWFSPN (SEQ ID NO: 44) | 15 | 1.947 | 11.1 | 0/4 | -0.92 |
| KKNSRFLTYWFFQPI M (SEQ ID NO: 45) | 16 | 2.106 | 10.29 | 0/3 | -0.375 |
| GDWGWFWYVPRPGDP AM (SEQ ID NO: 46) | 17 | 2.037 | 4.21 | 2/1 | -0.635 |
| TYADFLRAYQSWNTF VNPDRPNL (SEQ ID NO: 47) | 23 | 2.789 | 5.63 | 2/2 | -0.778 |
| VSDRVKQMLSHWWNF RNPDTANL (SEQ ID NO: 48) | 23 | 2.815 | 8.72 | 2/3 | -0.883 |

TABLE 5-continued

| Physicochemical properties of functionally verified peptide ligands, ordered by peptide length | | | | | |
|---|---|---|---|---|---|
| Sequence | Length | MW | IP | Charge (-/+) | GRAVY[a] |
| TYEDFLRVYKNWWSF QNPDRPDL (SEQ ID NO: 49) | 23 | 2.990 | 4.68 | 4/3 | -1.265 |

[a]The GRAVY value is the average hydropathy of the given sequence. Positive values indicate overall hydrophilicity of the sequence and negative values relative hydrophobicity. Index range is -4.5 to 4.5

6.8.1. Key Characteristics of Fungal GPCRs

Candidate receptors for biosenosor engineering were identified by searching protein and genomic databases (NCBI, UniProt) for proteins and/or genes with homology to *S. cerevisiae* Ste2 receptor. Functionally characterized receptors (described below) had an average amino acid sequence homology of 33% to *S. cerevisiae* Ste2, ranging from 66% to 15% as calculated with Clustal Omega [Sievers (2014)].

Additionally, all receptors were predicted to have seven transmembrane helices, an extracellular N-terminus, an intracellular C-terminus, three extracellular loops and three intracellular loops when analyzed by TMHMM v2.0 [Krogh et al. (2001)]. Notably, while large portions of the extracellular loops and transmembrane helices had low conservation across receptors, three key regions with increased homology (see FIG. 11) were observed. Based on previous mutational studies of the *S. cerevisiae* Ste2 receptor, these three regions have been shown to be important in mediating signal transduction and interactions with the downstream G-protein. [Ćelić et al. (2003); Martin et al. (2002)]. Thus, cell surface receptors with homology to these key regions have a high likelihood of functioning in a *S. cerevisiae* biosensor.

6.8.2. List of Functionally Characterized Receptors

Twenty three receptor-peptide pairs were cloned and functionally characterized in sensor strain, as shown in FIGS. 9 and 10 (see Table 6 for sequences).

Human pathogen: *C. albicans, C. glabrata, P. brasiliensis, L. elongisporous, P. rubens, C. guillermondi, C. tropicalis, C. parapsilosis,*

Plant pathogen: *F. graminearum, M. oryzea, B. cinerea, G. candidum.*

Food Safety/Spoilage: *Z. bailii. Z. rouxii*

Industrial/Model fungi: *S. cerevisiae, K lactis, S. pombe, V. polyspora* (receptor 1), *V. polyspora* (receptor 2), *S. stipitis, S. japonicas, S. castellii, S. octosporus.*

6.8.3. List of Additional Cloned Receptors (See Table 6 for Sequences)

*A. nidulans, A. oryzae, B. bassiana, C. lusitaniae, C. tenuis, N. fischeri, N. crassa, P. destructans, H. jecorina, T. melanosporum, D. haptotyla, S. scheckii, Y. lipolytica, T. delbrueckii, K. pastoris*

TABLE 6

| Sequences of Fungal GPCRs and Peptide Ligands | | | |
|---|---|---|---|
| Fungi | sequence of peptide analyte used | sequence of GPCRs used (all sequences are wild type) | DNA coding sequence of corresponding GPCRs that senses peptide analyte (WT or codon-optimized noted) |
| *Saccharomyces cerevisiae* | WHWLQL<br>KPGQPM<br>Y<br>(SEQ ID<br>NO: 38) | MSDAAPSLSNLFY<br>DPTYNPGQSTINY<br>TSIYGNGSTITFDE<br>LQGLVNSTVTQAI<br>MFGVRCGAAALT<br>LIVMWMTSRSRKT<br>PIFIINQVSLFLIILH<br>SALYFKYLLSNYS<br>SVTYALTGFPQFIS<br>RGDVHVYGATNII<br>QVLLVASIETSLVF<br>QIKVIFTGDNFKRI<br>GLMLTSISFTLGIA<br>TVTMYFVSAVKG<br>MIVTYNDVSATQD<br>KYFNASTILLASSI<br>NFMSFVLVVKLIL<br>AIRSRRFLGLKQFD<br>SFHILLIMSCQSLL<br>VPSIIFILAYSLKPN<br>QGTDVLTTVATLL<br>AVLSLPLSSMWAT<br>AANNASKTNTITS<br>DFTTSTDRFYPGTL<br>SSFQTDSINNDAKS<br>SLRSRLYDLYPRR<br>KETTSDKHSERTF<br>VSETADDIEKNQF<br>YQLPTPTSSKNTRI<br>GPFADASYKEGEV<br>EPVDMYTPDTAA<br>DEEARKFWTEDN<br>NNL (SEQ ID<br>NO: 50) | (wild type)<br>ATGTCTGATGCGGCTCCTTCATTGAGC<br>AATCTATTTTATGATCCAACGTATAAT<br>CCTGGTCAAAGCACCATTAACTACAC<br>TTCCATATATGGGAATGGATCTACCAT<br>CACTTTCGATGAGTTGCAAGGTTTAGT<br>TAACAGTACTGTTACTCAGGCCATTAT<br>GTTTGGTGTCAGATGTGGTGCAGCTGC<br>TTTGACTTTGATTGTCATGTGGATGAC<br>ATCGAGAAGCAGAAAAACGCCGATTT<br>TCATTATCAACCAAGTTTCATTGTTTT<br>TAATCATTTTGCATTCTGCACTCTATT<br>TTAAATATTTACTGTCTAATTACTCTT<br>CAGTGACTTACGCTCTCACCGGATTTC<br>CTCAGTTCATCAGTAGAGGTGACGTTC<br>ATGTTTATGGTGCTACAAATATAATTC<br>AAGTCCTTCTTGTGGCTTCTATTGAGA<br>CTTCACTGGTGTTTCAGATAAAAGTTA<br>TTTTCACAGGCGACAACTTCAAAAGG<br>ATAGGTTTGATGCTGACGTCGATATCT<br>TTCACTTTAGGGATTGCTACAGTTACC<br>ATGTATTTTGTAAGCGCTGTTAAAGGT<br>ATGATTGTGACTTATAATGATGTTAGT<br>GCCACCCAAGATAAATACTTCAATGC<br>ATCCACAATTTTACTTGCATCCTCAAT<br>AAACTTTATGTCATTTGTCCTGGTAGT<br>TAAATTGATTTTAGCTATTAGATCAAG<br>AAGATTCCTTGGTCTCAAGCAGTTCGA<br>TAGTTTCCATATTTTACTCATAATGTC<br>ATGTCAATCTTTGTTGGTTCCATCGAT<br>AATATTCATCCTCGCATACAGTTTGAA<br>ACCAAACCAGGGAACAGATGTCTTGA<br>CTACTGTTGCAACATTACTTGCTGTAT<br>TGTCTTTACCATTATCATCAATGTGGG |

TABLE 6-continued

Sequences of Fungal GPCRs and Peptide Ligands

| Fungi | sequence of peptide analyte used | sequence of GPCRs used (all sequences are wild type) | DNA coding sequence of corresponding GPCRs that senses peptide analyte (WT or codon-optimized noted) |
|---|---|---|---|
| | | | CCACGGCTGCTAATAATGCATCCAAA<br>ACAAACACAATTACTTCAGACTTTAC<br>AACATCCACAGATAGGTTTTATCCAG<br>GCACGCTGTCTAGCTTTCAAACTGATA<br>GTATCAACAACGATGCTAAAAGCAGT<br>CTCAGAAGTAGATTATATGACCTATAT<br>CCTAGAAGGAAGGAAACAACATCGGA<br>TAAACATTCGGAAAGAACTTTTGTTTC<br>TGAGACTGCAGATGATATAGAGAAAA<br>ATCAGTTTTATCAGTTGCCCACACCTA<br>CGAGTTCAAAAAATACTAGGATAGGA<br>CCGTTTGCTGATGCAAGTTACAAAGA<br>GGGAGAAGTTGAACCCGTCGACATGT<br>ACACTCCCGATACGGCAGCTGATGAG<br>GAAGCCAGAAAGTTCTGGACTGAAGA<br>TAATAATAATTTATAG (SEQ ID<br>NO: 51) |
| *Candida albicans* | GFRLTNF<br>GYFEPG<br>(SEQ ID<br>NO: 5) | MNINSTFIPDKPGD<br>IIISYSIPGLDQPIQI<br>PFHSLDSFQTDQA<br>KIALVMGITIGSCS<br>MTLIFLISIMYKTN<br>KLTNLKLKLKLKY<br>ILQWINQKIFTKKR<br>NDNKQQQQQQQQ<br>QIESSSYNNTTTTL<br>GGYKLFLFYLNSLI<br>LLIGIIRSGCYLNY<br>NLGPLNSLSFVFTG<br>WYDGSSFISSDVT<br>NGFKCILYALVEIS<br>LGFQVYVMFKTSN<br>LKIWGIMASLLSIG<br>LGLIVVAFQINLTI<br>LSHIRFSRAISTNRS<br>EEESSSSLSSDSVG<br>YVINSIWMDLPTIL<br>FSISINIMTILLIGKL<br>IIAIRTRRYLGLKQ<br>FDSFHILLIGFSQTL<br>IIPSIILVVHYFYLS<br>QNKDSLLQQISLLL<br>IILMLPLSSLWAQT<br>ANNTHNINSSPSLS<br>FISRHHLSDSSRSG<br>GSNTIVSNGGSNG<br>GGGGGGNFPVSGI<br>DAQLPPDIEKILHE<br>DNNYKLLNSNNES<br>VNDGDIIINDEGMI<br>TKQITIKRV | (wild type)<br>ATGAATATCAATTCAACTTTCATACCT<br>GATAAACCAGGCGATATAATTATTAG<br>TTATTCAATTCCAGGATTAGATCAACC<br>AATTCAAATTCCTTTCCATTCATTAGA<br>TTCATTTCAAACCGATCAAGCTAAAAT<br>AGCTTTAGTCATGGGGATAACTATTG<br>GGAGTTGTTCAATGACATTAATTTTTT<br>TGATTTCTATAATGTATAAAACTAATA<br>AATTAACAAATTTAAAATTAAAATTA<br>AAATTAAAATATATCTTGCAATGGAT<br>AAATCAAAAAATCTTCACCAAAAAAA<br>GGAATGACAACAAACAACAACAACA<br>ACAACAACAACAACAAATTGAATCAT<br>CATCATATAACAATACTACTACTACGC<br>TGGGGGGTTATAAATTATTTTTATTTT<br>ATCTTAATTCATTGATTTTATTAATTG<br>GTATTATTCGATCAGGTTGTTATTTAA<br>ATTATAATTTAGGTCCATTAAATTCAC<br>TTAGTTTTGTATTTACTGGTTGGTATG<br>ATGGATCATCATTTATATCATCCGATG<br>TAACTAATGGATTTAAATGTATTTTAT<br>ATGCTTTAGTGGAAATTTCATTAGGTT<br>TCCAAGTTTATGTGATGTTCAAAACTT<br>CAAATTTAAAAATTTGGGGGATAATG<br>GCATCATTATTATCAATTGGTTTAGGA<br>TTGATTGTTGTTGCCTTTCAAATCAAT<br>TTAACAATTTTATCTCATATTCGATTT<br>TCCCGGGCTATATCAACTAACAGAAG<br>TGAAGAAGAATCATCATCATCATTAT<br>CATCTGATTCGGTTGGGTATGTGATTA<br>ATTCAATATGGATGGATTTACCAACA<br>ATATTATTTTCCATTAGTATTAATATA<br>ATGACAATATTATTGATTGGTAAACTT<br>ATAATTGCTATTAGAACAAGACGTTA<br>TTTAGGATTGAAACAATTTGATAGTTT<br>CCATATTTTATTAATTGGTTTCAGTCA<br>AACATTAATTATTCCTTCAATTATTTT<br>GGTGGTTCATTATTTTTATTTATCACA<br>AAATAAAGATTCTTTATTACAACAAA<br>TTAGTCTTTTATTGATTATTTTAATGTT<br>ACCATTAAGTTCTTTATGGGCTCAAAC<br>TGCTAATAATACTCATAATATTAATTC<br>ATCTCCAAGTTTATCATTCATATCTCG<br>TCATCATCTGTCTGATAGTAGTCGTAG<br>TGGTGGTTCCAATACAATTGTTAGTAA<br>TGGTGGTAGTAATGGTGGTGGTGGTG<br>GTGGTGGGAATTTCCCTGTTTCAGGTA<br>TTGATGCACAATTACCACCTGATATTG<br>AAAAAATCTTACATGAAGATAATAAT<br>TATAAATTACTTAATAGTAATAATGA<br>AAGTGTAAATGATGGAGATATTATCA<br>TTAATGATGAAGGTATGATTACTAAA<br>CAAATCACCATCAAAAGAGTGTAG |

TABLE 6-continued

Sequences of Fungal GPCRs and Peptide Ligands

| Fungi | sequence of peptide analyte used | sequence of GPCRs used (all sequences are wild type) | DNA coding sequence of corresponding GPCRs that senses peptide analyte (WT or codon-optimized noted) |
|---|---|---|---|
| *Candida* | WHWVRL | MEMGYDPRMYNP | (wild type) |
| *glabrata* | RKGQGLF | RNEYLNFTSVYDV | ATGGAGATGGGCTACGATCCAAGAAT |
| | | NDTIRFSTLDAIVK | GTATAATCCAAGAAATGAATACTTGA |
| | | GLLRIAIVHGVRL | ATTTCACGTCGGTATATGATGTAAATG |
| | | GAIFMTLIIMFISSN | ACACAATCAGATTTTCGACTCTGGAC |
| | | TWKKPIFIINMVSL | GCCATTGTAAAAGGATTGCTTAGAAT |
| | | MLVMIHSALSFHY | TGCCATTGTTCATGGAGTTAGATTGGG |
| | | LLSNYSSISYILTGF | AGCAATATTCATGACGTTAATAATAA |
| | | PQLITSNNKRIQDA | TGTTTATCTCATCAAATACATGGAAAA |
| | | ASIVQVLLVAAIEA | AACCCATATTTATAATTAACATGGTGT |
| | | SLVFQIHVMFTIEN | CGTTGATGTTAGTTATGATTCATTCCG |
| | | IKLIREIVLSISIAM | CACTTAGCTTCCATTACCTTTTATCGA |
| | | GLATVATYLAAAI | ATTATTCTTCAATTTCTTATATACTGA |
| | | KLIRGLHDEVMPQ | CAGGGTTTCCTCAGTTGATTACAAGCA |
| | | THLIFNLSIILLASSI | ATAATAAACGAATTCAAGATGCAGCG |
| | | NFMTFILVIKLFFAI | AGTATAGTCCAAGTTTTATTGGTTGCT |
| | | RSRRYLGLRQFDA | GCGATAGAAGCATCATTGGTATTTCA |
| | | FHILLIMFCQSLLIP | GATTCATGTTATGTTTACGATTGAAAA |
| | | SVLYIIVYAVDSRS | CATTAAGCTTATTAGAGAAATAGTAC |
| | | NQDYLIPIANLFVV | TCTCTATATCGATAGCAATGGGATTGG |
| | | LSLPLSSIWANTSN | CAACAGTGGCTACATATCTTGCTGCA |
| | | NSSRSPKYWKNSQ | GCAATAAAGCTGATAAGAGGACTGCA |
| | | TNKSNGSFVSSISV | TGATGAGGTAATGCCACAAACACATC |
| | | NSDSQNPLYKKIV | TTATTTTCAATTTATCTATAATATTGCT |
| | | RFTSKGDTTRSIVS | TGCATCCTCCATAAATTTTATGACATT |
| | | DSTLAEVGKYSM | TATATTGGTCATTAAACTTTTCTTCGC |
| | | QDVSNSNFECRDL | TATTAGATCTAGAAGATATCTCGGTCT |
| | | DFEKVKHTCENFG | TCGTCAATTCGATGCTTTTCATATTTT |
| | | RISETYSELSTLDT | ATTAATCATGTTCTGCCAGTCATTATT |
| | | TALNETRLFWKQQ | GATACCCTCAGTATTATATATTATAGT |
| | | SQCDK | TTACGCGGTTGATAGCAGATCTAATC |
| | | | AGGATTATCTGATTCCAATTGCCAATT |
| | | | TATTTGTTGTTTTATCTTTGCCATTATC |
| | | | CTCTATCTGGGCTAACACATCAAATA |
| | | | ACTCATCCAGATCTCCAAAATATTGG |
| | | | AAAAACTCTCAAACGAATAAGAGCAA |
| | | | TGGGTCTTTTGTCTCTTCAATATCTGT |
| | | | CAATAGTGACTCACAAAACCCTTTGT |
| | | | ACAAAAAGATTGTACGTTTTACATCA |
| | | | AAAGGCGACACTACCCGTAGTATTGT |
| | | | AAGTGATTCAACATTAGCAGAGGTGG |
| | | | GAAAATACTCTATGCAAGACGTTAGC |
| | | | AATTCAAACTTTGAATGTCGAGACCTT |
| | | | GATTTTGAGAAGGTAAAACATACTTG |
| | | | CGAAAATTTTGGCAGAATATCTGAAA |
| | | | CATATAGTGAGTTAAGTACTTTAGATA |
| | | | CCACTGCCCTCAATGAGACTCGGTTGT |
| | | | TTTGGAAACAACAAAGTCAGTGTGAC |
| | | | AAATAG |
| *Paracoccidioides* | WCTRPG | MAPSFDPFNQSVV | (wild type) |
| *brasiliensis* | QGC | FHKADGTPFNVSI | ATGGCACCCTCATTCGACCCCTTCAAC |
| | | HELDDFVQYNTK | CAAAGCGTGGTCTTCCACAAGGCCGA |
| | | VCINYSSQLGASVI | CGGAACTCCATTCAACGTCTCAATCCA |
| | | AGLMLAMLTHSE | TGAACTAGACGACTTCGTGCAGTACA |
| | | KRRLPVFFLNTFA | ACACCAAAGTCTGCATCAACTACTCTT |
| | | LAMNFARLLCMTI | CCCAGCTCGGAGCATCTGTCATTGCA |
| | | YFTTGFNKSYAYF | GGACTCATGCTTGCCATGCTGACACA |
| | | GQDYSQVPGSAY | CTCAGAAAAGCGTCGTCTGCCAGTTTT |
| | | AASVLGVVFTTLL | CTTCCTAAACACATTCGCACTGGCCAT |
| | | VISMEMSLLIQTRV | GAACTTTGCCCGCCTGCTCTGCATGAC |
| | | VCTTLPDIQRYLL | CATCTACTTCACCACGGGCTTCAACAA |
| | | MAVSSAISLMAIG | GTCCTATGCCTACTTTGGTCAGGATTA |
| | | FRLGLMVENCIAI | CTCCCAGGTGCCTGGGAGCGCCTACG |
| | | VQASNFAPFIWLQ | CAGCCTCTGTCTTGGGCGTTGTCTTCA |
| | | SASNITITISTCFFS | CCACTCTCCTGGTAATCAGCATGGAA |
| | | AVFVTKLAYALVT | ATGTCCCTCCTGATCCAAACAAGGGTT |
| | | RIRLGLTRFGAMQ | GTCTGCACGACCCTTCCGGATATCCAA |
| | | VMFIMSCQTMVIP | CGTTATCTACTCATGGCAGTTTCCTCC |
| | | AIFSILQYPLPKYE | GCGATTTCCCTGATGGCCATCGGGTTC |
| | | MNSNLFTLVAIFLP | CGCCTTGGCTTAATGGTTGAGAACTGC |

TABLE 6-continued

Sequences of Fungal GPCRs and Peptide Ligands

| Fungi | sequence of peptide analyte used | sequence of GPCRs used (all sequences are wild type) | DNA coding sequence of corresponding GPCRs that senses peptide analyte (WT or codon-optimized noted) |
|---|---|---|---|
| | | LSSLWASVATRSS<br>FETSSSGRHQYLW<br>PSEQSNNVTNSEIK<br>YQVSFSQNHTTLR<br>SGGSVATTLSPDR<br>LDPVYCEVEAGTK<br>A | ATTGCCATTGTGCAGGCGTCGAATTTC<br>GCCCCTTTTATCTGGCTTCAAAGCGCC<br>TCGAACATCACCATTACGATCAGCAC<br>ATGTTTCTTCAGTGCCGTCTTTGTTAC<br>GAAATTGGCATATGCACTCGTCACTC<br>GTATACGACTAGGCTTGACGAGGTTT<br>GGTGCTATGCAGGTTATGTTCATCATG<br>TCCTGCCAGACTATGGTGATTCCAGCC<br>ATCTTCTCAATTCTCCAATACCCACTC<br>CCCAAGTACGAAATGAACTCCAACCT<br>CTTTACGCTGGTGGCCATTTTCCTCCC<br>TCTTTCCTCGCTATGGGCTTCAGTTGC<br>TACGAGATCCAGTTTCGAGACGTCTTC<br>TTCCGGCCGCCATCAGTATCTTTGGCC<br>AAGCGAACAGAGCAATAACGTCACCA<br>ATTCGGAAATTAAGTATCAGGTCAGC<br>TTCTCTCAGAACCACACTACGTTGCGG<br>TCTGGAGGGTCTGTGGCCACGACACT<br>CTCCCCGGACCGGCTCGACCCGGTTTA<br>TTGTGAAGTTGAAGCTGGCACAAAGG<br>CCTAG |
| *Fusarium graminearum* | WCWWK<br>GQPCW | MSKEVFDPFTQNV<br>TFFAPDGKTEISIP<br>VAAIDQVRRMMV<br>NTTINYATQLGAC<br>LIMLVVLLVMVPK<br>EKFRRPFMILQITS<br>LVISCCRMLLLSIF<br>HSSQFLDFYVFWG<br>DDHSRIPRSAYAPS<br>VAGNTMSLCLVIS<br>VETMLMSQAWTM<br>VRLWPNVWKYIIA<br>GVSLIVSIMAISVR<br>LAYTIIQNNAVLK<br>LEPAFHMFWLIKW<br>TVIMNVASISWWC<br>AIFNIKLVWHLISN<br>RGILPSYKTFTPME<br>VLIMTNGILMIIPVI<br>FASLEWAHFVNFE<br>SASLTLTSVAVILP<br>LGTLAAQRIASSAP<br>SSANSTGASSGIRY<br>GVSGPSSFTGFKAP<br>SFSTGTTDRPHVSI<br>YARCEAGTSSREH<br>INPQGVELAKLDP<br>ETDHHVRVDRAFL<br>QREERIRAPL | (codon optimized)<br>ATGTCTAAGGAAGTTTTCGACCCATTC<br>ACTCAAAACGTTACTTTCTTCGCTCCA<br>GACGGTAAGACTGAAATCTCTATCCC<br>AGTTGCTGCTATCGACCAAGTTAGAA<br>GAATGATGGTTAACACTACTATCAAC<br>TACGCTACTCAATTGGGTGCTTGTTTG<br>ATCATGTTGGTTGTTTTGTTGGTTATG<br>GTTCCAAAGGAAAAGTTCAGAAGACC<br>ATTCATGATCTTGCAAATCACTTCTTT<br>GGTTATCTCTTGTTGTAGAATGTTGTT<br>GTTGTCTATCTTCCACTCTTCTCAATTC<br>TTGGACTTCTACGTTTTCTGGGGTGAC<br>GACCACTCTAGAATCCCAAGATCTGC<br>TTACGCTCCATCTGTTGCTGGTAACAC<br>TATGTCTTTGTGTTTGGTTATCTCTGTT<br>GAAACTATGTTGATGTCTCAAGCTTGG<br>ACTATGGTTAGATTGTGGCCAAACGTT<br>TGGAAGTACATCATCGCTGGTGTTTCT<br>TTGATCGTTTCTATCATGGCTATCTCT<br>GTTAGATTGGCTTACACTATCATCCAA<br>AACAACGCTGTTTTGAAGTTGGAACC<br>AGCTTTCCACATGTTCTGGTTGATCAA<br>GTGGACTGTTATCATGAACGTTGCTTC<br>TATCTCTTGGTGGTGTGCTATCTTCAA<br>CATCAAGTTGGTTTGGCACTTGATCTC<br>TAACAGAGGTATCTTGCCATCTTACAA<br>GACTTTCACTCCAATGGAAGTTTTGAT<br>CATGACTAACGGTATCTTGATGATCAT<br>CCCAGTTATCTTCGCTTCTTTGGAATG<br>GGCTCACTTCGTTAACTTCGAATCTGC<br>TTCTTTGACTTTGACTTCTGTTGCTGTT<br>ATCTTGCCATTGGGTACTTTGGCTGCT<br>CAAAGAATCGCTTCTTCTGCTCCATCT<br>TCTGCTAACTCTACTGGTGCTTCTTCT<br>GGTATCAGATACGGTGTTTCTGGTCCA<br>TCTTCTTTCACTGGTTTCAAGGCTCCA<br>TCTTTCTCTACTGGTACTACTGACAGA<br>CCACACGTTTCTATCTACGCTAGATGT<br>GAAGCTGGTACTTCTTCTAGAGAACA<br>CATCAACCCACAAGGTGTTGAATTGG<br>CTAAGTTGGACCCAGAAACTGACCAC<br>CACGTTAGAGTTGACAGAGCTTTCTTG<br>CAAAGAGAAGAAAGAATCAGAGCTCC<br>ATTGTAG |
| *Magnaporthe oryzea* | QWCPRR<br>GQPCW | MDQTLSATGTATS<br>PPGPALTVDPRFQ<br>TITMLTPALMGQG<br>FEEVQTTPAEINDV | (codon optimized)<br>ATGGACCAAACTTTGTCTGCTACTGGT<br>ACTGCTACTTCTCCACCAGGTCCAGCT<br>TTGACTGTTGACCCAAGATTCCAAACT |

TABLE 6-continued

Sequences of Fungal GPCRs and Peptide Ligands

| Fungi | sequence of peptide analyte used | sequence of GPCRs used (all sequences are wild type) | DNA coding sequence of corresponding GPCRs that senses peptide analyte (WT or codon-optimized noted) |
|---|---|---|---|
| | | YFLAFNTAIGYST | ATCACTATGTTGACTCCAGCTTTGATG |
| | | QIGACFIMLLVLLT | GGTCAAGGTTTCGAAGAAGTTCAAAC |
| | | MTAKARFARIPTII | TACTCCAGCTGAAATCAACGACGTTT |
| | | NTAALVVSIIRCTL | ACTTCTTGGCTTTCAACACTGCTATCG |
| | | LVIFFTSTMMEFYT | GTTACTCTACTCAAATCGGTGCTTGTT |
| | | IFSDDFSFVHPNDI | TCATCATGTTGTTGGTTTTGTTGACTA |
| | | RRSVAATVFAPLQ | TGACTGCTAAGGCTAGATTCGCTAGA |
| | | LALVEAALMVQA | ATCCCAACTATCATCAACACTGCTGCT |
| | | WAMVELWPRAW | TTGGTTGTTTCTATCATCAGATGTACT |
| | | KVSGIAFSLILATV | TTGTTGGTTATCTTCTTCACTTCTACTA |
| | | TVAFKCASAAVTV | TGATGGAATTCTACACTATCTTCTCTG |
| | | KSALEPLDPRPYL | ACGACTTCTCTTTCGTTCACCCAAACG |
| | | WIRQTDLAFTTAM | ACATCAGAAGATCTGTTGCTGCTACTG |
| | | VTWFCFLFNVRLI | TTTTCGCTCCATTGCAATTGGCTTTGG |
| | | MHMWQNRSILPT | TTGAAGCTGCTTTGATGGTTCAAGCTT |
| | | VKGLSPMEVLVM | GGGCTATGGTTGAATTGTGGCCAAGA |
| | | ANGLLMVFPVLFA | GCTTGGAAGGTTTCTGGTATCGCTTTC |
| | | GLYYGNFGQFESA | TCTTTGATCTTGGCTACTGTTACTGTT |
| | | SLTITSVVLVLPLG | GCTTTCAAGTGTGCTTCTGCTGCTGTT |
| | | TLVAQRLAVNNT | ACTGTTAAGTCTGCTTTGGAACCATTG |
| | | VAGSSANTDMDD | GACCCAAGACCATACTTGTGGATCAG |
| | | KLAFLGNATTVTS | ACAAACTGACTTGGCTTTCACTACTGC |
| | | SAAGFAGSSASAT | TATGGTTACTTGGTTCTGTTTCTTGTTC |
| | | RSRLASPRQNSQL | AACGTTAGATTGATCATGCACATGTG |
| | | STSVSAGKPRADPI | GCAAAACAGATCTATCTTGCCAACTG |
| | | DLELQRIDDEDDD | TTAAGGGTTTGTCTCCAATGGAAGTTT |
| | | FSRSGSAGGVRVE | TGGTTATGGCTAACGGTTTGTTGATGG |
| | | RSIERREERL | TTTTCCCAGTTTTGTTCGCTGGTTTGTA |
| | | | CTACGGTAACTTCGGTCAATTCGAATC |
| | | | TGCTTCTTTGACTATCACTTCTGTTGTT |
| | | | TTGGTTTTGCCATTGGGTACTTTGGTT |
| | | | GCTCAAAGATTGGCTGTTAACAACAC |
| | | | TGTTGCTGGTTCTTCTGCTAACACTGA |
| | | | CATGGACGACAAGTTGGCTTTCTTGG |
| | | | GTAACGCTACTACTGTTACTTCTTCTG |
| | | | CTGCTGGTTTCGCTGGTTCTTCTGCTT |
| | | | CTGCTACTAGATCTAGATTGGCTTCTC |
| | | | CAAGACAAAACTCTCAATTGTCTACTT |
| | | | CTGTTTCTGCTGGTAAGCCAAGAGCTG |
| | | | ACCCAATCGACTTGGAATTGCAAAGA |
| | | | ATCGACGACGAAGACGACGACTTCTC |
| | | | TAGATCTGGTTCTGCTGGTGGTGTTAG |
| | | | AGTTGAAAGATCTATCGAAAGAAGAG |
| | | | AAGAAAGATTGTAG |
| *Botrytis* | WCGRPG | MASNSSNFDPLTQ | (codon optimized) |
| *cinerea* | QPC | SITILMADGITTVS | ATGGCTTCTAACTCTTCTAACTTCGAC |
| | | FTPLDIDFFYYYNV | CCATTGACTCAATCTATCACTATCTTG |
| | | ACCINYGAQAGAC | ATGGCTGACGGTATCACTACTGTTTCT |
| | | LLMFFVVVVLTKA | TTCACTCCATTGGACATCGACTTCTTC |
| | | VKRKTLLFVLNVL | TACTACTACAACGTTGCTTGTTGTATC |
| | | SLIFGFLRAMLYAI | AACTACGGTGCTCAAGCTGGTGCTTGT |
| | | YFLQGFNDFYAAF | TTGTTGATGTTCTTCGTTGTTGTTGTTT |
| | | TFDFSRVPRSSYAS | TGACTAAGGCTGTTAAGAGAAAGACT |
| | | SVAGSVIPLCMTIT | TTGTTGTTCGTTTTGAACGTTTTGTCTT |
| | | VNMSLYLQAYTV | TGATCTTCGGTTTCTTGAGAGCTATGT |
| | | CKNLDDIKRIILTT | TGTACGCTATCTACTTCTTGCAAGGTT |
| | | LSAIVALLAIGFRF | TCAACGACTTCTACGCTGCTTTCACTT |
| | | AATVVNSVAILAT | TCGACTTCTCTAGAGTTCCAAGATCTT |
| | | SASSVPMQWLVK | CTTACGCTTCTTCTGTTGCTGGTTCTGT |
| | | GTLVTETISIWFFS | TATCCCATTGTGTATGACTATCACTGT |
| | | LIFTGKLVWTLYN | TAACATGTCTTTGTACTTGCAAGCTTA |
| | | RRRNGWRQWSAV | CACTGTTTGTAAGAACTTGGACGACA |
| | | RILAAMGGCTMVI | TCAAGAGAATCATCTTGACTACTTTGT |
| | | PSIFAILEYVTPVSF | CTGCTATCGTTGCTTTGTTGGCTATCG |
| | | PEAGSIALTSVALL | GTTTCAGATTCGCTGCTACTGTTGTTA |
| | | LPISSLWAGMVTD | ACTCTGTTGCTATCTTGGCTACTTCTG |
| | | EETSAIDVSNLTGS | CTTCTTCTGTTCCAATGCAATGGTTGG |
| | | RTMLGSQSGNFSR | TTAAGGGTACTTTGGTTACTGAAACTA |
| | | KTHASDITAQSSH | TCTCTATCTGGTTCTTCTCTTTGATCTT |
| | | LDFSSRKGSNATM | CACTGGTAAGTTGGTTTGGACTTTGTA |
| | | MRKGSNAMDQVT | CAACAGAAGAAGAAACGGTTGGAGA |

TABLE 6-continued

Sequences of Fungal GPCRs and Peptide Ligands

| Fungi | sequence of peptide analyte used | sequence of GPCRs used (all sequences are wild type) | DNA coding sequence of corresponding GPCRs that senses peptide analyte (WT or codon-optimized noted) |
|---|---|---|---|
| | | TIDCVVEDNQANRGLRDSTEMDLEAMGVRVNKSYGVQKA | CAATGGTCTGCTGTTAGAATCTTGGCTGCTATGGGTGGTTGTACTATGGTTATCCCATCTATCTTCGCTATCTTGGAATACGTTACTCCAGTTTCTTTCCCAGAAGCTGGTTCTATCGCTTTGACTTCTGTTGCTTTGTTGTTGCCAATCTCTTCTTTGTGGGCTGGTATGGTTACTGACGAAGAAACTTCTGCTATCGACGTTTCTAACTTGACTGGTTCTAGAACTATGTTGGGTTCTCAATCTGGTAACTTCTCTAGAAAGACTCACGCTTCTGACATCACTGCTCAATCTTCTCACTTGGACTTCTCTTCTAGAAAGGGTTCTAACGCTACTATGATGAGAAAGGGTTCTAACGCTATGGACCAAGTTACTACTATCGACTGTGTTGTTGAAGACAACCAAGCTAACAGAGGTTTGAGAGACTCTACTGAAATGGACTTGGAAGCTATGGGTGTTAGAGTTAACAAGTCTTACGGTGTTCAAAAGGCTTAG |
| *Lodderomyces elongisporous* | WMWTRYGRFSPV | MDEAINANLVSGDIIVSFNIPGLPEPVQVPFSEFDSFHKDQLIGVIILGVTIGACSLLLILLLGMLYKSREKYWKSLLFMLNVCILAATILRSGCFLDYYLSDLASISYTFTGVYNGTSFASSDAANVFKTIMFALIETSLTFQVYVMFQGTTWKNWGHAVTALSGLLSVASVAFQIYTTILSHNNFNATISGTGTLTSGVWMDLPTLLFAASINFMTILLLFKLGMAIRQRRYLGLKQFDGFHILFIMFTQTLFIPSILLVIHYFYQAMSGPFIINMALFLVVAFLPLSSLWAQTANTTKKIESSPSMSFITRRKSEDESPLAANDEDRLRKFTTTLDLSGNKNNTTNNNNNSNNINNNMSNINYPSTGLGEDDKSFIFEMEPSRERAAIEEIDLGARIDTGLPRDLEKFLVDGFDDSDDGEGMIAREVTMLKK (SEQ ID NO: 52) | (wild type) ATGGACGAAGCAATCAATGCAAACCTTGTTTCTGGAGATATTATAGTCTCTTTTAACATTCCTGGTTTGCCAGAACCGGTACAAGTGCCATTCAGCGAATTTGATTCGTTTCATAAAGACCAGCTCATTGGAGTCATCATTCTTGGAGTCACTATTGGAGCATGCTCGCTTTTGTTGATATTGCTACTTGGAATGTTATACAAGAGCCGTGAAAAGTATTGGAAATCACTATTATTTATGCTCAATGTATGCATCTTGGCTGCCACAATCTTAAGGAGCGGTTGCTTCTTAGACTATTATCTAAGTGATTTGGCCAGTATCAGTTATACATTTACTGGAGTATACAATGGTACCAGCTTTGCTAGCTCTGACGCGGCAAATGTGTTCAAGACTATTATGTTTGCCTTGATTGAAACTTCGTTAACCTTTCAAGTGTATGTCATGTTTCAAGGGACCACTTGGAAAAATTGGGGCCATGCTGTCACTGCATTATCGGGTCTCTTGTCTGTTGCCTCAGTGGCGTTCCAGATCTACACCACGATTTTATCCCACAATAATTTCAATGCTACAATCTCGGGAACCGGTACATTAACTTCAGGTGTTTGGATGGACTTACCAACACTCTTGTTTGCCGCAAGTATCAATTTTATGACCATTTTGTTGTTATTTAAGTTGGGAATGGCCATTAGACAAAGAAGGTATTTAGGTTTAAAACAGTTTGATGGGTTCCATATCTTATTCATCATGTTTACCCAAACATTGTTCATACCCTCGATTTTGCTTGTGATCCACTACTTTTACCAGGCAATGTCTGGACCATTCATCATCAACATGGCGTTGTTCTTGGTGGTGGCATTCTTGCCATTGAGTTCATTATGGGCACAAACTGCAAACACTACTAAAAAGATTGAATCTTCGCCAAGTATGAGCTTTATTACTAGACGAAAATCAGAGGATGAGTCACCACTGGCTGCTAACGACGAGGATAGGTTACGAAAATTCACCACAACTTTGGATTTGTCGGGCAACAAGAACAATACAACAAACAATAATAACAATAGCAACAACATTAACAACAATATGAGCAACATCAACTACCCTTCTACAGGACTGGGAGAAGACGATAAATCCTTTATATTTGAGATGGAACCCAGTCGGGAAAGAGCTGCAATAGAAGAGATTGATCTTGGAGCAAGGATCGATACCGGTTTGCCCAGAGATTTAGAGAAATTTCTAGTTGATGGGTTTGACGATAGTGATGACGGAGAGAAGGAATGATAGCCAGAGAAGTGACTATGTTGAAAAAATAG (SEQ ID NO: 53) |

TABLE 6-continued

Sequences of Fungal GPCRs and Peptide Ligands

| Fungi | sequence of peptide analyte used | sequence of GPCRs used (all sequences are wild type) | DNA coding sequence of corresponding GPCRs that senses peptide analyte (WT or codon-optimized noted) |
|---|---|---|---|
| *Penicillium rubens* | WCGHIG QGC | MATSSPIQPFDPFT QNVTFRLQDGTEF PVSVKALDVFVM YNVRVCINYGCQF GASFVLLVILVLLT QSDKRRSAVFILN GLALFLNSSRLLFQ VIHFSTAFEQVYPY VSGDYSSVPWSAY AISIVAVVLTTLVV VCIEASLVIQVHV VCSTLRRRYRHPL LAISILVALVPIGFR CAWMVANCKAII KLTYTNDVWWIES ATNICVTISICFFCV IFVTKLGFAIKQRR RLGVREFGPMKVI FVMGCQTMVVPAI FSITQYYVVVPEFS SNVVTLVVISLPLS SIWAGAVLENARR TGSQDRQRRRNL WRALVGGAESLLS PTKDSPTSLSAMT AAQTLCYSDHTMS KGSPTSRDTDAFY GISVEHDISINRVQ RNNSIV (SEQ ID NO: 54) | (codon optimized) ATGGCTACCTCTTCCCCAATCCAACCA TTTGACCCATTCACCCAAAACGTTACC TTCCGTTTGCAAGACGGTACCGAATTC CCAGTTTCTGTCAAGGCTTTGGACGTC TTCGTCATGTACAACGTTAGAGTCTGT ATTAACTACGGTTGTCAATTCGGTGCC TCCTTCGTCTTGTTAGTCATTTTAGTCT TGTTAACTCAATCCGACAAGAGAAGA TCTGCTGTCTTCATTTTGAACGGTTTG GCTTTGTTCTTGAACTCTTCTAGATTG TTGTTTCAAGTTATTCACTTCTCCACT GCCTTCGAACAAGTCTACCCATACGTC TCTGGTGACTACTCCTCTGTCCCATGG TCCGCTTACGCTATCTCCATTGTCGCT GTTGTTTTGACTACCTTGGTCGTTGTT TGTATCGAAGCTTCTTTGGTTATTCAA GTTCACGTTGTCTGTTCCACCTTGAGA CGTAGATACAGACACCCATTATTAGC TATTTCTATTTTGGTCGCTTTGGTTCCA ATCGGTTTCAGATGTGCTTGGATGGTC GCTAACTGTAAGGCTATTATTAAATTG ACCTACACCAACGACGTTTGGTGGAT CGAATCTGCTACTAACATCTGTGTCAC TATCTCCATCTGTTTCTTCTGTGTTATC TTCGTTACCAAGTTGGGTTTCGCCATC AAGCAAAGAAGAAGATTGGGTGTTAG AGAATTCGGTCCAATGAAGGTTATTTT CGTCATGGGTTGTCAAACTATGGTTGT TCCAGCTATTTTCTCCATCACCCAATA CTACGTCGTCGTCCCAGAATTCTCCTC TAACGTCGTTACTTTGGTTGTCATTTC TTTACCATTATCTTCCATTTGGGCCGG TGCTGTCTTGGAAAACGCTAGAAGAA CCGGTTCCCAAGATAGACAAAGAAGA CGTAACTTGTGGAGAGCTTTGGTTGGT GGTGCTGAATCCTTGTTATCCCCAACT AAGGACTCTCCAACCTCTTTGTCTGCT ATGACTGCTGCTCAAACCTTATGTTAC TCTGATCACACCATGTCCAAGGGTTCT CCAACTTCCAGAGACACCGATGCTTTC TACGGTATCTCCGTTGAACACGACATC TCCATTAACAGAGTTCAACGTAACAA CTCCATCGTCTAG (SEQ ID NO: 55) |
| *Candida guilliermondii* | KKNSRFL TYWFFQP IM | MKSCSIGFGIPFINE PNFETVSILTMDVS FIDADVNPDNILLN FTIPGYQNGFSVP MVVINELQKSQM KYAIVYGCGVGAS LILLFVVWILCSRK TPLFIMNNIPLVLY VISSSLNLAYITGP LSSVSVFLTGILTS HDAINVVYASNAL QMLLIFSIQSTMAY HVYVMFKSPQIKY LRYMLVGFLGCLQ IVTTCLYINYNVLY SRRMHKLYETGQT YQDGTVMTFVPFI LFQCSVNFSSIFLV LKLIMAIRTRRYL GLRQFGGFHILMI VSLQTMLVPSILVL VNYAAHKAVPSN LLSSVSMMIIVLSL PASSMWAAAANA SSAPSSAASSLFRY TTSDSDRTLETKS | (codon optimized) ATGAAGTCCTGCTCCATCGGTTTCGGT ATCCCATTCATTAATGAACCAAACTTC GAAACTGTTTCTATTTTGACCATGGAC GTTTCTTTCATTGACGCTGACGTCAAT CCTGACAATATCTTGTTGAACTTCACC ATTCCTGGTTACCAAAACGGTTTCTCT GTTCCAATGGTTGTTATTAACGAATTG CAAAAGTCTCAAATGAAATACGCTAT TGTTTACGGTTGTGGTGTCGGTGCCTC CTTGATTTTGTTGTTTGTCGTCTGGATT TTGTGTTCTAGAAAGACTCCATTGTTT ATCATGAACAACATTCCATTAGTTTTG TACGTCATCTCCTCTTCTTTGAACTTG GCTTACATTACCGGTCCATTGTCTTCT GTTTCCGTCTTCTTGACCGGTATCTTG ACTTCTCACGATGCCATTAACGTCGTT TACGCTTCCAACGCTTTGCAAATGTTG TTGATCTTTTCTATCCAATCTACCATG GCCTACCACGTTTACGTTATGTTCAAA TCTCCACAAATTAAATACTTGAGATAC ATGTTAGTCGGTTTCTTGGGTTGTTTA CAAATTGTCACCACCTGTTTATACATC AACTACAATGTTTTGTACTCTCGTAGA ATGCACAAATTGTACGAAACTGGTCA AACCTACCAAGATGGTACCGTTATGA |

TABLE 6-continued

| Sequences of Fungal GPCRs and Peptide Ligands | | | |
|---|---|---|---|
| Fungi | sequence of peptide analyte used | sequence of GPCRs used (all sequences are wild type) | DNA coding sequence of corresponding GPCRs that senses peptide analyte (WT or codon-optimized noted) |
| | | DHFIMKHESHNSS<br>PNSSPLTLVQKRIS<br>DATLELPKELEDLI<br>DSTSI (SEQ ID<br>NO: 56) | CTTTCGTTCCATTCATCTTGTTCCAAT<br>GTTCTGTCAACTTCTCTTCTATTTTCTT<br>GGTTTTGAAGTTGATTATGGCCATTAG<br>AACCAGACGTTACTTGGGTTTGCGTCA<br>ATTCGGTGGTTTTCATATTTTGATGAT<br>CGTTTCTTTACAAACTATGTTGGTCCC<br>ATCTATTTTGGTTTTGGTTAACTACGC<br>CGCTCATAAGGCTGTTCCTTCCAACTT<br>GTTATCTTCCGTTTCTATGATGATCAT<br>TGTTTTGTCTTTACCAGCTTCTTCTATG<br>TGGGCCGCTGCTGCTAACGCCTCTTCT<br>GCCCCTTCCTCCGCTGCTTCCTCCTTG<br>TTCAGATACACCACTTCTGATTCCGAT<br>AGAACTTTGGAAACTAAATCTGACCA<br>CTTCATCATGAAGCATGAGTCCCACA<br>ACTCTTCTCCAAATTCCTCCCCATTGA<br>CTTTGGTTCAAAAGAGAATTTCTGATG<br>CCACCTTAGAATTACCAAAAGAGTTA<br>GAAGACTTGATCGACTCCACCTCCATC<br>TAG (SEQ ID NO: 57) |
| *Candida tropicalis* | KFKFRLT<br>RYGWFSP<br>N | MDINNTIQSSGDIII<br>TYTIPGIEEPFELPF<br>EVLNHFQSEQSKN<br>CLVMGVMIGSCSV<br>LLIFLVGILFKTNK<br>FSTIGKSKNLSKNF<br>LFYLNCLITFIGIIR<br>AACFSNYLLGPLN<br>SASFAFTGWYNGE<br>SYASSEAANGFRV<br>ILFALIETSMVFQV<br>FVMFRGAGMKKL<br>AYSVTILCTALAL<br>VVVGFQINSAVLS<br>HRRFVNTVNEIGD<br>TGLSSIWLDLPTIL<br>FSVSVNLMSVLLI<br>GKLIMAIKTRRYL<br>GLKQFDSFHVLLIC<br>STQTLLVPSLILFV<br>HYFLFFRNANVML<br>INISILLIVLMLPFS<br>SLWAQTANTTQYI<br>NSSPSFSFISREPSA<br>NSTLHSSSGHYSE<br>KSYGINKLNTQGS<br>SPATLKDDHNSVI<br>LEATNPMSGFDAQ<br>LPPDIARFLQDDIRI<br>EPSSTQDFVSTEVT<br>YKKV (SEQ ID<br>NO: 58) | (codon optimized)<br>ATGGACATCAACAACACCATCCAATC<br>TTCCGGTGACATCATCATTACCTACAC<br>CATCCCAGGTATCGAAGAACCATTCG<br>AATTGCCATTCGAAGTTTTGAACCACT<br>TCCAATCTGAACAATCCAAGAACTGT<br>TTGGTCATGGGTGTTATGATCGGTTCT<br>TGTTCCGTTTTGTTGATCTTCTTGGTCG<br>GTATTTTGTTCAAAACCAACAAATTCT<br>CTACTATTGGTAAGTCTAAGAACTTGT<br>CTAAGAACTTCTTGTTCTACTTGAACT<br>GTTTGATCACCTTCATCGGTATCATTC<br>GTGCTGCCTGTTTTTCTAACTACTTGT<br>TGGGTCCATTGAACTCTGCTTCTTTCG<br>CTTTCACTGGTTGGTACAACGGTGAAT<br>CTTACGCTTCTTCCGAAGCTGCTAACG<br>GTTTCAGAGTCATCTTGTTCGCTTTGA<br>TTGAAACTTCTATGGTCTTCCAAGTTT<br>TCGTTATGTTCAGAGGTGCTGGTATGA<br>AAAAGTTGGCTTACTCCGTTACCATTT<br>TGTGTACCGCTTTGGCTTTGGTCGTTG<br>TTGGTTTCCAAATTAACTCCGCTGTCT<br>TATCTCACAGAAGATTCGTCAACACC<br>GTTAACGAAATTGGTGATACTGGTTTG<br>TCCTCCATTTGGTTGGACTTGCCAACC<br>ATCTTGTTCTCCGTCTCTGTCAACTTA<br>ATGTCTGTTTTGTTGATCGGTAAATTG<br>ATCATGGCTATTAAGACTAGAAGATA<br>CTTGGGTTTGAAACAATTCGATTCCTT<br>CCACGTTTTGTTAATTTGTTCCACTCA<br>AACTTTGTTGGTCCCATCTTTAATCTT<br>GTTCGTTCACTACTTCTTGTTCTTTAG<br>AAACGCCAACGTTATGTTGATTAACA<br>TTTCCATCTTGTTGATCGTCTTGATGTT<br>GCCATTCTCTTCCTTGTGGGCTCAAAC<br>CGCCAACACCACCCAATACATCAACT<br>CTTCCCCATCCTTCTCTTTCATCTCTAG<br>AGAACCATCTGCTAACTCTACTTTGCA<br>CTCCTCTTCCGGTCACTACTCTGAAAA<br>GTCCTACGGTATTAACAAATTGAACA<br>CCCAAGGTTCTTCCCCAGCCACCTTAA<br>AGGATGATCACAACTCCGTCATCTTG<br>GAAGCTACCAACCCAATGTCTGGTTTC<br>GACGCCCAATTGCCACCAGACATTGC<br>TAGATTCTTGCAAGATGACATCAGAA<br>TTGAACCATCTTCTACCCAAGATTTCG<br>TTTCCACTGAAGTCACCTACAAGAAG<br>GTCTAG (SEQ ID NO: 59) |

TABLE 6-continued

Sequences of Fungal GPCRs and Peptide Ligands

| Fungi | sequence of peptide analyte used | sequence of GPCRs used (all sequences are wild type) | DNA coding sequence of corresponding GPCRs that senses peptide analyte (WT or codon-optimized noted) |
|---|---|---|---|
| *Candida parapsilosis* | KPHWTT<br>YGYYEPQ | MNKIVSKLSSSDVI<br>VTVTIPNEEDGTY<br>EVPFYAIDNYHYS<br>RMENAVVLGATIG<br>ACSMLLIMLIGILF<br>KNFQRLRKSLLFNI<br>NFAILLMLILRSAC<br>YINYLMNNLSSISF<br>FFTGIFDDESFMSS<br>DAANAFKVILVAL<br>IEVSLTYQIYVMFK<br>TPMLKSWGIFASV<br>LAGVLGLATLATQ<br>IYTTVMSHVNFVN<br>GTTGSPSQVTSAW<br>MDMPTILFSVSINV<br>LSMFLVCKLGLAI<br>RTRRYLGLKQFDA<br>FHILFIMSTQTMIIP<br>SIILFVHYFDQNDS<br>QTTLVNISLLLVVI<br>SLPLSSLWAQTAN<br>NVRRIDTSPSMSFI<br>SREASNRSGNETL<br>HSGATISKYNTSN<br>TVNTTPGTSKDDS<br>LFILDRSIPEQRIVD<br>TGLPKDLEKFINN<br>DFYEDDGGMIARE<br>VTMLKTAHNNQ<br>(SEQ ID<br>NO: 60) | (codon optimized)<br>ATGAACAAGATTGTCTCCAAGTTGTCT<br>TCTTCTGACGTCATCGTTACCGTCACC<br>ATCCCAAACGAAGAAGATGGTACTTA<br>CGAAGTCCCATTCTACGCTATTGACAA<br>CTACCACTACTCCCGTATGGAAAACG<br>CTGTTGTTTTAGGTGCTACCATTGGTG<br>CTTGTTCTATGTTGTTGATCATGTTGA<br>TTGGTATTTTGTTCAAGAACTTCCAAA<br>GATTGAGAAAGTCTTTGTTGTTCAACA<br>TCAACTTCGCTATCTTATTGATGTTGA<br>TTTTGAGATCCGCTTGTTACATCAACT<br>ACTTGATGAACAACTTGTCTTCCATTT<br>CTTTCTTCTTCACCGGTATTTTCGATG<br>ATGAATCTTTCATGTCTTCCGACGCTG<br>CCAACGCCTTCAAGGTTATCTTGGTTG<br>CCTTGATTGAAGTTTCCTTGACCTACC<br>AAATTTACGTTATGTTCAAGACCCCAA<br>TGTTGAAGTCCTGGGGTATTTTCGCCT<br>CTGTCTTGGCCGGTGTTTTGGGTTTGG<br>CTACTTTGGCTACCCAAATCTACACTA<br>CCGTTATGTCTCACGTTAACTTCGTCA<br>ACGGTACCACCGGTTCTCCATCTCAAG<br>TTACTTCCGCTTGGATGGACATGCCAA<br>CTATCTTATTCTCCGTTTCTATTAACGT<br>TTTGTCTATGTTCTTGGTTTGTAAGTT<br>GGGTTTGGCCATCAGAACCAGACGTT<br>ACTTGGGTTTAAAGCAATTCGACGCTT<br>TCCACATTTTATTCATTATGTCCACTC<br>AAACCATGATCATTCCATCCATCATCT<br>TGTTCGTTCACTACTTCGATCAAAACG<br>ACTCTCAAACCACCTTGGTCAACATCT<br>CTTTGTTATTGGTCGTCATTTCCTTGCC<br>ATTGTCTTCTTTGTGGGCTCAAACTGC<br>TAACAACGTTAGAAGAATTGACACTT<br>CTCCATCCATGTCCTTCATCTCTAGAG<br>AAGCTTCCAACAGATCTGGTAACGAA<br>ACCTTGCACTCTGGTGCTACTATCTCT<br>AAGTACAACACCTCCAACACCGTTAA<br>CACTACCCCAGGTACTTCTAAGGATG<br>ACTCTTTGTTCATCTTGGACAGATCCA<br>TTCCAGAACAAAGAATTGTCGACACT<br>GGTTTGCCAAAGGACTTGGAAAAGTT<br>CATTAACAACGATTTTTACGAAGACG<br>ATGGTGGTATGATTGCCAGAGAAGTC<br>ACCATGTTGAAGACCGCTCACAACAA<br>CCAATAG (SEQ ID NO: 61) |
| *Geotrichum candidum* | GDWGWF<br>WYVPRP<br>GDPAM | MAEDSIFPNNSTSP<br>LTNPIVVETIKGTA<br>YIPLHYLDDLQYE<br>KMLLASLFSVRIA<br>TSFVVIIWYFVAV<br>NKAKRSKFLYIVN<br>QVSLLIVFIQSILSL<br>IYVFSNFSKMSTIL<br>TGDYTGITKRDIN<br>VSCVASVFQFLFIA<br>CIELALFIQATVVF<br>QKSVRWLKFSVSL<br>IQGSVALTTTALY<br>MAIIVQSIYATLNP<br>YAGNLIKGRFGYL<br>LASLGKIFFSISVTS<br>CMCIFVGKLVFAI<br>HQRRTLGIKQFDG<br>LQILVIMSTQSMIIP<br>TIIVLMSFLRRNAG<br>SVYTMATLLVALS<br>LPLSSLWAEAKTT<br>RDSASYTAYRPSG<br>SPNNRSLFAIFSDR | (codon optimized)<br>ATGGCCGAAGACTCCATCTTCCCAAA<br>CAACTCCACCTCTCCATTGACCAACCC<br>AATTGTTGTTGAAACCATTAAGGGTA<br>CCGCTTACATTCCATTACACTACTTGG<br>ATGATTTGCAATACGAAAAGATGTTG<br>TTGGCTTCCTTGTTCTCCGTTAGAATT<br>GCTACTTCCTTCGTTGTTATTATTTGGT<br>ACTTCGTCGCTGTCAACAAGGCTAAG<br>AGATCTAAGTTTTTGTACATTGTCAAC<br>CAAGTTTCTTTGTTGATCGTTTTTATCC<br>AATCCATTTTGTCTTTGATTTACGTCTT<br>CTCCAACTTCTCCAAGATGTCTACCAT<br>TTTGACCGGTGATTACACCGGTATCAC<br>TAAGAGAGACATTAACGTCTCTTGTGT<br>TGCCTCCGTTTTCCAATTCTTGTTCATC<br>GCTTGTATCGAATTGGCTTTGTTCATC<br>CAAGCTACTGTCGTTTTCCAAAAATCT<br>GTTAGATGGTTGAAGTTTTCCGTTTCT<br>TTGATCCAAGGTTCCGTCGCTTTGACT<br>ACTACCGCCTTGTACATGGCCATTATT<br>GTCCAATCCATCTACGCTACTTTGAAC<br>CCATACGCTGGTAACTTGATTAAAGG<br>TCGTTTCGGTTACTTATTAGCTTCTTTG |

TABLE 6-continued

| Sequences of Fungal GPCRs and Peptide Ligands | | | |
|---|---|---|---|
| Fungi | sequence of peptide analyte used | sequence of GPCRs used (all sequences are wild type) | DNA coding sequence of corresponding GPCRs that senses peptide analyte (WT or codon-optimized noted) |
| | | LACGSGRNNRHD DDSRGNGSVNAR KADVESTIEMSSC YTDSPTYSKFEAG LDARGIVFYNEHG LPVVSGEVGGSSS NGTKLGSGHKYE VNTTVVLSDVDSP SPTDVTRK (SEQ ID NO: 62) | GGTAAGATTTTCTTCTCTATTTCTGTT ACTTCTTGTATGTGTATCTTCGTTGGT AAGTTGGTCTTTGCTATTCACCAAAGA AGAACTTTGGGTATTAAGCAATTCGA CGGTTTGCAAATTTTGGTCATTATGTC TACTCAATCCATGATCATCCCAACTAT TATCGTCTTGATGTCTTTTTTGAGACG TAACGCTGGTTCTGTTTACACCATGGC TACCTTGTTGGTCGCTTTGTCCTTGCC ATTGTCCTCCTTGTGGGCTGAAGCCAA GACTACCAGAGACTCTGCTTCTTACAC CGCTTACAGACCATCTGGTTCTCCAAA CAACCGTTCTTTGTTCGCCATCTTCTC TGATAGATTGGCTTGTGGTTCTGGTAG AAACAACAGACACGATGATGATTCTA GAGGTAACGGTTCTGTTAACGCCAGA AAGGCTGACGTCGAATCTACTATCGA AATGTCCTCTTGTTACACTGATTCCCC AACCTACTCCAAGTTCGAAGCTGGTTT GGACGCTAGAGGTATCGTCTTCTACA ACGAACACGGTTTGCCAGTTGTCTCCG GTGAAGTTGGTGGTTCTTCCTCCAACG GTACTAAGTTGGGTTCTGGTCATAAGT ACGAAGTCAACACTACTGTTGTTTTGT CTGATGTTGACTCTCCATCTCCAACCG ACGTCACCCGTAAGTAG (SEQ ID NO: 63) |
| *Zygosaccharomyces bailii* | HLVRLSP GAAMF | MSGLANNTSYNPL ESFIIFTSVYGGDT MVKFEDLQLVFTK RITEGILFGVKVGA ASLTMIVMWMISR RRTSPIFIMNQLSL VFTILHASFYFKYL LDGFGSIVYTLTLF PQLITSSDLHVFAT ANVVEVLLVSSIE ASLVFQVNVMFA GSNHRKFAWLLV GFSLGLALATVAL YFVTAVKMIASAY ASQPPTNPIYFNVS LFLLAASVFLMTL MLTVKLILAIRSRR FLGLKQFDSFHILL IMSCQTLIAPSVLY ILGFILDHRKGND YLITVAQLLVVLS LPLSSMWATTAND ASSGTSMSSKESV YGSDSLYSKSKCS QFTRTFMNRFSTK PTKNDEISDSAFVA VDSLEKNAPQGIS EHVCEFPQSDLSD QATSISSRKKEAV VYASTVDEDKGSF SSDINGYTVTNMP LASAASANCENSP CHVPRPYEENEGV VETRKIILKKNVK W (SEQ ID NO: 64) | (codon optimized) ATGTCTGGTTTGGCTAACAACACCTCT TACAACCCATTGGAATCTTTCATTATT TTCACTTCTGTTTACGGTGGTGATACC ATGGTTAAGTTCGAAGACTTGCAATT AGTCTTCACCAAGCGTATTACTGAAG GTATTTTGTTCGGTGTCAAGGTTGGTG CCGCTTCTTTGACTATGATTGTTATGT GGATGATTTCCAGAAGAAGAACCTCC CCAATCTTCATCATGAACCAATTGTCT TTGGTTTTCACCATCTTGCACGCTTCT TTTTACTTTAAGTACTTATTGGACGGT TTCGGTTCTATTGTCTACACTTTGACC TTGTTCCCACAATTAATTACTTCCTCT GACTTGCACGTTTTCGCTACTGCTAAC GTTGTTGAAGTCTTATTGGTTTCTTCC ATCGAAGCCTCTTTGGTTTTCCAAGTC AACGTCATGTTCGCTGGTTCTAACCAC AGAAAGTTCGCTTGGTTGTTGGTCGGT TTCTCTTTGGGTTTGGCTTTGGCCACT GTCGCTTTGTACTTCGTTACTGCTGTC AAGATGATCGCTTCCGCTTACGCTTCT CAACCACCAACTAACCCAATCTACTTC AACGTTTCCTTGTTCTTGTTGGCTGCC TCCGTTTTCTTGATGACTTTAATGTTG ACCGTCAAGTTGATCTTGGCTATCAGA TCCAGAAGATTCTTGGGTTTGAAGCA ATTCGACTCTTTCCACATTTTGTTGAT TATGTCTTGTCAAACTTTGATCGCTCC ATCTGTTTTGTACATCTTGGGTTTTATT TTGGATCACAGAAAGGGTAACGACTA CTTGATTACCGTCGCTCAATTGTTGGT CGTTTTGTCTTTGCCATTGTCCTCCAT GTGGGCCACTACTGCTAACGATGCTTC CTCCGGTACTTCTATGTCTTCCAAGGA ATCCGTCTACGGTTCTGATTCCTTATA CTCTAAGTCTAAGTGTTCCCAATTCAC CAGAACCTTCATGAACAGATTCTCTAC TAAGCCAACTAAGAACGACGAAATTT CTGATTCCGCTTTCGTCGCTGTTGATT CCTTGGAAAAGAACGCTCCACAAGGT ATCTCTGAACACGTTTGTGAATTCCCA CAATCTGACTTATCTGATCAAGCTACT TCCATCTCCTCCAGAAAAAAGGAAGC |

TABLE 6-continued

Sequences of Fungal GPCRs and Peptide Ligands

| Fungi | sequence of peptide analyte used | sequence of GPCRs used (all sequences are wild type) | DNA coding sequence of corresponding GPCRs that senses peptide analyte (WT or codon-optimized noted) |
|---|---|---|---|
| | | | TGTTGTTTACGCTTCCACTGTTGATGA<br>AGATAAGGGTTCTTTCTCCTCTGACAT<br>CAACGGTTACACTGTTACCAACATGC<br>CATTGGCTTCCGCTGCTTCTGCTAACT<br>GTGAAAACTCCCCATGTCACGTTCCA<br>AGACCATACGAAGAAAACGAAGGTGT<br>CGTCGAAACCAGAAAAATTATTTTGA<br>AGAAGAACGTCAAATGGTAG<br>(SEQ ID NO: 65) |
| *Zygosaccharomyces rouxii* | HFIELDP GQPMF | MSEINNSTYNPMN<br>AYVTFTSIYGDDT<br>MVRFKDVELVVN<br>KRVTEAIMFGVKV<br>GAASLTLIIMWMIS<br>KKRTTPIFIINQSSL<br>VFTIIHASLYFGYL<br>LSGFGSIVYNMTSF<br>PQLISSNDVRVYA<br>ATNIFEVLLVASIEI<br>SLVFQVKVMFAN<br>NNGRRWTWCLM<br>VVSIGMALATVGL<br>YFATAVELIRAAY<br>SNDTVSRHVFYNV<br>SLILLASSVNLMTL<br>MLVVKLVLAIRSR<br>RFLGLKQFDSFHIL<br>LIMSCQTLIAPSILF<br>ILGWTLDPHTGNE<br>VLITVGQLLIVLSL<br>PLSSMWATTANNT<br>SSSSSSVSCNDSSF<br>GNDNLCSKSSQFR<br>RTFMNRFRPKSVN<br>GDGNSENTFVTID<br>DLEKSVFQELSTP<br>VSGESKIDHDHAS<br>SISCQKTCNHVHA<br>STVNSDKGSWSSD<br>GSCGSSPLRKTSTV<br>NSEDLPPHILSAYD<br>DDRGIVESKKIILK<br>KL (SEQ ID NO: 66) | (wild type)<br>ATGAGTGAGATTAACAATTCTACCTA<br>CAATCCAATGAATGCATATGTAACGT<br>TTACATCAATATATGGTGATGATACTA<br>TGGTACGTTTCAAAGATGTGGAATTG<br>GTAGTTAACAAAAGGGTTACAGAAGC<br>CATTATGTTCGGCGTCAAAGTTGGTGC<br>AGCTTCGTTGACACTCATCATCATGTG<br>GATGATCTCTAAGAAAAGAACAACAC<br>CGATATTTATCATAAATCAGTCTTCGC<br>TTGTATTTACCATAATACATGCTTCGC<br>TTTATTTTGGGTACCTTTTGTCAGGAT<br>TTGGTAGTATAGTTTACAATATGACAT<br>CGTTCCCGCAGTTAATAAGCTCCAATG<br>ACGTTCGTGTGTACGCAGCTACAAAT<br>ATTTTTGAGGTCCTGTTGGTAGCATCT<br>ATCGAAATCTCTCTGGTTTTTCAGGTC<br>AAAGTTATGTTTGCCAACAATAATGG<br>TCGAAGATGGACTTGGTGTTTGATGGT<br>AGTTTCCATAGGGATGGCACTAGCTA<br>CTGTAGGACTTTATTTTGCCACTGCCG<br>TTGAGTTGATCAGAGCTGCTTACAGC<br>AATGATACTGTTAGCCGCCATGTTTTT<br>TACAATGTTTCTCTGATCTTACTAGCG<br>TCATCTGTCAATCTAATGACACTAATG<br>CTAGTGGTAAAATTAGTATTAGCGAT<br>CAGATCAAGAAGATTTTTGGGGTTAA<br>AACAGTTTGACAGTTTCCACATATTAC<br>TTATAATGTCTTGCCAGACTCTAATAG<br>CACCTTCCATTCTATTCATTTTGGGTT<br>GGACCTTAGACCCTCATACTGGTAAT<br>GAGGTTTTAATTACAGTTGGTCAATTG<br>CTAATAGTACTGTCATTACCGCTGTCA<br>TCTATGTGGGCTACAACCGCTAACAA<br>TACCAGTTCATCTAGTAGTTCGGTGTC<br>CTGTAATGACAGCTCTTTTGGTAATGA<br>CAATCTCTGTTCCAAGAGTTCGCAATT<br>TAGAAGAACTTTTATGAATAGATTCC<br>GTCCCAAGTCGGTTAATGGTGACGGT<br>AATTCTGAAAATACCTTTGTTACAATT<br>GATGATTTGGAAAAAAGCGTTTTTCA<br>AGAATTATCAACACCTGTTAGCGGAG<br>AATCAAAGATAGATCATGATCATGCA<br>AGTAGTATTTCATGTCAAAAGACATG<br>TAATCATGTTCATGCTTCGACAGTGAA<br>TTCAGATAAGGGATCTTGGTCCTCTGA<br>TGGTAGTTGTGGCAGTTCTCCGTTAAG<br>AAAGACTTCCACCGTTAATTCTGAAG<br>ATTTACCTCCACATATATTGAGCGCCT<br>ACGATGACGATCGAGGTATAGTAGAA<br>AGTAAAAAAATTATCCTAAAGAAATT<br>ATAG (SEQ ID NO: 67) |
| *Kluyveromyces lactis* | WSWITLR PGQPIF | MSEEIPSLNPLFYN<br>ETYNPLQSVLTYS<br>SIYGDGTEITFQQL<br>QNLVHENITQAIIF<br>GTRIGAAGLALIIM<br>WMVSKNRKTPIFII<br>NQSSLVLTIVQSAL<br>YLSYLLSNFGGVP<br>FALTLFPQMIGDR | (wild type)<br>ATGTCAGAAGAGATACCCAGTTTGAA<br>CCCATTGTTCTACAATGAGACATATAA<br>TCCATTGCAGTCCGTCCTAACATACAG<br>TTCAATTTACGGAGATGGGACTGAAA<br>TAACATTTCAACAGCTACAAAATCTTG<br>TCCATGAAAACATCACCCAAGCAATT<br>ATTTTTGGAACAAGGATCGGCGCTGC<br>TGGATTAGCGTTGATTATAATGTGGAT |

TABLE 6-continued

Sequences of Fungal GPCRs and Peptide Ligands

| Fungi | sequence of peptide analyte used | sequence of GPCRs used (all sequences are wild type) | DNA coding sequence of corresponding GPCRs that senses peptide analyte (WT or codon-optimized noted) |
|---|---|---|---|
| | | DKHLYGAVTLIQC<br>LLVACIEVSLVFQ<br>VRVIFKADRYRKI<br>GIILTGVSASFGAA<br>TVAMWMITAIKSII<br>VVYDSPLNKVDTY<br>YYNIAVILLACSIN<br>FITLLLSVKLFLAF<br>RARRHLGLKQFDS<br>FHILLIMSTQTLIGP<br>SVLYILAYALNNK<br>GVKSLTSIATLLVV<br>LSLPLTSIWAAAA<br>NDAPSASTFYRQF<br>NPYSAQNRDDSSS<br>YSYGKAFSDKYSF<br>SNSPQTSDGCSSKE<br>LELSTQLEMDLES<br>GESFMDRAKRSDF<br>VSSPGSTDATVIKQ<br>LKASNIYTSETDA<br>DEEARAFWVNAIH<br>ENKDDGLMQSKT<br>VFKELR (SEQ ID<br>NO: 68) | GGTCTCTAAGAATAGAAAGACGCCGA<br>TATTCATAATAAATCAGAGTTCTTTGG<br>TTCTTACAATTGTTCAATCTGCTTTAT<br>ATCTATCATATTTGTTGAGCAATTTTG<br>GAGGAGTTCCCTTTGCTCTAACTTTGT<br>TCCCACAGATGATAGGCGACCGTGAC<br>AAACATCTTTACGGTGCCGTGACTCTA<br>ATTCAATGTCTATTGGTTGCGTGTATT<br>GAGGTCTCGTTAGTCTTTCAGGTAAGA<br>GTCATTTTCAAAGCAGATAGATATAG<br>GAAGATAGGAATCATTTTGACTGGCG<br>TCTCCGCTAGTTTTGGTGCTGCAACTG<br>TAGCCATGTGGATGATTACTGCAATA<br>AAATCTATTATTGTAGTGTATGATAGT<br>CCATTGAACAAAGTTGACACATATTA<br>TTACAACATAGCAGTTATTTTACTTGC<br>ATGTTCAATAAATTTCATCACTCTTCT<br>TCTATCAGTGAAACTTTTCCTGGCTTT<br>CAGAGCTAGGAGACATTTAGGTTTGA<br>AACAATTTGACTCATTTCACATTCTAC<br>TCATCATGTCTACTCAGACATTAATAG<br>GTCCATCGGTTTTGTATATTCTCGCCT<br>ACGCGCTGAACAATAAAGGAGTTAAG<br>TCGTTGACTTCTATTGCTACATTGCTT<br>GTAGTTCTTTCCCTACCTTTGACATCT<br>ATCTGGGCTGCTGCTGCAAATGATGC<br>ACCAAGTGCCAGTACTTTCTATCGCCA<br>ATTCAACCCTTACTCTGCACAAAATCG<br>TGATGATTCATCATCCTACTCTTATGG<br>TAAAGCCTTTAGTGACAAATACTCTTT<br>CAGTAACTCACCACAAACTTCGGATG<br>GTTGTAGTTCAAAGGAACTTGAACTA<br>TCTACACAGTTGGAGATGGATTTAGA<br>GTCTGGCGAATCTTTTATGGATAGAGC<br>AAAAAGGTCCGATTTTGTTTCTTCTCC<br>AGGATCAACAGATGCAACAGTGATTA<br>AACAATTGAAAGCTTCCAACATCTAT<br>ACCTCAGAAACAGATGCTGATGAAGA<br>GGCAAGGGCATTTTGGGTGAATGCAA<br>TTCATGAAAACAAAGATGACGGTTTA<br>ATGCAATCGAAAACCGTATTCAAAGA<br>ATTAAGATAG (SEQ ID NO: 69) |
| *Schizosaccharomyces pombe* | TYADFLR<br>AYQSWN<br>TFVNPDR<br>PNL | MRQPWWKDFTIP<br>DASAIIHQNITIVSI<br>VGEIEVPVSTIDAY<br>ERDRLLTGMTLSA<br>QLALGVLTILMVC<br>LLSSSEKRKHPVF<br>VFNSASIVAMCLR<br>AILNIVTICSNSYSI<br>LVNYGFILNMVH<br>MYVHVFNILILLL<br>APVIIFTAEMSMMI<br>QVRIICAHDRKTQ<br>RIMTVISACLTVLV<br>LAFWITNMCQQIQ<br>YLLWLTPLSSKTIV<br>GYSWPYFIAKILFA<br>FSIIFHSGVFSYKLF<br>RAILIRKKIGQFPF<br>GPMQCILVISCQCL<br>IVPATFTIIDSFIHT<br>YDGFSSMTQCLLII<br>SLPLSSLWASSTAL<br>KLQSMKTSSAQGE<br>TTEVSIRVDRTFDI<br>KHTPSDDYSISDES<br>ETKKWT (SEQ ID<br>NO: 70) | (wild type)<br>ATGAGACAACCATGGTGGAAAGACTT<br>TACTATTCCCGATGCATCCGCAATTAT<br>TCACCAAAATATTACCATTGTCTCTAT<br>TGTAGGAGAGATTGAAGTGCCAGTTT<br>CAACAATTGATGCATATGAAAGAGAT<br>AGACTTTTAACTGGAATGACTTTGTCT<br>GCCCAACTTGCTTTAGGAGTCCTTACC<br>ATTTTGATGGTTTGTCTATTGTCATCA<br>TCCGAAAAACGAAAACACCCAGTTTT<br>TGTTTTTAATTCGGCAAGTATTGTTGC<br>AATGTGTCTTCGGGCCATTTTGAATAT<br>AGTGACCATATGCAGCAATAGCTACA<br>GTATCCTGGTTAATTACGGGTTTATCT<br>TAAACATGGTTCATATGTATGTCCATG<br>TGTTTAATATTTTAATTTTGTTGCTTGC<br>ACCGGTCATCATTTTTACTGCTGAGAT<br>GAGCATGATGATTCAAGTTCGTATAA<br>TTTGTGCACATGATAGAAAGACACAA<br>AGGATAATGACTGTTATTAGTGCCTGC<br>TTAACTGTTTTGGTTCTCGCATTTTGG<br>ATTACTAACATGTGTCAACAGATTCA<br>GTATCTGTTATGGTTAACTCCACTTAG<br>CAGCAAGACCATTGTTGGATACTCTTG<br>GCCCTACTTTATTGCTAAAATACTTTT<br>TGCTTTTAGCATTATTTTTCACAGTGG<br>TGTTTTTTCATACAAACTCTTTCGTGC<br>CATATTAATACGGAAAAAAATTGGGC<br>AATTTCCATTTGGTCCGATGCAGTGTA |

TABLE 6-continued

Sequences of Fungal GPCRs and Peptide Ligands

| Fungi | sequence of peptide analyte used | sequence of GPCRs used (all sequences are wild type) | DNA coding sequence of corresponding GPCRs that senses peptide analyte (WT or codon-optimized noted) |
|---|---|---|---|
| | | | TTTTAGTTATTAGCTGCCAATGTCTTA<br>TTGTTCCAGCTACCTTTACTATAATAG<br>ATAGTTTTATCCATACGTATGATGGCT<br>TTAGCTCTATGACTCAATGTCTGCTAA<br>TCATTTCTCTTCCTCTTTCGAGTTTATG<br>GGCGTCTAGTACAGCTCTGAAATTGC<br>AAAGCATGAAAACTTCATCTGCGCAA<br>GGAGAAACCACCGAGGTTTCGATTAG<br>AGTTGATAGAACGTTTGATATCAAAC<br>ATACTCCCAGTGACGATTATTCGATTT<br>CTGATGAATCTGAAACTAAAAAGTGG<br>ACGTAG (SEQ ID NO: 71) |
| *Vanderwaltozyma polyspora* (receptor 1) | WHWLEL<br>DNGQPIY | MSSQSHPPLIDLFY<br>DSSYDPGESLIYYT<br>SIYGNNTYITFDEL<br>QTIVNKKVTQGILF<br>GVRCGAAFLMLV<br>AMWLISKNKRSRI<br>FITNQCCLVFMIM<br>HSGLYFRYLLSRY<br>GSVTFILTGFQQLL<br>TRNDIHIYGATDFI<br>QVALVACIELSLIF<br>QIKVIFAGTNYGK<br>LANYFITLGSLLGL<br>ATFGMYMLTAING<br>TIKLYNNEYDPNQ<br>RKYFNISTILLASSI<br>NMLTLILILKLVAA<br>IRTRRYLGLKQFD<br>SFHILLIMSTQTLII<br>PSILFILSYSLRED<br>MHTDQLIIIGNLIV<br>VLSLPLSSMWASS<br>LNNSSKPTSLNTDF<br>SGPKSSEEGTAISL<br>LSQNMEPSIVTKY<br>TRRSPGLYPVSVG<br>TPIEKEASYTLFEA<br>TDIDFESSSNDITR<br>TS (SEQ ID<br>NO: 72) | (wild type)<br>ATGAGTTCCCAATCACACCCACCGCT<br>AATCGATTTATTTTACGATTCCAGTTA<br>TGACCCTGGTGAAAGTTTAATTTATTA<br>CACATCCATCTATGGTAATAATACATA<br>CATAACTTTTGATGAACTCCAGACGAT<br>AGTGAACAAGAAGGTCACACAAGGTA<br>TCTTATTTGGTGTCAGATGTGGTGCTG<br>CTTTCCTGATGTTGGTAGCAATGTGGT<br>TGATTTCCAAAAATAAAAGATCTAGA<br>ATTTTCATTACCAACCAATGTTGTCTG<br>GTCTTCATGATAATGCATTCTGGTCTT<br>TATTTTAGGTACCTGCTTTCAAGGTAC<br>GGTTCAGTTACTTTCATTCTAACAGGG<br>TTCCAACAACTGCTTACAAGAAATGA<br>CATTCATATTTATGGAGCTACTGATTT<br>TATCCAAGTAGCTTTGGTAGCTTGCAT<br>AGAATTATCTCTTATTTTCCAAATAAA<br>AGTGATATTCGCTGGTACAAACTATG<br>GTAAGTTGGCTAATTATTTCATCACTC<br>TAGGTTCATTATTGGGTTTAGCCACCT<br>TTGGTATGTACATGCTTACTGCTATTA<br>ACGGTACAATAAAATTATACAATAAC<br>GAATATGACCCAAACCAAAGGAAATA<br>CTTTAACATTTCTACAATATTGCTTGC<br>ATCATCAATTAATATGCTAACGCTGAT<br>ACTTATATTGAAGCTGGTGGCAGCAA<br>TTAGAACAAGACGTTACTTAGGTTTG<br>AAGCAATTCGATAGTTTTCACATCCTA<br>TTAATCATGTCGACTCAAACATTAATA<br>ATTCCTTCTATCTTATTTATTCTATCAT<br>ACAGTTTGAGAGAGGATATGCATACT<br>GATCAATTAATAATCATCGGAAATCT<br>GATCGTGGTATTGTCATTACCATTGTC<br>CTCAATGTGGGCTTCGTCTCTAAACAA<br>TTCAAGTAAACCTACATCTTTGAATAC<br>TGATTTCTCAGGGCCAAAATCAAGTG<br>AAGAAGGGACAGCAATAAGTTTGCTA<br>TCACAAAACATGGAACCATCAATAGT<br>CACTAAATATACAAGAAGATCACCTG<br>GGTTATACCCAGTAAGCGTGGGTACA<br>CCAATTGAAAAAGAAGCATCATACAC<br>TCTTTTTGAAGCTACTGACATTGATTT<br>TGAAAGCAGTAGTAACGATATCACAA<br>GGACTTCATAG (SEQ ID NO: 73) |
| *Vanderwaltozyma polyspora* (receptor 2) | WHWLRL<br>RYGEPIY | MSGIDDMGDKPDI<br>LGLFYDANYDPGQ<br>GILTFISMYGNTTI<br>TFDELQLEVNSLIT<br>SGIMFGVRCGAAC<br>LTLLIMWMISKNK<br>KTPIFIINQCSLILII<br>MHSGLYFKNILSN<br>LNSLSYILTGFTQN<br>ITKNNIHVFGAANI<br>IQVLLVATIELSLV<br>FQIRVMFKGDSFR<br>KAGYGLLSIASGL | (wild type)<br>ATGTCAGGAATTGATGATATGGGTGA<br>TAAACCAGATATTTTAGGTTTATTTTA<br>TGATGCTAACTATGATCCAGGTCAAG<br>GTATACTCACATTTATTTCAATGTACG<br>GGAATACTACTATAACTTTTGATGAGT<br>TACAGTTAGAGGTCAATAGTTTAATTA<br>CAAGTGGTATTATGTTCGGCGTCAGAT<br>GTGGTGCTGCTTGTTTGACATTGTTAA<br>TAATGTGGATGATTTCTAAGAATAAG<br>AAGACTCCAATTTTTATTATTAATCAA<br>TGCTCGCTAATCCTTATTATTATGCAT<br>TCAGGTTTATATTTTAAGAATATTCTA |

TABLE 6-continued

| Sequences of Fungal GPCRs and Peptide Ligands | | | |
|---|---|---|---|
| Fungi | sequence of peptide analyte used | sequence of GPCRs used (all sequences are wild type) | DNA coding sequence of corresponding GPCRs that senses peptide analyte (WT or codon-optimized noted) |
| | | GIATVVMYFYSAI<br>TNMIAVYNQTYNS<br>TAKLFNVANILLST<br>SINFMTVVLIVKLF<br>LAVRSRRYLGLKQ<br>FDSFHILLIMSCQT<br>LIVPSILFILSYALS<br>TKLYTDHLVVIAT<br>LLVVLSLPLSSMW<br>ASAANNSPKPSSFT<br>TDYSNKNPSDTPS<br>FYSQSISSSMKSKF<br>PSKFIPFNFKSKDN<br>SSDTRSENTYIGNY<br>DMEKNGSPNHSYS<br>SKDQSEVYTIGVSS<br>MHTDIKSQKNISG<br>QHLYTPSTEIDEEA<br>RDFWAGRAVNNS<br>VPNDYQPSELPASI<br>LEELNSLDENNEG<br>FLETKRITFRKQ<br>(SEQ ID<br>NO: 74) | TCAAATTTGAATTCTTTATCATATATC<br>TTAACTGGGTTTACTCAAAATATCACT<br>AAAAATAATATACATGTCTTTGGTGCC<br>GCTAATATTATTCAAGTTTTATTAGTA<br>GCAACCATTGAACTGTCGTTAGTGTTT<br>CAAATTCGAGTCATGTTTAAAGGTGA<br>CAGTTTTAGAAAAGCTGGTTACGGTTT<br>GTTGTCAATTGCGTCTGGTTTGGGTAT<br>AGCTACTGTCGTCATGTATTTTTACTC<br>TGCCATTACAAATATGATTGCTGTTTA<br>TAATCAAACTTACAACTCCACTGCTAA<br>ATTATTTAACGTTGCAAACATTCTTCT<br>GTCTACATCGATAAATTTTATGACGGT<br>AGTATTAATTGTTAAATTATTTTTGGC<br>TGTTAGATCAAGAAGATATTTGGGTTT<br>AAAGCAGTTCGATAGTTTCCATATTTT<br>ATTGATTATGTCATGTCAAACATTGAT<br>TGTACCATCAATTCTTTTTATCTTATC<br>ATACGCTTTAAGTACTAAGCTGTACAC<br>TGATCATTTAGTTGTCATTGCAACTTT<br>ATTAGTCGTTCTATCTTTACCATTATC<br>TTCGATGTGGGCAAGCGCTGCAAATA<br>ATTCTCCTAAACCAAGCTCGTTTACAA<br>CCGATTATTCAAACAAGAATCCTAGT<br>GACACACCAAGCTTCTACAGTCAAAG<br>TATTAGTTCCTCGATGAAAAGCAAATT<br>CCCAAGCAAATTCATACCCTTCAATTT<br>CAAGTCTAAAGACAATTCTTCTGACA<br>CTAGATCAGAAAATACATATATTGGC<br>AATTATGACATGGAAAAGAATGGATC<br>ACCAAATCACTCTTATTCTTCCAAAGA<br>TCAAAGTGAAGTTTACACTATAGGTG<br>TAAGCTCTATGCACACAGATATAAAG<br>TCACAAAAGAATATCAGTGGACAGCA<br>TTTATATACCCCAAGTACAGAGATTG<br>ATGAAGAAGCTAGAGACTTCTGGGCG<br>GGCAGAGCTGTTAATAATTCAGTTCC<br>AAATGACTATCAACCATCTGAGTTAC<br>CAGCATCGATTCTTGAAGAATTGAATT<br>CACTGGATGAAAATAATGAAGGTTTC<br>TTGGAGACAAAAAGAATAACATTTAG<br>AAAACAATAG (SEQ ID NO: 75) |
| *Scheffersomyces stipitis* | WHWTSY<br>GVFEPG | MDTSINTLNPANII<br>VNYTLPNDPRVIS<br>VPFGAFDEYVNQS<br>MQKAIIHGVSIGSC<br>TIMLLIILIFNVKRK<br>KSPAFYLNSVTLT<br>AMIIRSALNLAYLL<br>GPLAGLSFTFSGLV<br>TPETNFSVSEATN<br>AFQVIVVALIEAS<br>MTFQVFVVFQSPE<br>VKKLGIALTSISAF<br>TGAAAVGFTINSTI<br>QQSRIYHSVVNGT<br>PTPTVATWSWVR<br>DVPTILFSTSVNIM<br>SFILILKLGFAIKTR<br>RYLGLRQFGSLHIL<br>LMMATQTLLAPSI<br>LILVHYGYGTSLN<br>SQLILISYLLVVLS<br>LPVSSIWAATANN<br>SPQLPSSATLSFMN<br>KTTSHFSES (SEQ<br>ID NO: 76) | (wild type)<br>ATGGATACTAGTATCAATACTCTCAAC<br>CCTGCGAATATCATTGTCAACTACACC<br>TTGCCAAATGATCCTAGAGTAATTAGT<br>GTCCCATTTGGAGCTTTTGACGAATAT<br>GTTAACCAATCTATGCAAAAGGCCAT<br>TATCCATGGAGTTTCCATTGGTTCATG<br>CACCATAATGCTTTTAATTATTTTGAT<br>CTTCAATGTCAAACGCAAGAAGTCGC<br>CAGCTTTCTATCTTAATTCGGTTACGT<br>TGACTGCAATGATTATTCGGTCTGCTC<br>TTAATTTGGCATATTTGCTAGGTCCTT<br>TGGCTGGATTAAGTTTTACGTTCTCCG<br>GCTTGGTAACTCCAGAAACCAATTTCT<br>CTGTCTCTGAAGCCACCAATGCTTTCC<br>AGGTTATTGTTGTTGCTCTTATCGAGG<br>CGTCCATGACATTTCAGGTGTTCGTCG<br>TCTTCCAATCACCAGAAGTGAAGAAG<br>TTGGGTATAGCTCTTACCTCCATATCT<br>GCATTCACGGGTGCTGCTGCTGTAGG<br>ATTTACTATCAATAGTACAATCCAACA<br>ATCGAGAATTTATCATTCAGTTGTCAA<br>TGGAACTCCTACGCCAACGGTCGCTA<br>CCTGGTCTTGGGTTAGAGATGTGCCTA<br>CGATACTTTTTTCTACTTCGGTTAACA<br>TAATGTCTTTCATCTTGATTCTCAAGT<br>TAGGGTTTGCCATAAAGACAAGAAGA<br>TACCTTGGCCTTCGGCAATTTGGCAGT<br>TTGCACATCTTATTGATGATGGCTACT |

TABLE 6-continued

| Sequences of Fungal GPCRs and Peptide Ligands | | | |
|---|---|---|---|
| Fungi | sequence of peptide analyte used | sequence of GPCRs used (all sequences are wild type) | DNA coding sequence of corresponding GPCRs that senses peptide analyte (WT or codon-optimized noted) |
| | | | CAAACATTATTGGCCCCATCTATTCTC<br>ATTCTTGTACATTACGGATATGGCACA<br>TCTCTGAATAGCCAGCTCATTCTTATA<br>AGTTACTTGCTTGTTGTTTTGTCTTTAC<br>CAGTATCCTCTATCTGGGCAGCAACA<br>GCCAACAATTCTCCTCAACTTCCATCT<br>TCCGCAACTCTTTCATTCATGAACAAA<br>ACGACCTCTCACTTTTCTGAAAGCTAG<br>(SEQ ID NO: 77) |
| *Schizosaccharomyces japonicus* | VSDRVK<br>QMLSHW<br>WNFRNP<br>DTANL | MYSWDEFRSPKQ<br>AEVLNQTVTLETI<br>VSTIQLPISEIDSME<br>RNRLLTGMTVAV<br>QVGLGSFILVLMCI<br>FSSSEKRKKPVFIF<br>NFAGNLVMTLRAI<br>FEVIVLASNNYSIA<br>VQYGFAFAAVRQ<br>YVHAFNIIILLLGPF<br>ILFIAEMSLMLQVR<br>IICSQHRPTMITTT<br>VISCIFTVVTLAFW<br>ITDMSQEIAYQLFL<br>KNYNMKQIVGYS<br>WLYFIAKITFAASII<br>FHSSVFSFKLMRAI<br>YIRRKIGQFPFGPM<br>QCIFIVSCQCLIVP<br>AIFTLIDSFTHTYD<br>GFSSMTQCLLIISL<br>PLSSLWATHTAQK<br>LQTMKDNTNPPSG<br>TQLTIRVDRTFDM<br>KFVSDSSDGSFTE<br>KTEETLP<br>(SEQ ID<br>NO: 78) | (codon optimized)<br>ATGTACTCCTGGGACGAATTCAGATC<br>CCCAAAGCAAGCTGAAGTTTTGAACC<br>AAACCGTTACCTTGGAAACTATTGTTT<br>CCACCATTCAATTGCCAATCTCTGAAA<br>TTGACTCCATGGAAAGAAACAGATTG<br>TTGACCGGTATGACTGTCGCTGTTCAA<br>GTTGGTTTAGGTTCCTTCATTTTAGTTT<br>TGATGTGTATTTTCTCTTCCTCTGAAA<br>AGAGAAAGAAGCCAGTCTTCATCTTC<br>AACTTCGCTGGTAACTTGGTTATGACT<br>TTGAGAGCTATTTTCGAAGTTATCGTT<br>TTGGCTTCTAACAACTACTCTATCGCT<br>GTTCAATACGGTTTCGCTTTTGCTGCC<br>GTCAGACAATACGTTCACGCCTTCAA<br>CATTATCATCTTGTTGTTGGGTCCATT<br>CATCTTGTTCATCGCTGAAATGTCTTT<br>GATGTTGCAAGTTAGAATCATTTGTTC<br>CCAACACAGACCAACTATGATTACCA<br>CCACTGTTATCTCTTGTATTTTCACTGT<br>TGTTACCTTGGCCTTCTGGATCACCGA<br>CATGTCTCAAGAAATTGCTTACCAATT<br>GTTCTTGAAAAACTACAACATGAAGC<br>AAATTGTTGGTTACTCCTGGTTGTACT<br>TTATCGCTAAGATCACCTTCGCTGCTT<br>CCATTATCTTCCATTCCTCCGTCTTCTC<br>CTTCAAATTGATGCGTGCTATTTACAT<br>TCGTAGAAAGATCGGTCAATTCCCATT<br>CGGTCCAATGCAATGTATCTTCATTGT<br>TTCCTGTCAATGTTTGATCGTTCCAGC<br>TATTTTCACTTTGATCGATTCTTTCACC<br>CACACTTACGATGGTTTCTCCTCCATG<br>ACTCAATGTTTGTTGATCATCTCCTTA<br>CCATTGTCTTCCTTGTGGGCCACCCAC<br>ACCGCTCAAAAGTTGCAAACCATGAA<br>GGATAACACTAACCCACCATCTGGTA<br>CCCAATTAACCATCAGAGTTGATCGT<br>ACTTTCGACATGAAGTTCGTTTCCGAC<br>TCCTCTGACGGTTCTTTCACTGAAAAG<br>ACCGAAGAAACTTTGCCA (SEQ ID<br>NO: 79) |
| *Saccharomyces castellii* | NWHWLR<br>LDPGQPL<br>Y | MSDAPPPLSELFY<br>NSSYNPGLSIISYTS<br>IYGNGTEVTFNEL<br>QSIVNKKITEAIMF<br>GVRCGAAILTIIVM<br>WMISKKKKTPIFII<br>NQVSLFLILLHSAF<br>NFRYLLSNYSSVT<br>FALTGFPQFIHRND<br>VHVYAAASIFQVL<br>LVASIEISLMFQIR<br>VIFKGDNFKRIGTI<br>LTALSSSLGLATV<br>AMYFVTAIKGIIAT<br>YKDVNDTQQKYF<br>NVATILLASSINFM<br>TLILVIKLILAIRSR<br>RFLGLKQFDSFHIL<br>LIMSFQSLLAPSILF<br>ILAYSLDPNQGTD | (codon optimized)<br>ATGTCTGACGCTCCACCACCATTGTCC<br>GAATTGTTCTACAACTCCTCCTACAAC<br>CCAGGTTTGTCTATCATTTCTTACACT<br>TCCATTTACGGTAACGGTACTGAAGTT<br>ACCTTTAACGAATTACAATCTATCGTC<br>AACAAGAAGATTACTGAAGCTATCAT<br>GTTCGGTGTCAGATGTGGTGCCGCTAT<br>TTTGACTATCATTGTCATGTGGATGAT<br>TTCTAAGAAGAAAAAGACCCCAATTT<br>TCATCATCAACCAAGTTTCTTTATTCT<br>TGATTTTGTTGCACTCCGCTTTCAACT<br>TCAGATACTTGTTGTCTAACTACTCTT<br>CCGTCACTTTCGCCTTGACCGGTTTCC<br>CACAATTCATCCACAGAAACGACGTC<br>CACGTCTACGCTGCTGCTTCTATCTTC<br>CAAGTCTTGTTGGTCGCTTCTATTGAA<br>ATTTCCTTAATGTTCCAAATCAGAGTC<br>ATTTTCAAGGGTGATAACTTCAAGAG<br>AATTGGTACTATCTTGACCGCTTTGTC |

TABLE 6-continued

Sequences of Fungal GPCRs and Peptide Ligands

| Fungi | sequence of peptide analyte used | sequence of GPCRs used (all sequences are wild type) | DNA coding sequence of corresponding GPCRs that senses peptide analyte (WT or codon-optimized noted) |
|---|---|---|---|
| | | VLVTVATLLVVLS LPLSSMWATAAN NASRPSSVGSDWT PSNSDYYSNGPSS VKTESVKSDEKVS LRSRIYNLYPKSKS EFEQSSEHTYVDK VDLENNFYELSTPI TERSPSSIIKKGKQ GISTRETVKKLDSL DDIYTPNTAADEE ARKFWSEDVSNEL DSLQKIETETSDEL SPEMLQLMIGQEE EDDNLLATKKITV KKQ (SEQ ID NO: 80) | CTCTTCTTTGGGTTTAGCTACTGTTGC TATGTACTTTGTCACCGCTATTAAGGG TATTATTGCTACCTACAAGGATGTTAA CGATACTCAACAAAAGTACTTCAACG TTGCTACTATCTTGTTGGCTTCCTCTAT CAACTTTATGACCTTGATCTTGGTTAT CAAGTTGATCTTGGCTATCAGATCCAG AAGATTCTTGGGTTTGAAACAATTCG ACTCTTTCCATATCTTGTTGATCATGT CTTTTCAATCTTTGTTGGCCCCATCCA TTTTGTTCATTTTGGCTTACTCTTTGGA CCCAAACCAAGGTACCGACGTCTTGG TTACTGTCGCTACTTTGTTGGTCGTCT TATCTTTGCCATTGTCCTCCATGTGGG CTACTGCTGCTAACAACGCCTCCAGA CCATCCTCTGTTGGTTCCGACTGGACT CCATCTAACTCCGACTACTACTCTAAC GGTCCATCTTCTGTCAAGACCGAATCT GTCAAATCTGATGAAAAGGTCTCCTT GAGATCCAGAATTTACAACTTGTACC CAAAGTCTAAGTCTGAATTCGAACAA TCCTCCGAACACACTTACGTTGACAA GGTCGACTTGGAAAACAACTTCTACG AATTGTCCACCCCAATCACCGAAAGA TCTCCATCTTCTATCATTAAGAAGGGT AAGCAAGGTATTTCTACTAGAGAAAC CGTCAAAAAGTTGGACTCCTTGGATG ACATTTACACTCCAAACACTGCTGCTG ATGAAGAAGCCAGAAAGTTCTGGTCT GAAGATGTTTCTAACGAATTGGATTCC TTACAAAAAATCGAAACTGAAACTTC CGATGAATTATCCCCAGAAATGTTAC AATTGATGATTGGTCAAGAAGAAGAA GACGATAACTTATTGGCTACCAAGAA GATCACCGTCAAGAAGCAA (SEQ ID NO: 81) |
| Schizosaccharomyces octosporus | TYEDFLR VYKNWW SFQNPDR PDL | MREPWWKNYYT MNGTQVQNQSIPI LSTQGYIQVPLSTI DKAERNRILTGMT VSAQLALGVLIMV MSILLSSPEKRKTP VFIVNSASIISMCIR AILMIVNLCSESYS LAVMYGFVFELV GQYVHVFDILVMII GTIIIITAEVSMLLQ VRIICAHDRKTQRI VTCISSGLSLIVVA FWFTDMCQEIKYL LWLTPYNNHQISG YYWVYFVGKILFA VSIMFHSAVFSYK LFHAIQIRKKIGQF PFGPMQCILIISCQ CLFVPAIFTIIDSFI HTYDGFSSMTQCL LIVSLPLSSLWASS TALKLQSLKSTTSP GDTTQVSIRVDRT YDIKRIPTEELSSV DETEIKKWP (SEQ ID NO: 82) | (codon optimized) ATGCGTGAACCATGGTGGAAGAACTA CTACACCATGAACGGTACCCAAGTCC AAAACCAATCCATCCCAATTTTGTCCA CCCAAGGTTACATTCAAGTTCCATTGT CCACCATCGATAAGGCTGAAAGAAAC AGAATTTTGACTGGTATGACCGTTTCT GCTCAATTGGCCTTGGGTGTCTTGATC ATGGTCATGTCTATTTTGTTGTCCTCC CCAGAAAAGAGAAAGACCCCAGTTTT CATCGTCAACTCTGCCTCTATCATTTC CATGTGTATTAGAGCTATCTTGATGAT TGTCAACTTGTGTTCTGAATCCTACTC TTTGGCTGTTATGTACGGTTTCGTCTT CGAATTGGTTGGTCAATACGTTCACGT TTTTGACATTTTGGTTATGATTATTGG TACCATCATCATTATTACCGCTGAAGT TTCCATGTTGTTGCAAGTCAGAATTAT TTGTGCTCACGACAGAAAGACTCAAA GAATTGTTACCTGTATCTCTTCTGGTT TATCCTTGATCGTCGTTGCCTTCTGGT TCACTGATATGTGTCAAGAAATTAAG TACTTGTTGTGGTTGACCCCATACAAC AACCACCAAATCTCTGGTTACTACTGG GTTTACTTCGTCGGTAAGATCTTGTTC GCCGTTTCCATTATGTTCCACTCTGCC GTCTTCTCCTACAAGTTGTTCCACGCT ATCCAAATTAGAAAGAAGATTGGTCA ATTCCCATTCGGTCCAATGCAATGTAT TTTAATTATTTCCTGTCAATGTTTGTTC GTTCCAGCTATTTTCACTATCATCGAC TCTTTCATCCACACTTACGACGGTTTT TCCTCCATGACCCAATGTTTGTTGATC GTCTCTTTGCCATTGTCCTCCTTGTGG GCCTCTTCCACTGCTTTAAAGTTGCAA |

TABLE 6-continued

Sequences of Fungal GPCRs and Peptide Ligands

| Fungi | sequence of peptide analyte used | sequence of GPCRs used (all sequences are wild type) | DNA coding sequence of corresponding GPCRs that senses peptide analyte (WT or codon-optimized noted) |
|---|---|---|---|
| | | | TCTTTGAAGTCTACCACCTCTCCAGGT<br>GACACTACTCAAGTTTCCATTAGAGTC<br>GACAGAACCTACGACATCAAGAGAAT<br>CCCAACTGAAGAATTGTCTTCTGTTGA<br>CGAAACCGAAATCAAGAAGTGGCCA<br>(SEQ ID NO: 83) |
| *Aspergillus nidulans* | WCRFRG<br>QVCG | MATHNQISDQCQ<br>WSYPEVFTTQAVE<br>EPTAEPASYHLHS<br>TLTIMASNFDPWN<br>QTITFRLEDGTPFD<br>ISVDYLDGILQYSI<br>RACVNYAAQLGA<br>SVILFVILVLLTRA<br>EKRASCLFWLNSL<br>ALLLNFARLLCDV<br>LFFTGNFVRIYTLI<br>SADESRVTASDLA<br>TSIVGAIMTALLLT<br>TIEISLVLQVQVVC<br>SNLRRIYRRALLC<br>VSAVVATATIAIR<br>YSLLAVNIRAILEF<br>SDPTTYNWLESLA<br>TVALTISICYFCVIF<br>VTKLGFAIRLRRK<br>LGLSELGPMKVVF<br>IMGCQTLVIPGKR<br>TLSSLIPPVIVSITH<br>YVSDVPELQTNVL<br>TIVALSLPLSSIWA<br>GTTIDKPVTHSNV<br>RNLWQILSFSGYR<br>PKQSTYIATTTTAT<br>TNAKQCTHCYSES<br>RLLTEKESGRNND<br>TSSKSSSQYGIAVE<br>HDISVRSARRESFD<br>V (SEQ ID<br>NO: 84) | (codon optimized)<br>ATGGCTACCCACAACCAAATCTCTGA<br>TCAATGTCAATGGTCTTACCCAGAAGT<br>CTTCACCACTCAAGCTGTCGAAGAAC<br>CAACCGCCGAACCAGCTTCTTACCACT<br>TGCACTCTACCTTGACTATTATGGCTT<br>CTAACTTCGACCCATGGAACCAAACC<br>ATTACCTTCAGATTGGAAGACGGTAC<br>TCCATTCGACATTTCTGTCGACTACTT<br>GGACGGTATCTTGCAATACTCTATCAG<br>AGCTTGTGTCAACTACGCTGCTCAATT<br>GGGTGCTTCTGTCATTTTGTTTGTTAT<br>CTTGGTCTTGTTGACTAGAGCCGAAA<br>AAAGAGCTTCTTGTTTGTTCTGGTTAA<br>ACTCCTTAGCTTTGTTGTTGAACTTCG<br>CCAGATTGTTGTGTGACGTCTTGTTCT<br>TCACCGGTAACTTCGTCAGAATTTACA<br>CTTTGATCTCCGCTGACGAATCTAGAG<br>TTACTGCTTCCGACTTGGCTACTTCCA<br>TCGTCGGTGCTATCATGACCGCTTTGT<br>TGTTGACCACTATTGAAATTTCTTTGG<br>TTTTGCAAGTCCAAGTCGTTTGTTCTA<br>ACTTGAGAAGAATCTACAGAAGAGCC<br>TTGTTGTGTGTTTCCGCCGTCGTTGCC<br>ACTGCTACCATTGCTATTAGATACTCC<br>TTGTTGGCTGTCAACATTAGAGCTATT<br>TTGGAATTCTCCGACCCAACTACTTAC<br>AACTGGTTGGAATCTTTAGCTACCGTC<br>GCCTTGACCATCTCCATCTGTTACTTC<br>TGTGTCATCTTCGTCACCAAGTTAGGT<br>TTCGCTATTAGATTGAGAAGAAAGTT<br>GGGTTTATCTGAATTGGGTCCAATGA<br>AGGTCGTCTTCATCATGGGTTGTCAAA<br>CCTTGGTCATCCCAGGTAAAAGAACC<br>TTGTCTTCTTTGATTCCACCAGTCATT<br>GTTTCTATTACTCACTACGTCTCCGAC<br>GTCCCAGAATTGCAAACTAACGTTTTG<br>ACTATCGTCGCCTTGTCCTTGCCATTG<br>TCCTCTATTTGGGCTGGTACCACCATT<br>GACAAGCCAGTCACTCACTCTAACGT<br>TAGAAACTTGTGGCAAATCTTGTCCTT<br>CTCTGGTTACAGACCAAAGCAATCTA<br>CCTACATTGCTACCACTACTACCGCTA<br>CTACCAACGCTAAGCAATGTACCCAC<br>TGTTACTCTGAATCTAGATTGTTGACT<br>GAAAAGGAATCTGGTCGTAACAACGA<br>CACTTCTTCTAAGTCTTCCTCCCAATA<br>CGGTATCGCTGTCGAACACGATATTTC<br>CGTTAGATCTGCTCGTCGTGAATCTTT<br>TGACGTCTAG (SEQ ID NO: 85) |
| *Aspergillus oryzae* | WCALPG<br>QGC | MDSKFDPYSQNLT<br>FHAADGTPFQVPV<br>MTLNDFYQYCIQI<br>CINYGAQFGASVII<br>FIILLLLTRPDKRA<br>SSVFFLNGGALLL<br>NMGRLLCHMIYFT<br>TDFVKAYQYFSSD<br>YSRAPTSAYANSIL<br>GVVLTTLLLVCIET<br>SLVLQVQVVCANL<br>RRRYRTVLLCVSIL<br>VALIPVGLRLGYM<br>VENCKTIVQTDTP | (codon optimized)<br>ATGGACTCTAAGTTCGACCCATACTCT<br>CAAAACTTGACTTTCCACGCTGCTGAC<br>GGTACCCCATTTCAAGTTCCAGTCATG<br>ACCTTGAACGACTTTTACCAATACTGT<br>ATTCAAATTTGTATCAACTACGGTGCT<br>CAATTCGGTGCTTCCGTCATCATTTTC<br>ATTATCTTGTTGTTATTGACTAGACCA<br>GACAAAAGAGCTTCTTCTGTTTTCTTC<br>TTAAACGGTGGTGCCTTGTTGTTGAAC<br>ATGGGTAGATTGTTGTGTCACATGATT<br>TACTTCACTACTGACTTCGTCAAGGCT<br>TACCAATACTTCTCTTCTGATTACTCT<br>AGAGCCCCAACCTCTGCCTACGCTAA |

TABLE 6-continued

Sequences of Fungal GPCRs and Peptide Ligands

| Fungi | sequence of peptide analyte used | sequence of GPCRs used (all sequences are wild type) | DNA coding sequence of corresponding GPCRs that senses peptide analyte (WT or codon-optimized noted) |
|---|---|---|---|
| | | LSLVWLESATNIVI<br>TISICFFCSIFIIKLG<br>FAIHQRRRLGVRD<br>FGPMKVIFVMGCQ<br>TLTVPALLSILQYA<br>VSVPELNSNIMTL<br>VTISLPLSSIWAGV<br>SLTRSSSTENSPSR<br>GALWNRLTDSTGT<br>RSNQTSSTDTAVA<br>MTYPSNKSSTVCY<br>ADQSSVKRQYDPE<br>QGHGISVEHDVSV<br>HSCQRL<br>(SEQ ID<br>NO: 86) | CTCCATTTTGGGTGTCGTCTTGACCAC<br>CTTGTTGTTGGTTTGTATCGAAACCTC<br>CTTGGTTTTACAAGTCCAAGTCGTCTG<br>TGCTAACTTGAGACGTAGATACAGAA<br>CCGTCTTATTGTGTGTTTCTATCTTGGT<br>CGCCTTGATCCCAGTCGGTTTGAGATT<br>GGGTTACATGGTTGAAAACTGTAAGA<br>CTATTGTTCAAACTGATACCCCATTGT<br>CTTTGGTTTGGTTGGAATCTGCTACTA<br>ACATCGTCATTACCATCTCCATCTGTT<br>TCTTCTGTTCTATCTTCATCATCAAGTT<br>GGGTTTCGCCATTCACCAAAGAAGAA<br>GATTGGGTGTCAGAGATTTCGGTCCA<br>ATGAAGGTCATTTTCGTCATGGGTTGT<br>CAAACTTTGACTGTTCCAGCTTTGTTG<br>TCTATTTTGCAATACGCTGTCTCTGTC<br>CCAGAATTGAACTCTAACATTATGACT<br>TTGGTTACTATCTCTTTGCCATTGTCCT<br>CCATTTGGGCTGGTGTTTCTTTGACCC<br>GTTCTTCCTCCACCGAAAACTCTCCAT<br>CCAGAGGTGCTTTGTGGAACCGTTTG<br>ACCGACTCTACCGGTACCAGATCTAA<br>CCAAACCTCTTCCACCGACACCGCCGT<br>CGCTATGACCTACCCATCTAACAAGTC<br>TTCTACTGTCTGTTACGCCGATCAATC<br>TTCTGTCAAGAGACAATACGATCCAG<br>AACAAGGTCACGGTATCTCTGTTGAA<br>CACGATGTTTCTGTCCACTCCTGTCAA<br>AGATTGTAG (SEQ ID NO: 87) |
| *Beauvaria bassiana* | WCMRPG<br>QPCW | MDGSSAPSSPTPDP<br>TFDRFAGNVTFFL<br>ADHITTTSVPMPV<br>LNAYYDESLCTTM<br>NYGAQLGACLVM<br>LVVVVALTPAAKL<br>ARRPASALHLVGL<br>LLCAVRSGLLFAY<br>FVSPISHFYQVWA<br>GDFSAVSRRYWD<br>ASLAANTLAFPLV<br>VVVEAALINQAW<br>TMVAFWPRAAKA<br>AACACSAVIVLLTI<br>GTRLAYTIVQNHA<br>IVTAVPPEHFLWAI<br>QWSAVMGAVSIF<br>WFCAVFNVKLVC<br>HLVANRGILPSISV<br>VNPMEVLVMTNG<br>TLMIIPSIFAGLEW<br>AKFTNFESGSLTLT<br>SVIIILPLGTLAAQR<br>ISGQGSQGYQAGH<br>LFHEQQQQARTR<br>SGAFGSASQQSHP<br>TNKVPSSITLSTSG<br>TPITPQISAGSRPEL<br>PLVDRSERLDPIDL<br>ELGRIDAFRGSSDF<br>SPSTARPKRMQRD<br>NFA (SEQ ID<br>NO: 88) | (codon optimized)<br>ATGGATGGTTCTTCTGCTCCATCTTCT<br>CCAACTCCAGATCCAACCTTCGACAG<br>ATTCGCCGGTAACGTCACTTTCTTCTT<br>GGCTGACCACATCACCACTACCTCCGT<br>TCCAATGCCAGTCTTGAACGCCTACTA<br>CGACGAATCCTTGTGTACTACCATGA<br>ACTACGGTGCTCAATTAGGTGCTTGTT<br>TAGTTATGTTGGTTGTCGTTGTTGCTT<br>TGACCCCAGCTGCTAAGTTGGCTAGA<br>AGACCAGCTTCTGCTTTGCATTTGGTT<br>GGTTTGTTGTTGTGTGCTGTTAGATCC<br>GGTTTGTTGTTTGCTTACTTCGTCTCCC<br>CAATCTCTCACTTTTACCAAGTTTGGG<br>CTGGTGACTTCTCTGCCGTTTCCAGAA<br>GATACTGGGACGCTTCTTTGGCTGCCA<br>ACACTTTAGCTTTCCCATTGGTTGTCG<br>TCGTTGAAGCTGCTTTGATCAACCAAG<br>CTTGGACCATGGTTGCTTTCTGGCCAA<br>GAGCCGCTAAGGCCGCTGCCTGTGCT<br>TGTTCTGCTGTCATTGTCTTGTTGACT<br>ATTGGTACTAGATTGGCCTACACTATC<br>GTCCAAAACCACGCTATTGTTACTGCC<br>GTCCCACCAGAACACTTCTTGTGGGCT<br>ATTCAATGGTCCGCTGTTATGGGTGCT<br>GTTTCCATCTTCTGGTTTTGTGCCGTTT<br>TCAACGTCAAGTTGGTCTGTCACTTAG<br>TCGCTAACAGAGGTATCTTGCCATCTA<br>TCTCTGTTGTTAACCCAATGGAAGTCT<br>TGGTTATGACTAACGGTACCTTGATGA<br>TTATCCCATCTATCTTCGCTGGTTTGG<br>AATGGGCTAAGTTCACCAACTTCGAA<br>TCCGGTTCTTTGACTTTGACTTCCGTT<br>ATTATTATCTTGCCATTGGGTACTTTG<br>GCTGCCCAACGTATTTCTGGTCAAGGT<br>TCCCAAGGTTACCAAGCTGGTCACTTA<br>TTCCACGAACAACAACAACAACAAGC<br>TCGTACCCGTTCCGGTGCCTTCGGTTC<br>CGCTTCTCAACAATCCCATCCAACTAA<br>CAAGGTTCCATCCTCTATTACCTTGTC<br>TACCTCTGGTACTCCAATTACTCCACA<br>AATCTCTGCCGGTTCCCGTCCAGAATT |

TABLE 6-continued

Sequences of Fungal GPCRs and Peptide Ligands

| Fungi | sequence of peptide analyte used | sequence of GPCRs used (all sequences are wild type) | DNA coding sequence of corresponding GPCRs that senses peptide analyte (WT or codon-optimized noted) |
|---|---|---|---|
| | | | ACCATTGGTTGATAGATCCGAACGTTT<br>GGACCCAATTGACTTGGAATTGGGTA<br>GAATCGATGCTTTCAGAGGTTCTTCCG<br>ACTTCTCTCCATCCACCGCTAGACCAA<br>AGCGTATGCAACGTGATAACTTCGCC<br>TAG (SEQ ID NO: 89) |
| *Candida lustianiae* | KWKWIK<br>FRNTDVI<br>G | MNPADINIEYTLG<br>DTAFSSTFADFEA<br>WKTRNTQFAIVNG<br>VALACGIILMVVS<br>WIIIVNKRAPIFAM<br>NQTMLVIMVIKSA<br>MYLKHIMGPLNSL<br>TFRFTGLMEESWA<br>PYNVYVTINVLHV<br>LLVAAVESSLVFQI<br>HVVFKSSRARVAG<br>RAIVSAMSTLALLI<br>VSLYLYSTVRHAQ<br>TLRAELSHGDTTT<br>VEPWVDNVPLILF<br>SASLNVLCLLLAL<br>KLVFAVRTRRHLG<br>LRQFDSFHILIIMA<br>TQTFVIPSSLVIAN<br>YRYASSPLLSSISII<br>VAVCNLPLCSLWA<br>CSNNNSSYPTSSQ<br>NTILSRYETETSQA<br>TDASSTTCAGIAE<br>KGFDKSPDSPTFG<br>DQDSVSISHILDSL<br>EKDVEGVTTHRLT<br>(SEQ ID<br>NO: 90) | (codon optimized)<br>ATGAACCCAGCTGACATCAACATCGA<br>ATACACCTTGGGTGATACTGCTTTCTC<br>TTCCACTTTCGCTGATTTCGAAGCTTG<br>GAAAACTAGAAACACTCAATTCGCTA<br>TTGTCAACGGTGTCGCTTTGGCTTGTG<br>GTATTATCTTGATGGTCGTTTCTTGGA<br>TTATTATTGTTAACAAGAGAGCTCCAA<br>TCTTCGCTATGAACCAAACTATGTTGG<br>TTATCATGGTTATTAAGTCCGCTATGT<br>ACTTGAAGCATATCATGGGTCCATTG<br>AACTCCTTGACCTTCCGTTTCACCGGT<br>TTAATGGAAGAATCCTGGGCTCCATA<br>CAACGTTTACGTCACTATTAACGTCTT<br>GCATGTTTTGTTGGTCGCTGCTGTCGA<br>ATCCTCTTTGGTCTTCCAAATCCATGT<br>TGTTTTCAAGTCTTCTAGAGCCAGAGT<br>TGCTGGTAGAGCCATTGTTTCTGCTAT<br>GTCCACTTTGGCCTTGTTGATCGTTTC<br>TTTGTACTTGTACTCTACTGTTAGACA<br>TGCTCAAACTTTGCGTGCTGAATTATC<br>TCATGGTGACACTACCACTGTTGAACC<br>ATGGGTCGATAACGTTCCATTGATTTT<br>GTTTTCCGCTTCTTTGAACGTTTTGTGT<br>TTGTTGTTGGCCTTGAAATTGGTTTTC<br>GCTGTCAGAACCAGAAGACATTTAGG<br>TTTAAGACAATTCGACTCTTTCCACAT<br>CTTGATTATTATGGCCACTCAAACTTT<br>CGTTATCCCATCCTCTTTGGTCATCGC<br>TAACTACAGATACGCTTCTTCCCCATT<br>GTTGTCTTCCATTTCCATCATCGTCGC<br>CGTCTGTAACTTGCCATTGTGTTCCTT<br>GTGGGCTTGTTCTAACAACAACTCTTC<br>CTACCCAACTTCTTCTCAAAACACTAT<br>TTTGTCCAGATACGAAACTGAAACCT<br>CTCAAGCTACTGACGCTTCCTCTACCA<br>CCTGTGCCGGTATTGCTGAAAAGGGT<br>TTCGACAAGTCTCCAGACTCTCCAACT<br>TTCGGTGACCAAGACTCCGTCTCTATC<br>TCCCATATCTTGGACTCTTTGGAAAAG<br>GATGTTGAAGGTGTCACCACCCATAG<br>ATTGACTTAG (SEQ ID NO: 91) |
| *Candida tenuis* | FSWNYRL<br>KWQPIS | MDSYLLNHPGDIS<br>LNFALPLSDEVYTI<br>TFNDLDSQSSFSIQ<br>YLVIHSCAITVCLT<br>LLVLLNLFIRNKKT<br>PVFVLNQVILFFAI<br>VRSSLFIGFMKSPL<br>STITASFTGIISDDQ<br>KHFYKVSVAANA<br>ALIILVMLIQVSFT<br>YQIYIIFRSPEVRKF<br>GVFMTSALGVLM<br>AVTFGFYVNSAVA<br>STKQYQHIFYSTDP<br>YIMDSWVTGLPPI<br>LYSASVIAMSLVL<br>VLKLVAAVRTRR<br>YLGLKQFSSYHILL<br>IMFTQTLFVPTILTI<br>LAYAFYGYNDILI<br>HISTTITVVLLPFTS<br>IWASIANNSRSLM | (codon optimized)<br>ATGGACTCCTACTTGTTGAACCATCCA<br>GGTGACATCTCTTTGAACTTCGCCTTG<br>CCATTGTCCGATGAAGTCTACACTATT<br>ACCTTCAACGACTTAGACTCTCAATCT<br>TCTTTTTCCATTCAATACTTGGTCATC<br>CACTCTTGTGCCATTACCGTCTGTTTG<br>ACCTTGTTGGTTTTGTTGAACTTGTTC<br>ATCAGAAACAAGAAGACTCCAGTCTT<br>CGTTTTGAACCAAGTCATCTTGTTCTT<br>CGCTATCGTCAGATCTTCTTTGTTCAT<br>CGGTTTTATGAAGTCTCCATTGTCCAC<br>CATCACCGCCTCTTTCACCGGTATCAT<br>TTCTGATGACCAAAAACACTTCTACA<br>AGGTCTCCGTCGCTGCTAACGCCGCTT<br>TGATCATTTTGGTCATGTTGATTCAAG<br>TTTCTTTCACTTACCAAATCTACATTA<br>TTTTCAGATCCCCAGAAGTTAGAAAG<br>TTCGGTGTCTTCATGACCTCCGCCTTG<br>GGTGTCTTGATGGCTGTTACCTTCGGT<br>TTTTACGTTAACTCCGCTGTCGCTTCT<br>ACCAAGCAATACCAACACATCTTCTA |

TABLE 6-continued

| Sequences of Fungal GPCRs and Peptide Ligands | | | |
|---|---|---|---|
| Fungi | sequence of peptide analyte used | sequence of GPCRs used (all sequences are wild type) | DNA coding sequence of corresponding GPCRs that senses peptide analyte (WT or codon-optimized noted) |
| | | SAASLYFSGSNSSL SELSSPSPSDNDTL NENVFAFFPDKLQ KMNSSEAVSAVD KVVVHDHFDTISQ KSIPHDILEILQGN EGGQMKEHISVYS DDSFSKTTPPIVGG NLLITNTDIGMK (SEQ ID NO: 92) | CTCTACCGACCCATACATCATGGACTC TTGGGTCACTGGTTTGCCACCAATCTT GTACTCTGCTTCCGTCATCGCTATGTC TTTGGTCTTGGTTTTGAAGTTGGTCGC TGCTGTCAGAACCAGAAGATACTTGG GTTTGAAGCAATTCTCCTCCTACCACA TCTTGTTGATTATGTTCACCCAAACCT TGTTCGTTCCAACCATCTTGACCATCT TAGCTTACGCTTTCTACGGTTACAACG ATATCTTGATCCATATTTCTACCACCA TCACCGTTGTCTTGTTGCCATTCACCT CCATTTGGGCTTCTATCGCCAACAACT CTAGATCCTTGATGTCTGCCGCTTCCT TGTACTTCTCCGGTTCCAACTCCTCTT TGTCTGAATTGTCTTCTCCATCTCCAT CTGATAACGACACTTTGAACGAAAAC GTCTTCGCCTTTTTTCCAGACAAGTTG CAAAAGATGAACTCTTCTGAAGCCGT TTCTGCTGTCGACAAGGTCGTTGTTCA CGACCACTTTGATACCATCTCCCAAAA GTCTATCCCACACGACATCTTGGAAAT TTTGCAAGGTAACGAAGGTGGTCAAA TGAAGGAACACATCTCTGTCTACTCTG ATGACTCTTTCTCCAAGACTACTCCAC CAATTGTCGGTGGTAACTTGTTGATCA CCAACACCGACATCGGTATGAAG (SEQ ID NO: 93) |
| *Neosartorya fischeri* | WCHLPG QGC | MNSTFDPWTQNIT LTQSDGTTVISSLA LADDYLHYMIRLG INYGAQLGACAVL LLVLLLLTRPEKR VSSVFVLNVAALL ANIIRLGCQLSYFS TGFARMYALLAG DFSRVSRGAYAGQ VMASVFFTIVFICV EASLVLQVQVVCS NLRRQYRILLLGA STLAALVPIGVRLT YSVLNCMVIMHA GTMDHLDWLESA TNIVTTVSICFFCA VFVVKLGLAIKMR KRLGVKQFGPMR VIFIMGCQTMTIPA IFAICQYFSRIPEFS HNVLTLVIISLPLSS IWAGFALVQANST ARSTESRHHLWNI LSSDGATRDKPSQ CVSSPMTSPTTTC YSEQSTSKPQQDP ENGFGISVAHDISI HSFRKDAHGDI (SEQ ID NO: 94) | (codon optimized) ATGAACTCCACCTTCGACCCATGGAC CCAAAACATTACTTTGACTCAATCCGA CGGTACCACTGTCATCTCCTCTTTGGC TTTGGCCGATGACTACTTGCACTACAT GATTAGATTGGGTATCAACTACGGTG CCCAATTGGGTGCTTGTGCTGTTTTGT TGTTGGTTTTGTTATTGTTGACTAGAC CAGAAAAGAGAGTTTCTTCTGTCTTCG TTTTGAACGTCGCTGCTTTGTTGGCTA ACATCATCAGATTGGGTTGTCAATTGT CCTACTTCTCTACCGGTTTCGCTAGAA TGTACGCCTTGTTGGCCGGTGACTTCT CCAGAGTCTCTCGTGGTGCTTACGCCG GTCAAGTTATGGCCTCCGTCTTCTTCA CCATTGTCTTCATTTGTGTTGAAGCTT CTTTGGTTTTGCAAGTTCAAGTCGTCT GTTCTAACTTGAGAAGACAATACAGA ATCTTGTTATTGGGTGCTTCCACTTTG GCTGCCTTGGTTCCAATTGGTGTTCGT TTGACTTACTCCGTTTTAAACTGTATG GTTATTATGCACGCTGGTACTATGGAC CACTTGGATTGGTTGGAATCTGCTACC AACATCGTTACTACCGTTTCTATTTGT TTCTTCTGTGCTGTTTTCGTTGTCAAAT TAGGTTTGGCTATCAAGATGAGAAAG CGTTTGGGTGTCAAACAATTCGGTCCA ATGAGAGTTATCTTCATCATGGGTTGT CAAACCATGACCATCCCAGCTATTTTC GCTATTTGTCAATACTTCTCTAGAATT CCAGAATTTTCTCATAACGTTTTGACT TTGGTTATCATCTCTTTGCCATTGTCTT CTATCTGGGCCGGTTTTGCTTTGGTCC AAGCCAACTCTACCGCCAGATCTACC GAATCTAGACATCATTTGTGGAACATT TTGTCTTCCGATGGTGCTACCAGAGAC AAGCCATCCCAATGTGTTTCTTCTCCA ATGACCTCTCCAACCACTACCTGTTAC TCCGAACAATCCACCTCTAAGCCACA ACAAGACCCAGAAAACGGTTTTGGTA TTTCTGTTGCCCACGATATTTCCATCC ACTCTTTCAGAAAGGACGCCCACGGT GATATTTAG (SEQ ID NO: 95) |

TABLE 6-continued

Sequences of Fungal GPCRs and Peptide Ligands

| Fungi | sequence of peptide analyte used | sequence of GPCRs used (all sequences are wild type) | DNA coding sequence of corresponding GPCRs that senses peptide analyte (WT or codon-optimized noted) |
|---|---|---|---|
| *Neurospora* | QWCRIHG | MASSSSPPADIFSG | (codon optimized) |
| *crassa* | QSCW | ITQSLNSTHATLTL | ATGGCGTCCTCTTCCTCACCACCTGCA |
| | | PIPPADRDHLENQ | GACATTTTCTCAGGGATCACGCAATC |
| | | VLFLFDNHGQLLN | ACTAAATAGTACACACGCGACGCTTA |
| | | VTTTYIDAFNNML | CACTACCGATTCCGCCAGCGGACAGG |
| | | VSTTINYATQIGAT | GATCATCTGGAAAATCAAGTATTATTT |
| | | FIMLAIMLLMTPR | TTGTTTGACAATCACGGTCAGTTACTT |
| | | RRFKRLPTIISLLAL | AATGTAACTACAACTTACATTGACGCT |
| | | CINLIRVVLLALFF | TTTAACAATATGCTGGTCTCTACTACT |
| | | PSHWTDFYVLYSG | ATAAACTATGCAACGCAAATTGGAGC |
| | | DWQFVPPGDMQIS | TACTTTTATAATGCTAGCCATTATGTT |
| | | VAATVLSIPVTALL | ATTAATGACTCCCAGAAGGAGGTTCA |
| | | LSALMVQAWSMM | AACGTTTACCAACAATTATTAGCTTGT |
| | | QLWTPLWRALVV | TAGCCTTATGTATTAATTTGATCAGGG |
| | | LVSGLLSLVTVAM | TGGTTTTGCTGGCCCTGTTTTTTCCTTC |
| | | SFANCIFQAKNILY | TCACTGGACAGACTTCTACGTGTTGTA |
| | | ADPLPSYWVRKLY | TTCCGGTGACTGGCAGTTTGTACCTCC |
| | | LALTTGSISWFTFL | AGGGGATATGCAAATATCTGTTGCTG |
| | | FMIRLVMHMWTN | CTACGGTTTTGTCTATCCCAGTGACGG |
| | | RSILPSMKGLKAM | CATTATTATTGAGCGCATTGATGGTTC |
| | | DVLIITNSILMLIPV | AAGCCTGGTCAATGATGCAATTATGG |
| | | LFAGLEFLDSASGF | ACACCACTGTGGAGGGCACTAGTGGT |
| | | ESGSLTQTSVVIVL | ACTAGTGTCCGGGCTATTGTCACTGGT |
| | | PLGTLVAQRIATR | AACTGTGGCAATGAGTTTCGCGAATT |
| | | GYMPDSLEASSGP | GCATTTTCCAAGCGAAAAATATTTTGT |
| | | NGSLPLSNLSFAG | ATGCCGACCCTTTACCCTCCTACTGGG |
| | | GGGGGSGGHKDK | TCAGAAAATTGTACTTAGCATTAACG |
| | | ENGGGIIPPTTNNT | ACTGGGTCTATAAGTTGGTTCACATTC |
| | | AATNFSSSIACSGI | CTTTTTATGATAAGATTGGTTATGCAT |
| | | SCLPKVKRMTASS | ATGTGGACAAACAGATCTATATTACC |
| | | ASSSQRPLLTMTN | AAGCATGAAGGGTTTGAAGGCTATGG |
| | | STIASNDSSGFPSP | ATGTATTGATTATTACGAATTCTATAT |
| | | GIHNTTTTTTQYQ | TGATGTTAATCCCAGTGTTGTTTGCAG |
| | | YSMGMNMPNFPP | GCTTGGAATTTCTGGATAGTGCCTCTG |
| | | VPFPGYQSRTTGV | GATTTGAGTCCGGGTCTTTGACTCAAA |
| | | TSHIVSDGRHHQG | CCTCTGTAGTGATTGTCCTGCCTTTGG |
| | | MNRHPSVDHFDRE | GTACTTTAGTAGCACAAAGAATAGCT |
| | | LARIDDEDDDGYP | ACGAGGGGTTACATGCCCGATAGTCT |
| | | FASSEKAVMHGD | GGAGGCTTCTAGCGGACCAAATGGTT |
| | | DDDDVERGRRRA | CATTGCCGTTATCTAATTTAAGTTTCG |
| | | LPPSLGGVRVERTI | CTGGAGGGGGCGGTGGTGGTTCTGGG |
| | | ETRSEERMPSPDPL | GGACATAAAGATAAAGAAAACGGTG |
| | | GVTKPRSFE (SEQ | GCGGTATTATACCGCCTACTACGAAC |
| | | ID NO: 96) | AATACTGCTGCTACTAATTTTTCTTCA |
| | | | TCAATCGCGTGTTCTGGTATATCTTGT |
| | | | TTACCAAAAGTCAAAAGAATGACCGC |
| | | | GAGTTCAGCCTCAAGTAGCCAGAGAC |
| | | | CGTTGTTGACAATGACTAACTCAACC |
| | | | ATAGCGAGTAATGACAGTTCAGGTTT |
| | | | CCCTTCTCCTGGCATACATAATACCAC |
| | | | TACTACGACAACACAATACCAATATT |
| | | | CCATGGGAATGAACATGCCGAACTTT |
| | | | CCTCCAGTCCCGTTCCCAGGTTACCAG |
| | | | TCACGTACTACCGGTGTTACTTCCCAT |
| | | | ATTGTGTCCGACGGTAGACATCACCA |
| | | | GGGTATGAACAGGCACCCATCTGTTG |
| | | | ACCATTTTGATAGGGAACTTGCTAGG |
| | | | ATTGATGATGAAGATGACGATGGTTA |
| | | | CCCTTTCGCATCAAGTGAAAAGGCCG |
| | | | TTATGCACGGAGACGATGACGACGAT |
| | | | GTGGAAAGGGGACGTCGTAGAGCTCT |
| | | | ACCACCATCCTTAGGTGGAGTTAGAG |
| | | | TTGAAAGGACGATCGAGACCAGGAGC |
| | | | GAGGAACGTATGCCATCTCCGGACCC |
| | | | ATTGGGTGTTACGAAGCCTAGATCATT |
| | | | CGAGTAG (SEQ ID NO: 97) |
| *Pseudogymnoascus* | FCWRPG | MSTANVHLPADFD | (codon optimized) |
| *destructans* | QPCG | PTRQNITIYTPDGT | ATGTCCACTGCCAACGTTCATTTACCA |
| | | PVVATLPMINLFN | GCTGATTTCGATCCAACTAGACAAAA |
| | | RQNNEICVVYGCQ | CATCACTATCTATACCCCAGACGGTAC |
| | | LGASLIMFLVVLL | CCCAGTTGTTGCTACCTTGCCAATGAT |

TABLE 6-continued

Sequences of Fungal GPCRs and Peptide Ligands

| Fungi | sequence of peptide analyte used | sequence of GPCRs used (all sequences are wild type) | DNA coding sequence of corresponding GPCRs that senses peptide analyte (WT or codon-optimized noted) |
|---|---|---|---|
| | | TTRVSKRKSPIFVLNVLSLIISCLRSLLQILYYIGPWTEIYRYLSFDYSTVPASAYANSVAATLLTLFLLITIEASLVLQTNVVCKSMSSHIRWPVTALSMVVSLLAISFRFGLTIRNIEGILGATVKSDSLMFSGASLISETASIWFFCTIFVIKLGWTLYQRKKMGLKQWGPMQIITIMAGCTMLIPSLFTVLEFFPEETFYEAGTLAICLVAILLPLSSVWAAAAIDGDEPVRPHGSTPKFASFNMGSDYKSSSAHLPRSIRKASVPAEHLSRTSEEELGDDGTLNRGGAYGMDRMSGSISPRGVRIERTYEVHTAGRGGSIEREDIF (SEQ ID NO: 98) | CAATTTGTTTAACAGACAAAACAACGAAATCTGTGTTGTTTACGGTTGTCAATTGGGTGCCTCTTTAATTATGTTCTTGGTTGTTTTGTTGACCACCAGAGTTTCCAAGAGAAAATCTCCAATCTTCGTCTTGAACGTTTTGTCTTTGATTATTTCTTGTTTAAGATCCTTGTTGCAAATTTTATACTATATTGGTCCATGGACCGAGATCTACAGATACTTGTCTTTCGATTACTCTACTGTCCCAGCTTCCGCTTACGCTAATTCTGTTGCTGCCACTTTATTAACCTTATTCTTATTGATTACCATTGAAGCTTCTTTAGTTTTACAAACTAACGTTGTCTGCAAGTCTATGTCTTCTCACATTCGTTGGCCAGTTACTGCTTTGTCCATGGTTGTCTCTTTATTGGCTATTTCTTTTAGATTCGGTTTGACCATCCGTAACATCGAAGGTATCTTAGGTGCTACTGTCAAATCCGACTCCTTAATGTTCTCTGGTGCCTCTTTGATCTCTGAAACTGCTTCTATCTGGTTCTTCTGCACTATTTTCGTTATTAAATTGGGTTGGACCTTGTACCAAAGAAAGAAGATGGGTTTGAAGCAATGGGGTCCAATGCAAATTATCACTATCATGGCTGGTTGCACCATGTTGATCCCATCCTTGTTCACTGTTTTGGAATTCTTCCCTGAAGAAACTTTCTACGAGGCCGGTACTTTGGCTATCTGTTTGGTTGCTATTTTGTTGCCATTATCTTCCGTCTGGGCTGCCGCTGCTATTGATGGTGATGAACCAGTCCGTCCACATGGTTCTACCCCAAAATTCGCTTCTTTCAACATGGGTTCCGACTACAAATCTTCTTCTGCTCACTTGCCAAGATCTATTAGAAAGGCCTCCGTCCCAGCTGAACATTTATCTAGAACTTCTGAAGAAGAGTTAGGTGACGACGGTACTTTGAACAGAGGTGGTGCCTACGGTATGGACAGAATGTCCGGTTCTATCTCCCCTAGAGGTGTCAGAATTGAAAGAACTTACGAAGTTCATACCGCTGGTAGAGGTGGTTCTATCGAGAGAGAGGACATCTTCTAG (SEQ ID NO: 99) |
| *Hypocrea jecorina* | WCYRIGEPCW | MSSFDPYTQNITILVSPSSPPISIPIPVIDAFNDETASIITNYAAQLGAALAMLLVLLAATPTARLLRADGPSLLHALALLVCVVRTVLLIYFFLTPFSHFYQVWTGDFSQVPAWNYRASIAGTVLSTLLTVVTDAALVNQAWTMVSLFAPRTKRAVCVLSLLITLLAISFRVAYTVIQCEGIAELAAPRQYAWLIRATLIFNICSIAWFCALFNSKLVAHLVTNRGVLPSRRAMSPMEVLIMANGILMIVPVVFAILEWHHFINFEAGSLTPTSIAIILPLSSLAAQRIANTSSS (SEQ ID NO: 100) | (codon optimized) ATGTCTTCCTTCGACCCATACACTCAAAACATTACTATTTTGGTTTCTCCATCCTCTCCACCAATTTCCATTCCAATCCCAGTTATCGACGCTTTCAACGACGAAACCGCTTCTATCATTACTAACTACGCCGCTCAATTAGGTGCTGCTTTGGCCATGTTATTAGTTTTGTTGGCCGCTACTCCAACCGCTAGATTGTTAAGAGCTGATGGTCCATCCTTGTTGCACGCTTTGGCCTTGTTAGTCTGTGTCGTCAGAACTGTCTTATTGATCTACTTCTTCTTGACCCCATTCTCTCACTTCTACCAAGTCTGGACCGGTGACTTCTCTCAAGTTCCAGCTTGGAACTACAGAGCTTCTATTGCTGGTACCGTTTTGTCTACTTTGTTGACCGTTGTTACCGACGCTGCTTTGGTTAACCAAGCTTGGACTATGGTTTCTTTATTCGCTCCAAGAACTAAGAGAGCCGTTTGTGTTTTGTCCTTGTTAATCACCTTGTTGGCCATTTCTTTCAGAGTCGCTTACACCGTCATTCAATGTGAAGGTATCGCTGAATTGGCTGCTCCAAGACAATACGCTTGGTTGATCAGAGCCACTTTGATCTTTAACATCTGTTCCATTGCCTGGTTCTGTGCTTTGTTCAACTCTAAGTTGGTTGCTCACTTGGTTACCAACAGAGGTGTCTTGCCATCCCGTAGAGCCATGTCCCCAATGGAAGTTTTGATTATGGCCAACGGTATCTTGATGATT |

TABLE 6-continued

| Sequences of Fungal GPCRs and Peptide Ligands | | | |
|---|---|---|---|
| Fungi | sequence of peptide analyte used | sequence of GPCRs used (all sequences are wild type) | DNA coding sequence of corresponding GPCRs that senses peptide analyte (WT or codon-optimized noted) |
| | | | GTTCCAGTTGTTTTCGCTATCTTGGAA<br>TGGCACCACTTCATTAACTTCGAAGCT<br>GGTTCTTTAACCCCAACCTCCATCGCC<br>ATTATCTTGCCATTGTCCTCTTTGGCC<br>GCCCAAAGAATCGCCAACACTTCTTC<br>CTCTTAG (SEQ ID NO: 101) |
| *Tubermelanosporum* | WTPRPGR<br>GAY | MEQIPVYERPGFN<br>PHKQNITLFKHDG<br>STVTVGLHELDAM<br>FTHSIRVAVVFAS<br>QIGACALLSVIVA<br>MVTKREKRRALFF<br>LHIISLLLVVVRSV<br>LQILYFVGPWAET<br>YNYVAYYYEDIPL<br>SDKLISIWAGIIQLI<br>LNICILLSLILQVRV<br>VYATSPKLNTIMT<br>LVSCVIASISVGFF<br>FTVIVQISEAILNG<br>VGYDGWVYKVHR<br>GVFAGAIAFFSFIFI<br>FKLAFAIRRRKAL<br>GLQRFGPLQVIFIM<br>GCQTMIVPAIFATL<br>ENGVGFEGMSSLT<br>ATLAVISLPLSSM<br>WAAAQTDGPSPQS<br>TPRDGYRRFSTRR<br>SALNRSDPSGGRS<br>VDMNTLDSTGND<br>SLALHVDKTFTVE<br>SSPSSQSQAGPHKE<br>RGFEFA (SEQ ID<br>NO: 102) | (codon optimized)<br>ATGGAGCAAATCCCAGTCTACGAGCG<br>TCCAGGTTTCAACCCACACAAGCAAA<br>ACATTACCTTGTTCAAGCATGATGGTT<br>CTACTGTTACTGTCGGTTTGCATGAGT<br>TGGACGCCATGTTCACTCATTCCATCA<br>GAGTTGCTGTCGTCTTCGCCTCTCAAA<br>TTGGTGCTTGTGCTTTGTTGTCTGTTAT<br>CGTTGCTATGGTCACCAAGAGAGAAA<br>AGAGACGTGCTTTGTTCTTCTTGCACA<br>TTATTTCCTTGTTGTTGGTCGTTGTTCG<br>TTCCGTCTTGCAAATCTTGTACTTCGT<br>CGGTCCATGGGCTGAAACTTATAATT<br>ACGTCGCCTACTACTATGAAGACATTC<br>CTTTGTCTGACAAATTGATTTCCATTT<br>GGGCTGGTATTATCCAATTGATTTTGA<br>ATATCTGTATTTTGTTATCTTTGATCTT<br>GCAAGTTCGTGTCGTTTACGCCACCTC<br>TCCAAAATTGAACACTATTATGACTTT<br>AGTCTCTTGTGTTATCGCTTCTATTTCT<br>GTCGGTTTCTTCTTTACTGTCATCGTTC<br>AAATTTCTGAGGCTATTTTAAACGGTG<br>TTGGTTACGACGGTTGGGTTTACAAA<br>GTCCATAGAGGTGTCTTCGCTGGTGCT<br>ATCGCCTTCTTCTCTTTCATCTTCATCT<br>TTAAGTTGGCCTTCGCTATCAGAAGA<br>AGAAAGGCTTTGGGTTTGCAAAGATT<br>CGGTCCATTGCAAGTTATCTTCATCAT<br>GGGTTGTCAAACTATGATTGTTCCAGC<br>TATCTTTGCTACTTTGGAAAACGGTGT<br>TGGTTTCGAAGGTATGTCCTCTTTGAC<br>TGCTACCTTGGCTGTCATTTCCTTACC<br>ATTGTCTTCTATGTGGGCCGCCGCTCA<br>AACCGACGGTCCATCTCCACAATCCA<br>CTCCAAGAGACGGTTATAGAAGATTC<br>TCTACTCGTAGATCTGCCTTGAACAGA<br>TCTGACCCATCTGGTGGTAGATCTGTT<br>GACATGAACACCTTGGACTCTACCGG<br>TAACGATTCCTTAGCTTTGCACGTTGA<br>TAAGACTTTTACTGTTGAATCTTCCCC<br>ATCCTCCCAATCTCAAGCTGGTCCACA<br>CAAGGAAAGAGGTTTCGAATTCGCCT<br>AG (SEQ ID NO: 103) |
| *Dactylellina haptotyla* | WCVYNS<br>CP | MDHNTQHFNRPE<br>YIEIPVPPSKGFNP<br>HTNPAFFIYPDGSN<br>MTFWFGQIDDFRR<br>DQLFTNTIFSIQIGA<br>ALVILCVMFCVTH<br>ADKRKTIVYLLNV<br>SNLFVVIIRGVFFV<br>HYFMGGLARTYT<br>TFTWDTSDVQQSE<br>KATSIVSSICSLILM<br>IGTQISLLLQVRIC<br>YALNPRSKTAILV<br>TCGSISGIATTAYL<br>LLGAYTIQLREKPP<br>DMKFMKWAKPV<br>VNALVALSIVSFSG<br>IFSWRMFQSVRNR<br>RRMGFTGIGSLESL<br>LASGFQCLVFPGL<br>VTTALTVAGSTW | (codon optimized)<br>ATGGACCACAACACCCAACACTTCAA<br>CAGACCTGAATACATTGAAATCCCAG<br>TTCCACCATCTAAGGGTTTCAACCCAC<br>ACACCAACCCTGCTTTCTTCATCTACC<br>CAGACGGTTCTAATATGACCTTTTGGT<br>TCGGTCAAATCGACGATTTCAGACGT<br>GACCAATTATTCACTAACACCATCTTT<br>TCCATTCAAATTGGTGCCGCTTTGGTC<br>ATCTTATGTGTCATGTTTTGTGTTACC<br>CACGCTGATAAGCGTAAAACCATTGT<br>CTACTTGTTAAACGTTTCCAACTTGTT<br>CGTTGTTATCATTAGAGGTGTTTTCTT<br>TGTTCATTACTTCATGGGTGGTTTGGC<br>CAGAACCTATACCACTTTCACCTGGG<br>ATACTTCTGATGTTCAACAATCTGAGA<br>AGGCTACTTCCATTGTCTCCTCTATTT<br>GTTCTTTGATTTTGATGATCGGTACTC<br>AAATCTCCTTATTGTTGCAAGTCAGAA<br>TCTGTTACGCTTTGAACCCAAGATCCA<br>AGACCGCTATCTTGGTTACTTGTGGTT |

TABLE 6-continued

Sequences of Fungal GPCRs and Peptide Ligands

| Fungi | sequence of peptide analyte used | sequence of GPCRs used (all sequences are wild type) | DNA coding sequence of corresponding GPCRs that senses peptide analyte (WT or codon-optimized noted) |
|---|---|---|---|
| | | YIAVNLTTPSDLTA | CTATTTCCGGTATTGCTACCACTGCTT |
| | | IYNCSAFFAYAFSI | ATTTATTGTTGGGTGCTTACACTATTC |
| | | PLLKERAQVEKTIS | AATTGAGAGAAAAGCCACCAGACATG |
| | | VVIAIAGVLVVAY | AAGTTCATGAAGTGGGCTAAGCCAGT |
| | | GDGADDGSTSNGE | TGTTAACGCTTTGGTTGCCTTGTCCAT |
| | | KARLGGNVLIGIG | TGTCTCCTTTTCTGGTATTTTCTCTTGG |
| | | SVLYGLYEVLYKK | AGAATGTTCCAATCTGTCAGAAACAG |
| | | LLCPPSGASPGRSV | AAGAAGAATGGGTTTCACTGGTATCG |
| | | VFSNTVCACIGAF | GTTCCTTGGAATCTTTGTTGGCTTCTG |
| | | TLLFLWIPLPLLH | GTTTCCAATGTTTAGTCTTCCCTGGTT |
| | | WSGWEIFELPTGK | TGGTTACTACCGCTTTGACCGTCGCCG |
| | | TAKLLGISIAANAT | GTTCCACTTGGTATATCGCTGTTAACT |
| | | FSGSFLILISLTGPV | TAACTACTCCATCTGACTTGACCGCTA |
| | | LSSVAALLTIFLVA | TTTACAACTGTTCCGCTTTTTTCGCTTA |
| | | ITDRILFGRELTSA | TGCTTTCTCCATTCCATTGTTAAAGGA |
| | | AILGGLLIIAAFAL | AAGAGCTCAAGTTGAAAAGACCATTT |
| | | LSWATWKEMIEE | CTGTTGTCATTGCTATCGCTGGTGTCT |
| | | NEKDTIDSISDVGD | TAGTCGTTGCTTACGGTGACGGTGCTG |
| | | HDD (SEQ ID | ACGACGGTTCCACCTCTAACGGTGAA |
| | | NO: 104) | AAGGCTAGATTGGGTGGTAACGTCTT |
| | | | GATCGGTATCGGTTCTGTCTTGTATGG |
| | | | TTTATACGAAGTCTTGTATAAGAAGTT |
| | | | ATTATGTCCACCATCTGGTGCTTCCCC |
| | | | AGGTAGATCTGTTGTTTTCTCTAATAC |
| | | | CGTTTGTGCTTGCATCGGTGCTTTCAC |
| | | | TTTGTTATTCTTGTGGATCCCATTGCC |
| | | | ATTGTTGCACTGGTCCGGTTGGGAAAT |
| | | | TTTTGAATTGCCAACCGGTAAGACTGC |
| | | | TAAGTTATTGGGTATTTCCATTGCCGC |
| | | | TAACGCCACCTTCTCTGGTTCTTTCTT |
| | | | GATCTTAATTTCTTTGACTGGTCCAGT |
| | | | TTTGTCCTCTGTTGCCGCCTTGTTGAC |
| | | | CATTTTCTTGGTTGCTATTACTGACAG |
| | | | AATTTTATTCGGTAGAGAATTGACTTC |
| | | | TGCTGCCATTTTGGGTGGTTTGTTGAT |
| | | | CATCGCTGCCTTCGCTTTGTTATCTTG |
| | | | GGCTACTTGGAAGGAAATGATTGAAG |
| | | | AGAACGAGAAGGATACTATCGATTCC |
| | | | ATCTCTGACGTTGGTGACCACGATGA |
| | | | CTAG (SEQ ID NO: 105) |
| *Sporothrix* | YCPLKGQ | MKPAAGPASSPFD | (codon optimized) |
| *scheckii* | SCW | PFNQTFYLTGPDN | ATGAAACCCGCCGCTGGACCTGCATC |
| | | TTVPVSVPQVDYI | TAGTCCATTCGACCCATTTAACCAAAC |
| | | WHYIIGTSINYGSQ | GTTTTACCTGACCGGTCCAGATAATAC |
| | | IGACLLMLLVMLT | CACTGTACCAGTCTCAGTCCCACAAGT |
| | | LTSKSRFSRAATLI | TGACTATATCTGGCATTATATTATTGG |
| | | NVASLLIGVIRCVL | AACATCCATCAACTATGGTTCTCAGAT |
| | | LAVYFTSSLTELY | CGGAGCCTGTTTACTTATGCTTCTTGT |
| | | ALFVGDYSQVRRS | GATGTTGACATTGACTTCAAAGTCAA |
| | | DLCVSAVATFFSL | GATTTTCTCGTGCGGCCACTCTGATTA |
| | | PQLVLIEAALFLQA | ACGTAGCAAGCTTATTGATTGGAGTA |
| | | YSMIKMWPSLWR | ATTCGTTGTGTTCTTTTAGCTGTCTACT |
| | | AVVLAMSVVVAV | TTACTTCTTCTCTAACTGAATTGTATG |
| | | CAIGFKFASVVMR | CTCTGTTCGTTGGCGATTACAGCCAGG |
| | | MRSTLTLDDSLDF | TCCGTAGGTCTGATCTTTGTGTCTCTG |
| | | WLVEVDLAFTATT | CTGTGGCAACCTTCTTTAGTCTACCAC |
| | | IFWFCFIYIIRLVIH | AATTAGTTCTAATAGAAGCTGCTTTGT |
| | | MWEYRSILPPMGS | TTCTACAGGCTTATAGTATGATCAAAA |
| | | VSAMEVLVMTNG | TGTGGCCATCCCTGTGGAGAGCAGTG |
| | | ALMLVPVIFAAIEI | GTTTTAGCTATGTCAGTGGTGGTGGCT |
| | | NGLSSFESGSLVHT | GTGTGTGCAATCGGTTTTAAGTTCGCG |
| | | SVIVLLPLGSLIAQ | TCCGTTGTTATGCGTATGAGGTCAACA |
| | | AMTRPDGYVQRT | TTAACATTGGACGATTCTTTGGATTTC |
| | | NTSGASGASGAHP | TGGCTAGTGGAAGTCGATCTGGCTTTT |
| | | GRNGSGHGGHGG | ACAGCAACTACTATTTTTTGGTTTTGT |
| | | AYSRAMTNTLNTL | TTCATCTACATTATAAGGTTGGTTATT |
| | | DTLDTVDSKTSIM | CATATGTGGGAATATAGAAGCATTTT |
| | | HHHHHHHRNHSN | ACCACCAATGGGGTCTGTTTCTGCTAT |
| | | GMSKTKANSGTW | GGAGGTTCTTGTTATGACCAATGGAG |
| | | SHASDANSTNAMI | CGTTGATGTTAGTTCCAGTGATTTTCG |
| | | SGGIATQVRIQAN | CCGCAATAGAAATCAATGGTTTATCA |

TABLE 6-continued

Sequences of Fungal GPCRs and Peptide Ligands

| Fungi | sequence of peptide analyte used | sequence of GPCRs used (all sequences are wild type) | DNA coding sequence of corresponding GPCRs that senses peptide analyte (WT or codon-optimized noted) |
|---|---|---|---|
| | | QSTLGNTGMSGGSGAPNSHTRNNSLAAMEPVEKQLHDIDATPLSASDCRVWVDREVEVRRDMV (SEQ ID NO: 106) | AGCTTTGAATCAGGGTCACTGGTTCATACATCAGTGATTGTATTATTACCTTTAGGTAGCTTGATAGCGCAAGCAATGACACGTCCAGATGGGTATGTCCAAAGAACGAATACATCTGGAGCATCAGGCGCAAGTGGTGCACATCCTGGTAGAAATGGATCCGGACACGGTGGTCATGGTGGTGCGTACTCAAGAGCCATGACTAATACCCTAAATACATTGGATACATTGGATACCGTAGACAGTAAGACATCCATAATGCATCATCATCATCACCATCATAGAAACCACTCAAATGGCATGAGTAAGACGAAGGCAAATAGTGGAACATGGAGCCATGCGTCAGATGCTAACTCCACCAATGCTATGATCAGCGGTGGTATCGCAACTCAAGTTAGGATTCAAGCTAATCAGTCAACCTTAGGAAATACGGGGATGTCCGGGGGCTCTGGAGCCCCTAATTCTCATACTCGTAATAACTCATTGGCTGCTATGGAACCAGTGGAGAAGCAACTGCATGATATCGATGCCACACCTTTAAGCGCATCTGATTGCAGGGTCTGGGTTGATCGTGAGGTCGAGGTCAGAAGGGACATGGTCTAG (SEQ ID NO: 107) |
| *Yarrowia lipolytica* | WRWFWLPGYGEPNW | MQLPPRPDFDIATLVASITVPETELVLGQMPLGALEQLYQNRLRLAILFGVRVGAAVLTLIAMHLISKKNRTKILFLANQMSLIMLIIHAALYFRFLLGPFASMLMMVAYIVDPRSNVSNDISVSVATNVFMMLMIMSVQLSLAVQTRSVFHAWLKSRIYVTVGLILLSLVVFVFWTTHTIVSCIVLTHPTRDLPSMGWTRLASDVSFACSISFASLVLLAKLVTAIRVRKTLGKKPLGYTKVLVIMSTQSLVVPSILIIVNYALPEKNSWILSGVAYLMVVLSLPLSSIWATAVHDDEMQSNYLLSALKDGHVQPSESKLKTVFLNRLRPFSTTTNRDDESSVDSPAMPSPESDVTFLNTGFECDEKM (SEQ ID NO: 108) | (codon optimized) ATGCAATTGCCACCACGTCCAGACTTCGACATTGCCACTTTGGTTGCCTCTATCACTGTTCCAGAAACTGAATTGGTCTTGGGTCAAATGCCATTGGGTGCTTTAGAACAATTGTACCAAAACAGATTGCGTTTGGCTATTTTGTTCGGTGTCAGAGTCGGTGCTGCTGTTTTGACCTTGATTGCTATGCACTTAATCTCCAAGAAGAACAGAACCAAGATCTTGTTCTTGGCTAACCAAATGTCTTTGATCATGTTGATCATCCATGCTGCTTTGTACTTCAGATTCTTGTTGGGTCCATTCGCCTCCATGTTGATGATGGTTGCTTACATCGTTGATCCAAGATCTAACGTCTCTAACGATATCTCTGTTTCTGTTGCCACCAACGTTTTCATGATGTTGATGATTATGTCCGTCCAATTGTCTTTGGCTGTTCAAACCCGTTCTGTTTTCCACGCTTGGTTGAAGTCTCGTATTTACGTTACCGTTGGTTTAATCTTGTTGTCCTTGGTCGTCTTCGTCTTCTGGACCACCCACACTATCGTTTCTTGTATCGTTTTAACCCATCCAACTAGAGACTTGCCATCTATGGGTTGGACTAGATTAGCTTCTGACGTTTCCTTCGCTTGTTCTATCTCTTTCGCTTCTTTGGTCTTGTTGGCTAAGTTGGTCACCGCCATCAGAGTTAGAAAGACCTTGGGTAAGAAGCCATTGGGTTACACCAAGGTTTTGGTCATCATGTCCACTCAATCTTTAGTCGTTCCATCTATCTTGATTATCGTTAACTACGCTTTGCCAGAAAAAAACTCTTGGATCTTGTCTGGTGTCGCTTACTTGATGGTTGTTTTGTCCTTACCATTGTCCTCCATTTGGGCTACCGCCGTCCATGACGACGAAATGCAATCCAACTACTTGTTGTCTGCCTTGAAAGATGGTCACGTTCAACCATCCGAATCTAAGTTGAAGACTGTTTTCTTGAACAGATTGAGACCATTCTCTACTACCACTAACAGAGACGATGAATCCTCTGTTGATTCCCCAGCCATGCCATCTCCAGAATCTGATGTTACCTTCTTGAACACTGGTTTCGAATGTGACGAAAAGATGTAG (SEQ ID NO: 109) |

TABLE 6-continued

Sequences of Fungal GPCRs and Peptide Ligands

| Fungi | sequence of peptide analyte used | sequence of GPCRs used (all sequences are wild type) | DNA coding sequence of corresponding GPCRs that senses peptide analyte (WT or codon-optimized noted) |
|---|---|---|---|
| *Torulaspora delbrueckii* | GWMRLR<br>LGQPL | MSDSAQNLSDLAF<br>NSSYNPLDSFITFT<br>SIYGDNTAVKFSV<br>LQDMVDVNTNEAI<br>VYGTRCGASVLTQ<br>IIMWMISKNRRTP<br>VFIINQVSLTLILIH<br>SALYFKYLLSGFG<br>SVVYGLTAFPQLI<br>KPGDLRAFAAANI<br>VMVLLVASIEASLI<br>FQVKVIFTGDNMK<br>RVGLILTIICTCMG<br>LATVTMYFITAVK<br>SIVSLYRDMSGSST<br>VLYNVSLIMLASSI<br>HFMALILVVKLFL<br>AVRSRRFLGLKQF<br>DSFHILLIISCQTLL<br>VPSLLFIIAYSFPSS<br>KNIESLKAIAVLTV<br>VLSLPLSSMWATA<br>ANNFTNSSSSGSDS<br>APTNGGFYGRGSS<br>NLYPEKTDNRSPK<br>GARNALYELRSKN<br>NAEGQADIYTVTD<br>IENDIFNDLSKPVE<br>QNIFSDVQIIDSHS<br>LHKACSKEDPVMT<br>LYTPNTAIEGEERK<br>LWTSDCSCSTNGS<br>TPVKKKSTGEYAN<br>LPPHLLRYDENYD<br>EEAGGRRKASLK<br>W (SEQ ID<br>NO: 110) | (codon optimized)<br>ATGTCTGACTCCGCCCAAAACTTGTCC<br>GATTTGGCCTTCAACTCTTCTTATAAC<br>CCATTGGACTCCTTTATTACCTTTACC<br>TCTATCTACGGTGATAACACTGCTGTT<br>AAGTTCTCCGTTTTACAAGACATGGTT<br>GACGTTAATACTAATGAAGCCATCGT<br>TTACGGTACCCGTTGTGGTGCTTCTGT<br>CTTGACCCAAATTATCATGTGGATGAT<br>TTCTAAAAACAGAAGAACCCCAGTCT<br>TTATTATTAACCAAGTTTCTTTGACTT<br>TGATTTTAATTCACTCTGCCTTGTACT<br>TCAAGTACTTGTTGTCTGGTTTCGGTT<br>CCGTTGTCTACGGTTTGACTGCTTTCC<br>CACAATTGATTAAGCCAGGTGATTTG<br>AGAGCTTTCGCTGCTGCTAACATCGTT<br>ATGGTCTTGTTGGTCGCTTCTATTGAA<br>GCTTCCTTAATCTTCCAAGTCAAAGTT<br>ATCTTCACCGGTGATAACATGAAGAG<br>AGTCGGTTTAATCTTGACTATTATTTG<br>TACTTGTATGGGTTTAGCTACTGTTAC<br>CATGTACTTTATTACTGCCGTCAAGTC<br>TATTGTCTCTTTGTACCGTGACATGTC<br>TGGTTCCTCCACCGTTTTATATAACGT<br>TTCTTTAATTATGTTGGCTTCCTCCATC<br>CACTTTATGGCTTTGATCTTGGTTGTC<br>AAATTGTTCTTGGCTGTTAGATCTAGA<br>AGATTCTTGGGTTTGAAACAATTCGAT<br>TCTTTCCACATTTTGTTGATCATCTCTT<br>GTCAAACTTTGTTGGTTCCATCTTTAT<br>TATTCATTATTGCTTACTCTTTTCCATC<br>TTCTAAGAACATTGAATCTTTGAAGGC<br>TATCGCTGTTTTGACCGTCGTTTTGTC<br>TTTGCCATTGTCTTCTATGTGGGCTAC<br>TGCTGCTAATAACTTCACTAACTCTTC<br>CTCCTCCGGTTCCGACTCCGCTCCAAC<br>CAATGGTGGTTTCTACGGTAGAGGTTC<br>TTCCAACTTGTATCCTGAAAAGACTGA<br>TAACAGATCCCCAAAGGGTGCCAGAA<br>ACGCTTTATACGAATTAAGATCTAAG<br>AACAATGCTGAGGGTCAAGCTGATAT<br>TTACACCGTTACCGATATTGAAAACG<br>ATATTTTCAACGATTTGTCCAAGCCAG<br>TTGAGCAAAACATTTTCTCTGATGTTC<br>AAATTATTGATTCTCATTCTTTGCATA<br>AGGCTTGTTCTAAAGAAGACCCAGTC<br>ATGACTTTGTACACTCCAAACACTGCT<br>ATTGAAGGTGAGGAGAGAAAATTGTG<br>GACTTCTGACTGTTCCTGTTCCACTAA<br>CGGTTCCACCCCAGTTAAGAAGAAGT<br>CCACCGGTGAATACGCCAATTTACCA<br>CCACACTTATTAAGATATGATGAAAA<br>CTACGATGAAGAAGCTGGTGGTAGAC<br>GTAAGGCCTCCTTGAAATGGTAG<br>(SEQ ID NO: 111) |
| *Komagataella pastoris* | FRWRNN<br>EKNQPFG | MEEYSDSFDPSQQ<br>LLNFTSLYGETDA<br>TFAELDDYHFYVV<br>KYAIVYGARIGVG<br>MFCTLMLFVVSKS<br>WKTPIFVLNQSSLI<br>LLIIHSGFYIHYLT<br>NQFSSLTYMFTRIP<br>NETHAGVDLRINV<br>VTNTLYALLILSIEI<br>SLIYQVFVIFKGVY<br>ENSLRWIVTIFTAL<br>FAAAVVAINFYVT<br>TLQSVSMYNSNVD<br>FPRWASNVPLILFA<br>SSVNWACLLLSLK | (codon optimized)<br>ATGGAAGAATACTCCGACTCCTTCGA<br>CCCATCCCAACAATTGTTGAACTTCAC<br>TTCCTTATACGGTGAAACCGATGCTAC<br>TTTCGCTGAATTGGACGACTACCACTT<br>CTACGTCGTTAAGTACGCCATCGTTTA<br>CGGTGCCAGAATTGGTGTCGGTATGTT<br>TTGTACTTTGATGTTGTTCGTTGTTTCC<br>AAGTCTTGGAAGACTCCAATCTTCGTC<br>TTGAACCAATCTTCTTTGATTTTGTTG<br>ATTATTCACTCCGGTTTCTACATCCAC<br>TACTTGACCAACCAATTCTCTTCCTTG<br>ACCTACATGTTCACTAGAATCCCAAA<br>CGAAACCCATGCTGGTGTCGATTTGC<br>GTATTAACGTCGTTACCAACACCTTGT<br>ACGCTTTGTTGATCTTATCTATTGAAA |

TABLE 6-continued

Sequences of Fungal GPCRs and Peptide Ligands

| Fungi | sequence of peptide analyte used | sequence of GPCRs used (all sequences are wild type) | DNA coding sequence of corresponding GPCRs that senses peptide analyte (WT or codon-optimized noted) |
|---|---|---|---|
| | | LFFAIKVRRSLGLR QFDTFHILAIMFSQ TLIIPSILIVLGYTG TRDRDSLASLGFL LIVVSLPFSSMWA ATANNSNIPTSTGS FAWKNRYSPSTYS DDTTAVSKSFTIM TAKDECFTTDTEG SPRFIKGDRTSEDL HF (SEQ ID NO: 112) | TTTCCTTAATTTACCAAGTCTTCGTTA TCTTCAAAGGTGTCTACGAAAACTCTT TAAGATGGATTGTTACTATTTTCACCG CTTTATTCGCCGCCGCCGTCGTTGCTA TTAACTTCTACGTCACTACTTTGCAAT CTGTCTCTATGTACAACTCTAACGTTG ACTTTCCAAGATGGGCTTCTAACGTCC CATTGATCTTGTTCGCTTCTTCTGTCA ACTGGGCTTGTTTGTTGTTGTCCTTGA AGTTGTTCTTCGCTATCAAGGTTAGAA GATCTTTGGGTTTGAGACAATTCGACA CTTTTCACATCTTGGCCATCATGTTCT CTCAAACTTTGATTATCCCATCCATTT TGATTGTCTTGGGTTACACTGGTACCA GAGACAGAGACTCCTTGGCTTCTTTGG GTTTCTTGTTGATCGTTGTTTCTTTGCC ATTTTCCTCTATGTGGGCTGCCACTGC TAACAACTCCAACATCCCAACCTCTAC CGGTTCTTTCGCCTGGAAGAACAGAT ACTCCCCATCTACTTACTCCGACGATA CCACTGCTGTTTCCAAGTCCTTCACTA TTATGACCGCTAAGGATGAATGTTTCA CCACTGATACCGAAGGTTCTCCAAGA TTCATCAAGGGTGACAGAACCTCCGA AGATTTGCACTTCTAG (SEQ ID NO: 113) |

6.8.4. Key Characteristics of Peptide Ligands

Twenty three natural fungal peptides were synthesized and tested for activation of their corresponding receptor in the biosensor strain. Physico-chemical properties, e.g., peptide length, overall charge, charge distribution and hydrophobicity/hydrophilicity were determined for all 23 functionally verified peptide ligands using the program ProtParam on the Expasy server [Walker (2005) ISBN 978-1-59259-890-8]. Sequence variability and conserved sequence motifs within the set of peptide ligands were determined using an alignment and clustering method described in [Andreatta et al. (2013)].

A. Physicochemical Characteristics of Peptide Ligands

Natural mating peptide ligands featured diversity in length (9-23 residues), overall charge and number of charged residues as well as hydrophobicity (GRAVY, Grand average of hydropathy [Kyte and Doolittle (1982)] ranging from hydrophobic to mildly hydrophilic (see Table 9).

B. Sequence-Function Relationship and Sequence Diversity

Functional Domains within Alpha-Factor:

previously reported Alanine scanning mutagenesis revealed defined functional domains within the *S. cerevisiae* mating pheromone alpha-factor [Naider et al. (2004)]. Residues at the C-terminus were found to be mainly involved in binding to the receptor, while residues at the N-terminus were shown to contribute to signaling due to receptor activation. NMR studies also showed that alpha factor adopts a bended secondary structure due to the tendency of the internal residue stretch to form a loop [Higashijima et al. (1983)].

Sequence Motifs of Peptide Ligands:

A motif search for the peptides listed below was performed using a 13-residue motif length as an input parameter, because this is the length of the well characterized alpha factor. The peptides were clustered into 3 groups by conservation of residues (see FIG. 12B): all three clusters showed conservation of internal prolines and Cluster 1 and cluster 3 sequence motif featured the conservation of the aromatic N-terminal “activation domain” also found in *S. cerevisiae* alpha factor.

Correlation Between Sequence Motifs and Physicochemical Properties:

The peptide alignments within the clusters showed that sequences within the same cluster varied in length, overall charge, distribution of charged residues and hydrophobicity/hydrophilicity (see FIG. 12). Cluster 1 featured high variability in overall charge (from negative to positive) and charge distribution across the sequence as well as hydrophobic and hydrophilic members. Cluster 1 and 2 featured variability in the length of group members showing a variation of up to 3 additional residues.

6.9. Example 9: Identification of Biomarkers Specific for a Disease Sample

The design of *S. cerevisiae* biosensor allowed for simple plug-and-play engineering of new receptor-ligand pairs into the existing biosensor strain. The first step in developing yeast biosensors for additional targets using this platform was the identification of specific peptide biomarkers, for which specific receptors can be adapted via receptor engineering and directed evolution. As shown in FIG. 15, a pipeline for identification of viable peptide biomarkers was developed.

First, mass spectrometric analysis is used to identify the peptidome of a given sample. A sample can be anything from a blood sample to a nasal swab or water sample. The peptidome of a sample includes peptides a priori present in the sample or otherwise released after proteolytic treatment (e.g. treatment with trypsin or chemotrypsin).

The resulting peptides are then compared against our existing fungal ligand library to identify the highest homology match. The inventors' fungal ligand library is a list of fungal peptide pheromones—unmodified peptides between 9-15 residues in length—which are predicted or have been validated to activate their cognate fungal mating GPCR. The GPCR corresponding to homologous library peptide is then used as parent for biosensor engineering and provides an advantageous starting point for directed evolution experiments towards the peptide target.

6.10. Example 10: Trypsination of Cholera Toxin to Release Target Ligands

Cholera toxin (CTx) is a heteromeric protein complex secreted by the bacterium *Vibrio cholerae*. It is responsible for the massive, watery diarrhea characteristic of cholera infection and it was shown to be an abundant protein in stool samples of cholera-infected patients. [LaRocque et al. (2008)]. CTx is composed of 2 subunits, CtxA (27 kDa) and CtxB (11.6 kDa), where CtxB assembles in a pentameric ring around a single CtxA subunit.

Trypsin digestion of un-denatured, completely folded Ctx (the protein form expected in an untreated stool sample) was performed and the resulting peptidome was determined by mass spectrometry (see peptide list in Table 7). Then, a similarity search of the resulting Ctx peptidome was performed with the inventors' existing library of functional peptides tested in their sensor strain. A peptide HFGVLDEQLHR (SEQ ID NO: 132) with 36% identity to a functional member of the inventors' fungal peptide library, the fungi *Zygosaccharomyces rouxii* (see FIG. 16) was detected.

The conservation of N-termini of these peptides is encouraging since the N-terminal end of mating pheromones was shown to be significant for receptor activation. [Naider et al. (2004)]. In addition, while tryptic release of some peptides may be less efficient than others because several predicted trypsin cleavage sites might not be solvent exposed and accessible, the high peptide count of the identified peptide (Table 7) indicates its high abundance in the analyzed sample. Importantly, the same peptide identified in this work was previously reported in tryptic digests of clinical stool samples from cholera infected patients. [LaRocque et al. (2008)]. Directed evolution experiments towards GPCR binding of the identified Ctx peptide is performed.

TABLE 7

Peptidome of Cholera Toxin after trypsin treatment

| Peptide released by trypsin digest | Peptide count |
|---|---|
| Cholera toxin subunit A | |
| ADGYGLAGFPPEHR (SEQ ID NO: 114) | 7 |
| ADSRPPDE (SEQ ID NO: 115) | 2 |
| ADSRPPDEIK (SEQ ID NO: 116) | 4 |
| ADSRPPDEIKQS (SEQ ID NO: 117) | 1 |
| ADSRPPDEIKQSGGLMPR (SEQ ID NO: 118) | 9 |

TABLE 7-continued

Peptidome of Cholera Toxin after trypsin treatment

| Peptide released by trypsin digest | Peptide count |
|---|---|
| AGFPPEHR (SEQ ID NO: 119) | 2 |
| ALGGIPYSQIYGWYR (SEQ ID NO: 120) | 1 |
| APAADGYGLAGFPPEHR (SEQ ID NO: 121) | 5 |
| ATAPNMFNVNDVLGAYSPHPDEQEVSALGGIPYSQIYGWYR (SEQ ID NO: 122) | 4 |
| AYSPHPDEQEVSALGGIPYSQIYGWYR (SEQ ID NO: 123) | 1 |
| DIAPAADGYGLAGFPPEHR (SEQ ID NO: 124) | 1 |
| DRYYSNLDIAPAADGYGLAGFPPEHR (SEQ ID NO: 125) | 34 |
| DSRPPDEIK (SEQ ID NO: 126) | 3 |
| DVLGAYSPHPDEQEVSALGGIPYSQIYGWYR (SEQ ID NO: 127) | 1 |
| FGVLDEQLHR (SEQ ID NO: 128) | 8 |
| FLDEYQSKVKRQIFSGYQSDIDTHNR (SEQ ID NO: 129) | 2 |
| FLDEYQSKVKRQIFSGYQSDIDTHNRIKDEL (SEQ ID NO: 130) | 5 |
| FNVNDVLGAYSPHPDEQEVSALGGIPYSQIYGWYR (SEQ ID NO: 131) | 1 |
| GAYSPHPDEQEVSALGGIPYSQIYGWYR (SEQ ID NO: 132) | 2 |
| GGIPYSQIYGWYR (SEQ ID NO: 133) | 2 |
| GQSEYFDR (SEQ ID NO: 134) | 4 |
| GQSEYFDRGTQMNINLYDHAR (SEQ ID NO: 135) | 6 |
| GTQMNINLYDHAR (SEQ ID NO: 136) | 45 |
| GTQTGFVR (SEQ ID NO: 137) | 15 |
| GTQTGFVRHDDGYVSTSISLR (SEQ ID NO: 138) | 3 |
| GYQSDIDTHNR (SEQ ID NO: 139) | 1 |
| GYRDRYYSNLDIAPAADGYGLAGFPPEHR (SEQ ID NO: 140) | 3 |
| HDDGYVSTS (SEQ ID NO: 141) | 1 |
| HDDGYVSTSISLR (SEQ ID NO: 142) | 38 |

TABLE 7-continued

| Peptidome of Cholera Toxin after trypsin treatment | |
|---|---|
| Peptide released by trypsin digest | Peptide count |
| HFGVLDEQLHR (SEQ ID NO: 143) | 76 |
| KQSGGLMPR (SEQ ID NO: 144) | 5 |
| LDIAPAADGYGLAGFPPEHR (SEQ ID NO: 145) | 2 |
| NVNDVLGAYSPHPDEQEVSALGGIPYSQIYGWYR (SEQ ID NO: 146) | 11 |
| QEVSALGGIPYSQIYGWYR (SEQ ID NO: 147) | 1 |
| QIFSGYQSDIDTH (SEQ ID NO: 148) | 1 |
| QIFSGYQSDIDTHN (SEQ ID NO: 149) | 1 |
| QIFSGYQSDIDTHNR (SEQ ID NO: 150) | 41 |
| QSDIDTHNR (SEQ ID NO: 151) | 2 |
| QSGGLMPR (SEQ ID NO: 152) | 6 |
| RHDDGYVSTSISLR (SEQ ID NO: 153) | 21 |
| RQIFSGYQSDIDTHNR (SEQ ID NO: 154) | 7 |
| SAHLVGQTILSGH (SEQ ID NO: 155) | 1 |
| SAHLVGQTILSGHSTY (SEQ ID NO: 156) | 1 |
| SAHLVGQTILSGHSTYY (SEQ ID NO: 157) | 5 |
| SAHLVGQTILSGHSTYYIYVIATAPNMF (SEQ ID NO: 158) | 5 |
| SDIDTHNR (SEQ ID NO: 159) | 98 |
| SGYQSDIDTHNR (SEQ ID NO: 160) | 6 |
| SNLDIAPAADGYGLAGFPPEHR (SEQ ID NO: 161) | 14 |
| SQIYGWYR (SEQ ID NO: 162) | 4 |
| SRPPDEIKQSGGLMPR (SEQ ID NO: 163) | 1 |
| TAPNMFNVNDVLGAYSPHPDEQEVSALGGIPYSQIYGWYR (SEQ ID NO: 164) | 2 |
| VIATAPNMFNVNDVLGAYSPHPDEQEVSALGGIPYSQIYGWYR (SEQ ID NO: 165) | 1 |
| VKRQIFSGYQSDIDTHNRIKDEL (SEQ ID NO: 166) | 2 |

TABLE 7-continued

| Peptidome of Cholera Toxin after trypsin treatment | |
|---|---|
| Peptide released by trypsin digest | Peptide count |
| VLDEQLHR (SEQ ID NO: 167) | 1 |
| YQSDIDTHNHR (SEQ ID NO: 168) | 2 |
| YSNLDIAPAADGYGLAGFPPEHR (SEQ ID NO: 169) | 17 |
| YSPHPDEQEVSALGGIPYSQIYGWYR (SEQ ID NO: 170) | 1 |
| YSQIYGWYR (SEQ ID NO: 171) | 1 |
| YYSNLDIAPAADGYGLA (SEQ ID NO: 172) | 1 |
| YYSNLDIAPAADGYGLAGFPPEHR (SEQ ID NO: 173) | 29 |
| Cholera subunit B | |
| AIAAISMAN (SEQ ID NO: 174) | 1 |
| EMAIITFK (SEQ ID NO: 175) | 1 |
| FSYTESLAGK (SEQ ID NO: 176) | 1 |
| IFSYTESLAGK (SEQ ID NO: 177) | 2 |
| NDKIFSYTESLAGK (SEQ ID NO: 178) | 2 |
| NGATFQVEVPGSQH (SEQ ID NO: 179) | 1 |
| NGATFQVEVPGSQHIDSQK (SEQ ID NO: 180) | 10 |
| NGATFQVEVPGSQHIDSQKK (SEQ ID NO: 181) | 18 |
| SYTESLAGKR (SEQ ID NO: 182) | 5 |
| TPHAIAAISMAN (SEQ ID NO: 183) | 2 |
| YTESLAGK (SEQ ID NO: 184) | 1 |

6.11 Example 11: Dipstick Test

Materials and Methods.

To assemble the dipstick, the biosensor strains were pre-cultured in 50 mL of yeast extract peptone dextrose media (YPD) at 30° C. at 300 RPM for 72 hours. The culture was diluted with water to an $OD_{600}$ of 2.5 and vacuum filtered onto a glass fiber filter paper (Thermo Scientific, DS0281-7500) using a plastic stencil to generate spots with a diameter of 5 mm. An appropriate culture volume was used to give about $5\times10^7$ cells per spot. The filter paper with biosensor spots was cut into small squares (8×8 mm, 1 biosensor spot) and placed onto a strip of wicking paper made of a standard brown paper towel (FIG. S8B, C). Each paper-based dipstick assay contained two different spots—an indicator (biosensor) spot and a control spot composed of *S. cerevisiae* carrying off-target receptor as a negative control.

To characterize its functionality, the dipstick was dipped into 1 mL of liquid sample and incubated at 30° C. The lycopene readout was inspected visually and quantitatively measured using time-lapse photography analyzed with ImageJ. A 24-well plate was used to easily array several dipsticks in the field of view of the camera. For all assays, a 10× stock of media was used and diluted to reach the appropriate 1× concentration. All measurements were performed in three or more replicates. For YPD assays (FIG. 17B-D), the dipstick was dipped into 1×YPD media supplemented with 1 μM of the indicated fungal pathogen peptide. For soil assays (FIG. 17D), 0.5 g of soil was pre-conditioned with 2 nmol (in 200 μL of water) of the indicated fungal pathogen peptide and allowed to air dry for 1 hour. The dipstick was inserted into the soil and 2 mL of 1×YPD media was added to give a concentration of 1 μM of fungal peptide. For urine and serum assays (FIG. 17D), the samples were vortexed briefly to resuspend particles, supplemented with 1×YPD media to give a concentration of 50% of urine or serum. For blood assays (FIG. 17D), the sample was supplemented with 1×YPD media to give a final concentration of 2% blood.

Additionally, we designed a small plastic holder to facilitate the ease of use of this dipstick assay. This plastic holder was 3D printed out of acrylonitrile butadiene styrene (ABS). We validated the holder it did not negatively impact the assay functionality.

To assay the long-term stability of the paper-dipstick, the biosensor spots were prepared on filter paper as described above and allowed to air-dry for 20 minutes at room temperature. The filter papers were then placed in plastic pouches, flushed with argon, sealed and stored in the dark at room temperature. After 38 weeks of storage the filter papers were removed from the storage pouches, and assembled with the paper towel wicking paper as described above. To characterize the functionality, the assembled paper dipsticks were rehydrated by dipping directly into 1 mL of liquid sample made of 1×YPD media supplemented either with 1 μM of the indicated fungal pathogen peptide or water as a control and incubated at 30° C. The lycopene readout was inspected visually and quantitatively measured using time-lapse photography. All measurements were performed in three or more replicates.

We also determined a visibility threshold for paper-based dipstick assay when measured by time-lapse photography and pixel color analysis. This was done by visually inspecting time-lapse clips. The visible threshold for the dipstick assay was determined to be 4 Δ Red Color units and is shown by a grey line in FIG. 17B, D).

To enable quantitative characterization of the paper-based dipstick assay we developed a method to measure lycopene production based on time-lapse photography and pixel color value analysis. Specifically, dipsticks dipped in samples and a tripod-mounted digital single-lens reflex camera (DSLR, Nikon D7000) were placed in a dark box kept at 30° C. Flash photographs were taken automatically every 5 minutes. The resulting sequence of photographs was analyzed using ImageJ[139]. For each time point, the average pixel color values were measured for each of the two dipstick spots using constant measurement areas. The apparent level of red color of each spot was first calculated by the following:

$$R_{apparent} = \frac{R - \left(\frac{G+B}{2}\right)}{R} \quad \text{(E1)}$$

where R, G, B are the measured red, green and blue color values, respectively. Since the color of the biosensor spots ranges from off-white to red-orange the color values are such that R>G>B is always true. Therefore, $R_{apparent}$ is a value that scores the level of red from 0 to 1. We then calculated the total level of positive lycopene readout produced by the dipstick by the following:

$$\Delta\text{Red Color} = R_{app,indicator} - R_{app,negative} \quad \text{(E2)}$$

where $R_{app}$, indicator and $R_{app,\ negative}$ are the apparent red color values of the indicator biosensor spot and the negative control yeast spot, respectively given by Eq. E1. Importantly, since the two yeast spots of the dipstick assay are always in close proximity to each other, the A Red Color value is not sensitive to variations in light levels and can be used to compare dipsticks placed anywhere in the field of view of the camera. Using these sequences of photographs we also generated time-lapse clips showing that the lycopene color change can be visualized by the naked eye. These clips are motion and exposure equalized to remove flicker between frames.

Results and Discussion.

Biosensor and control cells were spotted onto filter paper, and detection was performed by simply dipping the paper into liquid samples containing synthetic mating peptides (FIG. 17A). In addition to visual inspection, we quantified lycopene accumulation on paper using pixel color analysis.

Using a *P. brasiliensis* dipstick assay, we observed a robust and highly reproducible signal that surpassed the visible lycopene threshold to give a clear Yes/No readout (FIG. 17B). Similar results were achieved using a *C. albicans* dipstick assay (FIG. 17C). As expected, no cross-reactivity was observed between these two pathogens. Lastly, to ensure the signal remains visible in complex samples, we performed dipstick tests in soil, urine, serum and blood supplemented with synthetic mating peptides. In all sample types, micromolar levels of peptide were successfully detected (FIG. 17D). Importantly, the dipstick assay retained its functionality after being stored for 38 weeks at room temperature. Further, see FIG. 18A-E.

6.12 Example 12: Detection of Yeast Strains

Materials and Methods.

Preparation of Culture Supernatant from Clinically Isolated Fungal Pathogens.

*H. capsulatum*—Strains Hc01 and Hc06 are clinical isolates representing North America class 2 (NAm2) and North America class 1 (NAm1), respectively.[127] *H. capsulatum* strains were added to liquid SDA medium (40 g/L glucose, 10 g/L peptone) at $10^5$ cells/mL and incubated for 10 days at 26° C. without agitation to induce conversion to mycelia. Conversion to mycelia was confirmed by phase-contrast microscopy. Mycelia were then transferred to HMM media.[128] and the cultures incubated at 26° C. After 3 weeks of growth, mycelia were separated from the supernatant by filtration through a cellulose filter (Whatman qualitative filter paper #2, 8 μm-diameter pores) and the filtrate subsequently filtered through a polyethersulfone membrane (0.45 μm diameter pores) to obtain the final culture filtrate. The supernatants were lyophilized, resuspended in 0.1 volume of $H_2O$ (10× concentration) and kept at −20° C.

*Paracoccidioides—Strains P. brasiliensis* Pb18 and *P. lutzii* Pb01 are clinical isolates containing mating loci MAT1-2 and MAT1-1, respectively.[129] The mycelium form was grown at 24° C. at 150 rpm in synthetic McVeigh Morton (MMvM) liquid medium.[130] Supernatants were collected by filtration 10 days after the yeast-mycelium transition. The supernatants were lyophilized, resuspended in 0.1 volume of $H_2O$ (10× concentration) and kept at −20° C.

*C. albicans—Human isolates GC*75 with MTLα/MTLα[131] and ySB36[132] were utilized, the latter being found to be heterozygous for its mating loci, MTLa/MTLα. Homozygous MTLα/MTLα derivatives of ySB36 were obtained by selection on sorbose as previously described.[133] In brief: ySB36 was cultured for 16 hours in YPD liquid media at 30° C., washed once with water and ~$10^5$ cells were plated on 2% sorbose media (0.67% yeast nitrogen base without amino acids, 2% sorbose). Colonies were visible after 4 days incubation at 30° C. Several colonies were re-streaked on 2% sorbose media, followed by re-streaking on YPD media and genotyping by colony PCR (see primers Listed in Table 8 below). One homozygous MTLα/MTLα isolate (ySB45) was used for supernatant preparation. Phenotypically switched opaque colonies of GC75 and ySB45 were isolated by Phloxine B staining as previously described.[134] In brief: A single colony of GC75 or ySB45 was incubated for 24 h at 25° C. in liquid YPD media without agitation. In total ~$2\times10^3$ cells were plated on YPD agar supplemented with 5 μg/ml Phloxine B (Sigma Aldrich) and incubated at 25° C. for 4 days. Opaque colonies stained pink on Phloxine B containing media. For supernatant preparation, a single opaque colony of *C. albicans* GC75 or ySB45 was cultured overnight in YPD media at 25° C., and used to inoculate 50 ml of YPD liquid media. Cells were cultured for ~24 h at 25° C. to a final $OD_{600}$ of 9.5 (~$2.8\times10^8$ cells/ml) and 7.9 (~$2.3\times10^8$ cells/ml), respectively. Cells were pelleted by centrifugation, the supernatant was reduced to dryness by vacuum concentration and resuspended in 0.1 volume $H_2O$ (10× concentration) and kept at −20° C.

TABLE 8

| Primers for cloning of fungal receptors and for genotyping of *C. albicans* isolates. |
|---|
| Primers used for cloning fungal receptors from genomic DNA and pLPreB: |
| Sc.Ste2: |
| MJ492: |
| ACCAAGAACTTAGTTTCGACGGATACTAGTAAAATGTCTGATGCGGCTCCTTC (SEQ ID NO: 185) |
| MJ493: |
| ACGAAATTACTTTTTCAAAGCCGTCTCGAGCTATAAATTATTATTATCTTCAGTCCAGAA (SEQ ID NO: 186) |
| Ca.Ste2: |
| MJ440: |
| acgtcaaggagaaaaaaccccggaaactagtaAAATGAATATCAATTCAACTTTCATACC (SEQ ID NO: 187) |
| MJ362: |
| gcaagtctcgagCTACACTCTTTTGATGGTGATTTG (SEQ ID NO: 188) |
| Cg.Ste2: |
| MJ498: |
| ACCAAGAACTTAGTTTCGACGGATACTAGTAAAATGGAGATGGGCTACGATCC (SEQ ID NO: 189) |
| MJ499: |
| ACGAAATTACTTTTTCAAAGCCGTCTCGAGCTATTTGTCACACTGACTTTGTTG (SEQ ID NO: 190) |

TABLE 8-continued

| Primers for cloning of fungal receptors and for genotyping of *C. albicans* isolates. |
|---|
| Le.Ste2: |
| MJ504: |
| ACCAAGAACTTAGTTTCGACGGATACTAGTAAAATGGACGAAGCAATCAATGCAAAC (SEQ ID NO: 191) |
| MJ505: |
| ACGAAATTACTTTTTCAAAGCCGTCTCGAGCTATTTTTTCAACATAGTCACTTC (SEQ ID NO: 192) |
| Pb.Ste2: |
| MJ508: |
| ACCAAGAACTTAGTTTCGACGGATACTAGTAAAATGGCACCCTCATTCGACC (SEQ ID NO: 193) |
| MJ509: |
| ACGAAATTACTTTTTCAAAGCCGTCTCGAGCTAGGCCTTTGTGCCAGCTTC (SEQ ID NO: 194) |
| Zr.Ste2: |
| MJ518: |
| ACCAAGAACTTAGTTTCGACGGATACTAGTAAAATGAGTGAGATTAACAATTCTACCTAC (SEQ ID NO: 195) |
| MJ519: |
| ACGAAATTACTTTTTCAAAGCCGTCTCGAGCTATAATTTCTTTAGGATAATTTTTTTACT (SEQ ID NO: 196) |
| Primers used for genotyping MTL loci of *C. albicans* |
| MTLα: |
| SB469: TGTAAACATCCTCAATTGTACCCGA (SEQ ID NO: 197) |
| SB470: TTCGAGTACATTCTGGTCGCG (SEQ ID NO: 198) |
| MTLa1: |
| SB471: TTCGAGTACATTCTGGTCGCG (SEQ ID NO: 199) |
| SB472: ATCAATTCCCTTTCTCTTCGATTAGG (SEQ ID NO: 200) |

Gibson assembly was used for receptor cloning except where restriction sites are indicated.

*S. cerevisiae—samples were obtained from S. cerevisiae* strain FY250 with MTLα[135] and W303-1B with MTLα (ATCC 201238). Cells were cultured in 50 ml YPD media for 20 h at 30° C. to a final $OD_{600}$ of 9.8 (~$2.9\times10^8$ cells/ml) and 8.5 (~$2.5\times10^8$ cells/ml), respectively. Cells were pelleted by centrifugation, the supernatant of FY250 was reduced to dryness by vacuum concentration and resuspended in 0.1 volume $H_2O$ (10× concentration) and kept at −20° C. The supernatant of W303-1B was kept at 1× concentration at −20° C.

Detection of Mating Peptides in Supernatants of Clinically Isolated Fungal Strains.

*P. brasiliensis* or *C. albicans* biosensor strains (yMJ258 and yMJ260, respectively) and a control *S. cerevisiae* strain (yMJ251) were used to test for the presence of the respective mating peptides in supernatants derived from clinically isolated pathogenic fungi or *S. cerevisiae* (supernatants preparation described above). Cells were seeded at an $OD_{600}$ of 2 in the indicated supernatant mixed with standard complete synthetic media (2% dextrose) supplemented with 5% YPD in 96-well microtiter plates, cultured at 30° C. and 800 RPM, and lycopene production was measured by absorbance as described above. A 2× stock of media and a 10× stock of the supernatant were used and diluted to reach the appropriate 1× concentration. The control supernatant for W303-1B was diluted to 50% in the final assay. Statistical significance of signal (i.e. biosensor strain treated with its cognate-supernatant) over noise (same biosensor strain treated with non-cognate supernatants) was determined by performing a paired parametric t-test in Prism (GraphPad). The highest P-value resulting from sample comparisons is given as  P≤0.01, * P≤0.001 (FIG. 22E). All measurements were performed in triplicates.

Determination of Lycopene Content in Microtiter Plate Format.

To determine the relative lycopene content directly in a cell suspension, we adapted the method proposed by Myers et al.[140] to characterize pigmented cells through optical density measurements at multiple wavelengths. This method greatly reduces the noise due to variations in cell growth phase, cell density and other sample irregularities. This enabled the precise evaluation of lycopene content in a high throughput microtiter plate format.

As described by Myers et al.[140], the optical density of the cell suspension measured at a sensitive wavelength (i.e. corresponding to an absorption maxima of the pigment) is approximately composed of two additive components: scatter due to cells and absorbance due to the pigment. Therefore the pigment content in a cell suspension is proportional to the measured optical density corrected for the scattering component as follows:

$$[\text{pigment}] \propto Abs_{S,P} = OD_S - OD_{S,scat} \tag{E3}$$

where $Abs_{S,P}$ is the absorbance due to the pigment at the sensitive wavelength S, $OD_S$ is the measured optical density at the sensitive wavelength S, and $OD_{S,scat}$ is a calculated scattering component at the sensitive wavelength S. Since there was noticeable Raleigh-like wavelength dependence in the scatter of lycopene null strains we chose the following functional form to approximate scatter at a particular wavelength λ:

$$OD_{\lambda,scat} = B - \log_{10}\left(1 - \frac{A}{\lambda}\right) \tag{E4}$$

where A and B are constants that reflect changes in cell density and other sample irregularities. At each time point and for each sample, we can calculate the corresponding values of A and B by using the optical density values measured at two robust wavelengths (i.e. corresponding to wavelengths where scatter is the only or dominant component). Substituting these additional scatter-only optical density measurements into Eq. E4 and solving for A and B we get:

$$A = R1\left(\frac{1-T}{\frac{R1}{R2} - T}\right), \text{ where } T = 10^{OD_{R1} - OD_{R2}} \tag{E5}$$

$$B = OD_{R1} + \log_{10}\left(1 - \frac{A}{R2}\right) \tag{E6}$$

where $OD_{R1}$ and $OD_{R2}$ are the measured optical densities at the robust wavelengths R1 and R2. Therefore, by setting λ=S and substituting Eq. E4 into Eq. E3, the relative content of lycopene in a cell suspension is given by:

$$[\text{pigment}] \propto Abs_{S,P} = OD_S + \log_{10}\left(1 - \frac{A}{S}\right) - B \tag{E7}$$

To apply this method to lycopene in yeast, we determined the appropriate sensitive and robust wavelengths by obtaining the absorbance spectrum of lycopene directly in yeast cells. The spectrum was determined by subtracting the optical density spectrum of a lycopene null strain yMJ105 from that of a constitutive lycopene producing strain LW2671 (FIG. 19B). This spectrum showed the characteristic profile of lycopene absorbance and had two major absorbance maxima at 485 nm and 520 nm (FIG. 19C). Based on this spectrum, 520 nm was chosen as the sensitive wavelength (S=520) since it is furthest away from other natural chromophores in yeast that absorb below 500 nm (e.g. flavins). 395 nm and 600 nm were chosen as the two robust wavelengths (R1=600 and R2=395) with low absorbance from lycopene and other natural chromophores.

Three additional considerations were crucial to yield reproducible lycopene measurements in a microtiter plate format. First, all three optical density measurements (at 395 nm, 520 nm and 600 nm) were taken at the same time for each well to reduce errors due to the settling of cells during the measurement of a whole microtiter plate. Second, assay wells were blanked using a reference well on the same microtiter plate containing identical media conditions as the assay wells but with no cells. This was particularly important when colored media was used. Finally, high cell densities ($OD_{600} \geq 2$) were used to yield larger bulk lycopene signals even with the short path length of micro titer plates (~3 mm). Since these high optical density values were outside the linear range of the photodetector, all optical density values were first corrected using the following formula to give true optical density values:

$$OD_{true} = \frac{k \cdot OD_{meas}}{OD_{sat} - OD_{meas}} \tag{E8}$$

where $OD_{meas}$ is the measured optical density, $OD_{sat}$ is the saturation value of the photodetector and k is the true optical density at which the detector reaches half saturation of the measured optical density. Appropriate values for $OD_{sat}$ and k were determined by plotting direct optical density measurements of a range of cultures of several strains, against the true optical densities determined by dilution to the linear range. Optical densities were taken at 395 nm, 520 nm and 600 nm. All points were fit once with Eq. E8 using Prism (GraphPad) to give $OD_{sat}$=3.57 and k=3.16. These values were used to correct all optical density measurements in this study.

Results and Discussion.

Next, we challenged our biosensor for detection of naturally secreted mating peptides using clinically-isolated *Paracoccidioides* strains. Paracoccidioidomycosis (PCM), an invasive fungal infection endemic to Latin America, is one of many neglected tropical diseases that primarily affect poor populations and lack systematic surveillance.[141] PCM is caused by inhalation of airborne conidia produced by mycelium of the soil ascomycete *P. brasiliensis*.[136] Recent identification of the genetic components underlying its mating system[137] enabled us to pursue specific yeast-based detection of *P. brasiliensis*, which could facilitate detection of its environmental reservoir.

Specifically, we challenged our yeast biosensor to detect cultured mycelial *P. brasiliensis* isolated from human patients. Biosensor cells expressing *P. brasiliensis* mating receptor, which exhibited specific and sensitive detection of its synthetic mating peptide (FIGS. 20A-B and 21A-D), were mixed with spent supernatants from two clinically isolated *Paracoccidioides* strains (Table 10). In response, we observed lycopene production well above the visible threshold (FIG. 22E). Secreted mating peptides were similarly detected from clinical isolates of *C. albicans* and *H. capsulatum* (FIG. 22E). Interestingly, the peptide produced by *H. capsulatum*[137], the causative agent of Histoplasmosis,[138] is identical to that of *P. brasiliensis* and could be detected using both biosensor strains (FIG. 22A-D).

TABLE 9

| Species | Association | Pathogenic Target | Synthetic Peptide Sequence | Receptor UniProt ID | Receptor Source |
|---|---|---|---|---|---|
| *Saccharomyces cerevisiae* | Baker's yeast | — | WHWLQLK PGQPMY | D6VTK4 | ATCC 200895 |
| *Candida glabrata* | Candidiasis | Human | WHWVRLR KGQGIF | Q6FLY8 | ATCC 2001 |
| *Candida albicans* | Candidiasis | Human | GFRLTNF GYFEPG | Q59Q04 | ATCC MYA-2876 |
| *Lodderomyces elongisporus* | Candidiasis | Human | WMWTRY GRFSPV | A5E1D9 | ATCC 11503 |
| *Paracoccidioides brasiliensis* (*lutzii*) | Paracoccidioidomycosis | Human | WCTRP GQGC | C1GFU7 | Plasmid pLPreB (30) |
| *Botrytis cinerea* (*Botryotinia fuckeliana*) | Gray mold | Plants | WCGRP GQPC | G2YE05 | codon-optimized synthetic DNA |

TABLE 9-continued

| Species | Association | Pathogenic Target | Synthetic Peptide Sequence | Receptor UniProt ID | Receptor Source |
|---|---|---|---|---|---|
| *Fusarium graminearum* (*Gibberella zeae*) | Wheat head blight | Plants | WCWWK GQPCW | I1RG07 | codon-optimized synthetic DNA |
| *Magnaporthe oryzae* | Rice blast | Plants | QWCPRR GQPCW | G4MR89 | codon-optimized synthetic DNA |
| *Zygosaccharomyces bailii* | Spoilage | Food spoilage | HLVRLS PGAAMF | S6EXB4 | codon-optimized synthetic DNA |
| *Zygosaccharomyces rouxii* | Spoilage | Food spoilage | HFIELD PGQPMF | C5DX97 | ATCC 2623 |
| *Histoplasma capsulatum* | Histoplasmosis | Human | WCTRP GQGC | C0NQ16 | codon-optimized synthetic DNA |

TABLE 10

| Strain | Genotype | Comments |
|---|---|---|
| FY251 | MATa his3-Δ200, leu2-Δ1 trp1-Δ63, ura3-52 | ATCC 96098 |
| BY4733 | MATa his3Δ200 leu2Δ0 met15Δ0 trp1A63 ura3Δ0 | ATCC 200895 |
| LW2591 | BY4733 MATa-inc HOΔ::ReRec | Reiterative Recombination acceptor strain (32) |
| LW2671 | BY4733 derivative overexpressing CrtEBI | Constitutive lycopene producing strain (40) |
| yMJ105 | LW2591 sst2-Δ far 1-Δ | Parental biosensor strain |
| | Fluorescence Readout Strains | |
| yMJ183 | yMJ105 ste2-A fus1Δ::pFUS1-HIS3-tHIS3 ReRec[1]::pFUS1-yCherry-tACT1 | Receptor-less fluorescence biosensor strain |
| yMJ281 | yMJ183 + pMJ093 | *S. cerevisiae* biosensor |
| yMJ282 | yMJ183 + pMJ090 | *C. albicans* biosensor |
| yMJ284 | yMJ183 + pMJ095 | *B. cinerea* biosensor |
| yMJ285 | yMJ183 + pMJ096 | *C. glabrata* biosensor |
| yMJ286 | yMJ183 + pMJ097 | *F. graminearum* biosensor |
| yMJ288 | yMJ183 + pMJ099 | *L. elongisporous* biosensor |
| yMJ289 | yMJ183 + pMJI00 | *M. oryzea* biosensor |
| yMJ290 | yMJ183 + pMJ101 | *P. brasiliensis* biosensor |
| yMJ294 | yMJ183 + pMJ105 | *Z. bailii* biosensor |
| yMJ295 | yMJ183 + pMJ106 | *Z. rouxii* biosensor |
| yMJ312 | yMJ183 + pMJ117 | *H. capsulatum* biosensor |
| yJM06 | yMJ183 + pJM13 | Codon-optimized *C. glabrata* biosensor |
| | Lycopene Biosensor Strains | |
| yMJ116 | yMJ105 ReRec[1]:: pTEF1-CrtE-tADH1-(CrtB-pPGK1, rev) | Lycopene null strain |
| yMJ118 | yMJ105 ReRec[1]::pTEF1-CrtE-tADH1-(CrtB-pPGK1, rev) ReRec[2]::pFUS1-CrtI-tACT1 | Unoptimized lycopene biosensor Lyco-1 |
| yMJ151 | yMJ118 + pMJ006 | "+2X CrtI" intermediate |
| yMJ152 | yMJ118 + pMJ009 | "+tHMG1" intermediate |

TABLE 10-continued

| Strain | Genotype | Comments |
|---|---|---|
| yMJ165 | yMJ118 + pMJ012 | "+FAD1" intermediate |
| yMJ251 | yMJ105 met15Δ::pFUS1-CrtI-tACT1-MET15 ReRec[1]::pTEF1-CrtE-tADH1-(CrtB-pPGK1, rev) ReRec[2]::pFUS1-CrtI-tACT1 ReRec[3]::pTDH3-FAD1-tPGK1 | Optimized lycopene biosensor Lyco-2 (Sc biosensor) |
| yMJ258 | yMJ251 ste2Δ::pTDH3-Pb.Ste2-tSTE2 | Pb biosensor |
| yMJ260 | yMJ251 ste2Δ::pTDH3-Ca.Ste2-tSTE2 | Ca biosensor |
| | Strains Used to Generate Pathogen and Control Supernatants | |
| W303-1B | MATα leu2-3, 112 trp1-1 can1-100 ura3-1 ade2-1 his3-11, 15 | ATCC 201238 |
| FY250 | MATα his3-Δ200, leu2-Δ1 trp1-Δ63, ura3-52 | (50) |
| GC75 | *Candida albicans*, MTLα/MTLα | Genebank assembly number GCA_000773735.1 (46) |
| ySB36 | *Candida albicans*, MTLa/MTLα | Clinical isolate obtained from A-C. Uhlemann, mating loci (MTL) were genotyped by PCR |
| ySB45 | *Candida albicans*, MTLα/MTLα | sorbose selected isolate, derivative of isolate ySB36, MTL were genotyped by PCR |
| Pb01 | *Paracoccidioides lutzii*, MAT1-1 | Supernatant prepared by Prof. Fernando Rodrigues (44) |
| Pb18 | *Paracoccidioides brasiliensis*, MAT1-2 | Supernatant prepared by Prof. Fernando Rodrigues (44) |
| Hc01 | *Histoplasma capsulatum*, NAm2 | Supernatant prepared by Prof. Chad Rappleye (42) |
| Hc06 | *Histoplasma capsulatum*, NAm1 | Supernatant prepared by Prof. Chad Rappleye (42) |

7. REFERENCE LIST

1 Gu, M. B., Choi, S. H. & Kim, S. W. Some observations in freeze-drying of recombinant bioluminescent *Escherichia coli* for toxicity monitoring. *J Biotechnol* 88, 95-105 (2001).

2 Yagi, K. Applications of whole-cell bacterial sensors in biotechnology and environmental science. *Appl Microbiol Biotechnol* 73, 1251-1258 (2007).

3 Ptitsyn, L. R. et al. A biosensor for environmental genotoxin screening based on an SOS lux assay in recombinant *Escherichia coli* cells. *Appl Environ Microbiol* 63, 4377-4384 (1997).

4 Van Dyk, T. K. et al. Rapid and sensitive pollutant detection by induction of heat shock gene-bioluminescence gene fusions. *Appl Environ Microbiol* 60, 1414-1420 (1994).

5 Belkin, S., Smulski, D. R., Vollmer, A. C., Van Dyk, T. K. & LaRossa, R. A. Oxidative stress detection with *Escherichia coli* harboring a katG'::lux fusion. *Appl Environ Microbiol* 62, 2252-2256 (1996).

6 Werlen, C., Jaspers, M. C. & van der Meer, J. R. Measurement of biologically available naphthalene in gas and aqueous phases by use of a *Pseudomonas putida* biosensor. *Appl Environ Microbiol* 70, 43-51 (2004).

7 Stocker, J. et al. Development of a set of simple bacterial biosensors for quantitative and rapid measurements of arsenite and arsenate in potable water. *Environ Sci Technol* 37, 4743-4750 (2003).

8 Hansen, L. H. & Sorensen, S. J. Versatile biosensor vectors for detection and quantification of mercury. *FEMS Microbiol Lett* 193, 123-127 (2000).

9 Olivo, P. D., Collins, P. L., Peeples, M. E. & Schlesinger, S. Detection and quantitation of human respiratory syncytial virus (RSV) using minigenome cDNA and a Sindbis virus replicon: a prototype assay for negative-strand RNA viruses. *Virology* 251, 198-205 (1998).

10 Levskaya, A. et al. Synthetic biology: engineering *Escherichia coli* to see light. *Nature* 438, 441-442 (2005).

11 Sauer, S. & Kliem, M. Mass spectrometry tools for the classification and identification of bacteria. *Nat Rev Microbiol* 8, 74-82, (2010).

12 Mischak, H. et al. Capillary electrophoresis-mass spectrometry as a powerful tool in biomarker discovery and clinical diagnosis: an update of recent developments. *Mass Spectrom Rev* 28, 703-724 (2009).

13 Conklin, B. R. et al. Engineering GPCR signaling pathways with RASSLs. *Nat Methods* 5, 673-678 (2008).

14 Dong, S., Rogan, S. C. & Roth, B. L. Directed molecular evolution of DREADDs: a generic approach to creating next-generation RASSLs. *Nat Protoc* 5, 561-573 (2010).

15 Wendland, J., Dunkler, A. & Walther, A. Characterization of alpha-factor pheromone and pheromone receptor genes of *Ashbya gossypii. FEMS Yeast Res* 11, 418-429 (2011).

16 Gomes-Rezende, J. A. et al. Functionality of the *Paracoccidioides* Mating α-Pheromone-Receptor System. *PLoS ONE* 7, e47033, (2012).

17 Janiak, A. M. et al. Functional expression of the *Candida albicans* α-factor receptor in *Saccharomyces cerevisiae. Fungal Genetics and Biology* 42, 328-338 (2005).

18 Mayrhofer, S. & Poggeler, S. Functional characterization of an alpha-factor-like *Sordaria macrospora* peptide pheromone and analysis of its interaction with its cognate receptor in *Saccharomyces cerevisiae. Eukaryot Cell* 4, 661-672 (2005).

19 Pierce, K. L., Premont, R. T. & Lefkowitz, R. J. Seven-transmembrane receptors. *Nat Rev Mol Cell Biol* 3, 639-650 (2002).

20 Wang, Y. & Dohlman, H. G. Pheromone signaling mechanisms in yeast: a prototypical sex machine. *Science* 306, 1508-1509 (2004).

21 King, K., Dohlman, H. G., Thorner, J., Caron, M. G. & Lefkowitz, R. J. Control of yeast mating signal transduction by a mammalian beta 2-adrenergic receptor and Gs alpha subunit. *Science* 250, 121-123 (1990).

22 Sander, P. et al. Heterologous expression of the human D2S dopamine receptor in protease-deficient *Saccharomyces cerevisiae* strains. *Eur J Biochem* 226, 697-705 (1994).

23 Harris, J. R. et al. Field evaluation of crystal VC Rapid Dipstick test for cholera during a cholera outbreak in Guinea-Bissau. *Trop Med Int Health* 14, 1117-1121 (2009).

24 Miret, J. J., Rakhilina, L., Silverman, L. & Oehlen, B. Functional expression of heteromeric calcitonin gene-related peptide and adrenomedullin receptors in yeast. *J Biol Chem* 277, 6881-6887 (2002).

25 Ignatovica, V., Megnis, K., Lapins, M., Schioth, H. B. & Klovins, J. Identification and analysis of functionally important amino acids in human purinergic 12 receptor using a *Saccharomyces cerevisiae* expression system. *FEBS J* 279, 180-191 (2012).

26 Erickson, J. R. et al. Edg-2/Vzg-1 couples to the yeast pheromone response pathway selectively in response to lysophosphatidic acid. *J Biol Chem* 273, 1506-1510 (1998).

27 Price, L. A., Kajkowski, E. M., Hadcock, J. R., Ozenberger, B. A. & Pausch, M. H. Functional coupling of a mammalian somatostatin receptor to the yeast pheromone response pathway. *Mol Cell Biol* 15, 6188-6195 (1995).

28 Price, L. A., Strnad, J., Pausch, M. H. & Hadcock, J. R. Pharmacological characterization of the rat A2a adenosine receptor functionally coupled to the yeast pheromone response pathway. *Mol Pharmacol* 50, 829-837 (1996).

29 Erlenbach, I. et al. Functional expression of M(1), M(3) and M(5) muscarinic acetylcholine receptors in yeast. *J Neurochem* 77, 1327-1337 (2001).

30 Armbruster, B. N., Li, X., Pausch, M. H., Herlitze, S. & Roth, B. L. Evolving the lock to fit the key to create a family of G protein-coupled receptors potently activated by an inert ligand. *Proc Natl Acad Sci USA* 104, 5163-5168 (2007).

31 Pei, Y., Rogan, S. C., Yan, F. & Roth, B. L. Engineered GPCRs as tools to modulate signal transduction. *Physiology* (*Bethesda*) 23, 313-321, (2008).

32 Ault, A. D. & Broach, J. R. Creation of GPCR-based chemical sensors by directed evolution in yeast. *Protein Eng Des Sel* 19, 1-8 (2006).

33 Martin, S. H., Wingfield, B. D., Wingfield, M. J. & Steenkamp, E. T. Causes and Consequences of Variability in Peptide Mating Pheromones of Ascomycete Fungi. *Molecular Biology and Evolution* 28, 1987-2003 (2011).

34 Martin, S. H., Steenkamp, E. T., Wingfield, M. J., Wingfield, B. D. Mate-recognition and species boundaries in the ascomycetes. *Fungal Diversity* 58, 1-12 (2013).

35 Leavitt, L. M., Macaluso, C. R., Kim, K. S., Martin, N. P. & Dumont, M. E. Dominant negative mutations in the alpha-factor receptor, a G protein-coupled receptor encoded by the STE2 gene of the yeast *Saccharomyces cerevisiae. Mol Gen Genet* 261, 917-932 (1999).

36 Martin, N. P., Celic, A. & Dumont, M. E. Mutagenic mapping of helical structures in the transmembrane segments of the yeast alpha-factor receptor. *J Mol Biol* 317, 765-788 (2002).

37 Naider, F. & Becker, J. M. The alpha-factor mating pheromone of *Saccharomyces cerevisiae*: a model for studying the interaction of peptide hormones and G protein-coupled receptors. *Peptides* 25, 1441-1463 (2004).

38 Mathew, E. et al. Differential interactions of fluorescent agonists and antagonists with the yeast G protein coupled receptor Ste2p. *J Mot Biol* 409, 513-528 (2011).

39 Hauser, M., Kauffman, S., Lee, B. K., Naider, F. & Becker, J. M. The first extracellular loop of the *Saccharomyces cerevisiae* G protein-coupled receptor Ste2p undergoes a conformational change upon ligand binding. *J Biol Chem* 282, 10387-10397 (2007).

40 Lin, J. C., Parrish, W., Eilers, M., Smith, S. O. & Konopka, J. B. Aromatic residues at the extracellular ends of transmembrane domains 5 and 6 promote ligand activation of the G protein-coupled alpha-factor receptor. *Biochemistry* 42, 293-301 (2003).

41 Umanah, G. K., Huang, L. Y., Maccarone, J. M., Naider, F. & Becker, J. M. Changes in conformation at the cytoplasmic ends of the fifth and sixth transmembrane helices of a yeast G protein-coupled receptor in response to ligand binding. *Biochemistry* 50, 6841-6854 (2011).

42 Umanah, G. K. et al. Identification of residue-to-residue contact between a peptide ligand and its G protein-coupled receptor using periodate-mediated dihydroxyphenylalanine cross-linking and mass spectrometry. *J Biol Chem* 285, 39425-39436 (2010).

43 Son, C. D., Sargsyan, H., Naider, F. & Becker, J. M. Identification of ligand binding regions of the *Saccharomyces cerevisiae* alpha-factor pheromone receptor by photoaffinity cross-linking. *Biochemistry* 43, 13193-13203 (2004).

44 Minic, J. et al. Functional expression of olfactory receptors in yeast and development of a bioassay for odorant screening. *FEBS J* 272, 524-537 (2005).

45 Alper, H., Jin, Y. S., Moxley, J. F. & Stephanopoulos, G. Identifying gene targets for the metabolic engineering of lycopene biosynthesis in *Escherichia coli. Metab Eng* 7, 155-164 (2005).

46 Armstrong, G. A. Genetics of eubacterial carotenoid biosynthesis: a colorful tale. *Annu Rev Microbiol* 51, 629-659 (1997).

47 Chemler, J. A., Yan, Y. & Koffas, M. A. Biosynthesis of isoprenoids, polyunsaturated fatty acids and flavonoids in *Saccharomyces cerevisiae. Microb Cell Fact* 5, 20 (2006).

48 van der Meer, J. R. & Belkin, S. Where microbiology meets microengineering: design and applications of reporter bacteria. *Nat Rev Microbiol* 8, 511-522 (2010).

49 Radhika, V. et al. Chemical sensing of DNT by engineered olfactory yeast strain. *Nat Chem Biol* 3, 325-330 (2007).

50 Xu, Y., Ault, A. D., Broach, J. R. Yeast That Smell. *J. Biochem. Technol.* 1 (2008).

51 Struss, A. K., Pasini, P., Daunert S. in *Recognition Receptors in Biosensors* (ed M. Zourob) 565-598 (Springer New York, 2010).

52 MacKay, V. L. et al. Gene expression analyzed by high-resolution state array analysis and quantitative proteomics: response of yeast to mating pheromone. *Mol Cell Proteomics* 3, 478-489 (2004).

53 Hagen, D. C., McCaffrey, G. & Sprague, G. F., Jr. Pheromone response elements are necessary and sufficient for basal and pheromone-induced transcription of the FUS1 gene of *Saccharomyces cerevisiae. Mol Cell Biol* 11, 2952-2961 (1991).

54 Wang, Y. & Dohlman, H. G. Pheromone-regulated sumoylation of transcription factors that mediate the invasive to mating developmental switch in yeast. *J Biol Chem* 281, 1964-1969 (2006).
55 Fukuda, N., Ishii, J., Kaishima, M. & Kondo, A. Amplification of agonist stimulation of human G-protein-coupled receptor signaling in yeast. *Anal Biochem* 417, 182-187 (2011).
56 Takahashi, S. & Pryciak, P. M. Membrane localization of scaffold proteins promotes graded signaling in the yeast MAP kinase cascade. *Curr Biol* 18, 1184-1191 (2008).
57 Cairns, B. R., Ramer, S. W. & Kornberg, R. D. Order of action of components in the yeast pheromone response pathway revealed with a dominant allele of the STE11 kinase and the multiple phosphorylation of the STET kinase. *Genes Dev* 6, 1305-1318 (1992).
58 Bashor, C. J., Helman, N. C., Yan, S. & Lim, W. A. Using engineered scaffold interactions to reshape MAP kinase pathway signaling dynamics. *Science* 319, 1539-1543 (2008).
59 Verwaal, R. et al. High-level production of beta-carotene in *Saccharomyces cerevisiae* by successive transformation with carotenogenic genes from *Xanthophyllomyces dendrorhous*. *Appl Environ Microbiol* 73, 4342-4350 (2007).
60 Ebert, M. P. et al. Identification of gastric cancer patients by serum protein profiling. *J Proteome Res* 3, 1261-1266 (2004).
61 Hingorani, S. R. et al. Preinvasive and invasive ductal pancreatic cancer and its early detection in the mouse. *Cancer Cell* 4, 437-450 (2003).
62 Villanueva, J. et al. Serum peptide profiling by magnetic particle-assisted, automated sample processing and MALDI-TOF mass spectrometry. *Anal Chem* 76, 1560-1570 (2004).
63 Villanueva, J. et al. Differential exoprotease activities confer tumor-specific serum peptidome patterns. *J Clin Invest* 116, 271-284 (2006).
64 Yang, H. et al. Prognostic polypeptide blood plasma biomarkers of Alzheimer's disease progression. *J Alzheimers Dis* 40, 659-666 (2014).
65 Lin, X. et al. DJ-1 isoforms in whole blood as potential biomarkers of Parkinson disease. *Sci Rep* 2, 954 (2012).
66 Niwa, T. Biomarker discovery for kidney diseases by mass spectrometry. *J Chromatogr B Analyt Technol Biomed Life Sci* 870, 148-153 (2008).
67 Gujraty, K. et al. Functional characterization of peptide-based anthrax toxin inhibitors. *Mol Pharm* 2, 367-372 (2005).
68 Ma, H., Zhou, B., Kim, Y. & Janda, K. D. A cyclic peptide-polymer probe for the detection of *Clostridium botulinum* neurotoxin serotype A. *Toxicon* 47, 901-908 (2006).
69 Higgins, D. A. et al. The major *Vibrio cholerae* autoinducer and its role in virulence factor production. *Nature* 450, 883-886 (2007).
70 Cloak, O. M., Solow, B. T., Briggs, C. E., Chen, C. Y. & Fratamico, P. M. Quorum sensing and production of autoinducer-2 in *Campylobacter* spp., *Escherichia coli* O157:H7, and *Salmonella enterica* serovar *Typhimurium* in foods. *Appl Environ Microbiol* 68, 4666-4671 (2002).
71 Pausch, M. H. G-protein-coupled receptors in *Saccharomyces cerevisiae*: high-throughput screening assays for drug discovery. *Trends Biotechnol* 15, 487-494 (1997).
72 Tracewell, C. A. & Arnold, F. H. Directed enzyme evolution: climbing fitness peaks one amino acid at a time. *Curr Opin Chem Biol* 13, 3-9 (2009).
73 Shin, H. J., Park, H. H. & Lim, W. K. Freeze-dried recombinant bacteria for on-site detection of phenolic compounds by color change. *J Biotechnol* 119, 36-43 (2005).
74. Su, L., Jia, W., Hou, C. & Lei, Y. Microbial biosensors: A review. *Biosens. Bioelectron.* 26, 1788-1799 (2011).
75. Eilam, Y. & Grossowicz, N. Nystatin Effects on Cellular Calcium in *Saccharomyces-Cerevisiae*. *Biochim. Biophys. Acta* 692, 238-243 (1982).
76. Garjonyte, R., Melvydas, V. & Malinauskas, A. Amperometric biosensors for lactic acid based on baker's and wine yeast. *Microchim. Acta* 164, 177-183 (2009).
77. Mavrodi, D. V. et al. Functional Analysis of Genes for Biosynthesis of Pyocyanin and Phenazine-1-Carboxamide from *Pseudomonas aeruginosa* PAO1. *J. Bacteriol.* 183, 6454-6465 (2001).
78. Bellin, D. L. et al. Integrated circuit-based electrochemical sensor for spatially resolved detection of redox-active metabolites in biofilms. *Nat. Commun.* 5, 3256 (2014).
79. Spira, M. E. & Hai, A. Multi-electrode array technologies for neuroscience and cardiology. *Nat. Nanotechnol.* 8, 83-94 (2013).
80. Ali, R., Zielinski, R. E. & Berkowitz, G. A. Expression of plant cyclic nucleotide-gated cation channels in yeast. *J Exp Bot* 57, 125-138 (2006).
81. Bourbonnais, Y., Bolin, D. & Shields, D. Secretion of somatostatin by *Saccharomyces cerevisiae*. Correct proteolytic processing of pro-alpha-factor-somatostatin hybrids requires the products of the KEX2 and STE13 genes. *J. Biol. Chem.* 263, 15342-15347 (1988).
82. Miyajima, A., Bond, M. W., Otsu, K., Arai, K. & Arai, N. Secretion of mature mouse interleukin-2 by *Saccharomyces cerevisiae*: use of a general secretion vector containing promoter and leader sequences of the mating pheromone α-factor. *Gene* 37, 155-161 (1985).
83. Ro, D. K. et al. Production of the antimalarial drug precursor artemisinic acid in engineered yeast. *Nature* 440, 940-943 (2006)
84. Huat, L. B. et al. *Entamoeba histolytica* acetyl-CoA synthetase: biomarker of acute amoebic liver abscess. *Asian Pac J Trop Biomed* 4, 446-450, (2014)
85. Rafati, S. et al. Amastin peptide-binding antibodies as biomarkers of active human visceral leishmaniasis. *Clin Vaccine Immunol* 13, 1104-1110 (2006).
86. Huzarewich, R. L., Siemens, C. G. & Booth, S. A. Application of "omics" to prion biomarker discovery. *J Biomed Biotechnol* 2010, 613504.
87. van Holten, T. C. et al. Circulating biomarkers for predicting cardiovascular disease risk; a systematic review and comprehensive overview of meta-analyses. *PLoS ONE* 8, e62080 (2013)
88. Van Everbroeck, B., Boons, J. & Cras, P. Cerebrospinal fluid biomarkers in Creutzfeldt-Jakob disease. *Clin Neurol Neurosurg* 107, 355-360 (2005)
89. Pisa, D., Alonso, R., Rabano, A., Rodal, I. & Carrasco, L. Different Brain Regions are Infected with Fungi in Alzheimer's Disease. *Sci Rep* 5, 15015 (2015)
90. Lee M E, Aswani A, Han A S, Tomlin C J, Dueber J E. Expression-level optimization of a multi-enzyme pathway in the absence of a high-throughput assay. Nucleic Acids Research 2013; 41(22):10668-10678
91. Hwan Han et al. Optimization of bio-indigo production by recombinant *E. coli* harboring fmo gene. Enzyme and Microbial Technology (2008).
92. Santos, C. N., and G. Stephanopoulos. 2008. Melanin-based high-throughput screen for L-tyrosine production in *Escherichia coli*. *Appl. Environ. Microbiol.* 74:1190-1197

93. Bourbonnais, Y., Bolin, D. & Shields, D. Secretion of somatostatin by *Saccharomyces cerevisiae*. Correct proteolytic processing of pro-alpha-factor-somatostatin hybrids requires the products of the KEX2 and STE13 genes. *J. Biol. Chem.* 263, 15342-15347 (1988)

94. Miyajima, A., Bond, M. W., Otsu, K., Arai, K. & Arai, N. Secretion of mature mouse interleukin-2 by *Saccharomyces cerevisiae*: use of a general secretion vector containing promoter and leader sequences of the mating pheromone α-factor. *Gene* 37, 155-161 (1985)

95. Ro, D. K. et al. Production of the antimalarial drug precursor artemisinic acid in engineered yeast. *Nature* 440, 940-943 (2006)

96. Su, L., Jia, W., Hou, C. & Lei, Y. Microbial biosensors: A review. Biosens. Bioelectron. 26, 1788-1799 (2011); Eilam, Y. & Grossowicz, N. Nystatin Effects on Cellular Calcium in *Saccharomyces-Cerevisiae. Biochim. Biophys. Acta* 692, 238-243 (1982)

97. Garjonyte, R., Melvydas, V. & Malinauskas, A. Amperometric biosensors for lactic acid based on baker's and wine yeast. *Microchim. Acta* 164, 177-183 (2009)

98. Mavrodi, D. V. et al. Functional Analysis of Genes for Biosynthesis of Pyocyanin and Phenazine-1-Carboxamide from *Pseudomonas aeruginosa* PAO1. *J. Bacteriol.* 183, 6454-6465 (2001)

99. Bellin, D. L. et al. Integrated circuit-based electrochemical sensor for spatially resolved detection of redox-active metabolites in biofilms. *Nat. Commun.* 5, 3256 (2014)

100. Spira, M. E. & Hai, A. Multi-electrode array technologies for neuroscience and cardiology. *Nat. Nanotechnol.* 8, 83-94 (2013)

101. Ali, R., Zielinski, R. E. & Berkowitz, G. A. Expression of plant cyclic nucleotide-gated cation channels in yeast. *J Exp Bot* 57, 125-138 (2006)

102. De Nobel J G and Barnett J A (1991), "Passage of molecules through yeast cell walls: A brief essay-review". Yeast 7(4):313-23

102. De Nobel J G, Klis F M, Munnik T, Priem J, van den Ende H (1990), "An assay of relative cell wall porosity in *Saccharomyces cerevisiae, Kluyveromyces lactis* and *Schizosaccharomyces pombe*". Yeast 6(6):483-90.

103. Hollis, R. P., Killham, K. & Glover, L. A. Design and Application of a Biosensor for Monitoring Toxicity of Compounds to Eukaryotes. Appl. Environ. Microbiol. 66, 1676-1679 (2000)

104. Radhika, V., Proikas-Cezanne, T., Jayaraman, M., Onesime, D., Ha, J. H. & Dhanasekaran, D. N. Chemical sensing of DNT by engineered olfactory yeast strain. Nat. Chem. Biol. 3, 325-330 (2007).

105. Rider, T. H., Petrovick, M. S., Nargi, F. E., Harper, J. D., Schwoebel, E. D., Mathews, R. H., Blanchard, D. J., Bortolin, L. T., Young, A. M., Chen, J. & Hollis, M. A. A B Cell-Based Sensor for Rapid Identification of Pathogens. Science 301, 213-215 (2003)

106. Andreatta M, Lund O, Nielsen M (2013), Simultaneous alignment and clustering of peptide data using a Gibbs sampling approach. Bioinformatics 29(1):8-14.

107. Huat et al. Asian Pac J Trop Biomed 4(6):446-50 (2014)

108. Rafati et al. Clin Vaccine Immunol 13(10) (2006).

109. Pi H, Chien C T, Fields S (1997) Transcriptional activation upon pheromone stimulation mediated by a small domain of *Saccharomyces cervisiae* Ste12. Molecular and Cellular Biology 17(11):6410-18

110. Sievers, F. et al. Fast, scalable generation of high-quality protein multiple sequence alignments using Clustal Omega. Molecular Systems Biology 7, 539-539 (2014)

111. Krogh, A., Larsson, B., von Heijne, G. & Sonnhammer, E. L. L. Predicting transmembrane protein topology with a hidden markov model: application to complete genomes1. Journal of Molecular Biology 305, 567-580 (2001).

112. Ćelić, A. et al. Sequences in the Intracellular Loops of the Yeast Pheromone Receptor Ste2p Required for G Protein Activation†. Biochemistry 42, 3004-3017 (2003)

113. Sánchez, C., Braña, A. F., Méndez, C. & Salas, J. A. Reevaluation of the Violacein Biosynthetic Pathway and its Relationship to Indolocarbazole Biosynthesis. ChemBioChem 7, 1231-1240 (2006).

114. Pfaller, M. A. & Diekema, D. J. Epidemiology of Invasive Candidiasis: a Persistent Public Health Problem. Clin. Microbiol. Rev. 20, 133-163 (2007).

115. Ramirez-Zavaleta, C. Y., Salas-Delgado, G. E., Peñas, A. D. L. & Castaño, I. Subtelomeric Silencing of the MTL3 Locus of *Candida glabrata* Requires yKu70, yKu80, and Rif1 Proteins. Eukaryotic Cell 9, 1602-1611 (2010).

116. Berman, J. & Sudbery, P. E. *Candida albicans*: A molecular revolution built on lessons from budding yeast. Nat Rev Genet 3, 918-932 (2002).

117. Brown, G. D. et al. Hidden Killers: Human Fungal Infections. Sci Transl Med 4, 165rv13-165rv13 (2012)

118. Ramirez-Zavala, B., Reuß, O., Park, Y.-N., Ohlsen, K. & Morschhäuser, J. Environmental Induction of White-Opaque Switching in *Candida albicans. PLoS Pathog* 4, e1000089 (2008)

119. Huang, G. et al. N-Acetylglucosamine Induces White to Opaque Switching, a Mating Prerequisite in *Candida albicans. PLoS Pathog* 6, e1000806 (2010)

120. Hull, C. M., Raisner, R. M. & Johnson, A. D. Evidence for Mating of the 'Asexual' Yeast *Candida albicans* in a Mammalian Host. Science 289, 307-310 (2000).

121. Lachke, S. A., Lockhart, S. R., Daniels, K. J. & Soll, D. R. Skin Facilitates *Candida albicans* Mating. Infect. Immun. 71, 4970-4976 (2003).

122. Dumitru, R. et al. In Vivo and In Vitro Anaerobic Mating in *Candida albicans*. Eukaryotic Cell 6, 465-472 (2007).

123. Lequin, R. M. Enzyme Immunoassay (EIA)/Enzyme-Linked Immunosorbent Assay (ELISA). Clinical Chemistry 51, 2415-2418 (2005).

124. Kyte, J. & Doolittle, R. F. A simple method for displaying the hydropathic character of a protein. Journal of Molecular Biology 157, 105-132 (1982).

125. Higashijima, T., Fujimura, K., Masui, Y., Sakakibara, S. & Miyazawa, T. Physiological activities of peptides are correlated with the conformations of membrane-bound molecules: α-Mating factor from *Saccharomyces cerevisiae* and analog peptides. FEBS Letters 159, 229-232 (1983).

126. LaRocque, R. C. et al. Proteomic Analysis of *Vibrio cholerae* in Human Stool. Infect. Immun. 76, 4145-4151 (2008).

127. K. D. Goughenour, J.-M. Balada-Llasat, C. A. Rappleye, Quantitative Microplate-Based Growth Assay for Determination of Antifungal Susceptibility of *Histoplasma capsulatum* Yeasts. J. Clin. Microbiol. 53, 3286-3295 (2015).

128. P. L. Worsham, W. E. Goldman, Quantitative plating of *Histoplasma capsulatum* without addition of conditioned medium or siderophores. J. Med. Vet. Mycol. 26, 137-143 (1988).

129. I. Tones, A. M. García, O. Hernandez, A. González, J. G. McEwen, A. Restrepo, M. Arango, Presence and expression of the mating type locus in *Paracoccidioides brasiliensis* isolates. Fungal Genet. Biol. 47, 373-380 (2010).

130. A. Restrepo, B. E. Jiménez, Growth of *Paracoccidioides brasiliensis* yeast phase in a chemically defined culture medium. J. Clin. Microbiol. 12, 279-281 (1980).

131. E. Blignaut, C. Pujol, S. Lockhart, S. Joly, D. R. Soll, Ca3 fingerprinting of *Candida albicans* isolates from human immunodeficiency virus-positive and healthy individuals reveals a new clade in South Africa. J. Clin. Microbiol. 40, 826-836 (2002).

132. B. B. Magee, P. T. Magee, Induction of mating in *Candida albicans* by construction of MTLa and MTLalpha strains. Science. 289, 310-313 (2000).

133. G. Janbon, F. Sherman, E. Rustchenko, Monosomy of a specific chromosome determines L-sorbose utilization: a novel regulatory mechanism in *Candida albicans. Proc. Natl. Acad. Sci. U.S.A.* 95, 5150-5155 (1998).

134. J. M. Anderson, D. R. Soll, Unique phenotype of opaque cells in the white-opaque transition of *Candida albicans*. J. Bacteriol. 169, 5579-5588 (1987).

135. P. W. Sherwood, M. Carlson, Mutations in GSF1 and GSF2 alter glucose signaling in *Saccharomyces cerevisiae*. Genetics. 147, 557-566 (1997).

136. M. S. S. Felipe, F. A. G. Tones, A. Q. Maranhão, I. Silva-Pereira, M. J. Poças-Fonseca, E. G. Campos, L. M. P. Moraes, F. B. M. Arraes, M. J. A. Carvalho, R. V. Andrade, A. M. Nicola, M. M. Teixeira, R. S. A. Jesuíno, M. Pereira, C. M. A. Soares, M. M. Brígido, Functional genome of the human pathogenic fungus *Paracoccidioides brasiliensis*. FEMS Immunol. Med. Microbiol. 45, 369-381 (2005).

137. J. A. Gomes-Rezende, A. G. Gomes-Alves, J. F. Menino, M. A. Coelho, P. Ludovico, P. Gonçalves, M. H. J. Sturme, F. Rodrigues, Functionality of the *Paracoccidioides* mating α-pheromone-receptor system. PLoS One. 7, e47033 (2012).

138. G. D. Brown, D. W. Denning, N. A. R. Gow, S. M. Levitz, M. G. Netea, T. C. White, Hidden killers: human fungal infections. Sci. Transl. Med. 4, 165rv13 (2012).

139. M. D. Abramoff, P. J. Magalhães, S. J. Ram, Image processing with ImageJ. Biophotonics international. 11, 36-42 (2004).

140. J. A. Myers, B. S. Curtis, W. R. Curtis, Improving accuracy of cell and chromophore concentration measurements using optical density. BMC Biophys. 6, 4 (2013).

141. P. J. Hotez, M. E. Bottazzi, C. Franco-Paredes, S. K. Ault, M. R. Periago, The neglected tropical diseases of Latin America and the Caribbean: a review of disease burden and distribution and a roadmap for control and elimination. PLoS Negl. Trop. Dis. 2, e300 (2008).

Various references are cited herein, the contents of which are hereby incorporated by reference in their entireties.

What is claimed is:

1. A sensor fungal cell comprising a fungal non-native G-protein coupled receptor (GPCR) that binds to a peptide analyte derived from an agent, wherein the peptide analyte is a ligand for the fungal non-native GPCR, wherein binding of the peptide analyte to the fungal non-native GPCR triggers an appearance of a reporter in the fungal cell, wherein the appearance of the reporter indicates the presence of the agent, and wherein the reporter is a biosynthesized visible-light pigment.

2. The sensor cell of claim 1, wherein the agent is selected from the group consisting of human pathogenic agents, agricultural agents, industrial/model organism agents, bioterrorism agents and heavy metal contaminants.

3. The sensor cell of claim 1, wherein the non-native fungal GPCR is engineered to bind to the peptide analyte.

4. The sensor cell of claim 3, wherein the non-native fungal GPCR receptor is engineered by directed evolution to bind the peptide analyte.

5. The sensor cell of claim 1, wherein the non-native fungal GPCR is a fungal pheromone GPCR.

6. The sensor cell of claim 1, wherein the non-native fungal GPCR is a GPCR comprising an amino acid sequence selected from the group consisting of SEQ ID NOs: 6, 9, 12, 15, 18, 21, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112 and 222.

7. The sensor cell of claim 1, wherein the peptide analyte is a cognate ligand for the non-native fungal GPCR or the analyte is a non-cognate ligand for the non-native GPCR.

8. The sensor cell of claim 1, wherein the peptide analyte is a peptide epitope of a polypeptide or protein.

9. The sensor cell of claim 1, wherein the peptide analyte is a fungal mating pheromone.

10. The sensor cell of claim 9, wherein the fungal mating pheromone is selected from the group consisting of a human fungal mating pheromone, a non-human animal fungal mating pheromone, a plant fungal mating pheromone, a food fungal mating pheromone and an industrial/model fungal mating pheromone.

11. The sensor cell of claim 10, wherein:

(a) the human fungal mating pheromone is selected from the group consisting of the mating pheromones of *C. albicans, C. glabrata, P. brasiliensis, L. elongisporous, P. rubens, C. guillermondi, C. tropicalis*, and *C. parapsilosis, C. lusitaniae, S. scheckii*, and *Candida krusei;*

(b) the non-human animal fungal mating pheromone is the mating pheromone of *P. destructans;*

(c) the plant fungal mating pheromone is selected from the group consisting of the mating pheromones of *F. graminearum, M. oryzea, B. cinerea, G. candidum*, and *C. purpurea;*

(d) the food fungal mating pheromone is selected from the group consisting of the mating pheromones of *Zygosaccharomyces bailii, Zygosaccharomyces rouxii*, and *N. fischeri*; or (e) the industrial/model fungal mating pheromone is selected from the group consisting of the mating pheromones of *S. cerevisiae, K. lactis, S. pombe, V. polyspora* (receptor 1), *V. polyspora* (receptor 2), *S. stipitis, S. japonicas, S. castellii, S. octosporus, A. oryzae, T. melanosporum, D. haptotyla, C. tenuis, Y. lipolytica, T. delbrueckii, B. bassiana, K. pastoris, A. nidulans, N. crassa* and *H. jecorina.*

12. The sensor cell of claim 1, wherein the peptide analyte comprises an amino acid sequence selected from the group consisting of SEQ ID NOs: 5, 8, 11, 14, 17, 20 and 34-49.

13. The sensor cell of claim 1, wherein the peptide analyte has a length of about 3-50 residues.

14. The sensor cell of claim 1, wherein the peptide analyte is derived from a bacterial pathogen.

15. The sensor cell of claim 1, wherein the peptide analyte is derived from *Vibrio cholera* or from cholera toxin.

16. The sensor cell of claim 15, wherein:

(a) the peptide analyte derived from *Vibrio cholerae* is selected from the group consisting of a peptide having an amino acid sequence set forth in VEVPGSQHIDSQKKA (SEQ ID NO: 26), a peptide having an amino acid sequence that is at least about 80%, at least about 90%, or at least about 95% homologous to SEQ ID NO: 26, a peptide having an amino acid sequence set forth in VPGSQHIDS (SEQ ID NO: 27), and a peptide having an amino acid sequence that is at least about 80%, at least about 90%, or at least about 95% homologous to SEQ ID NO: 27; or (b) the peptide analyte derived from cholera toxin is a peptide comprising an amino acid sequence selected from the group consisting of SEQ ID NOs: 114-184.

17. The sensor cell of claim 1, wherein the biosynthesized visible-light pigment is lycopene.

18. A sensor fungal cell comprising a fungal non-native G-protein coupled receptor (GPCR) that binds to a peptide analyte derived from an agent, wherein the peptide analyte is a ligand for the fungal non-native GPCR, wherein binding of the peptide analyte to the fungal non-native GPCR triggers an appearance of a reporter in the fungal cell, wherein the appearance of the reporter indicates the presence of the agent, and wherein the non-native fungal GPCR is an engineered GPCR and comprises an amino acid sequence selected from the group consisting of SEQ ID NOs: 6, 9, 12, 15, 18, 21, 52, 54, 56, 58, 74, 94, and 222.

19. The sensor cell of claim 18, wherein the fungal non-native GPCR is engineered to bind to the peptide analyte.

20. The sensor cell of claim 18, wherein the peptide analyte is a peptide epitope of a polypeptide or protein.

21. The sensor cell of claim 18, wherein the peptide analyte is a fungal mating pheromone.

22. The sensor cell of claim 21, wherein the fungal mating pheromone is selected from the group consisting of a human fungal mating pheromone, a non-human animal fungal mating pheromone, a plant fungal mating pheromone, a food fungal mating pheromone and an industrial/model fungal mating pheromone.

23. The sensor cell of claim 22, wherein:

(a) the human fungal mating pheromone is selected from the group consisting of the mating pheromones of *C. albicans, C. glabrata, P. brasiliensis, L. elongisporous, P. rubens, C. guillermondi, C. tropicalis*, and *C. parapsilosis, C. lusitaniae, S. scheckii*, and *C. krusei;*

(b) the non-human animal fungal mating pheromone is the mating pheromone of *P. destructans;*

(c) the plant fungal mating pheromone is selected from the group consisting of the mating pheromones of *F. graminearum, M. oryzea, B. cinerea, G. candidum*, and *C. purpurea;*

(d) the food fungal mating pheromone is selected from the group consisting of the mating pheromones of *Z. bailii, Z. rouxii*, and *N. fischeri*; or (e) the industrial/model fungal mating pheromone is selected from the group consisting of the mating pheromones of *K lactis, S. pombe, V. polyspora* (receptor 1), *V. polyspora* (receptor 2), *S. stipitis, S. japonicas, S. castellii, S. octosporus, A. oryzae, T. melanosporum, D. haptotyla, C. tenuis, Y. lipolytica, T. delbrueckii, B. bassiana, K. pastoris, A. nidulans, N. crassa* and *H. jecorina.*

24. The sensor cell of claim 18, wherein the peptide analyte is derived from *Vibrio cholera* or from cholera toxin.

25. The sensor cell of claim 18, wherein the peptide analyte comprises an amino acid sequence selected from the group consisting of SEQ ID NOs: 5, 8, 11, 14, 17, 20 and 34-49.

26. The sensor cell of claim 18, wherein the reporter is a biosynthesized visible-light pigment.

27. The sensor cell of claim 26, wherein the biosynthesized visible-light pigment is lycopene.

* * * * *

SEQUENCE LISTING

<160> NUMBER OF SEQ ID NOS: 222

<210> SEQ ID NO 1
<211> LENGTH: 1479
<212> TYPE: DNA
<213> ORGANISM: Erwinia herbicola

<400> SEQUENCE: 1
atgaagaaaa ccgtagtgat tggtgcaggt tttggtggtt tagctttggc tatacgtcta 60
caagctgcag gtattcctac agtgctattg gagcaaagag acaaaccagg aggaagagct 120
tatgtttggc acgatcaagg ctttaccttt gatgctggtc ctacagtcat cactgatcct 180
actgcattgg aagctttgtt caccttagct ggtagaagaa tggaagatta tgtccgtcta 240
ttgcctgtca agccgtttta cagattgtgt tgggaatctg gtaaaaccct agattacgcc 300
aatgacagtg ctgaactaga agctcagatt acgcagttta atcccagaga tgtcgaaggt 360
tacaggagat tccttgccta ttcccaagct gttttccaag agggttatct tcgtttgggt 420
tcagttccat tcctgtcctt tagggatatg cttagagcag gtcctcagtt gttgaagcta 480
caagcatggc aaagtgtgta tcagtctgtt tcgagattta tcgaggatga acatctgaga 540
caagcattct cattccacag tcttctagtt ggaggtaatc cctttaccac atcgagcata 600
tatacgttga ttcacgcttt ggaaagagaa tggggagttt ggtttcctga aggtggaaca 660
ggtgctttgg ttaatggtat ggtgaagcta ttcacggatt tgggtggaga aatagagctg 720
aatgcaagag tggaagaact tgttgtagca gacaacagag tctcacaagt tagacttgct 780
gatggtagga tcttcgatac agatgctgta gcttcaaacg cagatgtagt gaacacttat 840
aaaaagttgt tgggacatca tcctgttgga caaaagagag cagctgcttt ggagaggaaa 900
tctatgagca actcgttgtt tgtcctttac tttgggctga atcaaccaca ctcacaacta 960
gctcatcaca caatctgctt tggtcctaga tacagagagc tgatagatga aattttcact 1020
ggatctgctt tagcagacga tttttccctg tacttgcatt caccatgtgt tactgatccc 1080
tctttagcac cacctggttg tgctagcttc tatgtactag cacctgtacc acatttgggt 1140
aatgctccat tagattgggc acaagaagga ccgaaattga gggataggat cttcgactat 1200
ttggaagaac gttacatgcc aggtttgaga tctcagttgg ttacacagag gatattcaca 1260
ccagctgatt ttcatgatac tctagatgcg catttaggta gcgctttttc cattgagcca 1320
cttttgacgc aaagtgcttg gtttagacca cacaacagag attctgacat tgccaatctg 1380
tacctagtag gtgcaggaac tcatccagga gctggtattc ctggagttgt agcttctgct 1440
aaagctactg ctagtctgat gatcgaggat ttgcagtaa 1479

<210> SEQ ID NO 2
<211> LENGTH: 924
<212> TYPE: DNA
<213> ORGANISM: Erwinia herbicola

<400> SEQUENCE: 2
atggtttctg gttcgaaagc aggagtatca cctcataggg aaatcgaagt catgagacag 60
tccattgatg accacttagc aggattgttg ccagaaacag attcccagga tatcgttagc 120
cttgctatga gagaaggtgt tatggcacct ggtaaacgta tcagaccttt gctgatgtta 180
cttgctgcaa gagacctgag atatcagggt tctatgccta cactactgga tctagcttgt 240
gctgttgaac tgacacatac tgcttccttg atgctggatg acatgccttg tatggacaat 300
gcggaactta gaagaggtca accaacaacc cacaagaaat tcggagaatc tgttgccatt 360
ttggcttctg taggtctgtt gtcgaaagct tttggcttga ttgctgcaac tggtgatctt 420
ccaggtgaaa ggagagcaca agctgtaaac gagctatcta ctgcagttgg tgttcaaggt 480
ctagtcttag gacagttcag agatttgaat gacgcagctt tggacagaac tcctgatgct 540
atcctgtcta cgaaccatct gaagactggc atcttgttct cagctatgtt gcaaatcgta 600
gccattgctt ctgcttcttc accatctact agggaaacgt tacacgcatt cgcattggac 660
tttggtcaag cctttcaact gctagacgat ttgagggatg atcatccaga gacaggtaaa 720
gaccgtaaca aagacgctgg taaaagcact ctagtcaaca gattgggtgc tgatgcagct 780
agacagaaac tgagagagca cattgactct gctgacaaac acctgacatt tgcatgtcca 840
caaggaggtg ctataaggca gtttatgcac ctatggtttg gacaccatct tgctgattgg 900
tctccagtga tgaagatcgc ctaa 924

<210> SEQ ID NO 3
<211> LENGTH: 930
<212> TYPE: DNA
<213> ORGANISM: Erwinia herbicola

<400> SEQUENCE: 3
atgagtcaac cacctttgtt ggatcatgct actcaaacga tggctaatgg ttccaagtcc 60
tttgctacag cagctaaact gtttgaccca gctactagaa gatcagtgct tatgctgtac 120
acttggtgta gacactgtga tgacgttata gatgaccaga cacatggttt cgcatctgaa 180
gctgctgcag aagaagaggc tactcagaga ttggctagat tgagaacgct tacacttgca 240
gcttttgaag gtgctgagat gcaagatcct gcttttgctg cattccaaga agttgcacta 300
acacacggta ttacgccaag aatggcactt gatcacttgg atggtttcgc aatggatgtt 360
gctcaaactc gttacgtgac ctttgaagac accttgagat actgctacca tgttgctgga 420
gtagttggtt tgatgatggc aagagtaatg ggtgtaagag acgaaagggt tttggacaga 480

```
gcttgtgatc taggtttggc ttttcagctg acaaacatcg cgagagatat tatcgacgat    540

gcagctattg acagatgcta tctacctgct gaatggttgc aagatgctgg tctaactcct    600

gagaattacg ctgcaagaga gaacagagct gcattagcaa gagttgctga aaggctgata    660

gacgctgctg aaccctatta catctcaagt caagctggat tgcatgatct accacctaga    720

tgtgcttggg ctatagctac tgcaagatct gtctacagag agattggcat caaggtaaaa    780

gctgcaggtg gttctgcttg ggatagacgt caacacacta gcaaaggaga gaagattgcg    840

atgcttatgg ctgcaccagg acaagtcatt cgtgccaaaa caaccagagt tacaccaaga    900

cctgctggtt tatggcaaag acctgtctaa                                      930
```

```
<210> SEQ ID NO 4
<211> LENGTH: 921
<212> TYPE: DNA
<213> ORGANISM: Saccharomyces cerevisiae

<400> SEQUENCE: 4

atgcagttga gcaaggctgc tgagatgtgt tatgagataa caaactctta cttacacata     60

gaccagaaat ctcagataat agcaagtaca caagaagcga tacggttgac aagaaaatac    120

ttactaagtg aaatttttgt acgttggagt ccactgaatg ggaaaatatc attctcgtac    180

aacggaggaa aagattgcca ggtattacta ctgttatatc tgagttgctt atgggaatat    240

ttcttcatta aggctcaaaa ttcccaattc gatttcgagt ttcaaagctt ccccatgcaa    300

agacttccaa ctgttttcat tgatcaagaa gaaactttcc ctacattaga gaattttgta    360

ctggaaacct cagagcgata ttgcctttcc ttatacgaat cacaaaggca atctggtgca    420

tcggtcaata tggcagacgc atttagagat tttataaaga tataccctga gaccgaagct    480

atagtgatag gtattagaca cacagaccca tttggtgaag cattaaagcc tattcaaaga    540

acagattcta actggcctga ttttatgagg ttgcaacctc tcttacactg ggacttaacc    600

aatatatgga gtttcttact gtattctaat gagccaattt gtggactata tggtaaaggt    660

ttcacatcaa tcggcggaat taacaactca ttgcctaacc cacacttgag aaaggactcc    720

aataatccag ccttgcattt tgaatgggaa atcattcatg catttggcaa ggacgcagaa    780

ggcgaacgta gttccgctat aaacacgtca cctatttccg tggtggataa ggaaagattc    840

agcaaatacc atgacaatta ctatcctggc tggtatttgg ttgatgacac tttagagaga    900

gcaggcagga tcaagaatta a                                               921
```

```
<210> SEQ ID NO 5
<211> LENGTH: 13
<212> TYPE: PRT
<213> ORGANISM: Candida albicans

<400> SEQUENCE: 5

Gly Phe Arg Leu Thr Asn Phe Gly Tyr Phe Glu Pro Gly
1               5                   10
```

```
<210> SEQ ID NO 6
<211> LENGTH: 469
<212> TYPE: PRT
<213> ORGANISM: Candida albicans

<400> SEQUENCE: 6

Met Asn Ile Asn Ser Thr Phe Ile Pro Asp Lys Pro Gly Asp Ile Ile
1               5                   10                  15

Ile Ser Tyr Ser Ile Pro Gly Leu Asp Gln Pro Ile Gln Ile Pro Phe
```

-continued

```
            20                  25                  30

His Ser Leu Asp Ser Phe Gln Thr Asp Gln Ala Lys Ile Ala Leu Val
        35                  40                  45

Met Gly Ile Thr Ile Gly Ser Cys Ser Met Thr Leu Ile Phe Leu Ile
    50                  55                  60

Ser Ile Met Tyr Lys Thr Asn Lys Leu Thr Asn Leu Lys Leu Lys Leu
65                  70                  75                  80

Lys Leu Lys Tyr Ile Leu Gln Trp Ile Asn Gln Lys Ile Phe Thr Lys
                85                  90                  95

Lys Arg Asn Asp Asn Lys Gln Gln Gln Gln Gln Gln Gln Gln Gln Ile
            100                 105                 110

Glu Ser Ser Ser Tyr Asn Asn Thr Thr Thr Thr Leu Gly Gly Tyr Lys
        115                 120                 125

Leu Phe Leu Phe Tyr Leu Asn Ser Leu Ile Leu Leu Ile Gly Ile Ile
    130                 135                 140

Arg Ser Gly Cys Tyr Leu Asn Tyr Asn Leu Gly Pro Leu Asn Ser Leu
145                 150                 155                 160

Ser Phe Val Phe Thr Gly Trp Tyr Asp Gly Ser Ser Phe Ile Ser Ser
                165                 170                 175

Asp Val Thr Asn Gly Phe Lys Cys Ile Leu Tyr Ala Leu Val Glu Ile
            180                 185                 190

Ser Leu Gly Phe Gln Val Tyr Val Met Phe Lys Thr Ser Asn Leu Lys
        195                 200                 205

Ile Trp Gly Ile Met Ala Ser Leu Leu Ser Ile Gly Leu Gly Leu Ile
    210                 215                 220

Val Val Ala Phe Gln Ile Asn Leu Thr Ile Leu Ser His Ile Arg Phe
225                 230                 235                 240

Ser Arg Ala Ile Ser Thr Asn Arg Ser Glu Glu Glu Ser Ser Ser Ser
                245                 250                 255

Leu Ser Ser Asp Ser Val Gly Tyr Val Ile Asn Ser Ile Trp Met Asp
            260                 265                 270

Leu Pro Thr Ile Leu Phe Ser Ile Ser Ile Asn Ile Met Thr Ile Leu
        275                 280                 285

Leu Ile Gly Lys Leu Ile Ile Ala Ile Arg Thr Arg Arg Tyr Leu Gly
    290                 295                 300

Leu Lys Gln Phe Asp Ser Phe His Ile Leu Leu Ile Gly Phe Ser Gln
305                 310                 315                 320

Thr Leu Ile Ile Pro Ser Ile Ile Leu Val Val His Tyr Phe Tyr Leu
                325                 330                 335

Ser Gln Asn Lys Asp Ser Leu Leu Gln Gln Ile Ser Leu Leu Leu Ile
            340                 345                 350

Ile Leu Met Leu Pro Leu Ser Ser Leu Trp Ala Gln Thr Ala Asn Asn
        355                 360                 365

Thr His Asn Ile Asn Ser Ser Pro Ser Leu Ser Phe Ile Ser Arg His
    370                 375                 380

His Leu Ser Asp Ser Ser Arg Ser Gly Gly Ser Asn Thr Ile Val Ser
385                 390                 395                 400

Asn Gly Gly Ser Asn Gly Gly Gly Gly Gly Gly Gly Asn Phe Pro Val
                405                 410                 415

Ser Gly Ile Asp Ala Gln Leu Pro Pro Asp Ile Glu Lys Ile Leu His
            420                 425                 430

Glu Asp Asn Asn Tyr Lys Leu Leu Asn Ser Asn Asn Glu Ser Val Asn
        435                 440                 445
```

```
Asp Gly Asp Ile Ile Ile Asn Asp Glu Gly Met Ile Thr Lys Gln Ile
    450                 455                 460

Thr Ile Lys Arg Val
465


<210> SEQ ID NO 7
<211> LENGTH: 1410
<212> TYPE: DNA
<213> ORGANISM: Candida albicans

<400> SEQUENCE: 7

atgaatatca attcaacttt catacctgat aaaccaggcg atataattat tagttattca     60

attccaggat tagatcaacc aattcaaatt cctttccatt cattagattc atttcaaacc    120

gatcaagcta aaatagcttt agtcatgggg ataactattg ggagttgttc aatgacatta    180

atttttttga tttctataat gtataaaact aataaattaa caaatttaaa attaaaatta    240

aaattaaaat atatcttgca atggataaat caaaaaatct tcaccaaaaa aaggaatgac    300

aacaaacaac aacaacaaca acaacaacaa caaattgaat catcatcata taacaatact    360

actactacgc tgggggggtta taaattattt ttattttatc ttaattcatt gattttatta    420

attggtatta ttcgatcagg ttgttattta aattataatt taggtccatt aaattcactt    480

agttttgtat ttactggttg gtatgatgga tcatcattta tatcatccga tgtaactaat    540

ggatttaaat gtattttata tgctttagtg gaaatttcat taggtttcca agtttatgtg    600

atgttcaaaa cttcaaattt aaaaatttgg gggataatgg catcattatt atcaattggt    660

ttaggattga ttgttgttgc ctttcaaatc aatttaacaa ttttatctca tattcgattt    720

tcccgggcta tatcaactaa cagaagtgaa gaagaatcat catcatcatt atcatctgat    780

tcggttgggt atgtgattaa ttcaatatgg atggatttac caacaatatt attttccatt    840

agtattaata taatgacaat attattgatt ggtaaactta taattgctat tagaacaaga    900

cgttatttag gattgaaaca atttgatagt ttccatattt tattaattgg tttcagtcaa    960

acattaatta ttccttcaat tattttggtg gttcattatt tttatttatc acaaaataaa   1020

gattctttat tacaacaaat tagtctttta ttgattattt taatgttacc attaagttct   1080

ttatgggctc aaactgctaa taatactcat aatattaatt catctccaag tttatcattc   1140

atatctcgtc atcatctgtc tgatagtagt cgtagtggtg gttccaatac aattgttagt   1200

aatggtggta gtaatggtgg tggtggtggt ggtgggaatt tccctgtttc aggtattgat   1260

gcacaattac cacctgatat tgaaaaaatc ttacatgaag ataataatta taaattactt   1320

aatagtaata atgaaagtgt aaatgatgga gatattatca ttaatgatga aggtatgatt   1380

actaaacaaa tcaccatcaa aagagtgtag                                    1410


<210> SEQ ID NO 8
<211> LENGTH: 13
<212> TYPE: PRT
<213> ORGANISM: Candida glabrata

<400> SEQUENCE: 8

Trp His Trp Val Arg Leu Arg Lys Gly Gln Gly Leu Phe
1               5                   10


<210> SEQ ID NO 9
<211> LENGTH: 417
<212> TYPE: PRT
<213> ORGANISM: Candida glabrata
```

<400> SEQUENCE: 9

Met Glu Met Gly Tyr Asp Pro Arg Met Tyr Asn Pro Arg Asn Glu Tyr
1               5                   10                  15

Leu Asn Phe Thr Ser Val Tyr Asp Val Asn Asp Thr Ile Arg Phe Ser
            20                  25                  30

Thr Leu Asp Ala Ile Val Lys Gly Leu Leu Arg Ile Ala Ile Val His
        35                  40                  45

Gly Val Arg Leu Gly Ala Ile Phe Met Thr Leu Ile Ile Met Phe Ile
    50                  55                  60

Ser Ser Asn Thr Trp Lys Lys Pro Ile Phe Ile Ile Asn Met Val Ser
65                  70                  75                  80

Leu Met Leu Val Met Ile His Ser Ala Leu Ser Phe His Tyr Leu Leu
                85                  90                  95

Ser Asn Tyr Ser Ser Ile Ser Tyr Ile Leu Thr Gly Phe Pro Gln Leu
            100                 105                 110

Ile Thr Ser Asn Asn Lys Arg Ile Gln Asp Ala Ala Ser Ile Val Gln
        115                 120                 125

Val Leu Leu Val Ala Ala Ile Glu Ala Ser Leu Val Phe Gln Ile His
    130                 135                 140

Val Met Phe Thr Ile Glu Asn Ile Lys Leu Ile Arg Glu Ile Val Leu
145                 150                 155                 160

Ser Ile Ser Ile Ala Met Gly Leu Ala Thr Val Ala Thr Tyr Leu Ala
                165                 170                 175

Ala Ala Ile Lys Leu Ile Arg Gly Leu His Asp Glu Val Met Pro Gln
            180                 185                 190

Thr His Leu Ile Phe Asn Leu Ser Ile Ile Leu Leu Ala Ser Ser Ile
        195                 200                 205

Asn Phe Met Thr Phe Ile Leu Val Ile Lys Leu Phe Phe Ala Ile Arg
    210                 215                 220

Ser Arg Arg Tyr Leu Gly Leu Arg Gln Phe Asp Ala Phe His Ile Leu
225                 230                 235                 240

Leu Ile Met Phe Cys Gln Ser Leu Leu Ile Pro Ser Val Leu Tyr Ile
                245                 250                 255

Ile Val Tyr Ala Val Asp Ser Arg Ser Asn Gln Asp Tyr Leu Ile Pro
            260                 265                 270

Ile Ala Asn Leu Phe Val Val Leu Ser Leu Pro Leu Ser Ser Ile Trp
        275                 280                 285

Ala Asn Thr Ser Asn Asn Ser Ser Arg Ser Pro Lys Tyr Trp Lys Asn
    290                 295                 300

Ser Gln Thr Asn Lys Ser Asn Gly Ser Phe Val Ser Ser Ile Ser Val
305                 310                 315                 320

Asn Ser Asp Ser Gln Asn Pro Leu Tyr Lys Lys Ile Val Arg Phe Thr
                325                 330                 335

Ser Lys Gly Asp Thr Thr Arg Ser Ile Val Ser Asp Ser Thr Leu Ala
            340                 345                 350

Glu Val Gly Lys Tyr Ser Met Gln Asp Val Ser Asn Ser Asn Phe Glu
        355                 360                 365

Cys Arg Asp Leu Asp Phe Glu Lys Val Lys His Thr Cys Glu Asn Phe
    370                 375                 380

Gly Arg Ile Ser Glu Thr Tyr Ser Glu Leu Ser Thr Leu Asp Thr Thr
385                 390                 395                 400

Ala Leu Asn Glu Thr Arg Leu Phe Trp Lys Gln Gln Ser Gln Cys Asp

-continued 405 410 415

Lys

<210> SEQ ID NO 10
<211> LENGTH: 1254
<212> TYPE: DNA
<213> ORGANISM: Candida glabrata

<400> SEQUENCE: 10
atggagatgg gctacgatcc aagaatgtat aatccaagaa atgaatactt gaatttcacg 60
tcggtatatg atgtaaatga cacaatcaga ttttcgactc tggacgccat tgtaaaagga 120
ttgcttagaa ttgccattgt tcatggagtt agattgggag caatattcat gacgttaata 180
ataatgttta tctcatcaaa tacatggaaa aaacccatat ttataattaa catggtgtcg 240
ttgatgttag ttatgattca ttccgcactt agcttccatt accttttatc gaattattct 300
tcaatttctt atatactgac agggtttcct cagttgatta caagcaataa taaacgaatt 360
caagatgcag cgagtatagt ccaagtttta ttggttgctg cgatagaagc atcattggta 420
tttcagattc atgttatgtt tacgattgaa aacattaagc ttattagaga aatagtactc 480
tctatatcga tagcaatggg attggcaaca gtggctacat atcttgctgc agcaataaag 540
ctgataagag gactgcatga tgaggtaatg ccacaaacac atcttatttt caatttatct 600
ataatattgc ttgcatcctc cataaatttt atgacattta tattggtcat taaacttttc 660
ttcgctatta gatctagaag atatctcggt cttcgtcaat tcgatgcttt tcatatttta 720
ttaatcatgt tctgccagtc attattgata ccctcagtat tatatattat agtttacgcg 780
gttgatagca gatctaatca ggattatctg attccaattg ccaatttatt tgttgtttta 840
tctttgccat tatcctctat ctgggctaac acatcaaata actcatccag atctccaaaa 900
tattggaaaa actctcaaac gaataagagc aatgggtctt ttgtctcttc aatatctgtc 960
aatagtgact cacaaaaccc tttgtacaaa aagattgtac gttttacatc aaaaggcgac 1020
actacccgta gtattgtaag tgattcaaca ttagcagagg tgggaaaata ctctatgcaa 1080
gacgttagca attcaaactt tgaatgtcga gaccttgatt ttgagaaggt aaaacatact 1140
tgcgaaaatt ttggcagaat atctgaaaca tatagtgagt taagtacttt agataccact 1200
gccctcaatg agactcggtt gttttggaaa caacaaagtc agtgtgacaa atag 1254

<210> SEQ ID NO 11
<211> LENGTH: 9
<212> TYPE: PRT
<213> ORGANISM: Paracoccidioides brasiliensis

<400> SEQUENCE: 11

Trp Cys Thr Arg Pro Gly Gln Gly Cys
1 5

<210> SEQ ID NO 12
<211> LENGTH: 356
<212> TYPE: PRT
<213> ORGANISM: Paracoccidioides brasiliensis

<400> SEQUENCE: 12

Met Ala Pro Ser Phe Asp Pro Phe Asn Gln Ser Val Val Phe His Lys
1 5 10 15

Ala Asp Gly Thr Pro Phe Asn Val Ser Ile His Glu Leu Asp Asp Phe
20 25 30

```
Val Gln Tyr Asn Thr Lys Val Cys Ile Asn Tyr Ser Ser Gln Leu Gly
        35                  40                  45

Ala Ser Val Ile Ala Gly Leu Met Leu Ala Met Leu Thr His Ser Glu
    50                  55                  60

Lys Arg Arg Leu Pro Val Phe Phe Leu Asn Thr Phe Ala Leu Ala Met
65                  70                  75                  80

Asn Phe Ala Arg Leu Leu Cys Met Thr Ile Tyr Phe Thr Thr Gly Phe
                85                  90                  95

Asn Lys Ser Tyr Ala Tyr Phe Gly Gln Asp Tyr Ser Gln Val Pro Gly
            100                 105                 110

Ser Ala Tyr Ala Ala Ser Val Leu Gly Val Val Phe Thr Thr Leu Leu
        115                 120                 125

Val Ile Ser Met Glu Met Ser Leu Leu Ile Gln Thr Arg Val Val Cys
    130                 135                 140

Thr Thr Leu Pro Asp Ile Gln Arg Tyr Leu Leu Met Ala Val Ser Ser
145                 150                 155                 160

Ala Ile Ser Leu Met Ala Ile Gly Phe Arg Leu Gly Leu Met Val Glu
                165                 170                 175

Asn Cys Ile Ala Ile Val Gln Ala Ser Asn Phe Ala Pro Phe Ile Trp
            180                 185                 190

Leu Gln Ser Ala Ser Asn Ile Thr Ile Thr Ile Ser Thr Cys Phe Phe
        195                 200                 205

Ser Ala Val Phe Val Thr Lys Leu Ala Tyr Ala Leu Val Thr Arg Ile
    210                 215                 220

Arg Leu Gly Leu Thr Arg Phe Gly Ala Met Gln Val Met Phe Ile Met
225                 230                 235                 240

Ser Cys Gln Thr Met Val Ile Pro Ala Ile Phe Ser Ile Leu Gln Tyr
                245                 250                 255

Pro Leu Pro Lys Tyr Glu Met Asn Ser Asn Leu Phe Thr Leu Val Ala
            260                 265                 270

Ile Phe Leu Pro Leu Ser Ser Leu Trp Ala Ser Val Ala Thr Arg Ser
        275                 280                 285

Ser Phe Glu Thr Ser Ser Ser Gly Arg His Gln Tyr Leu Trp Pro Ser
    290                 295                 300

Glu Gln Ser Asn Asn Val Thr Asn Ser Glu Ile Lys Tyr Gln Val Ser
305                 310                 315                 320

Phe Ser Gln Asn His Thr Thr Leu Arg Ser Gly Gly Ser Val Ala Thr
                325                 330                 335

Thr Leu Ser Pro Asp Arg Leu Asp Pro Val Tyr Cys Glu Val Glu Ala
            340                 345                 350

Gly Thr Lys Ala
        355
```

<210> SEQ ID NO 13
<211> LENGTH: 1071
<212> TYPE: DNA
<213> ORGANISM: Paracoccidioides brasiliensis

<400> SEQUENCE: 13

```
atggcaccct cattcgaccc cttcaaccaa agcgtggtct tccacaaggc cgacggaact      60

ccattcaacg tctcaatcca tgaactagac gacttcgtgc agtacaacac caaagtctgc     120

atcaactact cttcccagct cggagcatct gtcattgcag gactcatgct tgccatgctg     180

acacactcag aaaagcgtcg tctgccagtt ttcttcctaa acacattcgc actggccatg     240
```

-continued

```
aactttgccc gcctgctctg catgaccatc tacttcacca cgggcttcaa caagtcctat    300

gcctactttg gtcaggatta ctcccaggtg cctgggagcg cctacgcagc ctctgtcttg    360

ggcgttgtct tcaccactct cctggtaatc agcatggaaa tgtccctcct gatccaaaca    420

agggttgtct gcacgaccct tccggatatc caacgttatc tactcatggc agtttcctcc    480

gcgatttccc tgatggccat cgggttccgc cttggcttaa tggttgagaa ctgcattgcc    540

attgtgcagg cgtcgaattt cgcccctttt atctggcttc aaagcgcctc gaacatcacc    600

attacgatca gcacatgttt cttcagtgcc gtctttgtta cgaaattggc atatgcactc    660

gtcactcgta tacgactagg cttgacgagg tttggtgcta tgcaggttat gttcatcatg    720

tcctgccaga ctatggtgat tccagccatc ttctcaattc tccaataccc actccccaag    780

tacgaaatga actccaacct ctttacgctg gtggccattt tcctccctct ttcctcgcta    840

tgggcttcag ttgctacgag atccagtttc gagacgtctt cttccggccg ccatcagtat    900

ctttggccaa gcgaacagag caataacgtc accaattcgg aaattaagta tcaggtcagc    960

ttctctcaga accacactac gttgcggtct ggagggtctg tggccacgac actctccccg   1020

gaccggctcg acccggttta ttgtgaagtt gaagctggca caaaggccta g            1071


<210> SEQ ID NO 14
<211> LENGTH: 10
<212> TYPE: PRT
<213> ORGANISM: Fusarium graminearum

<400> SEQUENCE: 14

Trp Cys Trp Trp Lys Gly Gln Pro Cys Trp
1               5                   10


<210> SEQ ID NO 15
<211> LENGTH: 386
<212> TYPE: PRT
<213> ORGANISM: Fusarium graminearum

<400> SEQUENCE: 15

Met Ser Lys Glu Val Phe Asp Pro Phe Thr Gln Asn Val Thr Phe Phe
1               5                   10                  15

Ala Pro Asp Gly Lys Thr Glu Ile Ser Ile Pro Val Ala Ala Ile Asp
            20                  25                  30

Gln Val Arg Arg Met Met Val Asn Thr Thr Ile Asn Tyr Ala Thr Gln
        35                  40                  45

Leu Gly Ala Cys Leu Ile Met Leu Val Val Leu Leu Val Met Val Pro
    50                  55                  60

Lys Glu Lys Phe Arg Arg Pro Phe Met Ile Leu Gln Ile Thr Ser Leu
65                  70                  75                  80

Val Ile Ser Cys Cys Arg Met Leu Leu Leu Ser Ile Phe His Ser Ser
                85                  90                  95

Gln Phe Leu Asp Phe Tyr Val Phe Trp Gly Asp Asp His Ser Arg Ile
            100                 105                 110

Pro Arg Ser Ala Tyr Ala Pro Ser Val Ala Gly Asn Thr Met Ser Leu
        115                 120                 125

Cys Leu Val Ile Ser Val Glu Thr Met Leu Met Ser Gln Ala Trp Thr
    130                 135                 140

Met Val Arg Leu Trp Pro Asn Val Trp Lys Tyr Ile Ile Ala Gly Val
145                 150                 155                 160

Ser Leu Ile Val Ser Ile Met Ala Ile Ser Val Arg Leu Ala Tyr Thr
                165                 170                 175
```

-continued

```
Ile Ile Gln Asn Asn Ala Val Leu Lys Leu Glu Pro Ala Phe His Met
            180                 185                 190

Phe Trp Leu Ile Lys Trp Thr Val Ile Met Asn Val Ala Ser Ile Ser
        195                 200                 205

Trp Trp Cys Ala Ile Phe Asn Ile Lys Leu Val Trp His Leu Ile Ser
    210                 215                 220

Asn Arg Gly Ile Leu Pro Ser Tyr Lys Thr Phe Thr Pro Met Glu Val
225                 230                 235                 240

Leu Ile Met Thr Asn Gly Ile Leu Met Ile Ile Pro Val Ile Phe Ala
                245                 250                 255

Ser Leu Glu Trp Ala His Phe Val Asn Phe Glu Ser Ala Ser Leu Thr
            260                 265                 270

Leu Thr Ser Val Ala Val Ile Leu Pro Leu Gly Thr Leu Ala Ala Gln
        275                 280                 285

Arg Ile Ala Ser Ser Ala Pro Ser Ser Ala Asn Ser Thr Gly Ala Ser
    290                 295                 300

Ser Gly Ile Arg Tyr Gly Val Ser Gly Pro Ser Ser Phe Thr Gly Phe
305                 310                 315                 320

Lys Ala Pro Ser Phe Ser Thr Gly Thr Thr Asp Arg Pro His Val Ser
                325                 330                 335

Ile Tyr Ala Arg Cys Glu Ala Gly Thr Ser Ser Arg Glu His Ile Asn
            340                 345                 350

Pro Gln Gly Val Glu Leu Ala Lys Leu Asp Pro Glu Thr Asp His His
        355                 360                 365

Val Arg Val Asp Arg Ala Phe Leu Gln Arg Glu Glu Arg Ile Arg Ala
    370                 375                 380

Pro Leu
385
```

<210> SEQ ID NO 16
<211> LENGTH: 1161
<212> TYPE: DNA
<213> ORGANISM: Fusarium graminearum

<400> SEQUENCE: 16

```
atgtctaagg aagttttcga cccattcact caaaacgtta ctttcttcgc tccagacggt     60

aagactgaaa tctctatccc agttgctgct atcgaccaag ttagaagaat gatggttaac    120

actactatca actacgctac tcaattgggt gcttgtttga tcatgttggt tgttttgttg    180

gttatggttc caaaggaaaa gttcagaaga ccattcatga tcttgcaaat cacttctttg    240

gttatctctt gttgtagaat gttgttgttg tctatcttcc actcttctca attcttggac    300

ttctacgttt tctggggtga cgaccactct agaatcccaa gatctgctta cgctccatct    360

gttgctggta acactatgtc tttgtgtttg gttatctctg ttgaaactat gttgatgtct    420

caagcttgga ctatggttag attgtggcca aacgtttgga agtacatcat cgctggtgtt    480

tctttgatcg tttctatcat ggctatctct gttagattgg cttacactat catccaaaac    540

aacgctgttt tgaagttgga accagctttc cacatgttct ggttgatcaa gtggactgtt    600

atcatgaacg ttgcttctat ctcttggtgg tgtgctatct tcaacatcaa gttggtttgg    660

cacttgatct ctaacagagg tatcttgcca tcttacaaga ctttcactcc aatggaagtt    720

ttgatcatga ctaacggtat cttgatgatc atcccagtta tcttcgcttc tttggaatgg    780

gctcacttcg ttaacttcga atctgcttct ttgactttga cttctgttgc tgttatcttg    840
```

-continued

```
ccattgggta ctttggctgc tcaaagaatc gcttcttctg ctccatcttc tgctaactct    900

actggtgctt cttctggtat cagatacggt gtttctggtc catcttcttt cactggtttc    960

aaggctccat ctttctctac tggtactact gacagaccac acgtttctat ctacgctaga   1020

tgtgaagctg gtacttcttc tagagaacac atcaacccac aaggtgttga attggctaag   1080

ttggacccag aaactgacca ccacgttaga gttgacagag ctttcttgca aagagaagaa   1140

agaatcagag ctccattgta g                                             1161


<210> SEQ ID NO 17
<211> LENGTH: 11
<212> TYPE: PRT
<213> ORGANISM: Magnaporthe oryzea

<400> SEQUENCE: 17

Gln Trp Cys Pro Arg Arg Gly Gln Pro Cys Trp
1               5                   10


<210> SEQ ID NO 18
<211> LENGTH: 415
<212> TYPE: PRT
<213> ORGANISM: Magnaporthe oryzea

<400> SEQUENCE: 18

Met Asp Gln Thr Leu Ser Ala Thr Gly Thr Ala Thr Ser Pro Pro Gly
1               5                   10                  15

Pro Ala Leu Thr Val Asp Pro Arg Phe Gln Thr Ile Thr Met Leu Thr
            20                  25                  30

Pro Ala Leu Met Gly Gln Gly Phe Glu Glu Val Gln Thr Thr Pro Ala
        35                  40                  45

Glu Ile Asn Asp Val Tyr Phe Leu Ala Phe Asn Thr Ala Ile Gly Tyr
    50                  55                  60

Ser Thr Gln Ile Gly Ala Cys Phe Ile Met Leu Leu Val Leu Leu Thr
65                  70                  75                  80

Met Thr Ala Lys Ala Arg Phe Ala Arg Ile Pro Thr Ile Ile Asn Thr
                85                  90                  95

Ala Ala Leu Val Val Ser Ile Ile Arg Cys Thr Leu Leu Val Ile Phe
            100                 105                 110

Phe Thr Ser Thr Met Met Glu Phe Tyr Thr Ile Phe Ser Asp Asp Phe
        115                 120                 125

Ser Phe Val His Pro Asn Asp Ile Arg Arg Ser Val Ala Ala Thr Val
    130                 135                 140

Phe Ala Pro Leu Gln Leu Ala Leu Val Glu Ala Ala Leu Met Val Gln
145                 150                 155                 160

Ala Trp Ala Met Val Glu Leu Trp Pro Arg Ala Trp Lys Val Ser Gly
                165                 170                 175

Ile Ala Phe Ser Leu Ile Leu Ala Thr Val Thr Val Ala Phe Lys Cys
            180                 185                 190

Ala Ser Ala Ala Val Thr Val Lys Ser Ala Leu Glu Pro Leu Asp Pro
        195                 200                 205

Arg Pro Tyr Leu Trp Ile Arg Gln Thr Asp Leu Ala Phe Thr Thr Ala
    210                 215                 220

Met Val Thr Trp Phe Cys Phe Leu Phe Asn Val Arg Leu Ile Met His
225                 230                 235                 240

Met Trp Gln Asn Arg Ser Ile Leu Pro Thr Val Lys Gly Leu Ser Pro
                245                 250                 255
```

-continued

```
Met Glu Val Leu Val Met Ala Asn Gly Leu Leu Met Val Phe Pro Val
            260                 265                 270

Leu Phe Ala Gly Leu Tyr Tyr Gly Asn Phe Gly Gln Phe Glu Ser Ala
        275                 280                 285

Ser Leu Thr Ile Thr Ser Val Val Leu Val Leu Pro Leu Gly Thr Leu
    290                 295                 300

Val Ala Gln Arg Leu Ala Val Asn Asn Thr Val Ala Gly Ser Ser Ala
305                 310                 315                 320

Asn Thr Asp Met Asp Asp Lys Leu Ala Phe Leu Gly Asn Ala Thr Thr
                325                 330                 335

Val Thr Ser Ser Ala Ala Gly Phe Ala Gly Ser Ser Ala Ser Ala Thr
            340                 345                 350

Arg Ser Arg Leu Ala Ser Pro Arg Gln Asn Ser Gln Leu Ser Thr Ser
        355                 360                 365

Val Ser Ala Gly Lys Pro Arg Ala Asp Pro Ile Asp Leu Glu Leu Gln
    370                 375                 380

Arg Ile Asp Asp Glu Asp Asp Asp Phe Ser Arg Ser Gly Ser Ala Gly
385                 390                 395                 400

Gly Val Arg Val Glu Arg Ser Ile Glu Arg Arg Glu Glu Arg Leu
                405                 410                 415
```

<210> SEQ ID NO 19
<211> LENGTH: 1248
<212> TYPE: DNA
<213> ORGANISM: Magnaporthe oryzea

<400> SEQUENCE: 19

```
atggaccaaa ctttgtctgc tactggtact gctacttctc caccaggtcc agctttgact     60

gttgacccaa gattccaaac tatcactatg ttgactccag ctttgatggg tcaaggtttc    120

gaagaagttc aaactactcc agctgaaatc aacgacgttt acttcttggc tttcaacact    180

gctatcggtt actctactca aatcggtgct tgtttcatca tgttgttggt tttgttgact    240

atgactgcta aggctagatt cgctagaatc ccaactatca tcaacactgc tgctttggtt    300

gtttctatca tcagatgtac tttgttggtt atcttcttca cttctactat gatggaattc    360

tacactatct tctctgacga cttctctttc gttcacccaa acgacatcag aagatctgtt    420

gctgctactg ttttcgctcc attgcaattg gctttggttg aagctgcttt gatggttcaa    480

gcttgggcta tggttgaatt gtggccaaga gcttggaagg tttctggtat cgctttctct    540

ttgatcttgg ctactgttac tgttgctttc aagtgtgctt ctgctgctgt tactgttaag    600

tctgctttgg aaccattgga cccaagacca tacttgtgga tcagacaaac tgacttggct    660

ttcactactg ctatggttac ttggttctgt ttcttgttca acgttagatt gatcatgcac    720

atgtggcaaa acagatctat cttgccaact gttaagggtt tgtctccaat ggaagttttg    780

gttatggcta acggtttgtt gatggttttc ccagttttgt tcgctggttt gtactacggt    840

aacttcggtc aattcgaatc tgcttctttg actatcactt ctgttgtttt ggttttgcca    900

ttgggtactt tggttgctca aagattggct gttaacaaca ctgttgctgg ttcttctgct    960

aacactgaca tggacgacaa gttggctttc ttgggtaacg ctactactgt tacttcttct   1020

gctgctggtt tcgctggttc ttctgcttct gctactagat ctagattggc ttctccaaga   1080

caaaactctc aattgtctac ttctgtttct gctggtaagc caagagctga cccaatcgac   1140

ttggaattgc aaagaatcga cgacgaagac gacgacttct ctagatctgg ttctgctggt   1200

ggtgttagag ttgaaagatc tatcgaaaga agagaagaaa gattgtag               1248
```

<210> SEQ ID NO 20
<211> LENGTH: 9
<212> TYPE: PRT
<213> ORGANISM: Botrytis cinerea

<400> SEQUENCE: 20

```
Trp Cys Gly Arg Pro Gly Gln Pro Cys
1               5
```

<210> SEQ ID NO 21
<211> LENGTH: 398
<212> TYPE: PRT
<213> ORGANISM: Botrytis cinerea

<400> SEQUENCE: 21

```
Met Ala Ser Asn Ser Ser Asn Phe Asp Pro Leu Thr Gln Ser Ile Thr
1               5                   10                  15

Ile Leu Met Ala Asp Gly Ile Thr Thr Val Ser Phe Thr Pro Leu Asp
            20                  25                  30

Ile Asp Phe Phe Tyr Tyr Tyr Asn Val Ala Cys Cys Ile Asn Tyr Gly
        35                  40                  45

Ala Gln Ala Gly Ala Cys Leu Leu Met Phe Phe Val Val Val Val Leu
    50                  55                  60

Thr Lys Ala Val Lys Arg Lys Thr Leu Leu Phe Val Leu Asn Val Leu
65                  70                  75                  80

Ser Leu Ile Phe Gly Phe Leu Arg Ala Met Leu Tyr Ala Ile Tyr Phe
                85                  90                  95

Leu Gln Gly Phe Asn Asp Phe Tyr Ala Ala Phe Thr Phe Asp Phe Ser
            100                 105                 110

Arg Val Pro Arg Ser Ser Tyr Ala Ser Ser Val Ala Gly Ser Val Ile
        115                 120                 125

Pro Leu Cys Met Thr Ile Thr Val Asn Met Ser Leu Tyr Leu Gln Ala
    130                 135                 140

Tyr Thr Val Cys Lys Asn Leu Asp Asp Ile Lys Arg Ile Ile Leu Thr
145                 150                 155                 160

Thr Leu Ser Ala Ile Val Ala Leu Leu Ala Ile Gly Phe Arg Phe Ala
                165                 170                 175

Ala Thr Val Val Asn Ser Val Ala Ile Leu Ala Thr Ser Ala Ser Ser
            180                 185                 190

Val Pro Met Gln Trp Leu Val Lys Gly Thr Leu Val Thr Glu Thr Ile
        195                 200                 205

Ser Ile Trp Phe Phe Ser Leu Ile Phe Thr Gly Lys Leu Val Trp Thr
    210                 215                 220

Leu Tyr Asn Arg Arg Arg Asn Gly Trp Arg Gln Trp Ser Ala Val Arg
225                 230                 235                 240

Ile Leu Ala Ala Met Gly Gly Cys Thr Met Val Ile Pro Ser Ile Phe
                245                 250                 255

Ala Ile Leu Glu Tyr Val Thr Pro Val Ser Phe Pro Glu Ala Gly Ser
            260                 265                 270

Ile Ala Leu Thr Ser Val Ala Leu Leu Leu Pro Ile Ser Ser Leu Trp
        275                 280                 285

Ala Gly Met Val Thr Asp Glu Glu Thr Ser Ala Ile Asp Val Ser Asn
    290                 295                 300

Leu Thr Gly Ser Arg Thr Met Leu Gly Ser Gln Ser Gly Asn Phe Ser
305                 310                 315                 320
```

Arg Lys Thr His Ala Ser Asp Ile Thr Ala Gln Ser Ser His Leu Asp
325 330 335

Phe Ser Ser Arg Lys Gly Ser Asn Ala Thr Met Met Arg Lys Gly Ser
340 345 350

Asn Ala Met Asp Gln Val Thr Thr Ile Asp Cys Val Val Glu Asp Asn
355 360 365

Gln Ala Asn Arg Gly Leu Arg Asp Ser Thr Glu Met Asp Leu Glu Ala
370 375 380

Met Gly Val Arg Val Asn Lys Ser Tyr Gly Val Gln Lys Ala
385 390 395

<210> SEQ ID NO 22
<211> LENGTH: 1197
<212> TYPE: DNA
<213> ORGANISM: Botrytis cinerea

<400> SEQUENCE: 22
atggcttcta actcttctaa cttcgaccca ttgactcaat ctatcactat cttgatggct 60
gacggtatca ctactgtttc tttcactcca ttggacatcg acttcttcta ctactacaac 120
gttgcttgtt gtatcaacta cggtgctcaa gctggtgctt gtttgttgat gttcttcgtt 180
gttgttgttt tgactaaggc tgttaagaga aagactttgt tgttcgtttt gaacgttttg 240
tctttgatct tcggtttctt gagagctatg ttgtacgcta tctacttctt gcaaggtttc 300
aacgacttct acgctgcttt cactttcgac ttctctagag ttccaagatc ttcttacgct 360
tcttctgttg ctggttctgt tatcccattg tgtatgacta tcactgttaa catgtctttg 420
tacttgcaag cttacactgt ttgtaagaac ttggacgaca tcaagagaat catcttgact 480
actttgtctg ctatcgttgc tttgttggct atcggtttca gattcgctgc tactgttgtt 540
aactctgttg ctatcttggc tacttctgct tcttctgttc caatgcaatg gttggttaag 600
ggtactttgg ttactgaaac tatctctatc tggttcttct ctttgatctt cactggtaag 660
ttggtttgga ctttgtacaa cagaagaaga aacggttgga gacaatggtc tgctgttaga 720
atcttggctg ctatgggtgg ttgtactatg gttatcccat ctatcttcgc tatcttggaa 780
tacgttactc cagtttcttt cccagaagct ggttctatcg ctttgacttc tgttgctttg 840
ttgttgccaa tctcttcttt gtgggctggt atggttactg acgaagaaac ttctgctatc 900
gacgtttcta acttgactgg ttctagaact atgttgggtt ctcaatctgg taacttctct 960
agaaagactc acgcttctga catcactgct caatcttctc acttggactt ctcttctaga 1020
aagggttcta acgctactat gatgagaaag ggttctaacg ctatggacca agttactact 1080
atcgactgtg ttgttgaaga caaccaagct aacagaggtt tgagagactc tactgaaatg 1140
gacttggaag ctatgggtgt tagagttaac aagtcttacg gtgttcaaaa ggcttag 1197

<210> SEQ ID NO 23
<211> LENGTH: 14
<212> TYPE: PRT
<213> ORGANISM: Vibrio cholerae

<400> SEQUENCE: 23

Trp His Trp Leu Glu Leu Pro Gly Ser Gln His Ile Asp Ser
1 5 10

<210> SEQ ID NO 24
<211> LENGTH: 13
<212> TYPE: PRT

-continued

<213> ORGANISM: Saccharomyces cerevisiae

<400> SEQUENCE: 24

Trp His Trp Leu Gln Leu Lys Pro Gly Gln Pro Met Tyr
1 5 10

<210> SEQ ID NO 25
<211> LENGTH: 13
<212> TYPE: PRT
<213> ORGANISM: Artificial Sequence
<220> FEATURE:
<223> OTHER INFORMATION: Description of Artificial Sequence: Synthetic peptide

<400> SEQUENCE: 25

Trp His Trp Leu Glu Val Pro Gly Ser Gln Pro Met Tyr
1 5 10

<210> SEQ ID NO 26
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 26

Trp His Trp Leu Glu Val Pro Gly Ser Gln His Ile Asp Ser
1 5 10

<210> SEQ ID NO 27
<211> LENGTH: 15
<212> TYPE: PRT
<213> ORGANISM: Vibrio cholerae

<400> SEQUENCE: 27

Val Glu Val Pro Gly Ser Gln His Ile Asp Ser Gln Lys Lys Ala
1 5 10 15

<210> SEQ ID NO 28
<211> LENGTH: 9
<212> TYPE: PRT
<213> ORGANISM: Vibrio cholerae

<400> SEQUENCE: 28

Val Pro Gly Ser Gln His Ile Asp Ser
1 5

<210> SEQ ID NO 29
<211> LENGTH: 431
<212> TYPE: PRT
<213> ORGANISM: Saccharomyces cerevisiae

<400> SEQUENCE: 29

Met Ser Asp Ala Ala Pro Ser Leu Ser Asn Leu Phe Tyr Asp Pro Thr
1 5 10 15

Tyr Asn Pro Gly Gln Ser Thr Ile Asn Tyr Thr Ser Ile Tyr Gly Asn
20 25 30

Gly Ser Thr Ile Thr Phe Asp Glu Leu Gln Gly Leu Val Asn Ser Thr
35 40 45

Val Thr Gln Ala Ile Met Phe Gly Val Arg Cys Gly Ala Ala Ala Leu
50 55 60

Thr Leu Ile Val Met Trp Met Thr Ser Arg Ser Arg Lys Thr Pro Ile
65 70 75 80

```
Phe Ile Ile Asn Gln Val Ser Leu Phe Leu Ile Ile Leu His Ser Ala
                85                  90                  95

Leu Tyr Phe Lys Tyr Leu Leu Ser Asn Tyr Ser Ser Val Thr Tyr Ala
            100                 105                 110

Leu Thr Gly Phe Pro Gln Phe Ile Ser Arg Gly Asp Val His Val Tyr
        115                 120                 125

Gly Ala Thr Asn Ile Ile Gln Val Leu Leu Val Ala Ser Ile Glu Thr
    130                 135                 140

Ser Leu Val Phe Gln Ile Lys Val Ile Phe Thr Gly Asp Asn Phe Lys
145                 150                 155                 160

Arg Ile Gly Leu Met Leu Thr Ser Ile Ser Phe Thr Leu Gly Ile Ala
                165                 170                 175

Thr Val Thr Met Tyr Phe Val Ser Ala Val Lys Gly Met Ile Val Thr
            180                 185                 190

Tyr Asn Asp Val Ser Ala Thr Gln Asp Lys Tyr Phe Asn Ala Ser Thr
        195                 200                 205

Ile Leu Leu Ala Ser Ser Ile Asn Phe Met Ser Phe Val Leu Val Val
    210                 215                 220

Lys Leu Ile Leu Ala Ile Arg Ser Arg Arg Phe Leu Gly Leu Lys Gln
225                 230                 235                 240

Phe Asp Ser Phe His Ile Leu Leu Ile Met Ser Cys Gln Ser Leu Leu
                245                 250                 255

Val Pro Ser Ile Ile Phe Ile Leu Ala Tyr Ser Leu Lys Pro Asn Gln
            260                 265                 270

Gly Thr Asp Val Leu Thr Thr Val Ala Thr Leu Leu Ala Val Leu Ser
        275                 280                 285

Leu Pro Leu Ser Ser Met Trp Ala Thr Ala Ala Asn Asn Ala Ser Lys
    290                 295                 300

Thr Asn Thr Ile Thr Ser Asp Phe Thr Thr Ser Thr Asp Arg Phe Tyr
305                 310                 315                 320

Pro Gly Thr Leu Ser Ser Phe Gln Thr Asp Ser Ile Asn Asn Asp Ala
                325                 330                 335

Lys Ser Ser Leu Arg Ser Arg Leu Tyr Asp Leu Tyr Pro Arg Arg Lys
            340                 345                 350

Glu Thr Thr Ser Asp Lys His Ser Glu Arg Thr Phe Val Ser Glu Thr
        355                 360                 365

Ala Asp Asp Ile Glu Lys Asn Gln Phe Tyr Gln Leu Pro Thr Pro Thr
    370                 375                 380

Ser Ser Lys Asn Thr Arg Ile Gly Pro Phe Ala Asp Ala Ser Tyr Lys
385                 390                 395                 400

Glu Gly Glu Val Glu Pro Val Asp Met Tyr Thr Pro Asp Thr Ala Ala
                405                 410                 415

Asp Glu Glu Ala Arg Lys Phe Trp Thr Glu Asp Asn Asn Asn Leu
            420                 425                 430
```

<210> SEQ ID NO 30
<211> LENGTH: 1293
<212> TYPE: DNA
<213> ORGANISM: Saccharomyces cerevisiae

<400> SEQUENCE: 30

```
atgtctgatg cggctccttc attgagcaat ctattttatg atccaacgta taatcctggt      60

caaagcacca ttaactacac ttccatatat gggaatggat ctaccatcac tttcgatgag     120
```

ttgcaaggtt tagttaacag tactgttact caggccatta tgtttggtgt cagatgtggt 180
gcagctgctt tgactttgat tgtcatgtgg atgacatcga gaagcagaaa aacgccgatt 240
ttcattatca accaagtttc attgttttta atcattttgc attctgcact ctattttaaa 300
tatttactgt ctaattactc ttcagtgact tacgctctca ccggatttcc tcagttcatc 360
agtagaggtg acgttcatgt ttatggtgct acaaatataa ttcaagtcct tcttgtggct 420
tctattgaga cttcactggt gtttcagata aaagttattt tcacaggcga caacttcaaa 480
aggataggtt tgatgctgac gtcgatatct ttcactttag ggattgctac agttaccatg 540
tattttgtaa gcgctgttaa aggtatgatt gtgacttata atgatgttag tgccacccaa 600
gataaatact tcaatgcatc cacaatttta cttgcatcct caataaactt tatgtcattt 660
gtcctggtag ttaaattgat tttagctatt agatcaagaa gattccttgg tctcaagcag 720
ttcgatagtt tccatatttt actcataatg tcatgtcaat ctttgttggt tccatcgata 780
atattcatcc tcgcatacag tttgaaacca aaccagggaa cagatgtctt gactactgtt 840
gcaacattac ttgctgtatt gtctttacca ttatcatcaa tgtgggccac ggctgctaat 900
aatgcatcca aaacaaacac aattacttca gactttacaa catccacaga taggttttat 960
ccaggcacgc tgtctagctt tcaaactgat agtatcaaca acgatgctaa aagcagtctc 1020
agaagtagat tatatgacct atatcctaga aggaaggaaa caacatcgga taaacattcg 1080
gaaagaactt ttgtttctga gactgcagat gatatagaga aaaatcagtt ttatcagttg 1140
cccacaccta cgagttcaaa aaatactagg ataggaccgt ttgctgatgc aagttacaaa 1200
gagggagaag ttgaacccgt cgacatgtac actcccgata cggcagctga tgaggaagcc 1260
agaaagttct ggactgaaga taataataat tta 1293

<210> SEQ ID NO 31
<211> LENGTH: 1293
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 31
atgtctgatg cggctccttc attgagcaat ctattttatg atccaacgta taatcctggt 60
caaagcacca ttaactacac ttccatatat gggaatggat ctaccatcac tttcgatgag 120
ttgcaaggtt tagttaacag tactgttact caggccatta tgtttggtgt cagatgtggt 180
gcagctgctt tgactttgat tgtcatgtgg atgacatcga gaagcagaaa aacgccgatt 240
ttcattatca accaagtttc attgttttta atcattttgc attctgcact ctattttaaa 300
tatttactgt ctaattactc ttcagtgact tacgctctca ccggatttcc tcagttcatc 360
agtagaggtg acgttcatgt ttatggtgct acaaatataa ttcaagtcct tcttgtggct 420
tctattgaga cttcactggt gtttcagata aaagttattt tcacaggcga caacttcaaa 480
aggataggtt tgatgctgac gtcgatatct ttcactttag ggattgctac agttaccatg 540
tattttgtaa gcgctgttaa aggtatgatt gtgacttata atgatgttag tgccacccaa 600
gataaatact tcaatgcatc cacaatttta cttgcatcct caataaactt tatgtcattt 660
gtcctggtag ttaaattgat tttagctatt agatcaagaa gattccttgg tctcaagcag 720
ttcgatagtt tccatatttt actcataatg tcatgtcaat ctttgttggt tccatcgata 780
atattcatcc tcgcatacag tttgaaacca aaccagggaa cagatgcctt gactactgtt 840

-continued gcaacattac ttgctgtatt gtctttacca ttatcatcaa tgtgggccac ggctgctaat 900
aatgcatcca aaacaaacac aattacttca gactttacaa catccacaga taggttttat 960
ccaggcacgc tgtctagctt tcaaactgat agtatcaaca acgatgctaa aagcagtctc 1020
agaagtagat tatatgacct atatcctaga aggaaggaaa caacatcgga taaacattcg 1080
gaaagaactt ttgtttctga gactgcagat gatatagaga aaaatcagtt ttatcagttg 1140
cccacaccta cgagttcaaa aaatactagg ataggaccgt ttgctgatgc aagttacaaa 1200
gagggagaag ttgaacccgt cgacatgtac actcccgata cggcagctga tgaggaagcc 1260
agaaagttct ggactgaaga taataataat tta 1293

<210> SEQ ID NO 32
<211> LENGTH: 1293
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 32
atgtctgatg cggctccttc attgagcaat ctattttatg atccaacgta taatcctggt 60
caaagcacca ttaactacac ttccatatat gggaatggat ctaccatcac tttcgatgag 120
ttgcaaggtt tagttaacag tactgttact caggccatta tgtttggtgt cagatgtggt 180
gcagctgctt tgactttgat tgtcatgtgg atgacatcga gaagcagaaa aacgccgatt 240
ttcattatca accaagtttc attgttttta atcattttgc attctgcact ctattttaaa 300
tatttactgt ctaattactc ttcagtgact tacgctctca ccggatttcc tcagttcatc 360
agtagaggtg acgttcatgt ttatggtgct acaaatataa ttcaagtcct tcttgtggct 420
tctattgaga cttcactggt gtttcagata aaagttattt tcacaggcga caacttcaaa 480
aggataggtt tgatgctgac gtcgatatct ttcactttag ggattgctac agttaccatg 540
tattttgtaa gcgctgttaa aggtatgatt gtgacttata atgatgttag tgccacccaa 600
gataaatact tcaatgcatc cacaattcta cttgcatcct caataaactt tatgtcattt 660
gtcctggtag ttaaattgat tttagctatt agatcaagaa gattccttgg tctcaagcag 720
ttcgatagtt tccatatttt actcataatg tcatgtcaat ctttgttggt tccatcgata 780
atattcatcc tcgcatacag tttgaaacca aaccagggaa cagatgcctt gactactgtt 840
gcaacattac ttgctgtatt gtctttacca ttatcatcaa tgtgggccac ggctgctaat 900
aatgcatcca aaacaaacac aattacttca gactttacaa catccacaga taggttttat 960
ccaggcacgc tgtctagctt tcaaactgat agtatcaaca acgatgctaa aagcagtctc 1020
agaagtagat tatatgacct atatcctaga aggaaggaaa caacatcgga taaacattcg 1080
gaaagaactt ttgtttctga gactgcagat gatatagaga aaaatcagtt ttatcagttg 1140
cccacaccta cgagttcaaa aaatactagg ataggaccgt ttgctgatgc aagttacaaa 1200
gagggagaag ttgaacccgt cgacatgtac actcccgata cggcagctga tgaggaagcc 1260
agaaagttct ggactgaaga taataataat tta 1293

<210> SEQ ID NO 33
<211> LENGTH: 9
<212> TYPE: PRT
<213> ORGANISM: Penicillium rubens

<400> SEQUENCE: 33

Trp Cys Gly His Ile Gly Gln Gly Cys
1 5

<210> SEQ ID NO 34
<211> LENGTH: 12
<212> TYPE: PRT
<213> ORGANISM: Lodderomyces elongisporous

<400> SEQUENCE: 34

Trp Met Trp Thr Arg Tyr Gly Arg Phe Ser Pro Val
1 5 10

<210> SEQ ID NO 35
<211> LENGTH: 12
<212> TYPE: PRT
<213> ORGANISM: Zygosaccharomyces bailii

<400> SEQUENCE: 35

His Leu Val Arg Leu Ser Pro Gly Ala Ala Met Phe
1 5 10

<210> SEQ ID NO 36
<211> LENGTH: 12
<212> TYPE: PRT
<213> ORGANISM: Zygosaccharomyces rouxii

<400> SEQUENCE: 36

His Phe Ile Glu Leu Asp Pro Gly Gln Pro Met Phe
1 5 10

<210> SEQ ID NO 37
<211> LENGTH: 12
<212> TYPE: PRT
<213> ORGANISM: Scheffersomyces stipitis

<400> SEQUENCE: 37

Trp His Trp Thr Ser Tyr Gly Val Phe Glu Pro Gly
1 5 10

<210> SEQ ID NO 38
<211> LENGTH: 13
<212> TYPE: PRT
<213> ORGANISM: Vibrio cholerae

<400> SEQUENCE: 38

Trp His Trp Leu Gln Leu Lys Pro Gly Gln Pro Met Tyr
1 5 10

<210> SEQ ID NO 39
<211> LENGTH: 13
<212> TYPE: PRT
<213> ORGANISM: Kluyveromyces lactis

<400> SEQUENCE: 39

Trp Ser Trp Ile Thr Leu Arg Pro Gly Gln Pro Ile Phe
1 5 10

<210> SEQ ID NO 40
<211> LENGTH: 13
<212> TYPE: PRT
<213> ORGANISM: Vanderwaltozyma polyspora

<400> SEQUENCE: 40

Trp His Trp Leu Glu Leu Asp Asn Gly Gln Pro Ile Tyr
1 5 10

<210> SEQ ID NO 41
<211> LENGTH: 13
<212> TYPE: PRT
<213> ORGANISM: Vanderwaltozyma polyspora

<400> SEQUENCE: 41

Trp His Trp Leu Arg Leu Arg Tyr Gly Glu Pro Ile Tyr
1 5 10

<210> SEQ ID NO 42
<211> LENGTH: 13
<212> TYPE: PRT
<213> ORGANISM: Candida parapsilosis

<400> SEQUENCE: 42

Lys Pro His Trp Thr Thr Tyr Gly Tyr Tyr Glu Pro Gln
1 5 10

<210> SEQ ID NO 43
<211> LENGTH: 14
<212> TYPE: PRT
<213> ORGANISM: Saccharomyces castellii

<400> SEQUENCE: 43

Asn Trp His Trp Leu Arg Leu Asp Pro Gly Gln Pro Leu Tyr
1 5 10

<210> SEQ ID NO 44
<211> LENGTH: 15
<212> TYPE: PRT
<213> ORGANISM: Candida tropicalis

<400> SEQUENCE: 44

Lys Phe Lys Phe Arg Leu Thr Arg Tyr Gly Trp Phe Ser Pro Asn
1 5 10 15

<210> SEQ ID NO 45
<211> LENGTH: 16
<212> TYPE: PRT
<213> ORGANISM: Candida guilliermondii

<400> SEQUENCE: 45

Lys Lys Asn Ser Arg Phe Leu Thr Tyr Trp Phe Phe Gln Pro Ile Met
1 5 10 15

<210> SEQ ID NO 46
<211> LENGTH: 17
<212> TYPE: PRT
<213> ORGANISM: Geotrichum candidum

<400> SEQUENCE: 46

Gly Asp Trp Gly Trp Phe Trp Tyr Val Pro Arg Pro Gly Asp Pro Ala
1 5 10 15

Met

<210> SEQ ID NO 47
<211> LENGTH: 23
<212> TYPE: PRT
<213> ORGANISM: Schizosaccharomyces pombe

<400> SEQUENCE: 47

Thr Tyr Ala Asp Phe Leu Arg Ala Tyr Gln Ser Trp Asn Thr Phe Val
1 5 10 15

```
Asn Pro Asp Arg Pro Asn Leu
            20


<210> SEQ ID NO 48
<211> LENGTH: 23
<212> TYPE: PRT
<213> ORGANISM: Schizosaccharomyces japonicus

<400> SEQUENCE: 48

Val Ser Asp Arg Val Lys Gln Met Leu Ser His Trp Trp Asn Phe Arg
1               5                   10                  15

Asn Pro Asp Thr Ala Asn Leu
            20


<210> SEQ ID NO 49
<211> LENGTH: 23
<212> TYPE: PRT
<213> ORGANISM: Schizosaccharomyces octosporus

<400> SEQUENCE: 49

Thr Tyr Glu Asp Phe Leu Arg Val Tyr Lys Asn Trp Trp Ser Phe Gln
1               5                   10                  15

Asn Pro Asp Arg Pro Asp Leu
            20


<210> SEQ ID NO 50
<211> LENGTH: 431
<212> TYPE: PRT
<213> ORGANISM: Saccharomyces cerevisiae

<400> SEQUENCE: 50

Met Ser Asp Ala Ala Pro Ser Leu Ser Asn Leu Phe Tyr Asp Pro Thr
1               5                   10                  15

Tyr Asn Pro Gly Gln Ser Thr Ile Asn Tyr Thr Ser Ile Tyr Gly Asn
            20                  25                  30

Gly Ser Thr Ile Thr Phe Asp Glu Leu Gln Gly Leu Val Asn Ser Thr
        35                  40                  45

Val Thr Gln Ala Ile Met Phe Gly Val Arg Cys Gly Ala Ala Ala Leu
    50                  55                  60

Thr Leu Ile Val Met Trp Met Thr Ser Arg Ser Arg Lys Thr Pro Ile
65                  70                  75                  80

Phe Ile Ile Asn Gln Val Ser Leu Phe Leu Ile Ile Leu His Ser Ala
                85                  90                  95

Leu Tyr Phe Lys Tyr Leu Leu Ser Asn Tyr Ser Ser Val Thr Tyr Ala
            100                 105                 110

Leu Thr Gly Phe Pro Gln Phe Ile Ser Arg Gly Asp Val His Val Tyr
        115                 120                 125

Gly Ala Thr Asn Ile Ile Gln Val Leu Leu Val Ala Ser Ile Glu Thr
    130                 135                 140

Ser Leu Val Phe Gln Ile Lys Val Ile Phe Thr Gly Asp Asn Phe Lys
145                 150                 155                 160

Arg Ile Gly Leu Met Leu Thr Ser Ile Ser Phe Thr Leu Gly Ile Ala
                165                 170                 175

Thr Val Thr Met Tyr Phe Val Ser Ala Val Lys Gly Met Ile Val Thr
            180                 185                 190

Tyr Asn Asp Val Ser Ala Thr Gln Asp Lys Tyr Phe Asn Ala Ser Thr
        195                 200                 205
```

-continued

```
Ile Leu Leu Ala Ser Ser Ile Asn Phe Met Ser Phe Val Leu Val Val
    210                 215                 220

Lys Leu Ile Leu Ala Ile Arg Ser Arg Arg Phe Leu Gly Leu Lys Gln
225                 230                 235                 240

Phe Asp Ser Phe His Ile Leu Leu Ile Met Ser Cys Gln Ser Leu Leu
                245                 250                 255

Val Pro Ser Ile Ile Phe Ile Leu Ala Tyr Ser Leu Lys Pro Asn Gln
            260                 265                 270

Gly Thr Asp Val Leu Thr Thr Val Ala Thr Leu Leu Ala Val Leu Ser
        275                 280                 285

Leu Pro Leu Ser Ser Met Trp Ala Thr Ala Ala Asn Asn Ala Ser Lys
    290                 295                 300

Thr Asn Thr Ile Thr Ser Asp Phe Thr Thr Ser Thr Asp Arg Phe Tyr
305                 310                 315                 320

Pro Gly Thr Leu Ser Ser Phe Gln Thr Asp Ser Ile Asn Asn Asp Ala
                325                 330                 335

Lys Ser Ser Leu Arg Ser Arg Leu Tyr Asp Leu Tyr Pro Arg Arg Lys
            340                 345                 350

Glu Thr Thr Ser Asp Lys His Ser Glu Arg Thr Phe Val Ser Glu Thr
        355                 360                 365

Ala Asp Asp Ile Glu Lys Asn Gln Phe Tyr Gln Leu Pro Thr Pro Thr
    370                 375                 380

Ser Ser Lys Asn Thr Arg Ile Gly Pro Phe Ala Asp Ala Ser Tyr Lys
385                 390                 395                 400

Glu Gly Glu Val Glu Pro Val Asp Met Tyr Thr Pro Asp Thr Ala Ala
                405                 410                 415

Asp Glu Glu Ala Arg Lys Phe Trp Thr Glu Asp Asn Asn Asn Leu
            420                 425                 430
```

<210> SEQ ID NO 51
<211> LENGTH: 1296
<212> TYPE: DNA
<213> ORGANISM: Saccharomyces cerevisiae

<400> SEQUENCE: 51

```
atgtctgatg cggctccttc attgagcaat ctattttatg atccaacgta taatcctggt      60

caaagcacca ttaactacac ttccatatat gggaatggat ctaccatcac tttcgatgag     120

ttgcaaggtt tagttaacag tactgttact caggccatta tgtttggtgt cagatgtggt     180

gcagctgctt tgactttgat tgtcatgtgg atgacatcga gaagcagaaa aacgccgatt     240

ttcattatca accaagtttc attgttttta atcattttgc attctgcact ctattttaaa     300

tatttactgt ctaattactc ttcagtgact tacgctctca ccggatttcc tcagttcatc     360

agtagaggtg acgttcatgt ttatggtgct acaaatataa ttcaagtcct tcttgtggct     420

tctattgaga cttcactggt gtttcagata aaagttattt tcacaggcga caacttcaaa     480

aggataggtt tgatgctgac gtcgatatct ttcactttag ggattgctac agttaccatg     540

tattttgtaa gcgctgttaa aggtatgatt gtgacttata atgatgttag tgccacccaa     600

gataaatact tcaatgcatc cacaatttta cttgcatcct caataaactt tatgtcattt     660

gtcctggtag ttaaattgat tttagctatt agatcaagaa gattccttgg tctcaagcag     720

ttcgatagtt tccatatttt actcataatg tcatgtcaat ctttgttggt tccatcgata     780

atattcatcc tcgcatacag tttgaaacca aaccagggaa cagatgtctt gactactgtt     840

gcaacattac ttgctgtatt gtctttacca ttatcatcaa tgtgggccac ggctgctaat     900
```

```
aatgcatcca aaacaaacac aattacttca gactttacaa catccacaga taggttttat    960

ccaggcacgc tgtctagctt tcaaactgat agtatcaaca acgatgctaa aagcagtctc   1020

agaagtagat tatatgacct atatcctaga aggaaggaaa caacatcgga taaacattcg   1080

gaaagaactt ttgtttctga gactgcagat gatatagaga aaaatcagtt ttatcagttg   1140

cccacaccta cgagttcaaa aaatactagg ataggaccgt ttgctgatgc aagttacaaa   1200

gagggagaag ttgaacccgt cgacatgtac actcccgata cggcagctga tgaggaagcc   1260

agaaagttct ggactgaaga taataataat ttatag                             1296


<210> SEQ ID NO 52
<211> LENGTH: 435
<212> TYPE: PRT
<213> ORGANISM: Lodderomyces elongisporous

<400> SEQUENCE: 52

Met Asp Glu Ala Ile Asn Ala Asn Leu Val Ser Gly Asp Ile Ile Val
1               5                   10                  15

Ser Phe Asn Ile Pro Gly Leu Pro Glu Pro Val Gln Val Pro Phe Ser
            20                  25                  30

Glu Phe Asp Ser Phe His Lys Asp Gln Leu Ile Gly Val Ile Ile Leu
        35                  40                  45

Gly Val Thr Ile Gly Ala Cys Ser Leu Leu Leu Ile Leu Leu Leu Gly
    50                  55                  60

Met Leu Tyr Lys Ser Arg Glu Lys Tyr Trp Lys Ser Leu Leu Phe Met
65                  70                  75                  80

Leu Asn Val Cys Ile Leu Ala Ala Thr Ile Leu Arg Ser Gly Cys Phe
                85                  90                  95

Leu Asp Tyr Tyr Leu Ser Asp Leu Ala Ser Ile Ser Tyr Thr Phe Thr
            100                 105                 110

Gly Val Tyr Asn Gly Thr Ser Phe Ala Ser Ser Asp Ala Ala Asn Val
        115                 120                 125

Phe Lys Thr Ile Met Phe Ala Leu Ile Glu Thr Ser Leu Thr Phe Gln
    130                 135                 140

Val Tyr Val Met Phe Gln Gly Thr Thr Trp Lys Asn Trp Gly His Ala
145                 150                 155                 160

Val Thr Ala Leu Ser Gly Leu Leu Ser Val Ala Ser Val Ala Phe Gln
                165                 170                 175

Ile Tyr Thr Thr Ile Leu Ser His Asn Asn Phe Asn Ala Thr Ile Ser
            180                 185                 190

Gly Thr Gly Thr Leu Thr Ser Gly Val Trp Met Asp Leu Pro Thr Leu
        195                 200                 205

Leu Phe Ala Ala Ser Ile Asn Phe Met Thr Ile Leu Leu Leu Phe Lys
    210                 215                 220

Leu Gly Met Ala Ile Arg Gln Arg Arg Tyr Leu Gly Leu Lys Gln Phe
225                 230                 235                 240

Asp Gly Phe His Ile Leu Phe Ile Met Phe Thr Gln Thr Leu Phe Ile
                245                 250                 255

Pro Ser Ile Leu Leu Val Ile His Tyr Phe Tyr Gln Ala Met Ser Gly
            260                 265                 270

Pro Phe Ile Ile Asn Met Ala Leu Phe Leu Val Val Ala Phe Leu Pro
        275                 280                 285

Leu Ser Ser Leu Trp Ala Gln Thr Ala Asn Thr Thr Lys Lys Ile Glu
    290                 295                 300
```

```
Ser Ser Pro Ser Met Ser Phe Ile Thr Arg Arg Lys Ser Glu Asp Glu
305                 310                 315                 320

Ser Pro Leu Ala Ala Asn Asp Glu Asp Arg Leu Arg Lys Phe Thr Thr
                325                 330                 335

Thr Leu Asp Leu Ser Gly Asn Lys Asn Asn Thr Thr Asn Asn Asn Asn
            340                 345                 350

Asn Ser Asn Asn Ile Asn Asn Asn Met Ser Asn Ile Asn Tyr Pro Ser
        355                 360                 365

Thr Gly Leu Gly Glu Asp Asp Lys Ser Phe Ile Phe Glu Met Glu Pro
    370                 375                 380

Ser Arg Glu Arg Ala Ala Ile Glu Glu Ile Asp Leu Gly Ala Arg Ile
385                 390                 395                 400

Asp Thr Gly Leu Pro Arg Asp Leu Glu Lys Phe Leu Val Asp Gly Phe
                405                 410                 415

Asp Asp Ser Asp Asp Gly Glu Gly Met Ile Ala Arg Glu Val Thr Met
            420                 425                 430

Leu Lys Lys
        435


<210> SEQ ID NO 53
<211> LENGTH: 1308
<212> TYPE: DNA
<213> ORGANISM: Lodderomyces elongisporous

<400> SEQUENCE: 53

atggacgaag caatcaatgc aaaccttgtt tctggagata ttatagtctc ttttaacatt     60

cctggtttgc cagaaccggt acaagtgcca ttcagcgaat ttgattcgtt tcataaagac    120

cagctcattg gagtcatcat tcttggagtc actattggag catgctcgct tttgttgata    180

ttgctacttg gaatgttata caagagccgt gaaaagtatt ggaaatcact attatttatg    240

ctcaatgtat gcatcttggc tgccacaatc ttaaggagcg gttgcttctt agactattat    300

ctaagtgatt tggccagtat cagttataca tttactggag tatacaatgg taccagcttt    360

gctagctctg acgcggcaaa tgtgttcaag actattatgt ttgccttgat tgaaacttcg    420

ttaacctttc aagtgtatgt catgtttcaa gggaccactt ggaaaaattg gggccatgct    480

gtcactgcat tatcgggtct cttgtctgtt gcctcagtgg cgttccagat ctacaccacg    540

attttatccc acaataattt caatgctaca atctcgggaa ccggtacatt aacttcaggt    600

gtttggatgg acttaccaac actcttgttt gccgcaagta tcaattttat gaccattttg    660

ttgttattta agttgggaat ggccattaga caaagaaggt atttaggttt aaaacagttt    720

gatgggttcc atatcttatt catcatgttt acccaaacat tgttcatacc ctcgattttg    780

cttgtgatcc actactttta ccaggcaatg tctggaccat tcatcatcaa catggcgttg    840

ttcttggtgg tggcattctt gccattgagt tcattatggg cacaaactgc aaacactact    900

aaaaagattg aatcttcgcc aagtatgagc tttattacta gacgaaaatc agaggatgag    960

tcaccactgg ctgctaacga cgaggatagg ttacgaaaat tcaccacaac tttggatttg   1020

tcgggcaaca agaacaatac aacaaacaat aataacaata gcaacaacat taacaacaat   1080

atgagcaaca tcaactaccc ttctacagga ctgggagaag acgataaatc ctttatattt   1140

gagatggaac ccagtcggga aagagctgca atagaagaga ttgatcttgg agcaaggatc   1200

gataccggtt tgcccagaga tttagagaaa tttctagttg atgggtttga cgatagtgat   1260

gacggagaag gaatgatagc cagagaagtg actatgttga aaaaatag                 1308
```

<210> SEQ ID NO 54
<211> LENGTH: 380
<212> TYPE: PRT
<213> ORGANISM: Penicillium rubens

<400> SEQUENCE: 54

```
Met Ala Thr Ser Ser Pro Ile Gln Pro Phe Asp Pro Phe Thr Gln Asn
1               5                   10                  15

Val Thr Phe Arg Leu Gln Asp Gly Thr Glu Phe Pro Val Ser Val Lys
            20                  25                  30

Ala Leu Asp Val Phe Val Met Tyr Asn Val Arg Val Cys Ile Asn Tyr
        35                  40                  45

Gly Cys Gln Phe Gly Ala Ser Phe Val Leu Leu Val Ile Leu Val Leu
    50                  55                  60

Leu Thr Gln Ser Asp Lys Arg Arg Ser Ala Val Phe Ile Leu Asn Gly
65                  70                  75                  80

Leu Ala Leu Phe Leu Asn Ser Ser Arg Leu Leu Phe Gln Val Ile His
                85                  90                  95

Phe Ser Thr Ala Phe Glu Gln Val Tyr Pro Tyr Val Ser Gly Asp Tyr
            100                 105                 110

Ser Ser Val Pro Trp Ser Ala Tyr Ala Ile Ser Ile Val Ala Val Val
        115                 120                 125

Leu Thr Thr Leu Val Val Val Cys Ile Glu Ala Ser Leu Val Ile Gln
    130                 135                 140

Val His Val Val Cys Ser Thr Leu Arg Arg Arg Tyr Arg His Pro Leu
145                 150                 155                 160

Leu Ala Ile Ser Ile Leu Val Ala Leu Val Pro Ile Gly Phe Arg Cys
                165                 170                 175

Ala Trp Met Val Ala Asn Cys Lys Ala Ile Ile Lys Leu Thr Tyr Thr
            180                 185                 190

Asn Asp Val Trp Trp Ile Glu Ser Ala Thr Asn Ile Cys Val Thr Ile
        195                 200                 205

Ser Ile Cys Phe Phe Cys Val Ile Phe Val Thr Lys Leu Gly Phe Ala
    210                 215                 220

Ile Lys Gln Arg Arg Arg Leu Gly Val Arg Glu Phe Gly Pro Met Lys
225                 230                 235                 240

Val Ile Phe Val Met Gly Cys Gln Thr Met Val Val Pro Ala Ile Phe
                245                 250                 255

Ser Ile Thr Gln Tyr Tyr Val Val Val Pro Glu Phe Ser Ser Asn Val
            260                 265                 270

Val Thr Leu Val Val Ile Ser Leu Pro Leu Ser Ser Ile Trp Ala Gly
        275                 280                 285

Ala Val Leu Glu Asn Ala Arg Arg Thr Gly Ser Gln Asp Arg Gln Arg
    290                 295                 300

Arg Arg Asn Leu Trp Arg Ala Leu Val Gly Gly Ala Glu Ser Leu Leu
305                 310                 315                 320

Ser Pro Thr Lys Asp Ser Pro Thr Ser Leu Ser Ala Met Thr Ala Ala
                325                 330                 335

Gln Thr Leu Cys Tyr Ser Asp His Thr Met Ser Lys Gly Ser Pro Thr
            340                 345                 350

Ser Arg Asp Thr Asp Ala Phe Tyr Gly Ile Ser Val Glu His Asp Ile
        355                 360                 365

Ser Ile Asn Arg Val Gln Arg Asn Asn Ser Ile Val
```

370 375 380

<210> SEQ ID NO 55
<211> LENGTH: 1143
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 55
atggctacct cttccccaat ccaaccattt gacccattca cccaaaacgt taccttccgt 60
ttgcaagacg gtaccgaatt cccagtttct gtcaaggctt tggacgtctt cgtcatgtac 120
aacgttagag tctgtattaa ctacggttgt caattcggtg cctccttcgt cttgttagtc 180
attttagtct tgttaactca atccgacaag agaagatctg ctgtcttcat tttgaacggt 240
ttggctttgt tcttgaactc ttctagattg ttgtttcaag ttattcactt ctccactgcc 300
ttcgaacaag tctacccata cgtctctggt gactactcct ctgtcccatg gtccgcttac 360
gctatctcca ttgtcgctgt tgttttgact accttggtcg ttgtttgtat cgaagcttct 420
ttggttattc aagttcacgt tgtctgttcc accttgagac gtagatacag acacccatta 480
ttagctattt ctattttggt cgctttggtt ccaatcggtt tcagatgtgc ttggatggtc 540
gctaactgta aggctattat taaattgacc tacaccaacg acgtttggtg gatcgaatct 600
gctactaaca tctgtgtcac tatctccatc tgtttcttct gtgttatctt cgttaccaag 660
ttgggtttcg ccatcaagca aagaagaaga ttgggtgtta gagaattcgg tccaatgaag 720
gttattttcg tcatgggttg tcaaactatg gttgttccag ctatttctc catcacccaa 780 tactacgtcg tcgtcccaga attctcctct aacgtcgtta ctttggttgt catttcttta 840
ccattatctt ccatttgggc cggtgctgtc ttggaaaacg ctagaagaac cggttcccaa 900
gatagacaaa gaagacgtaa cttgtggaga gctttggttg gtggtgctga atccttgtta 960
tccccaacta aggactctcc aacctctttg tctgctatga ctgctgctca aaccttatgt 1020
tactctgatc acaccatgtc caagggttct ccaacttcca gagacaccga tgctttctac 1080
ggtatctccg ttgaacacga catctccatt aacagagttc aacgtaacaa ctccatcgtc 1140
tag 1143

<210> SEQ ID NO 56
<211> LENGTH: 395
<212> TYPE: PRT
<213> ORGANISM: Candida guilliermondii

<400> SEQUENCE: 56

Met Lys Ser Cys Ser Ile Gly Phe Gly Ile Pro Phe Ile Asn Glu Pro
1 5 10 15

Asn Phe Glu Thr Val Ser Ile Leu Thr Met Asp Val Ser Phe Ile Asp
20 25 30

Ala Asp Val Asn Pro Asp Asn Ile Leu Leu Asn Phe Thr Ile Pro Gly
35 40 45

Tyr Gln Asn Gly Phe Ser Val Pro Met Val Val Ile Asn Glu Leu Gln
50 55 60

Lys Ser Gln Met Lys Tyr Ala Ile Val Tyr Gly Cys Gly Val Gly Ala
65 70 75 80

Ser Leu Ile Leu Leu Phe Val Val Trp Ile Leu Cys Ser Arg Lys Thr
85 90 95

-continued

```
Pro Leu Phe Ile Met Asn Asn Ile Pro Leu Val Leu Tyr Val Ile Ser
            100                 105                 110

Ser Ser Leu Asn Leu Ala Tyr Ile Thr Gly Pro Leu Ser Ser Val Ser
        115                 120                 125

Val Phe Leu Thr Gly Ile Leu Thr Ser His Asp Ala Ile Asn Val Val
    130                 135                 140

Tyr Ala Ser Asn Ala Leu Gln Met Leu Leu Ile Phe Ser Ile Gln Ser
145                 150                 155                 160

Thr Met Ala Tyr His Val Tyr Val Met Phe Lys Ser Pro Gln Ile Lys
                165                 170                 175

Tyr Leu Arg Tyr Met Leu Val Gly Phe Leu Gly Cys Leu Gln Ile Val
            180                 185                 190

Thr Thr Cys Leu Tyr Ile Asn Tyr Asn Val Leu Tyr Ser Arg Arg Met
        195                 200                 205

His Lys Leu Tyr Glu Thr Gly Gln Thr Tyr Gln Asp Gly Thr Val Met
    210                 215                 220

Thr Phe Val Pro Phe Ile Leu Phe Gln Cys Ser Val Asn Phe Ser Ser
225                 230                 235                 240

Ile Phe Leu Val Leu Lys Leu Ile Met Ala Ile Arg Thr Arg Arg Tyr
                245                 250                 255

Leu Gly Leu Arg Gln Phe Gly Gly Phe His Ile Leu Met Ile Val Ser
            260                 265                 270

Leu Gln Thr Met Leu Val Pro Ser Ile Leu Val Leu Val Asn Tyr Ala
        275                 280                 285

Ala His Lys Ala Val Pro Ser Asn Leu Leu Ser Ser Val Ser Met Met
    290                 295                 300

Ile Ile Val Leu Ser Leu Pro Ala Ser Ser Met Trp Ala Ala Ala Ala
305                 310                 315                 320

Asn Ala Ser Ser Ala Pro Ser Ser Ala Ala Ser Ser Leu Phe Arg Tyr
                325                 330                 335

Thr Thr Ser Asp Ser Asp Arg Thr Leu Glu Thr Lys Ser Asp His Phe
            340                 345                 350

Ile Met Lys His Glu Ser His Asn Ser Ser Pro Asn Ser Ser Pro Leu
        355                 360                 365

Thr Leu Val Gln Lys Arg Ile Ser Asp Ala Thr Leu Glu Leu Pro Lys
    370                 375                 380

Glu Leu Glu Asp Leu Ile Asp Ser Thr Ser Ile
385                 390                 395
```

<210> SEQ ID NO 57
<211> LENGTH: 1188
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 57

```
atgaagtcct gctccatcgg tttcggtatc ccattcatta atgaaccaaa cttcgaaact      60

gtttctattt tgaccatgga cgtttctttc attgacgctg acgtcaatcc tgacaatatc     120

ttgttgaact tcaccattcc tggttaccaa aacggtttct ctgttccaat ggttgttatt     180

aacgaattgc aaaagtctca aatgaaatac gctattgttt acggttgtgg tgtcggtgcc     240

tccttgattt tgttgtttgt cgtctggatt ttgtgttcta gaaagactcc attgtttatc     300

atgaacaaca ttccattagt tttgtacgtc atctcctctt ctttgaactt ggcttacatt     360
```

```
accggtccat tgtcttctgt ttccgtcttc ttgaccggta tcttgacttc tcacgatgcc    420

attaacgtcg tttacgcttc caacgctttg caaatgttgt tgatcttttc tatccaatct    480

accatggcct accacgttta cgttatgttc aaatctccac aaattaaata cttgagatac    540

atgttagtcg gtttcttggg ttgtttacaa attgtcacca cctgtttata catcaactac    600

aatgttttgt actctcgtag aatgcacaaa ttgtacgaaa ctggtcaaac ctaccaagat    660

ggtaccgtta tgactttcgt tccattcatc ttgttccaat gttctgtcaa cttctcttct    720

attttcttgg ttttgaagtt gattatggcc attagaacca gacgttactt gggtttgcgt    780

caattcggtg gttttcatat tttgatgatc gtttctttac aaactatgtt ggtcccatct    840

attttggttt tggttaacta cgccgctcat aaggctgttc cttccaactt gttatcttcc    900

gtttctatga tgatcattgt tttgtcttta ccagcttctt ctatgtgggc cgctgctgct    960

aacgcctctt ctgccccttc ctccgctgct tcctccttgt tcagatacac cacttctgat   1020

tccgatagaa ctttggaaac taaatctgac cacttcatca tgaagcatga gtcccacaac   1080

tcttctccaa attcctcccc attgactttg gttcaaaaga gaatttctga tgccacctta   1140

gaattaccaa aagagttaga agacttgatc gactccacct ccatctag                 1188


<210> SEQ ID NO 58
<211> LENGTH: 412
<212> TYPE: PRT
<213> ORGANISM: Candida tropicalis

<400> SEQUENCE: 58

Met Asp Ile Asn Asn Thr Ile Gln Ser Ser Gly Asp Ile Ile Ile Thr
1               5                   10                  15

Tyr Thr Ile Pro Gly Ile Glu Glu Pro Phe Glu Leu Pro Phe Glu Val
            20                  25                  30

Leu Asn His Phe Gln Ser Glu Gln Ser Lys Asn Cys Leu Val Met Gly
        35                  40                  45

Val Met Ile Gly Ser Cys Ser Val Leu Leu Ile Phe Leu Val Gly Ile
    50                  55                  60

Leu Phe Lys Thr Asn Lys Phe Ser Thr Ile Gly Lys Ser Lys Asn Leu
65                  70                  75                  80

Ser Lys Asn Phe Leu Phe Tyr Leu Asn Cys Leu Ile Thr Phe Ile Gly
                85                  90                  95

Ile Ile Arg Ala Ala Cys Phe Ser Asn Tyr Leu Leu Gly Pro Leu Asn
            100                 105                 110

Ser Ala Ser Phe Ala Phe Thr Gly Trp Tyr Asn Gly Glu Ser Tyr Ala
        115                 120                 125

Ser Ser Glu Ala Ala Asn Gly Phe Arg Val Ile Leu Phe Ala Leu Ile
    130                 135                 140

Glu Thr Ser Met Val Phe Gln Val Phe Val Met Phe Arg Gly Ala Gly
145                 150                 155                 160

Met Lys Lys Leu Ala Tyr Ser Val Thr Ile Leu Cys Thr Ala Leu Ala
                165                 170                 175

Leu Val Val Val Gly Phe Gln Ile Asn Ser Ala Val Leu Ser His Arg
            180                 185                 190

Arg Phe Val Asn Thr Val Asn Glu Ile Gly Asp Thr Gly Leu Ser Ser
        195                 200                 205

Ile Trp Leu Asp Leu Pro Thr Ile Leu Phe Ser Val Ser Val Asn Leu
    210                 215                 220
```

```
Met Ser Val Leu Leu Ile Gly Lys Leu Ile Met Ala Ile Lys Thr Arg
225                 230                 235                 240

Arg Tyr Leu Gly Leu Lys Gln Phe Asp Ser Phe His Val Leu Leu Ile
                245                 250                 255

Cys Ser Thr Gln Thr Leu Leu Val Pro Ser Leu Ile Leu Phe Val His
            260                 265                 270

Tyr Phe Leu Phe Phe Arg Asn Ala Asn Val Met Leu Ile Asn Ile Ser
        275                 280                 285

Ile Leu Leu Ile Val Leu Met Leu Pro Phe Ser Ser Leu Trp Ala Gln
    290                 295                 300

Thr Ala Asn Thr Thr Gln Tyr Ile Asn Ser Ser Pro Ser Phe Ser Phe
305                 310                 315                 320

Ile Ser Arg Glu Pro Ser Ala Asn Ser Thr Leu His Ser Ser Ser Gly
                325                 330                 335

His Tyr Ser Glu Lys Ser Tyr Gly Ile Asn Lys Leu Asn Thr Gln Gly
            340                 345                 350

Ser Ser Pro Ala Thr Leu Lys Asp Asp His Asn Ser Val Ile Leu Glu
        355                 360                 365

Ala Thr Asn Pro Met Ser Gly Phe Asp Ala Gln Leu Pro Pro Asp Ile
    370                 375                 380

Ala Arg Phe Leu Gln Asp Asp Ile Arg Ile Glu Pro Ser Ser Thr Gln
385                 390                 395                 400

Asp Phe Val Ser Thr Glu Val Thr Tyr Lys Lys Val
                405                 410
```

<210> SEQ ID NO 59
<211> LENGTH: 1239
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 59

```
atggacatca acaacaccat ccaatcttcc ggtgacatca tcattaccta caccatccca     60

ggtatcgaag aaccattcga attgccattc gaagttttga accacttcca atctgaacaa    120

tccaagaact gtttggtcat gggtgttatg atcggttctt gttccgtttt gttgatcttc    180

ttggtcggta ttttgttcaa aaccaacaaa ttctctacta ttggtaagtc taagaacttg    240

tctaagaact tcttgttcta cttgaactgt ttgatcacct tcatcggtat cattcgtgct    300

gcctgttttt ctaactactt gttgggtcca ttgaactctg cttctttcgc tttcactggt    360

tggtacaacg gtgaatctta cgcttcttcc gaagctgcta acggtttcag agtcatcttg    420

ttcgctttga ttgaaacttc tatggtcttc caagttttcg ttatgttcag aggtgctggt    480

atgaaaaagt tggcttactc cgttaccatt ttgtgtaccg ctttggcttt ggtcgttgtt    540

ggtttccaaa ttaactccgc tgtcttatct cacagaagat tcgtcaacac cgttaacgaa    600

attggtgata ctggtttgtc ctccatttgg ttggacttgc caaccatctt gttctccgtc    660

tctgtcaact taatgtctgt tttgttgatc ggtaaattga tcatggctat taagactaga    720

agatacttgg gtttgaaaca attcgattcc ttccacgttt tgttaatttg ttccactcaa    780

actttgttgg tcccatcttt aatcttgttc gttcactact tcttgttctt tagaaacgcc    840

aacgttatgt tgattaacat ttccatcttg ttgatcgtct tgatgttgcc attctcttcc    900

ttgtgggctc aaaccgccaa caccacccaa tacatcaact cttccccatc cttctctttc    960
```

atctctagag aaccatctgc taactctact ttgcactcct cttccggtca ctactctgaa 1020
aagtcctacg gtattaacaa attgaacacc caaggttctt ccccagccac cttaaaggat 1080
gatcacaact ccgtcatctt ggaagctacc aacccaatgt ctggtttcga cgcccaattg 1140
ccaccagaca ttgctagatt cttgcaagat gacatcagaa ttgaaccatc ttctacccaa 1200
gatttcgttt ccactgaagt cacctacaag aaggtctag 1239

<210> SEQ ID NO 60
<211> LENGTH: 403
<212> TYPE: PRT
<213> ORGANISM: Candida parapsilosis

<400> SEQUENCE: 60

Met Asn Lys Ile Val Ser Lys Leu Ser Ser Ser Asp Val Ile Val Thr
1               5                   10                  15

Val Thr Ile Pro Asn Glu Glu Asp Gly Thr Tyr Glu Val Pro Phe Tyr
            20                  25                  30

Ala Ile Asp Asn Tyr His Tyr Ser Arg Met Glu Asn Ala Val Val Leu
        35                  40                  45

Gly Ala Thr Ile Gly Ala Cys Ser Met Leu Leu Ile Met Leu Ile Gly
    50                  55                  60

Ile Leu Phe Lys Asn Phe Gln Arg Leu Arg Lys Ser Leu Leu Phe Asn
65                  70                  75                  80

Ile Asn Phe Ala Ile Leu Leu Met Leu Ile Leu Arg Ser Ala Cys Tyr
                85                  90                  95

Ile Asn Tyr Leu Met Asn Asn Leu Ser Ser Ile Ser Phe Phe Phe Thr
            100                 105                 110

Gly Ile Phe Asp Asp Glu Ser Phe Met Ser Ser Asp Ala Ala Asn Ala
        115                 120                 125

Phe Lys Val Ile Leu Val Ala Leu Ile Glu Val Ser Leu Thr Tyr Gln
    130                 135                 140

Ile Tyr Val Met Phe Lys Thr Pro Met Leu Lys Ser Trp Gly Ile Phe
145                 150                 155                 160

Ala Ser Val Leu Ala Gly Val Leu Gly Leu Ala Thr Leu Ala Thr Gln
                165                 170                 175

Ile Tyr Thr Thr Val Met Ser His Val Asn Phe Val Asn Gly Thr Thr
            180                 185                 190

Gly Ser Pro Ser Gln Val Thr Ser Ala Trp Met Asp Met Pro Thr Ile
        195                 200                 205

Leu Phe Ser Val Ser Ile Asn Val Leu Ser Met Phe Leu Val Cys Lys
    210                 215                 220

Leu Gly Leu Ala Ile Arg Thr Arg Arg Tyr Leu Gly Leu Lys Gln Phe
225                 230                 235                 240

Asp Ala Phe His Ile Leu Phe Ile Met Ser Thr Gln Thr Met Ile Ile
                245                 250                 255

Pro Ser Ile Ile Leu Phe Val His Tyr Phe Asp Gln Asn Asp Ser Gln
            260                 265                 270

Thr Thr Leu Val Asn Ile Ser Leu Leu Leu Val Val Ile Ser Leu Pro
        275                 280                 285

Leu Ser Ser Leu Trp Ala Gln Thr Ala Asn Asn Val Arg Arg Ile Asp
    290                 295                 300

Thr Ser Pro Ser Met Ser Phe Ile Ser Arg Glu Ala Ser Asn Arg Ser
305                 310                 315                 320

Gly Asn Glu Thr Leu His Ser Gly Ala Thr Ile Ser Lys Tyr Asn Thr

```
            325                 330                 335

Ser Asn Thr Val Asn Thr Thr Pro Gly Thr Ser Lys Asp Asp Ser Leu
            340                 345                 350

Phe Ile Leu Asp Arg Ser Ile Pro Glu Gln Arg Ile Val Asp Thr Gly
        355                 360                 365

Leu Pro Lys Asp Leu Glu Lys Phe Ile Asn Asn Asp Phe Tyr Glu Asp
    370                 375                 380

Asp Gly Gly Met Ile Ala Arg Glu Val Thr Met Leu Lys Thr Ala His
385                 390                 395                 400

Asn Asn Gln


<210> SEQ ID NO 61
<211> LENGTH: 1212
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 61

atgaacaaga ttgtctccaa gttgtcttct tctgacgtca tcgttaccgt caccatccca      60

aacgaagaag atggtactta cgaagtccca ttctacgcta ttgacaacta ccactactcc     120

cgtatggaaa acgctgttgt tttaggtgct accattggtg cttgttctat gttgttgatc     180

atgttgattg gtattttgtt caagaacttc caaagattga gaaagtcttt gttgttcaac     240

atcaacttcg ctatcttatt gatgttgatt ttgagatccg cttgttacat caactacttg     300

atgaacaact tgtcttccat ttctttcttc ttcaccggta ttttcgatga tgaatctttc     360

atgtcttccg acgctgccaa cgccttcaag gttatcttgg ttgccttgat tgaagtttcc     420

ttgacctacc aaatttacgt tatgttcaag accccaatgt tgaagtcctg ggtattttc      480

gcctctgtct tggccggtgt tttgggtttg gctactttgg ctacccaaat ctacactacc     540

gttatgtctc acgttaactt cgtcaacggt accaccggtt ctccatctca agttacttcc     600

gcttggatgg acatgccaac tatcttattc tccgtttcta ttaacgtttt gtctatgttc     660

ttggtttgta agttgggttt ggccatcaga accagacgtt acttgggttt aaagcaattc     720

gacgctttcc acattttatt cattatgtcc actcaaacca tgatcattcc atccatcatc     780

ttgttcgttc actacttcga tcaaaacgac tctcaaacca ccttggtcaa catctctttg     840

ttattggtcg tcatttcctt gccattgtct tctttgtggg ctcaaactgc taacaacgtt     900

agaagaattg acacttctcc atccatgtcc ttcatctcta gagaagcttc caacagatct     960

ggtaacgaaa ccttgcactc tggtgctact atctctaagt acaacacctc caacaccgtt    1020

aacactaccc caggtacttc taaggatgac tctttgttca tcttggacag atccattcca    1080

gaacaaagaa ttgtcgacac tggtttgcca aaggacttgg aaaagttcat taacaacgat    1140

ttttacgaag acgatggtgg tatgattgcc agagaagtca ccatgttgaa gaccgctcac    1200

aacaaccaat ag                                                        1212


<210> SEQ ID NO 62
<211> LENGTH: 435
<212> TYPE: PRT
<213> ORGANISM: Geotrichum candidum

<400> SEQUENCE: 62

Met Ala Glu Asp Ser Ile Phe Pro Asn Asn Ser Thr Ser Pro Leu Thr
1               5                   10                  15
```

-continued

```
Asn Pro Ile Val Val Glu Thr Ile Lys Gly Thr Ala Tyr Ile Pro Leu
            20                  25                  30

His Tyr Leu Asp Asp Leu Gln Tyr Glu Lys Met Leu Leu Ala Ser Leu
        35                  40                  45

Phe Ser Val Arg Ile Ala Thr Ser Phe Val Val Ile Ile Trp Tyr Phe
    50                  55                  60

Val Ala Val Asn Lys Ala Lys Arg Ser Lys Phe Leu Tyr Ile Val Asn
65                  70                  75                  80

Gln Val Ser Leu Leu Ile Val Phe Ile Gln Ser Ile Leu Ser Leu Ile
                85                  90                  95

Tyr Val Phe Ser Asn Phe Ser Lys Met Ser Thr Ile Leu Thr Gly Asp
            100                 105                 110

Tyr Thr Gly Ile Thr Lys Arg Asp Ile Asn Val Ser Cys Val Ala Ser
        115                 120                 125

Val Phe Gln Phe Leu Phe Ile Ala Cys Ile Glu Leu Ala Leu Phe Ile
    130                 135                 140

Gln Ala Thr Val Val Phe Gln Lys Ser Val Arg Trp Leu Lys Phe Ser
145                 150                 155                 160

Val Ser Leu Ile Gln Gly Ser Val Ala Leu Thr Thr Thr Ala Leu Tyr
                165                 170                 175

Met Ala Ile Ile Val Gln Ser Ile Tyr Ala Thr Leu Asn Pro Tyr Ala
            180                 185                 190

Gly Asn Leu Ile Lys Gly Arg Phe Gly Tyr Leu Leu Ala Ser Leu Gly
        195                 200                 205

Lys Ile Phe Phe Ser Ile Ser Val Thr Ser Cys Met Cys Ile Phe Val
    210                 215                 220

Gly Lys Leu Val Phe Ala Ile His Gln Arg Arg Thr Leu Gly Ile Lys
225                 230                 235                 240

Gln Phe Asp Gly Leu Gln Ile Leu Val Ile Met Ser Thr Gln Ser Met
                245                 250                 255

Ile Ile Pro Thr Ile Ile Val Leu Met Ser Phe Leu Arg Arg Asn Ala
            260                 265                 270

Gly Ser Val Tyr Thr Met Ala Thr Leu Leu Val Ala Leu Ser Leu Pro
        275                 280                 285

Leu Ser Ser Leu Trp Ala Glu Ala Lys Thr Thr Arg Asp Ser Ala Ser
    290                 295                 300

Tyr Thr Ala Tyr Arg Pro Ser Gly Ser Pro Asn Asn Arg Ser Leu Phe
305                 310                 315                 320

Ala Ile Phe Ser Asp Arg Leu Ala Cys Gly Ser Gly Arg Asn Asn Arg
                325                 330                 335

His Asp Asp Asp Ser Arg Gly Asn Gly Ser Val Asn Ala Arg Lys Ala
            340                 345                 350

Asp Val Glu Ser Thr Ile Glu Met Ser Ser Cys Tyr Thr Asp Ser Pro
        355                 360                 365

Thr Tyr Ser Lys Phe Glu Ala Gly Leu Asp Ala Arg Gly Ile Val Phe
    370                 375                 380

Tyr Asn Glu His Gly Leu Pro Val Val Ser Gly Glu Val Gly Gly Ser
385                 390                 395                 400

Ser Ser Asn Gly Thr Lys Leu Gly Ser Gly His Lys Tyr Glu Val Asn
                405                 410                 415

Thr Thr Val Val Leu Ser Asp Val Asp Ser Pro Ser Pro Thr Asp Val
            420                 425                 430
```

Thr Arg Lys
        435

<210> SEQ ID NO 63
<211> LENGTH: 1308
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 63
atggccgaag actccatctt cccaaacaac tccacctctc cattgaccaa cccaattgtt 60
gttgaaacca ttaagggtac cgcttacatt ccattacact acttggatga tttgcaatac 120
gaaaagatgt tgttggcttc cttgttctcc gttagaattg ctacttcctt cgttgttatt 180
atttggtact tcgtcgctgt caacaaggct aagagatcta agtttttgta cattgtcaac 240
caagtttctt tgttgatcgt ttttatccaa tccattttgt ctttgattta cgtcttctcc 300
aacttctcca agatgtctac cattttgacc ggtgattaca ccggtatcac taagagagac 360
attaacgtct cttgtgttgc ctccgttttc caattcttgt tcatcgcttg tatcgaattg 420
gctttgttca tccaagctac tgtcgttttc caaaaatctg ttagatggtt gaagttttcc 480
gtttctttga tccaaggttc cgtcgctttg actactaccg ccttgtacat ggccattatt 540
gtccaatcca tctacgctac tttgaaccca tacgctggta acttgattaa aggtcgtttc 600
ggttacttat tagcttcttt gggtaagatt ttcttctcta tttctgttac ttcttgtatg 660
tgtatcttcg ttggtaagtt ggtctttgct attcaccaaa gaagaacttt gggtattaag 720
caattcgacg gtttgcaaat tttggtcatt atgtctactc aatccatgat catcccaact 780
attatcgtct tgatgtcttt tttgagacgt aacgctggtt ctgtttacac catggctacc 840
ttgttggtcg ctttgtcctt gccattgtcc tccttgtggg ctgaagccaa gactaccaga 900
gactctgctt cttacaccgc ttacagacca tctggttctc caaacaaccg ttctttgttc 960
gccatcttct ctgatagatt ggcttgtggt tctggtagaa acaacagaca cgatgatgat 1020
tctagaggta acggttctgt taacgccaga aaggctgacg tcgaatctac tatcgaaatg 1080
tcctcttgtt acactgattc cccaacctac tccaagttcg aagctggttt ggacgctaga 1140
ggtatcgtct tctacaacga acacggtttg ccagttgtct ccggtgaagt tggtggttct 1200
tcctccaacg gtactaagtt gggttctggt cataagtacg aagtcaacac tactgttgtt 1260
ttgtctgatg ttgactctcc atctccaacc gacgtcaccc gtaagtag 1308

<210> SEQ ID NO 64
<211> LENGTH: 452
<212> TYPE: PRT
<213> ORGANISM: Zygosaccharomyces bailii

<400> SEQUENCE: 64

Met Ser Gly Leu Ala Asn Asn Thr Ser Tyr Asn Pro Leu Glu Ser Phe
1               5                   10                  15

Ile Ile Phe Thr Ser Val Tyr Gly Gly Asp Thr Met Val Lys Phe Glu
            20                  25                  30

Asp Leu Gln Leu Val Phe Thr Lys Arg Ile Thr Glu Gly Ile Leu Phe
        35                  40                  45

Gly Val Lys Val Gly Ala Ala Ser Leu Thr Met Ile Val Met Trp Met
    50                  55                  60

Ile Ser Arg Arg Arg Thr Ser Pro Ile Phe Ile Met Asn Gln Leu Ser

-continued

```
65                  70                  75                  80

Leu Val Phe Thr Ile Leu His Ala Ser Phe Tyr Phe Lys Tyr Leu Leu
                85                  90                  95

Asp Gly Phe Gly Ser Ile Val Tyr Thr Leu Thr Leu Phe Pro Gln Leu
            100                 105                 110

Ile Thr Ser Ser Asp Leu His Val Phe Ala Thr Ala Asn Val Val Glu
        115                 120                 125

Val Leu Leu Val Ser Ser Ile Glu Ala Ser Leu Val Phe Gln Val Asn
    130                 135                 140

Val Met Phe Ala Gly Ser Asn His Arg Lys Phe Ala Trp Leu Leu Val
145                 150                 155                 160

Gly Phe Ser Leu Gly Leu Ala Leu Ala Thr Val Ala Leu Tyr Phe Val
                165                 170                 175

Thr Ala Val Lys Met Ile Ala Ser Ala Tyr Ala Ser Gln Pro Pro Thr
            180                 185                 190

Asn Pro Ile Tyr Phe Asn Val Ser Leu Phe Leu Leu Ala Ala Ser Val
        195                 200                 205

Phe Leu Met Thr Leu Met Leu Thr Val Lys Leu Ile Leu Ala Ile Arg
    210                 215                 220

Ser Arg Arg Phe Leu Gly Leu Lys Gln Phe Asp Ser Phe His Ile Leu
225                 230                 235                 240

Leu Ile Met Ser Cys Gln Thr Leu Ile Ala Pro Ser Val Leu Tyr Ile
                245                 250                 255

Leu Gly Phe Ile Leu Asp His Arg Lys Gly Asn Asp Tyr Leu Ile Thr
            260                 265                 270

Val Ala Gln Leu Leu Val Val Leu Ser Leu Pro Leu Ser Ser Met Trp
        275                 280                 285

Ala Thr Thr Ala Asn Asp Ala Ser Ser Gly Thr Ser Met Ser Ser Lys
    290                 295                 300

Glu Ser Val Tyr Gly Ser Asp Ser Leu Tyr Ser Lys Ser Lys Cys Ser
305                 310                 315                 320

Gln Phe Thr Arg Thr Phe Met Asn Arg Phe Ser Thr Lys Pro Thr Lys
                325                 330                 335

Asn Asp Glu Ile Ser Asp Ser Ala Phe Val Ala Val Asp Ser Leu Glu
            340                 345                 350

Lys Asn Ala Pro Gln Gly Ile Ser Glu His Val Cys Glu Phe Pro Gln
        355                 360                 365

Ser Asp Leu Ser Asp Gln Ala Thr Ser Ile Ser Ser Arg Lys Lys Glu
    370                 375                 380

Ala Val Val Tyr Ala Ser Thr Val Asp Glu Asp Lys Gly Ser Phe Ser
385                 390                 395                 400

Ser Asp Ile Asn Gly Tyr Thr Val Thr Asn Met Pro Leu Ala Ser Ala
                405                 410                 415

Ala Ser Ala Asn Cys Glu Asn Ser Pro Cys His Val Pro Arg Pro Tyr
            420                 425                 430

Glu Glu Asn Glu Gly Val Val Glu Thr Arg Lys Ile Ile Leu Lys Lys
        435                 440                 445

Asn Val Lys Trp
    450
```

<210> SEQ ID NO 65
<211> LENGTH: 1359
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 65

```
atgtctggtt tggctaacaa cacctcttac aacccattgg aatctttcat tattttcact      60
tctgtttacg gtggtgatac catggttaag ttcgaagact tgcaattagt cttcaccaag     120
cgtattactg aaggtatttt gttcggtgtc aaggttggtg ccgcttcttt gactatgatt     180
gttatgtgga tgatttccag aagaagaacc tccccaatct tcatcatgaa ccaattgtct     240
ttggttttca ccatcttgca cgcttctttt tactttaagt acttattgga cggtttcggt     300
tctattgtct acactttgac cttgttccca caattaatta cttcctctga cttgcacgtt     360
ttcgctactg ctaacgttgt tgaagtctta ttggtttctt ccatcgaagc ctctttggtt     420
ttccaagtca acgtcatgtt cgctggttct aaccacagaa agttcgcttg gttgttggtc     480
ggtttctctt tgggtttggc tttggccact gtcgctttgt acttcgttac tgctgtcaag     540
atgatcgctt ccgcttacgc ttctcaacca ccaactaacc caatctactt caacgtttcc     600
ttgttcttgt tggctgcctc cgttttcttg atgactttaa tgttgaccgt caagttgatc     660
ttggctatca gatccagaag attcttgggt ttgaagcaat tcgactcttt ccacattttg     720
ttgattatgt cttgtcaaac tttgatcgct ccatctgttt tgtacatctt gggttttatt     780
ttggatcaca gaaagggtaa cgactacttg attaccgtcg ctcaattgtt ggtcgttttg     840
tctttgccat tgtcctccat gtgggccact actgctaacg atgcttcctc cggtacttct     900
atgtcttcca aggaatccgt ctacggttct gattccttat actctaagtc taagtgttcc     960
caattcacca gaaccttcat gaacagattc tctactaagc caactaagaa cgacgaaatt    1020
tctgattccg ctttcgtcgc tgttgattcc ttggaaaaga acgctccaca aggtatctct    1080
gaacacgttt gtgaattccc acaatctgac ttatctgatc aagctacttc catctcctcc    1140
agaaaaaagg aagctgttgt ttacgcttcc actgttgatg aagataaggg ttctttctcc    1200
tctgacatca acggttacac tgttaccaac atgccattgg cttccgctgc ttctgctaac    1260
tgtgaaaact ccccatgtca cgttccaaga ccatacgaag aaaacgaagg tgtcgtcgaa    1320
accagaaaaa ttattttgaa gaagaacgtc aaatggtag                           1359
```

<210> SEQ ID NO 66
<211> LENGTH: 443
<212> TYPE: PRT
<213> ORGANISM: Zygosaccharomyces rouxii

<400> SEQUENCE: 66

```
Met Ser Glu Ile Asn Asn Ser Thr Tyr Asn Pro Met Asn Ala Tyr Val
1               5                   10                  15

Thr Phe Thr Ser Ile Tyr Gly Asp Asp Thr Met Val Arg Phe Lys Asp
            20                  25                  30

Val Glu Leu Val Val Asn Lys Arg Val Thr Glu Ala Ile Met Phe Gly
        35                  40                  45

Val Lys Val Gly Ala Ala Ser Leu Thr Leu Ile Ile Met Trp Met Ile
    50                  55                  60

Ser Lys Lys Arg Thr Thr Pro Ile Phe Ile Ile Asn Gln Ser Ser Leu
65                  70                  75                  80

Val Phe Thr Ile Ile His Ala Ser Leu Tyr Phe Gly Tyr Leu Leu Ser
                85                  90                  95

Gly Phe Gly Ser Ile Val Tyr Asn Met Thr Ser Phe Pro Gln Leu Ile
```

```
            100                 105                 110

Ser Ser Asn Asp Val Arg Val Tyr Ala Ala Thr Asn Ile Phe Glu Val
        115                 120                 125

Leu Leu Val Ala Ser Ile Glu Ile Ser Leu Val Phe Gln Val Lys Val
    130                 135                 140

Met Phe Ala Asn Asn Asn Gly Arg Arg Trp Thr Trp Cys Leu Met Val
145                 150                 155                 160

Val Ser Ile Gly Met Ala Leu Ala Thr Val Gly Leu Tyr Phe Ala Thr
                165                 170                 175

Ala Val Glu Leu Ile Arg Ala Ala Tyr Ser Asn Asp Thr Val Ser Arg
            180                 185                 190

His Val Phe Tyr Asn Val Ser Leu Ile Leu Leu Ala Ser Ser Val Asn
        195                 200                 205

Leu Met Thr Leu Met Leu Val Val Lys Leu Val Leu Ala Ile Arg Ser
    210                 215                 220

Arg Arg Phe Leu Gly Leu Lys Gln Phe Asp Ser Phe His Ile Leu Leu
225                 230                 235                 240

Ile Met Ser Cys Gln Thr Leu Ile Ala Pro Ser Ile Leu Phe Ile Leu
                245                 250                 255

Gly Trp Thr Leu Asp Pro His Thr Gly Asn Glu Val Leu Ile Thr Val
            260                 265                 270

Gly Gln Leu Leu Ile Val Leu Ser Leu Pro Leu Ser Ser Met Trp Ala
        275                 280                 285

Thr Thr Ala Asn Asn Thr Ser Ser Ser Ser Ser Ser Val Ser Cys Asn
    290                 295                 300

Asp Ser Ser Phe Gly Asn Asp Asn Leu Cys Ser Lys Ser Ser Gln Phe
305                 310                 315                 320

Arg Arg Thr Phe Met Asn Arg Phe Arg Pro Lys Ser Val Asn Gly Asp
                325                 330                 335

Gly Asn Ser Glu Asn Thr Phe Val Thr Ile Asp Asp Leu Glu Lys Ser
            340                 345                 350

Val Phe Gln Glu Leu Ser Thr Pro Val Ser Gly Glu Ser Lys Ile Asp
        355                 360                 365

His Asp His Ala Ser Ser Ile Ser Cys Gln Lys Thr Cys Asn His Val
    370                 375                 380

His Ala Ser Thr Val Asn Ser Asp Lys Gly Ser Trp Ser Ser Asp Gly
385                 390                 395                 400

Ser Cys Gly Ser Ser Pro Leu Arg Lys Thr Ser Thr Val Asn Ser Glu
                405                 410                 415

Asp Leu Pro Pro His Ile Leu Ser Ala Tyr Asp Asp Asp Arg Gly Ile
            420                 425                 430

Val Glu Ser Lys Lys Ile Ile Leu Lys Lys Leu
        435                 440
```

<210> SEQ ID NO 67
<211> LENGTH: 1332
<212> TYPE: DNA
<213> ORGANISM: Zygosaccharomyces rouxii

<400> SEQUENCE: 67

```
atgagtgaga ttaacaattc tacctacaat ccaatgaatg catatgtaac gtttacatca     60

atatatggtg atgatactat ggtacgtttc aaagatgtgg aattggtagt taacaaaagg    120

gttacagaag ccattatgtt cggcgtcaaa gttggtgcag cttcgttgac actcatcatc    180
```

```
atgtggatga tctctaagaa aagaacaaca ccgatattta tcataaatca gtcttcgctt    240

gtatttacca taatacatgc ttcgctttat tttgggtacc ttttgtcagg atttggtagt    300

atagtttaca atatgacatc gttcccgcag ttaataagct ccaatgacgt tcgtgtgtac    360

gcagctacaa atatttttga ggtcctgttg gtagcatcta tcgaaatctc tctggttttt    420

caggtcaaag ttatgtttgc caacaataat ggtcgaagat ggacttggtg tttgatggta    480

gtttccatag ggatggcact agctactgta ggactttatt ttgccactgc cgttgagttg    540

atcagagctg cttacagcaa tgatactgtt agccgccatg ttttttacaa tgtttctctg    600

atcttactag cgtcatctgt caatctaatg acactaatgc tagtggtaaa attagtatta    660

gcgatcagat caagaagatt tttggggtta aaacagtttg acagtttcca catattactt    720

ataatgtctt gccagactct aatagcacct tccattctat tcattttggg ttggacctta    780

gaccctcata ctggtaatga ggttttaatt acagttggtc aattgctaat agtactgtca    840

ttaccgctgt catctatgtg ggctacaacc gctaacaata ccagttcatc tagtagttcg    900

gtgtcctgta atgacagctc ttttggtaat gacaatctct gttccaagag ttcgcaattt    960

agaagaactt ttatgaatag attccgtccc aagtcggtta atggtgacgg taattctgaa   1020

aataccttttg ttacaattga tgatttggaa aaaagcgttt ttcaagaatt atcaacacct   1080

gttagcggag aatcaaagat agatcatgat catgcaagta gtatttcatg tcaaaagaca   1140

tgtaatcatg ttcatgcttc gacagtgaat tcagataagg gatcttggtc ctctgatggt   1200

agttgtggca gttctccgtt aagaaagact tccaccgtta attctgaaga tttacctcca   1260

catatattga gcgcctacga tgacgatcga ggtatagtag aaagtaaaaa aattatccta   1320

aagaaattat ag                                                        1332
```

<210> SEQ ID NO 68
<211> LENGTH: 436
<212> TYPE: PRT
<213> ORGANISM: Kluyveromyces lactis

<400> SEQUENCE: 68

```
Met Ser Glu Glu Ile Pro Ser Leu Asn Pro Leu Phe Tyr Asn Glu Thr
1               5                   10                  15

Tyr Asn Pro Leu Gln Ser Val Leu Thr Tyr Ser Ser Ile Tyr Gly Asp
            20                  25                  30

Gly Thr Glu Ile Thr Phe Gln Gln Leu Gln Asn Leu Val His Glu Asn
        35                  40                  45

Ile Thr Gln Ala Ile Ile Phe Gly Thr Arg Ile Gly Ala Ala Gly Leu
    50                  55                  60

Ala Leu Ile Ile Met Trp Met Val Ser Lys Asn Arg Lys Thr Pro Ile
65                  70                  75                  80

Phe Ile Ile Asn Gln Ser Ser Leu Val Leu Thr Ile Val Gln Ser Ala
                85                  90                  95

Leu Tyr Leu Ser Tyr Leu Leu Ser Asn Phe Gly Gly Val Pro Phe Ala
            100                 105                 110

Leu Thr Leu Phe Pro Gln Met Ile Gly Asp Arg Asp Lys His Leu Tyr
        115                 120                 125

Gly Ala Val Thr Leu Ile Gln Cys Leu Leu Val Ala Cys Ile Glu Val
    130                 135                 140

Ser Leu Val Phe Gln Val Arg Val Ile Phe Lys Ala Asp Arg Tyr Arg
145                 150                 155                 160

Lys Ile Gly Ile Ile Leu Thr Gly Val Ser Ala Ser Phe Gly Ala Ala
```

```
                165                 170                 175

Thr Val Ala Met Trp Met Ile Thr Ala Ile Lys Ser Ile Ile Val Val
            180                 185                 190

Tyr Asp Ser Pro Leu Asn Lys Val Asp Thr Tyr Tyr Tyr Asn Ile Ala
        195                 200                 205

Val Ile Leu Leu Ala Cys Ser Ile Asn Phe Ile Thr Leu Leu Leu Ser
    210                 215                 220

Val Lys Leu Phe Leu Ala Phe Arg Ala Arg Arg His Leu Gly Leu Lys
225                 230                 235                 240

Gln Phe Asp Ser Phe His Ile Leu Leu Ile Met Ser Thr Gln Thr Leu
                245                 250                 255

Ile Gly Pro Ser Val Leu Tyr Ile Leu Ala Tyr Ala Leu Asn Asn Lys
            260                 265                 270

Gly Val Lys Ser Leu Thr Ser Ile Ala Thr Leu Leu Val Val Leu Ser
        275                 280                 285

Leu Pro Leu Thr Ser Ile Trp Ala Ala Ala Ala Asn Asp Ala Pro Ser
    290                 295                 300

Ala Ser Thr Phe Tyr Arg Gln Phe Asn Pro Tyr Ser Ala Gln Asn Arg
305                 310                 315                 320

Asp Asp Ser Ser Ser Tyr Ser Tyr Gly Lys Ala Phe Ser Asp Lys Tyr
                325                 330                 335

Ser Phe Ser Asn Ser Pro Gln Thr Ser Asp Gly Cys Ser Ser Lys Glu
            340                 345                 350

Leu Glu Leu Ser Thr Gln Leu Glu Met Asp Leu Glu Ser Gly Glu Ser
        355                 360                 365

Phe Met Asp Arg Ala Lys Arg Ser Asp Phe Val Ser Ser Pro Gly Ser
    370                 375                 380

Thr Asp Ala Thr Val Ile Lys Gln Leu Lys Ala Ser Asn Ile Tyr Thr
385                 390                 395                 400

Ser Glu Thr Asp Ala Asp Glu Glu Ala Arg Ala Phe Trp Val Asn Ala
                405                 410                 415

Ile His Glu Asn Lys Asp Asp Gly Leu Met Gln Ser Lys Thr Val Phe
            420                 425                 430

Lys Glu Leu Arg
        435
```

<210> SEQ ID NO 69
<211> LENGTH: 1311
<212> TYPE: DNA
<213> ORGANISM: Kluyveromyces lactis

<400> SEQUENCE: 69

```
atgtcagaag agatacccag tttgaaccca ttgttctaca atgagacata taatccattg     60

cagtccgtcc taacatacag ttcaatttac ggagatggga ctgaaataac atttcaacag    120

ctacaaaatc ttgtccatga aaacatcacc caagcaatta tttttggaac aaggatcggc    180

gctgctggat tagcgttgat tataatgtgg atggtctcta agaatagaaa gacgccgata    240

ttcataataa atcagagttc tttggttctt acaattgttc aatctgcttt atatctatca    300

tatttgttga gcaattttgg aggagttccc tttgctctaa ctttgttccc acagatgata    360

ggcgaccgtg acaaacatct ttacggtgcc gtgactctaa ttcaatgtct attggttgcg    420

tgtattgagg tctcgttagt ctttcaggta agagtcattt tcaaagcaga tagatatagg    480

aagataggaa tcattttgac tggcgtctcc gctagttttg gtgctgcaac tgtagccatg    540
```

```
tggatgatta ctgcaataaa atctattatt gtagtgtatg atagtccatt gaacaaagtt    600

gacacatatt attacaacat agcagttatt ttacttgcat gttcaataaa tttcatcact    660

cttcttctat cagtgaaact tttcctggct ttcagagcta ggagacattt aggtttgaaa    720

caatttgact catttcacat tctactcatc atgtctactc agacattaat aggtccatcg    780

gttttgtata ttctcgccta cgcgctgaac aataaaggag ttaagtcgtt gacttctatt    840

gctacattgc ttgtagttct ttccctacct ttgacatcta tctgggctgc tgctgcaaat    900

gatgcaccaa gtgccagtac tttctatcgc caattcaacc cttactctgc acaaaatcgt    960

gatgattcat catcctactc ttatggtaaa gcctttagtg acaaatactc tttcagtaac   1020

tcaccacaaa cttcggatgg ttgtagttca aaggaacttg aactatctac acagttggag   1080

atggatttag agtctggcga atcttttatg gatagagcaa aaaggtccga ttttgtttct   1140

tctccaggat caacagatgc aacagtgatt aaacaattga aagcttccaa catctatacc   1200

tcagaaacag atgctgatga agaggcaagg gcattttggg tgaatgcaat tcatgaaaac   1260

aaagatgacg gtttaatgca atcgaaaacc gtattcaaag aattaagata g            1311
```

```
<210> SEQ ID NO 70
<211> LENGTH: 348
<212> TYPE: PRT
<213> ORGANISM: Schizosaccharomyces pombe

<400> SEQUENCE: 70

Met Arg Gln Pro Trp Trp Lys Asp Phe Thr Ile Pro Asp Ala Ser Ala
1               5                   10                  15

Ile Ile His Gln Asn Ile Thr Ile Val Ser Ile Val Gly Glu Ile Glu
            20                  25                  30

Val Pro Val Ser Thr Ile Asp Ala Tyr Glu Arg Asp Arg Leu Leu Thr
        35                  40                  45

Gly Met Thr Leu Ser Ala Gln Leu Ala Leu Gly Val Leu Thr Ile Leu
    50                  55                  60

Met Val Cys Leu Leu Ser Ser Ser Glu Lys Arg Lys His Pro Val Phe
65                  70                  75                  80

Val Phe Asn Ser Ala Ser Ile Val Ala Met Cys Leu Arg Ala Ile Leu
                85                  90                  95

Asn Ile Val Thr Ile Cys Ser Asn Ser Tyr Ser Ile Leu Val Asn Tyr
            100                 105                 110

Gly Phe Ile Leu Asn Met Val His Met Tyr Val His Val Phe Asn Ile
        115                 120                 125

Leu Ile Leu Leu Leu Ala Pro Val Ile Ile Phe Thr Ala Glu Met Ser
    130                 135                 140

Met Met Ile Gln Val Arg Ile Ile Cys Ala His Asp Arg Lys Thr Gln
145                 150                 155                 160

Arg Ile Met Thr Val Ile Ser Ala Cys Leu Thr Val Leu Val Leu Ala
                165                 170                 175

Phe Trp Ile Thr Asn Met Cys Gln Gln Ile Gln Tyr Leu Leu Trp Leu
            180                 185                 190

Thr Pro Leu Ser Ser Lys Thr Ile Val Gly Tyr Ser Trp Pro Tyr Phe
        195                 200                 205

Ile Ala Lys Ile Leu Phe Ala Phe Ser Ile Ile Phe His Ser Gly Val
    210                 215                 220

Phe Ser Tyr Lys Leu Phe Arg Ala Ile Leu Ile Arg Lys Lys Ile Gly
225                 230                 235                 240
```

```
Gln Phe Pro Phe Gly Pro Met Gln Cys Ile Leu Val Ile Ser Cys Gln
                245                 250                 255

Cys Leu Ile Val Pro Ala Thr Phe Thr Ile Ile Asp Ser Phe Ile His
            260                 265                 270

Thr Tyr Asp Gly Phe Ser Ser Met Thr Gln Cys Leu Leu Ile Ile Ser
        275                 280                 285

Leu Pro Leu Ser Ser Leu Trp Ala Ser Ser Thr Ala Leu Lys Leu Gln
    290                 295                 300

Ser Met Lys Thr Ser Ser Ala Gln Gly Glu Thr Thr Glu Val Ser Ile
305                 310                 315                 320

Arg Val Asp Arg Thr Phe Asp Ile Lys His Thr Pro Ser Asp Asp Tyr
                325                 330                 335

Ser Ile Ser Asp Glu Ser Glu Thr Lys Lys Trp Thr
            340                 345
```

<210> SEQ ID NO 71
<211> LENGTH: 1047
<212> TYPE: DNA
<213> ORGANISM: Schizosaccharomyces pombe

<400> SEQUENCE: 71

```
atgagacaac catggtggaa agactttact attcccgatg catccgcaat tattcaccaa     60

aatattacca ttgtctctat tgtaggagag attgaagtgc cagtttcaac aattgatgca    120

tatgaaagag atagactttt aactggaatg actttgtctg cccaacttgc tttaggagtc    180

cttaccattt tgatggtttg tctattgtca tcatccgaaa aacgaaaaca cccagttttt    240

gtttttaatt cggcaagtat tgttgcaatg tgtcttcggg ccatttgaa tatagtgacc     300

atatgcagca atagctacag tatcctggtt aattacgggt ttatcttaaa catggttcat    360

atgtatgtcc atgtgtttaa tattttaatt ttgttgcttg caccggtcat cattttttact    420

gctgagatga gcatgatgat tcaagttcgt ataatttgtg cacatgatag aaagacacaa    480

aggataatga ctgttattag tgcctgctta actgttttgg ttctcgcatt ttggattact    540

aacatgtgtc aacagattca gtatctgtta tggttaactc cacttagcag caagaccatt    600

gttggatact cttggcccta ctttattgct aaaatacttt ttgcttttag cattattttt    660

cacagtggtg ttttttcata caaactcttt cgtgccatat taatacggaa aaaaattggg    720

caatttccat ttggtccgat gcagtgtatt ttagttatta gctgccaatg tcttattgtt    780

ccagctacct ttactataat agatagtttt atccatacgt atgatggctt tagctctatg    840

actcaatgtc tgctaatcat ttctcttcct ctttcgagtt tatgggcgtc tagtacagct    900

ctgaaattgc aaagcatgaa aacttcatct gcgcaaggag aaaccaccga ggtttcgatt    960

agagttgata gaacgtttga tatcaaacat actcccagtg acgattattc gatttctgat   1020

gaatctgaaa ctaaaaagtg gacgtag                                       1047
```

<210> SEQ ID NO 72
<211> LENGTH: 384
<212> TYPE: PRT
<213> ORGANISM: Vanderwaltozyma polyspora

<400> SEQUENCE: 72

```
Met Ser Ser Gln Ser His Pro Pro Leu Ile Asp Leu Phe Tyr Asp Ser
1               5                   10                  15

Ser Tyr Asp Pro Gly Glu Ser Leu Ile Tyr Tyr Thr Ser Ile Tyr Gly
            20                  25                  30
```

```
Asn Asn Thr Tyr Ile Thr Phe Asp Glu Leu Gln Thr Ile Val Asn Lys
        35                  40                  45

Lys Val Thr Gln Gly Ile Leu Phe Gly Val Arg Cys Gly Ala Ala Phe
    50                  55                  60

Leu Met Leu Val Ala Met Trp Leu Ile Ser Lys Asn Lys Arg Ser Arg
65                  70                  75                  80

Ile Phe Ile Thr Asn Gln Cys Cys Leu Val Phe Met Ile Met His Ser
                85                  90                  95

Gly Leu Tyr Phe Arg Tyr Leu Leu Ser Arg Tyr Gly Ser Val Thr Phe
            100                 105                 110

Ile Leu Thr Gly Phe Gln Gln Leu Leu Thr Arg Asn Asp Ile His Ile
        115                 120                 125

Tyr Gly Ala Thr Asp Phe Ile Gln Val Ala Leu Val Ala Cys Ile Glu
    130                 135                 140

Leu Ser Leu Ile Phe Gln Ile Lys Val Ile Phe Ala Gly Thr Asn Tyr
145                 150                 155                 160

Gly Lys Leu Ala Asn Tyr Phe Ile Thr Leu Gly Ser Leu Leu Gly Leu
                165                 170                 175

Ala Thr Phe Gly Met Tyr Met Leu Thr Ala Ile Asn Gly Thr Ile Lys
            180                 185                 190

Leu Tyr Asn Asn Glu Tyr Asp Pro Asn Gln Arg Lys Tyr Phe Asn Ile
        195                 200                 205

Ser Thr Ile Leu Leu Ala Ser Ser Ile Asn Met Leu Thr Leu Ile Leu
    210                 215                 220

Ile Leu Lys Leu Val Ala Ala Ile Arg Thr Arg Arg Tyr Leu Gly Leu
225                 230                 235                 240

Lys Gln Phe Asp Ser Phe His Ile Leu Leu Ile Met Ser Thr Gln Thr
                245                 250                 255

Leu Ile Ile Pro Ser Ile Leu Phe Ile Leu Ser Tyr Ser Leu Arg Glu
            260                 265                 270

Asp Met His Thr Asp Gln Leu Ile Ile Ile Gly Asn Leu Ile Val Val
        275                 280                 285

Leu Ser Leu Pro Leu Ser Ser Met Trp Ala Ser Ser Leu Asn Asn Ser
    290                 295                 300

Ser Lys Pro Thr Ser Leu Asn Thr Asp Phe Ser Gly Pro Lys Ser Ser
305                 310                 315                 320

Glu Glu Gly Thr Ala Ile Ser Leu Leu Ser Gln Asn Met Glu Pro Ser
                325                 330                 335

Ile Val Thr Lys Tyr Thr Arg Arg Ser Pro Gly Leu Tyr Pro Val Ser
            340                 345                 350

Val Gly Thr Pro Ile Glu Lys Glu Ala Ser Tyr Thr Leu Phe Glu Ala
        355                 360                 365

Thr Asp Ile Asp Phe Glu Ser Ser Ser Asn Asp Ile Thr Arg Thr Ser
    370                 375                 380
```

<210> SEQ ID NO 73
<211> LENGTH: 1155
<212> TYPE: DNA
<213> ORGANISM: Vanderwaltozyma polyspora

<400> SEQUENCE: 73

```
atgagttccc aatcacaccc accgctaatc gatttatttt acgattccag ttatgaccct      60

ggtgaaagtt taatttatta cacatccatc tatggtaata atacatacat aacttttgat     120

gaactccaga cgatagtgaa caagaaggtc acacaaggta tcttatttgg tgtcagatgt     180
```

```
ggtgctgctt tcctgatgtt ggtagcaatg tggttgattt ccaaaaataa aagatctaga    240

attttcatta ccaaccaatg ttgtctggtc ttcatgataa tgcattctgg tctttatttt    300

aggtacctgc tttcaaggta cggttcagtt actttcattc taacagggtt ccaacaactg    360

cttacaagaa atgacattca tatttatgga gctactgatt ttatccaagt agctttggta    420

gcttgcatag aattatctct tattttccaa ataaaagtga tattcgctgg tacaaactat    480

ggtaagttgg ctaattattt catcactcta ggttcattat tgggtttagc cacctttggt    540

atgtacatgc ttactgctat taacggtaca ataaaattat acaataacga atatgaccca    600

aaccaaagga aatactttaa catttctaca atattgcttg catcatcaat taatatgcta    660

acgctgatac ttatattgaa gctggtggca gcaattagaa caagacgtta cttaggtttg    720

aagcaattcg atagttttca catcctatta atcatgtcga ctcaaacatt aataattcct    780

tctatcttat ttattctatc atacagtttg agagaggata tgcatactga tcaattaata    840

atcatcggaa atctgatcgt ggtattgtca ttaccattgt cctcaatgtg ggcttcgtct    900

ctaaacaatt caagtaaacc tacatctttg aatactgatt tctcagggcc aaaatcaagt    960

gaagaaggga cagcaataag tttgctatca caaaacatgg aaccatcaat agtcactaaa   1020

tatacaagaa gatcacctgg gttataccca gtaagcgtgg gtacaccaat tgaaaaagaa   1080

gcatcataca ctctttttga agctactgac attgattttg aaagcagtag taacgatatc   1140

acaaggactt catag                                                     1155
```

```
<210> SEQ ID NO 74
<211> LENGTH: 473
<212> TYPE: PRT
<213> ORGANISM: Vanderwaltozyma polyspora

<400> SEQUENCE: 74

Met Ser Gly Ile Asp Asp Met Gly Asp Lys Pro Asp Ile Leu Gly Leu
1               5                   10                  15

Phe Tyr Asp Ala Asn Tyr Asp Pro Gly Gln Gly Ile Leu Thr Phe Ile
            20                  25                  30

Ser Met Tyr Gly Asn Thr Thr Ile Thr Phe Asp Glu Leu Gln Leu Glu
        35                  40                  45

Val Asn Ser Leu Ile Thr Ser Gly Ile Met Phe Gly Val Arg Cys Gly
    50                  55                  60

Ala Ala Cys Leu Thr Leu Leu Ile Met Trp Met Ile Ser Lys Asn Lys
65                  70                  75                  80

Lys Thr Pro Ile Phe Ile Ile Asn Gln Cys Ser Leu Ile Leu Ile Ile
                85                  90                  95

Met His Ser Gly Leu Tyr Phe Lys Asn Ile Leu Ser Asn Leu Asn Ser
            100                 105                 110

Leu Ser Tyr Ile Leu Thr Gly Phe Thr Gln Asn Ile Thr Lys Asn Asn
        115                 120                 125

Ile His Val Phe Gly Ala Ala Asn Ile Ile Gln Val Leu Leu Val Ala
    130                 135                 140

Thr Ile Glu Leu Ser Leu Val Phe Gln Ile Arg Val Met Phe Lys Gly
145                 150                 155                 160

Asp Ser Phe Arg Lys Ala Gly Tyr Gly Leu Leu Ser Ile Ala Ser Gly
                165                 170                 175

Leu Gly Ile Ala Thr Val Val Met Tyr Phe Tyr Ser Ala Ile Thr Asn
            180                 185                 190
```

```
Met Ile Ala Val Tyr Asn Gln Thr Tyr Asn Ser Thr Ala Lys Leu Phe
        195                 200                 205

Asn Val Ala Asn Ile Leu Leu Ser Thr Ser Ile Asn Phe Met Thr Val
    210                 215                 220

Val Leu Ile Val Lys Leu Phe Leu Ala Val Arg Ser Arg Arg Tyr Leu
225                 230                 235                 240

Gly Leu Lys Gln Phe Asp Ser Phe His Ile Leu Leu Ile Met Ser Cys
                245                 250                 255

Gln Thr Leu Ile Val Pro Ser Ile Leu Phe Ile Leu Ser Tyr Ala Leu
            260                 265                 270

Ser Thr Lys Leu Tyr Thr Asp His Leu Val Val Ile Ala Thr Leu Leu
        275                 280                 285

Val Val Leu Ser Leu Pro Leu Ser Ser Met Trp Ala Ser Ala Ala Asn
    290                 295                 300

Asn Ser Pro Lys Pro Ser Ser Phe Thr Thr Asp Tyr Ser Asn Lys Asn
305                 310                 315                 320

Pro Ser Asp Thr Pro Ser Phe Tyr Ser Gln Ser Ile Ser Ser Ser Met
                325                 330                 335

Lys Ser Lys Phe Pro Ser Lys Phe Ile Pro Phe Asn Phe Lys Ser Lys
            340                 345                 350

Asp Asn Ser Ser Asp Thr Arg Ser Glu Asn Thr Tyr Ile Gly Asn Tyr
        355                 360                 365

Asp Met Glu Lys Asn Gly Ser Pro Asn His Ser Tyr Ser Ser Lys Asp
    370                 375                 380

Gln Ser Glu Val Tyr Thr Ile Gly Val Ser Ser Met His Thr Asp Ile
385                 390                 395                 400

Lys Ser Gln Lys Asn Ile Ser Gly Gln His Leu Tyr Thr Pro Ser Thr
                405                 410                 415

Glu Ile Asp Glu Glu Ala Arg Asp Phe Trp Ala Gly Arg Ala Val Asn
            420                 425                 430

Asn Ser Val Pro Asn Asp Tyr Gln Pro Ser Glu Leu Pro Ala Ser Ile
        435                 440                 445

Leu Glu Glu Leu Asn Ser Leu Asp Glu Asn Asn Glu Gly Phe Leu Glu
    450                 455                 460

Thr Lys Arg Ile Thr Phe Arg Lys Gln
465                 470
```

<210> SEQ ID NO 75
<211> LENGTH: 1422
<212> TYPE: DNA
<213> ORGANISM: Vanderwaltozyma polyspora

<400> SEQUENCE: 75

```
atgtcaggaa ttgatgatat gggtgataaa ccagatattt taggtttatt ttatgatgct      60

aactatgatc caggtcaagg tatactcaca tttatttcaa tgtacgggaa tactactata     120

acttttgatg agttacagtt agaggtcaat agtttaatta caagtggtat tatgttcggc     180

gtcagatgtg gtgctgcttg tttgacattg ttaataatgt ggatgatttc taagaataag     240

aagactccaa tttttattat taatcaatgc tcgctaatcc ttattattat gcattcaggt     300

ttatatttta agaatattct atcaaatttg aattctttat catatatctt aactgggttt     360

actcaaaata tcactaaaaa taatatacat gtctttggtg ccgctaatat tattcaagtt     420

ttattagtag caaccattga actgtcgtta gtgtttcaaa ttcgagtcat gtttaaaggt     480

gacagtttta gaaaagctgg ttacggtttg ttgtcaattg cgtctggttt gggtatagct     540
```

```
actgtcgtca tgtattttta ctctgccatt acaaatatga ttgctgttta taatcaaact    600

tacaactcca ctgctaaatt atttaacgtt gcaaacattc ttctgtctac atcgataaat    660

tttatgacgg tagtattaat tgttaaatta tttttggctg ttagatcaag aagatatttg    720

ggtttaaagc agttcgatag tttccatatt ttattgatta tgtcatgtca aacattgatt    780

gtaccatcaa ttctttttat cttatcatac gctttaagta ctaagctgta cactgatcat    840

ttagttgtca ttgcaacttt attagtcgtt ctatctttac cattatcttc gatgtgggca    900

agcgctgcaa ataattctcc taaaccaagc tcgtttacaa ccgattattc aaacaagaat    960

cctagtgaca caccaagctt ctacagtcaa agtattagtt cctcgatgaa aagcaaattc   1020

ccaagcaaat tcataccctt caatttcaag tctaaagaca attcttctga cactagatca   1080

gaaaatacat atattggcaa ttatgacatg gaaaagaatg gatcaccaaa tcactcttat   1140

tcttccaaag atcaaagtga agtttacact ataggtgtaa gctctatgca cacagatata   1200

aagtcacaaa agaatatcag tggacagcat ttatataccc caagtacaga gattgatgaa   1260

gaagctagag acttctgggc gggcagagct gttaataatt cagttccaaa tgactatcaa   1320

ccatctgagt taccagcatc gattcttgaa gaattgaatt cactggatga aaataatgaa   1380

ggtttcttgg agacaaaaag aataacattt agaaaacaat ag                      1422
```

<210> SEQ ID NO 76
<211> LENGTH: 321
<212> TYPE: PRT
<213> ORGANISM: Scheffersomyces stipitis

<400> SEQUENCE: 76

```
Met Asp Thr Ser Ile Asn Thr Leu Asn Pro Ala Asn Ile Ile Val Asn
1               5                   10                  15

Tyr Thr Leu Pro Asn Asp Pro Arg Val Ile Ser Val Pro Phe Gly Ala
            20                  25                  30

Phe Asp Glu Tyr Val Asn Gln Ser Met Gln Lys Ala Ile Ile His Gly
        35                  40                  45

Val Ser Ile Gly Ser Cys Thr Ile Met Leu Leu Ile Ile Leu Ile Phe
    50                  55                  60

Asn Val Lys Arg Lys Lys Ser Pro Ala Phe Tyr Leu Asn Ser Val Thr
65                  70                  75                  80

Leu Thr Ala Met Ile Ile Arg Ser Ala Leu Asn Leu Ala Tyr Leu Leu
                85                  90                  95

Gly Pro Leu Ala Gly Leu Ser Phe Thr Phe Ser Gly Leu Val Thr Pro
            100                 105                 110

Glu Thr Asn Phe Ser Val Ser Glu Ala Thr Asn Ala Phe Gln Val Ile
        115                 120                 125

Val Val Ala Leu Ile Glu Ala Ser Met Thr Phe Gln Val Phe Val Val
    130                 135                 140

Phe Gln Ser Pro Glu Val Lys Lys Leu Gly Ile Ala Leu Thr Ser Ile
145                 150                 155                 160

Ser Ala Phe Thr Gly Ala Ala Ala Val Gly Phe Thr Ile Asn Ser Thr
                165                 170                 175

Ile Gln Gln Ser Arg Ile Tyr His Ser Val Val Asn Gly Thr Pro Thr
            180                 185                 190

Pro Thr Val Ala Thr Trp Ser Trp Val Arg Asp Val Pro Thr Ile Leu
        195                 200                 205

Phe Ser Thr Ser Val Asn Ile Met Ser Phe Ile Leu Ile Leu Lys Leu
```

-continued

```
    210                 215                 220

Gly Phe Ala Ile Lys Thr Arg Arg Tyr Leu Gly Leu Arg Gln Phe Gly
225                 230                 235                 240

Ser Leu His Ile Leu Leu Met Met Ala Thr Gln Thr Leu Leu Ala Pro
                245                 250                 255

Ser Ile Leu Ile Leu Val His Tyr Gly Tyr Gly Thr Ser Leu Asn Ser
            260                 265                 270

Gln Leu Ile Leu Ile Ser Tyr Leu Leu Val Val Leu Ser Leu Pro Val
        275                 280                 285

Ser Ser Ile Trp Ala Ala Thr Ala Asn Asn Ser Pro Gln Leu Pro Ser
    290                 295                 300

Ser Ala Thr Leu Ser Phe Met Asn Lys Thr Thr Ser His Phe Ser Glu
305                 310                 315                 320

Ser


<210> SEQ ID NO 77
<211> LENGTH: 966
<212> TYPE: DNA
<213> ORGANISM: Scheffersomyces stipitis

<400> SEQUENCE: 77

atggatacta gtatcaatac tctcaaccct gcgaatatca ttgtcaacta caccttgcca      60

aatgatccta gagtaattag tgtcccattt ggagcttttg acgaatatgt taaccaatct     120

atgcaaaagg ccattatcca tggagtttcc attggttcat gcaccataat gcttttaatt     180

attttgatct tcaatgtcaa acgcaagaag tcgccagctt tctatcttaa ttcggttacg     240

ttgactgcaa tgattattcg gtctgctctt aatttggcat atttgctagg tcctttggct     300

ggattaagtt ttacgttctc cggcttggta actccagaaa ccaatttctc tgtctctgaa     360

gccaccaatg ctttccaggt tattgttgtt gctcttatcg aggcgtccat gacatttcag     420

gtgttcgtcg tcttccaatc accagaagtg aagaagttgg gtatagctct tacctccata     480

tctgcattca cgggtgctgc tgctgtagga tttactatca atagtacaat ccaacaatcg     540

agaatttatc attcagttgt caatggaact cctacgccaa cggtcgctac ctggtcttgg     600

gttagagatg tgcctacgat actttttcct acttcggtta acataatgtc tttcatcttg     660

attctcaagt tagggtttgc cataaagaca agaagatacc ttggccttcg gcaatttggc     720

agtttgcaca tcttattgat gatggctact caaacattat tggccccatc tattctcatt     780

cttgtacatt acggatatgg cacatctctg aatagccagc tcattcttat aagttacttg     840

cttgttgttt tgtctttacc agtatcctct atctgggcag caacagccaa caattctcct     900

caacttccat cttccgcaac tctttcattc atgaacaaaa cgacctctca cttttctgaa     960

agctag                                                                966


<210> SEQ ID NO 78
<211> LENGTH: 346
<212> TYPE: PRT
<213> ORGANISM: Schizosaccharomyces japonicus

<400> SEQUENCE: 78

Met Tyr Ser Trp Asp Glu Phe Arg Ser Pro Lys Gln Ala Glu Val Leu
1               5                   10                  15

Asn Gln Thr Val Thr Leu Glu Thr Ile Val Ser Thr Ile Gln Leu Pro
            20                  25                  30

Ile Ser Glu Ile Asp Ser Met Glu Arg Asn Arg Leu Leu Thr Gly Met
```

```
        35                  40                  45

Thr Val Ala Val Gln Val Gly Leu Gly Ser Phe Ile Leu Val Leu Met
    50                  55                  60

Cys Ile Phe Ser Ser Ser Glu Lys Arg Lys Lys Pro Val Phe Ile Phe
65                  70                  75                  80

Asn Phe Ala Gly Asn Leu Val Met Thr Leu Arg Ala Ile Phe Glu Val
                85                  90                  95

Ile Val Leu Ala Ser Asn Asn Tyr Ser Ile Ala Val Gln Tyr Gly Phe
            100                 105                 110

Ala Phe Ala Ala Val Arg Gln Tyr Val His Ala Phe Asn Ile Ile Ile
        115                 120                 125

Leu Leu Leu Gly Pro Phe Ile Leu Phe Ile Ala Glu Met Ser Leu Met
    130                 135                 140

Leu Gln Val Arg Ile Ile Cys Ser Gln His Arg Pro Thr Met Ile Thr
145                 150                 155                 160

Thr Thr Val Ile Ser Cys Ile Phe Thr Val Val Thr Leu Ala Phe Trp
                165                 170                 175

Ile Thr Asp Met Ser Gln Glu Ile Ala Tyr Gln Leu Phe Leu Lys Asn
            180                 185                 190

Tyr Asn Met Lys Gln Ile Val Gly Tyr Ser Trp Leu Tyr Phe Ile Ala
        195                 200                 205

Lys Ile Thr Phe Ala Ala Ser Ile Ile Phe His Ser Ser Val Phe Ser
    210                 215                 220

Phe Lys Leu Met Arg Ala Ile Tyr Ile Arg Arg Lys Ile Gly Gln Phe
225                 230                 235                 240

Pro Phe Gly Pro Met Gln Cys Ile Phe Ile Val Ser Cys Gln Cys Leu
                245                 250                 255

Ile Val Pro Ala Ile Phe Thr Leu Ile Asp Ser Phe Thr His Thr Tyr
            260                 265                 270

Asp Gly Phe Ser Ser Met Thr Gln Cys Leu Leu Ile Ile Ser Leu Pro
        275                 280                 285

Leu Ser Ser Leu Trp Ala Thr His Thr Ala Gln Lys Leu Gln Thr Met
    290                 295                 300

Lys Asp Asn Thr Asn Pro Pro Ser Gly Thr Gln Leu Thr Ile Arg Val
305                 310                 315                 320

Asp Arg Thr Phe Asp Met Lys Phe Val Ser Asp Ser Ser Asp Gly Ser
                325                 330                 335

Phe Thr Glu Lys Thr Glu Glu Thr Leu Pro
            340                 345
```

<210> SEQ ID NO 79
<211> LENGTH: 1038
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 79

```
atgtactcct gggacgaatt cagatcccca aagcaagctg aagttttgaa ccaaaccgtt      60

accttggaaa ctattgtttc caccattcaa ttgccaatct ctgaaattga ctccatggaa     120

agaaacagat tgttgaccgg tatgactgtc gctgttcaag ttggtttagg ttccttcatt     180

ttagttttga tgtgtatttt ctcttcctct gaaaagagaa agaagccagt cttcatcttc     240

aacttcgctg gtaacttggt tatgactttg agagctattt tcgaagttat cgttttggct     300
```

```
tctaacaact actctatcgc tgttcaatac ggtttcgctt ttgctgccgt cagacaatac    360

gttcacgcct tcaacattat catcttgttg ttgggtccat tcatcttgtt catcgctgaa    420

atgtctttga tgttgcaagt tagaatcatt tgttcccaac acagaccaac tatgattacc    480

accactgtta tctcttgtat tttcactgtt gttaccttgg ccttctggat caccgacatg    540

tctcaagaaa ttgcttacca attgttcttg aaaaactaca acatgaagca aattgttggt    600

tactcctggt tgtactttat cgctaagatc accttcgctg cttccattat cttccattcc    660

tccgtcttct ccttcaaatt gatgcgtgct atttacattc gtagaaagat cggtcaattc    720

ccattcggtc caatgcaatg tatcttcatt gtttcctgtc aatgtttgat cgttccagct    780

attttcactt tgatcgattc tttcacccac acttacgatg gtttctcctc catgactcaa    840

tgtttgttga tcatctcctt accattgtct tccttgtggg ccacccacac cgctcaaaag    900

ttgcaaacca tgaaggataa cactaaccca ccatctggta cccaattaac catcagagtt    960

gatcgtactt tcgacatgaa gttcgtttcc gactcctctg acggttcttt cactgaaaag   1020

accgaagaaa ctttgcca                                                 1038
```

<210> SEQ ID NO 80
<211> LENGTH: 477
<212> TYPE: PRT
<213> ORGANISM: Saccharomyces castellii

<400> SEQUENCE: 80

```
Met Ser Asp Ala Pro Pro Pro Leu Ser Glu Leu Phe Tyr Asn Ser Ser
1               5                   10                  15

Tyr Asn Pro Gly Leu Ser Ile Ile Ser Tyr Thr Ser Ile Tyr Gly Asn
            20                  25                  30

Gly Thr Glu Val Thr Phe Asn Glu Leu Gln Ser Ile Val Asn Lys Lys
        35                  40                  45

Ile Thr Glu Ala Ile Met Phe Gly Val Arg Cys Gly Ala Ala Ile Leu
    50                  55                  60

Thr Ile Ile Val Met Trp Met Ile Ser Lys Lys Lys Lys Thr Pro Ile
65                  70                  75                  80

Phe Ile Ile Asn Gln Val Ser Leu Phe Leu Ile Leu Leu His Ser Ala
                85                  90                  95

Phe Asn Phe Arg Tyr Leu Leu Ser Asn Tyr Ser Ser Val Thr Phe Ala
            100                 105                 110

Leu Thr Gly Phe Pro Gln Phe Ile His Arg Asn Asp Val His Val Tyr
        115                 120                 125

Ala Ala Ala Ser Ile Phe Gln Val Leu Leu Val Ala Ser Ile Glu Ile
    130                 135                 140

Ser Leu Met Phe Gln Ile Arg Val Ile Phe Lys Gly Asp Asn Phe Lys
145                 150                 155                 160

Arg Ile Gly Thr Ile Leu Thr Ala Leu Ser Ser Ser Leu Gly Leu Ala
                165                 170                 175

Thr Val Ala Met Tyr Phe Val Thr Ala Ile Lys Gly Ile Ile Ala Thr
            180                 185                 190

Tyr Lys Asp Val Asn Asp Thr Gln Gln Lys Tyr Phe Asn Val Ala Thr
        195                 200                 205

Ile Leu Leu Ala Ser Ser Ile Asn Phe Met Thr Leu Ile Leu Val Ile
    210                 215                 220

Lys Leu Ile Leu Ala Ile Arg Ser Arg Arg Phe Leu Gly Leu Lys Gln
225                 230                 235                 240
```

```
Phe Asp Ser Phe His Ile Leu Leu Ile Met Ser Phe Gln Ser Leu Leu
                245                 250                 255

Ala Pro Ser Ile Leu Phe Ile Leu Ala Tyr Ser Leu Asp Pro Asn Gln
            260                 265                 270

Gly Thr Asp Val Leu Val Thr Val Ala Thr Leu Leu Val Val Leu Ser
        275                 280                 285

Leu Pro Leu Ser Ser Met Trp Ala Thr Ala Ala Asn Asn Ala Ser Arg
    290                 295                 300

Pro Ser Ser Val Gly Ser Asp Trp Thr Pro Ser Asn Ser Asp Tyr Tyr
305                 310                 315                 320

Ser Asn Gly Pro Ser Ser Val Lys Thr Glu Ser Val Lys Ser Asp Glu
                325                 330                 335

Lys Val Ser Leu Arg Ser Arg Ile Tyr Asn Leu Tyr Pro Lys Ser Lys
            340                 345                 350

Ser Glu Phe Glu Gln Ser Ser Glu His Thr Tyr Val Asp Lys Val Asp
        355                 360                 365

Leu Glu Asn Asn Phe Tyr Glu Leu Ser Thr Pro Ile Thr Glu Arg Ser
    370                 375                 380

Pro Ser Ser Ile Ile Lys Lys Gly Lys Gln Gly Ile Ser Thr Arg Glu
385                 390                 395                 400

Thr Val Lys Lys Leu Asp Ser Leu Asp Asp Ile Tyr Thr Pro Asn Thr
                405                 410                 415

Ala Ala Asp Glu Glu Ala Arg Lys Phe Trp Ser Glu Asp Val Ser Asn
            420                 425                 430

Glu Leu Asp Ser Leu Gln Lys Ile Glu Thr Glu Thr Ser Asp Glu Leu
        435                 440                 445

Ser Pro Glu Met Leu Gln Leu Met Ile Gly Gln Glu Glu Glu Asp Asp
    450                 455                 460

Asn Leu Leu Ala Thr Lys Lys Ile Thr Val Lys Lys Gln
465                 470                 475
```

```
<210> SEQ ID NO 81
<211> LENGTH: 1431
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 81

atgtctgacg ctccaccacc attgtccgaa ttgttctaca actcctccta caacccaggt      60

ttgtctatca tttcttacac ttccatttac ggtaacggta ctgaagttac ctttaacgaa     120

ttacaatcta tcgtcaacaa gaagattact gaagctatca tgttcggtgt cagatgtggt     180

gccgctattt tgactatcat tgtcatgtgg atgatttcta agaagaaaaa gaccccaatt     240

ttcatcatca accaagtttc tttattcttg attttgttgc actccgcttt caacttcaga     300

tacttgttgt ctaactactc ttccgtcact ttcgccttga ccggtttccc acaattcatc     360

cacagaaacg acgtccacgt ctacgctgct gcttctatct tccaagtctt gttggtcgct     420

tctattgaaa tttccttaat gttccaaatc agagtcattt tcaagggtga taacttcaag     480

agaattggta ctatcttgac cgctttgtcc tcttctttgg gtttagctac tgttgctatg     540

tactttgtca ccgctattaa gggtattatt gctacctaca aggatgttaa cgatactcaa     600

caaaagtact tcaacgttgc tactatcttg ttggcttcct ctatcaactt tatgaccttg     660
```

```
atcttggtta tcaagttgat cttggctatc agatccagaa gattcttggg tttgaaacaa    720

ttcgactctt tccatatctt gttgatcatg tcttttcaat ctttgttggc cccatccatt    780

ttgttcattt tggcttactc tttggaccca aaccaaggta ccgacgtctt ggttactgtc    840

gctactttgt tggtcgtctt atctttgcca ttgtcctcca tgtgggctac tgctgctaac    900

aacgcctcca gaccatcctc tgttggttcc gactggactc catctaactc cgactactac    960

tctaacggtc catcttctgt caagaccgaa tctgtcaaat ctgatgaaaa ggtctccttg   1020

agatccagaa tttacaactt gtacccaaag tctaagtctg aattcgaaca atcctccgaa   1080

cacacttacg ttgacaaggt cgacttggaa aacaacttct acgaattgtc caccccaatc   1140

accgaaagat ctccatcttc tatcattaag aagggtaagc aaggtatttc tactagagaa   1200

accgtcaaaa agttggactc cttggatgac atttacactc caaacactgc tgctgatgaa   1260

gaagccagaa agttctggtc tgaagatgtt tctaacgaat tggattcctt acaaaaaatc   1320

gaaactgaaa cttccgatga attatcccca gaaatgttac aattgatgat tggtcaagaa   1380

gaagaagacg ataacttatt ggctaccaag aagatcaccg tcaagaagca a            1431
```

<210> SEQ ID NO 82
<211> LENGTH: 348
<212> TYPE: PRT
<213> ORGANISM: Schizosaccharomyces octosporus

<400> SEQUENCE: 82

```
Met Arg Glu Pro Trp Trp Lys Asn Tyr Tyr Thr Met Asn Gly Thr Gln
1               5                   10                  15

Val Gln Asn Gln Ser Ile Pro Ile Leu Ser Thr Gln Gly Tyr Ile Gln
            20                  25                  30

Val Pro Leu Ser Thr Ile Asp Lys Ala Glu Arg Asn Arg Ile Leu Thr
        35                  40                  45

Gly Met Thr Val Ser Ala Gln Leu Ala Leu Gly Val Leu Ile Met Val
    50                  55                  60

Met Ser Ile Leu Leu Ser Ser Pro Glu Lys Arg Lys Thr Pro Val Phe
65                  70                  75                  80

Ile Val Asn Ser Ala Ser Ile Ile Ser Met Cys Ile Arg Ala Ile Leu
                85                  90                  95

Met Ile Val Asn Leu Cys Ser Glu Ser Tyr Ser Leu Ala Val Met Tyr
            100                 105                 110

Gly Phe Val Phe Glu Leu Val Gly Gln Tyr Val His Val Phe Asp Ile
        115                 120                 125

Leu Val Met Ile Ile Gly Thr Ile Ile Ile Ile Thr Ala Glu Val Ser
    130                 135                 140

Met Leu Leu Gln Val Arg Ile Ile Cys Ala His Asp Arg Lys Thr Gln
145                 150                 155                 160

Arg Ile Val Thr Cys Ile Ser Ser Gly Leu Ser Leu Ile Val Val Ala
                165                 170                 175

Phe Trp Phe Thr Asp Met Cys Gln Glu Ile Lys Tyr Leu Leu Trp Leu
            180                 185                 190

Thr Pro Tyr Asn Asn His Gln Ile Ser Gly Tyr Tyr Trp Val Tyr Phe
        195                 200                 205

Val Gly Lys Ile Leu Phe Ala Val Ser Ile Met Phe His Ser Ala Val
    210                 215                 220

Phe Ser Tyr Lys Leu Phe His Ala Ile Gln Ile Arg Lys Lys Ile Gly
225                 230                 235                 240
```

```
Gln Phe Pro Phe Gly Pro Met Gln Cys Ile Leu Ile Ile Ser Cys Gln
                245                 250                 255

Cys Leu Phe Val Pro Ala Ile Phe Thr Ile Ile Asp Ser Phe Ile His
            260                 265                 270

Thr Tyr Asp Gly Phe Ser Ser Met Thr Gln Cys Leu Leu Ile Val Ser
        275                 280                 285

Leu Pro Leu Ser Ser Leu Trp Ala Ser Ser Thr Ala Leu Lys Leu Gln
    290                 295                 300

Ser Leu Lys Ser Thr Thr Ser Pro Gly Asp Thr Thr Gln Val Ser Ile
305                 310                 315                 320

Arg Val Asp Arg Thr Tyr Asp Ile Lys Arg Ile Pro Thr Glu Glu Leu
                325                 330                 335

Ser Ser Val Asp Glu Thr Glu Ile Lys Lys Trp Pro
            340                 345
```

<210> SEQ ID NO 83
<211> LENGTH: 1044
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 83

```
atgcgtgaac catggtggaa gaactactac accatgaacg gtacccaagt ccaaaaccaa     60

tccatcccaa ttttgtccac ccaaggttac attcaagttc cattgtccac catcgataag    120

gctgaaagaa acagaatttt gactggtatg accgtttctg ctcaattggc cttgggtgtc    180

ttgatcatgg tcatgtctat tttgttgtcc tccccagaaa agagaaagac cccagttttc    240

atcgtcaact ctgcctctat catttccatg tgtattagag ctatcttgat gattgtcaac    300

ttgtgttctg aatcctactc tttggctgtt atgtacggtt tcgtcttcga attggttggt    360

caatacgttc acgtttttga cattttggtt atgattattg gtaccatcat cattattacc    420

gctgaagttt ccatgttgtt gcaagtcaga attatttgtg ctcacgacag aaagactcaa    480

agaattgtta cctgtatctc ttctggttta tccttgatcg tcgttgcctt ctggttcact    540

gatatgtgtc aagaaattaa gtacttgttg tggttgaccc catacaacaa ccaccaaatc    600

tctggttact actgggttta cttcgtcggt aagatcttgt tcgccgtttc cattatgttc    660

cactctgccg tcttctccta caagttgttc cacgctatcc aaattagaaa gaagattggt    720

caattcccat tcggtccaat gcaatgtatt ttaattattt cctgtcaatg tttgttcgtt    780

ccagctattt tcactatcat cgactctttc atccacactt acgacggttt ttcctccatg    840

acccaatgtt tgttgatcgt ctctttgcca ttgtcctcct tgtgggcctc ttccactgct    900

ttaaagttgc aatctttgaa gtctaccacc tctccaggtg acactactca agtttccatt    960

agagtcgaca gaacctacga catcaagaga atcccaactg aagaattgtc ttctgttgac   1020

gaaaccgaaa tcaagaagtg gcca                                          1044
```

<210> SEQ ID NO 84
<211> LENGTH: 430
<212> TYPE: PRT
<213> ORGANISM: Aspergillus nidulans

<400> SEQUENCE: 84

```
Met Ala Thr His Asn Gln Ile Ser Asp Gln Cys Gln Trp Ser Tyr Pro
1               5                   10                  15
```

-continued

```
Glu Val Phe Thr Thr Gln Ala Val Glu Glu Pro Thr Ala Glu Pro Ala
            20                  25                  30

Ser Tyr His Leu His Ser Thr Leu Thr Ile Met Ala Ser Asn Phe Asp
        35                  40                  45

Pro Trp Asn Gln Thr Ile Thr Phe Arg Leu Glu Asp Gly Thr Pro Phe
    50                  55                  60

Asp Ile Ser Val Asp Tyr Leu Asp Gly Ile Leu Gln Tyr Ser Ile Arg
65                  70                  75                  80

Ala Cys Val Asn Tyr Ala Ala Gln Leu Gly Ala Ser Val Ile Leu Phe
                85                  90                  95

Val Ile Leu Val Leu Leu Thr Arg Ala Glu Lys Arg Ala Ser Cys Leu
            100                 105                 110

Phe Trp Leu Asn Ser Leu Ala Leu Leu Leu Asn Phe Ala Arg Leu Leu
        115                 120                 125

Cys Asp Val Leu Phe Phe Thr Gly Asn Phe Val Arg Ile Tyr Thr Leu
    130                 135                 140

Ile Ser Ala Asp Glu Ser Arg Val Thr Ala Ser Asp Leu Ala Thr Ser
145                 150                 155                 160

Ile Val Gly Ala Ile Met Thr Ala Leu Leu Leu Thr Thr Ile Glu Ile
                165                 170                 175

Ser Leu Val Leu Gln Val Gln Val Val Cys Ser Asn Leu Arg Arg Ile
            180                 185                 190

Tyr Arg Arg Ala Leu Leu Cys Val Ser Ala Val Val Ala Thr Ala Thr
        195                 200                 205

Ile Ala Ile Arg Tyr Ser Leu Leu Ala Val Asn Ile Arg Ala Ile Leu
    210                 215                 220

Glu Phe Ser Asp Pro Thr Thr Tyr Asn Trp Leu Glu Ser Leu Ala Thr
225                 230                 235                 240

Val Ala Leu Thr Ile Ser Ile Cys Tyr Phe Cys Val Ile Phe Val Thr
                245                 250                 255

Lys Leu Gly Phe Ala Ile Arg Leu Arg Arg Lys Leu Gly Leu Ser Glu
            260                 265                 270

Leu Gly Pro Met Lys Val Val Phe Ile Met Gly Cys Gln Thr Leu Val
        275                 280                 285

Ile Pro Gly Lys Arg Thr Leu Ser Ser Leu Ile Pro Pro Val Ile Val
    290                 295                 300

Ser Ile Thr His Tyr Val Ser Asp Val Pro Glu Leu Gln Thr Asn Val
305                 310                 315                 320

Leu Thr Ile Val Ala Leu Ser Leu Pro Leu Ser Ser Ile Trp Ala Gly
                325                 330                 335

Thr Thr Ile Asp Lys Pro Val Thr His Ser Asn Val Arg Asn Leu Trp
            340                 345                 350

Gln Ile Leu Ser Phe Ser Gly Tyr Arg Pro Lys Gln Ser Thr Tyr Ile
        355                 360                 365

Ala Thr Thr Thr Thr Ala Thr Thr Asn Ala Lys Gln Cys Thr His Cys
    370                 375                 380

Tyr Ser Glu Ser Arg Leu Leu Thr Glu Lys Glu Ser Gly Arg Asn Asn
385                 390                 395                 400

Asp Thr Ser Ser Lys Ser Ser Ser Gln Tyr Gly Ile Ala Val Glu His
                405                 410                 415

Asp Ile Ser Val Arg Ser Ala Arg Arg Glu Ser Phe Asp Val
            420                 425                 430
```

<210> SEQ ID NO 85
<211> LENGTH: 1293
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 85

```
atggctaccc acaaccaaat ctctgatcaa tgtcaatggt cttacccaga agtcttcacc     60

actcaagctg tcgaagaacc aaccgccgaa ccagcttctt accacttgca ctctaccttg    120

actattatgg cttctaactt cgacccatgg aaccaaacca ttaccttcag attggaagac    180

ggtactccat tcgacatttc tgtcgactac ttggacggta tcttgcaata ctctatcaga    240

gcttgtgtca actacgctgc tcaattgggt gcttctgtca ttttgtttgt tatcttggtc    300

ttgttgacta gagccgaaaa aagagcttct tgtttgttct ggttaaactc cttagctttg    360

ttgttgaact tcgccagatt gttgtgtgac gtcttgttct tcaccggtaa cttcgtcaga    420

atttacactt tgatctccgc tgacgaatct agagttactg cttccgactt ggctacttcc    480

atcgtcggtg ctatcatgac cgctttgttg ttgaccacta ttgaaatttc tttggttttg    540

caagtccaag tcgtttgttc taacttgaga agaatctaca gaagagcctt gttgtgtgtt    600

tccgccgtcg ttgccactgc taccattgct attagatact ccttgttggc tgtcaacatt    660

agagctattt tggaattctc cgacccaact acttacaact ggttggaatc tttagctacc    720

gtcgccttga ccatctccat ctgttacttc tgtgtcatct tcgtcaccaa gttaggtttc    780

gctattagat tgagaagaaa gttgggttta tctgaattgg gtccaatgaa ggtcgtcttc    840

atcatgggtt gtcaaacctt ggtcatccca ggtaaaagaa ccttgtcttc tttgattcca    900

ccagtcattg tttctattac tcactacgtc tccgacgtcc cagaattgca aactaacgtt    960

ttgactatcg tcgccttgtc cttgccattg tcctctattt gggctggtac caccattgac   1020

aagccagtca ctcactctaa cgttagaaac ttgtggcaaa tcttgtcctt ctctggttac   1080

agaccaaagc aatctaccta cattgctacc actactaccg ctactaccaa cgctaagcaa   1140

tgtacccact gttactctga atctagattg ttgactgaaa aggaatctgg tcgtaacaac   1200

gacacttctt ctaagtcttc ctcccaatac ggtatcgctg tcgaacacga tatttccgtt   1260

agatctgctc gtcgtgaatc ttttgacgtc tag                                1293
```

<210> SEQ ID NO 86
<211> LENGTH: 369
<212> TYPE: PRT
<213> ORGANISM: Aspergillus oryzae

<400> SEQUENCE: 86

```
Met Asp Ser Lys Phe Asp Pro Tyr Ser Gln Asn Leu Thr Phe His Ala
1               5                   10                  15

Ala Asp Gly Thr Pro Phe Gln Val Pro Val Met Thr Leu Asn Asp Phe
            20                  25                  30

Tyr Gln Tyr Cys Ile Gln Ile Cys Ile Asn Tyr Gly Ala Gln Phe Gly
        35                  40                  45

Ala Ser Val Ile Ile Phe Ile Ile Leu Leu Leu Leu Thr Arg Pro Asp
    50                  55                  60

Lys Arg Ala Ser Ser Val Phe Phe Leu Asn Gly Gly Ala Leu Leu Leu
65                  70                  75                  80

Asn Met Gly Arg Leu Leu Cys His Met Ile Tyr Phe Thr Thr Asp Phe
                85                  90                  95
```

```
Val Lys Ala Tyr Gln Tyr Phe Ser Ser Asp Tyr Ser Arg Ala Pro Thr
            100                 105                 110

Ser Ala Tyr Ala Asn Ser Ile Leu Gly Val Val Leu Thr Thr Leu Leu
        115                 120                 125

Leu Val Cys Ile Glu Thr Ser Leu Val Leu Gln Val Gln Val Val Cys
    130                 135                 140

Ala Asn Leu Arg Arg Arg Tyr Arg Thr Val Leu Leu Cys Val Ser Ile
145                 150                 155                 160

Leu Val Ala Leu Ile Pro Val Gly Leu Arg Leu Gly Tyr Met Val Glu
                165                 170                 175

Asn Cys Lys Thr Ile Val Gln Thr Asp Thr Pro Leu Ser Leu Val Trp
            180                 185                 190

Leu Glu Ser Ala Thr Asn Ile Val Ile Thr Ile Ser Ile Cys Phe Phe
        195                 200                 205

Cys Ser Ile Phe Ile Ile Lys Leu Gly Phe Ala Ile His Gln Arg Arg
    210                 215                 220

Arg Leu Gly Val Arg Asp Phe Gly Pro Met Lys Val Ile Phe Val Met
225                 230                 235                 240

Gly Cys Gln Thr Leu Thr Val Pro Ala Leu Leu Ser Ile Leu Gln Tyr
                245                 250                 255

Ala Val Ser Val Pro Glu Leu Asn Ser Asn Ile Met Thr Leu Val Thr
            260                 265                 270

Ile Ser Leu Pro Leu Ser Ser Ile Trp Ala Gly Val Ser Leu Thr Arg
        275                 280                 285

Ser Ser Ser Thr Glu Asn Ser Pro Ser Arg Gly Ala Leu Trp Asn Arg
    290                 295                 300

Leu Thr Asp Ser Thr Gly Thr Arg Ser Asn Gln Thr Ser Ser Thr Asp
305                 310                 315                 320

Thr Ala Val Ala Met Thr Tyr Pro Ser Asn Lys Ser Ser Thr Val Cys
                325                 330                 335

Tyr Ala Asp Gln Ser Ser Val Lys Arg Gln Tyr Asp Pro Glu Gln Gly
            340                 345                 350

His Gly Ile Ser Val Glu His Asp Val Ser Val His Ser Cys Gln Arg
        355                 360                 365

Leu
```

<210> SEQ ID NO 87
<211> LENGTH: 1110
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 87

```
atggactcta agttcgaccc atactctcaa aacttgactt tccacgctgc tgacggtacc      60

ccatttcaag ttccagtcat gaccttgaac gacttttacc aatactgtat tcaaatttgt     120

atcaactacg gtgctcaatt cggtgcttcc gtcatcattt tcattatctt gttgttattg     180

actagaccag acaaaagagc ttcttctgtt ttcttcttaa acggtggtgc cttgttgttg     240

aacatgggta gattgttgtg tcacatgatt tacttcacta ctgacttcgt caaggcttac     300

caatacttct cttctgatta ctctagagcc ccaacctctg cctacgctaa ctccattttg     360

ggtgtcgtct tgaccacctt gttgttggtt tgtatcgaaa cctccttggt tttacaagtc     420
```

```
caagtcgtct gtgctaactt gagacgtaga tacagaaccg tcttattgtg tgtttctatc    480

ttggtcgcct tgatcccagt cggtttgaga ttgggttaca tggttgaaaa ctgtaagact    540

attgttcaaa ctgataccc  attgtctttg gtttggttgg aatctgctac taacatcgtc    600

attaccatct ccatctgttt cttctgttct atcttcatca tcaagttggg tttcgccatt    660

caccaaagaa gaagattggg tgtcagagat ttcggtccaa tgaaggtcat tttcgtcatg    720

ggttgtcaaa ctttgactgt tccagctttg ttgtctattt tgcaatacgc tgtctctgtc    780

ccagaattga actctaacat tatgactttg gttactatct ctttgccatt gtcctccatt    840

tgggctggtg tttctttgac ccgttcttcc tccaccgaaa actctccatc cagaggtgct    900

ttgtggaacc gtttgaccga ctctaccggt accagatcta accaaacctc ttccaccgac    960

accgccgtcg ctatgaccta cccatctaac aagtcttcta ctgtctgtta cgccgatcaa   1020

tcttctgtca agagacaata cgatccagaa caaggtcacg gtatctctgt tgaacacgat   1080

gtttctgtcc actcctgtca aagattgtag                                    1110
```

<210> SEQ ID NO 88
<211> LENGTH: 412
<212> TYPE: PRT
<213> ORGANISM: Beauvaria bassiana

<400> SEQUENCE: 88

```
Met Asp Gly Ser Ser Ala Pro Ser Ser Pro Thr Pro Asp Pro Thr Phe
1               5                   10                  15

Asp Arg Phe Ala Gly Asn Val Thr Phe Phe Leu Ala Asp His Ile Thr
            20                  25                  30

Thr Thr Ser Val Pro Met Pro Val Leu Asn Ala Tyr Tyr Asp Glu Ser
        35                  40                  45

Leu Cys Thr Thr Met Asn Tyr Gly Ala Gln Leu Gly Ala Cys Leu Val
    50                  55                  60

Met Leu Val Val Val Val Ala Leu Thr Pro Ala Ala Lys Leu Ala Arg
65                  70                  75                  80

Arg Pro Ala Ser Ala Leu His Leu Val Gly Leu Leu Leu Cys Ala Val
                85                  90                  95

Arg Ser Gly Leu Leu Phe Ala Tyr Phe Val Ser Pro Ile Ser His Phe
            100                 105                 110

Tyr Gln Val Trp Ala Gly Asp Phe Ser Ala Val Ser Arg Arg Tyr Trp
        115                 120                 125

Asp Ala Ser Leu Ala Ala Asn Thr Leu Ala Phe Pro Leu Val Val Val
    130                 135                 140

Val Glu Ala Ala Leu Ile Asn Gln Ala Trp Thr Met Val Ala Phe Trp
145                 150                 155                 160

Pro Arg Ala Ala Lys Ala Ala Ala Cys Ala Cys Ser Ala Val Ile Val
                165                 170                 175

Leu Leu Thr Ile Gly Thr Arg Leu Ala Tyr Thr Ile Val Gln Asn His
            180                 185                 190

Ala Ile Val Thr Ala Val Pro Pro Glu His Phe Leu Trp Ala Ile Gln
        195                 200                 205

Trp Ser Ala Val Met Gly Ala Val Ser Ile Phe Trp Phe Cys Ala Val
    210                 215                 220

Phe Asn Val Lys Leu Val Cys His Leu Val Ala Asn Arg Gly Ile Leu
225                 230                 235                 240

Pro Ser Ile Ser Val Val Asn Pro Met Glu Val Leu Val Met Thr Asn
                245                 250                 255
```

```
Gly Thr Leu Met Ile Ile Pro Ser Ile Phe Ala Gly Leu Glu Trp Ala
            260                 265                 270

Lys Phe Thr Asn Phe Glu Ser Gly Ser Leu Thr Leu Thr Ser Val Ile
        275                 280                 285

Ile Ile Leu Pro Leu Gly Thr Leu Ala Ala Gln Arg Ile Ser Gly Gln
    290                 295                 300

Gly Ser Gln Gly Tyr Gln Ala Gly His Leu Phe His Glu Gln Gln Gln
305                 310                 315                 320

Gln Gln Ala Arg Thr Arg Ser Gly Ala Phe Gly Ser Ala Ser Gln Gln
                325                 330                 335

Ser His Pro Thr Asn Lys Val Pro Ser Ser Ile Thr Leu Ser Thr Ser
            340                 345                 350

Gly Thr Pro Ile Thr Pro Gln Ile Ser Ala Gly Ser Arg Pro Glu Leu
        355                 360                 365

Pro Leu Val Asp Arg Ser Glu Arg Leu Asp Pro Ile Asp Leu Glu Leu
    370                 375                 380

Gly Arg Ile Asp Ala Phe Arg Gly Ser Ser Asp Phe Ser Pro Ser Thr
385                 390                 395                 400

Ala Arg Pro Lys Arg Met Gln Arg Asp Asn Phe Ala
                405                 410
```

<210> SEQ ID NO 89
<211> LENGTH: 1239
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 89

```
atggatggtt cttctgctcc atcttctcca actccagatc caaccttcga cagattcgcc     60

ggtaacgtca ctttcttctt ggctgaccac atcaccacta cctccgttcc aatgccagtc    120

ttgaacgcct actacgacga atccttgtgt actaccatga actacggtgc tcaattaggt    180

gcttgtttag ttatgttggt tgtcgttgtt gctttgaccc cagctgctaa gttggctaga    240

agaccagctt ctgctttgca tttggttggt ttgttgttgt gtgctgttag atccggtttg    300

ttgtttgctt acttcgtctc cccaatctct cacttttacc aagtttgggc tggtgacttc    360

tctgccgttt ccagaagata ctgggacgct tctttggctg ccaacacttt agctttccca    420

ttggttgtcg tcgttgaagc tgctttgatc aaccaagctt ggaccatggt tgctttctgg    480

ccaagagccg ctaaggccgc tgcctgtgct tgttctgctg tcattgtctt gttgactatt    540

ggtactagat tggcctacac tatcgtccaa aaccacgcta ttgttactgc cgtcccacca    600

gaacacttct tgtgggctat tcaatggtcc gctgttatgg gtgctgtttc catcttctgg    660

ttttgtgccg ttttcaacgt caagttggtc tgtcacttag tcgctaacag aggtatcttg    720

ccatctatct ctgttgttaa cccaatggaa gtcttggtta tgactaacgg taccttgatg    780

attatcccat ctatcttcgc tggtttggaa tgggctaagt tcaccaactt cgaatccggt    840

tctttgactt tgacttccgt tattattatc ttgccattgg gtactttggc tgcccaacgt    900

atttctggtc aaggttccca aggttaccaa gctggtcact tattccacga acaacaacaa    960

caacaagctc gtacccgttc cggtgccttc ggttccgctt ctcaacaatc ccatccaact   1020

aacaaggttc catcctctat taccttgtct acctctggta ctccaattac tccacaaatc   1080

tctgccggtt cccgtccaga attaccattg gttgatagat ccgaacgttt ggacccaatt   1140
```

gacttggaat tgggtagaat cgatgctttc agaggttctt ccgacttctc tccatccacc 1200
gctagaccaa agcgtatgca acgtgataac ttcgcctag 1239

<210> SEQ ID NO 90
<211> LENGTH: 360
<212> TYPE: PRT
<213> ORGANISM: Candida lustianiae

<400> SEQUENCE: 90

Met Asn Pro Ala Asp Ile Asn Ile Glu Tyr Thr Leu Gly Asp Thr Ala
1 5 10 15

Phe Ser Ser Thr Phe Ala Asp Phe Glu Ala Trp Lys Thr Arg Asn Thr
20 25 30

Gln Phe Ala Ile Val Asn Gly Val Ala Leu Ala Cys Gly Ile Ile Leu
35 40 45

Met Val Val Ser Trp Ile Ile Ile Val Asn Lys Arg Ala Pro Ile Phe
50 55 60

Ala Met Asn Gln Thr Met Leu Val Ile Met Val Ile Lys Ser Ala Met
65 70 75 80

Tyr Leu Lys His Ile Met Gly Pro Leu Asn Ser Leu Thr Phe Arg Phe
85 90 95

Thr Gly Leu Met Glu Glu Ser Trp Ala Pro Tyr Asn Val Tyr Val Thr
100 105 110

Ile Asn Val Leu His Val Leu Leu Val Ala Ala Val Glu Ser Ser Leu
115 120 125

Val Phe Gln Ile His Val Val Phe Lys Ser Ser Arg Ala Arg Val Ala
130 135 140

Gly Arg Ala Ile Val Ser Ala Met Ser Thr Leu Ala Leu Leu Ile Val
145 150 155 160

Ser Leu Tyr Leu Tyr Ser Thr Val Arg His Ala Gln Thr Leu Arg Ala
165 170 175

Glu Leu Ser His Gly Asp Thr Thr Thr Val Glu Pro Trp Val Asp Asn
180 185 190

Val Pro Leu Ile Leu Phe Ser Ala Ser Leu Asn Val Leu Cys Leu Leu
195 200 205

Leu Ala Leu Lys Leu Val Phe Ala Val Arg Thr Arg Arg His Leu Gly
210 215 220

Leu Arg Gln Phe Asp Ser Phe His Ile Leu Ile Ile Met Ala Thr Gln
225 230 235 240

Thr Phe Val Ile Pro Ser Ser Leu Val Ile Ala Asn Tyr Arg Tyr Ala
245 250 255

Ser Ser Pro Leu Leu Ser Ser Ile Ser Ile Ile Val Ala Val Cys Asn
260 265 270

Leu Pro Leu Cys Ser Leu Trp Ala Cys Ser Asn Asn Asn Ser Ser Tyr
275 280 285

Pro Thr Ser Ser Gln Asn Thr Ile Leu Ser Arg Tyr Glu Thr Glu Thr
290 295 300

Ser Gln Ala Thr Asp Ala Ser Ser Thr Thr Cys Ala Gly Ile Ala Glu
305 310 315 320

Lys Gly Phe Asp Lys Ser Pro Asp Ser Pro Thr Phe Gly Asp Gln Asp
325 330 335

Ser Val Ser Ile Ser His Ile Leu Asp Ser Leu Glu Lys Asp Val Glu
340 345 350

Gly Val Thr Thr His Arg Leu Thr
        355                 360

<210> SEQ ID NO 91
<211> LENGTH: 1083
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 91
atgaacccag ctgacatcaa catcgaatac accttgggtg atactgcttt ctcttccact 60
ttcgctgatt tcgaagcttg gaaaactaga aacactcaat tcgctattgt caacggtgtc 120
gctttggctt gtggtattat cttgatggtc gtttcttgga ttattattgt taacaagaga 180
gctccaatct tcgctatgaa ccaaactatg ttggttatca tggttattaa gtccgctatg 240
tacttgaagc atatcatggg tccattgaac tccttgacct tccgtttcac cggtttaatg 300
gaagaatcct gggctccata caacgtttac gtcactatta acgtcttgca tgttttgttg 360
gtcgctgctg tcgaatcctc tttggtcttc caaatccatg ttgttttcaa gtcttctaga 420
gccagagttg ctggtagagc cattgtttct gctatgtcca ctttggcctt gttgatcgtt 480
tctttgtact tgtactctac tgttagacat gctcaaactt tgcgtgctga attatctcat 540
ggtgacacta ccactgttga accatgggtc gataacgttc cattgatttt gttttccgct 600
tctttgaacg ttttgtgttt gttgttggcc ttgaaattgg ttttcgctgt cagaaccaga 660
agacatttag gtttaagaca attcgactct ttccacatct tgattattat ggccactcaa 720
actttcgtta tcccatcctc tttggtcatc gctaactaca gatacgcttc ttccccattg 780
ttgtcttcca tttccatcat cgtcgccgtc tgtaacttgc cattgtgttc cttgtgggct 840
tgttctaaca acaactcttc ctacccaact tcttctcaaa acactatttt gtccagatac 900
gaaactgaaa cctctcaagc tactgacgct tcctctacca cctgtgccgg tattgctgaa 960
aagggtttcg acaagtctcc agactctcca actttcggtg accaagactc cgtctctatc 1020
tcccatatct tggactcttt ggaaaaggat gttgaaggtg tcaccaccca tagattgact 1080
tag 1083

<210> SEQ ID NO 92
<211> LENGTH: 419
<212> TYPE: PRT
<213> ORGANISM: Candida tenuis

<400> SEQUENCE: 92

Met Asp Ser Tyr Leu Leu Asn His Pro Gly Asp Ile Ser Leu Asn Phe
1               5                   10                  15

Ala Leu Pro Leu Ser Asp Glu Val Tyr Thr Ile Thr Phe Asn Asp Leu
            20                  25                  30

Asp Ser Gln Ser Ser Phe Ser Ile Gln Tyr Leu Val Ile His Ser Cys
        35                  40                  45

Ala Ile Thr Val Cys Leu Thr Leu Leu Val Leu Leu Asn Leu Phe Ile
    50                  55                  60

Arg Asn Lys Lys Thr Pro Val Phe Val Leu Asn Gln Val Ile Leu Phe
65                  70                  75                  80

Phe Ala Ile Val Arg Ser Ser Leu Phe Ile Gly Phe Met Lys Ser Pro
                85                  90                  95

Leu Ser Thr Ile Thr Ala Ser Phe Thr Gly Ile Ile Ser Asp Asp Gln

-continued

```
            100                 105                 110

Lys His Phe Tyr Lys Val Ser Val Ala Ala Asn Ala Ala Leu Ile Ile
        115                 120                 125

Leu Val Met Leu Ile Gln Val Ser Phe Thr Tyr Gln Ile Tyr Ile Ile
    130                 135                 140

Phe Arg Ser Pro Glu Val Arg Lys Phe Gly Val Phe Met Thr Ser Ala
145                 150                 155                 160

Leu Gly Val Leu Met Ala Val Thr Phe Gly Phe Tyr Val Asn Ser Ala
                165                 170                 175

Val Ala Ser Thr Lys Gln Tyr Gln His Ile Phe Tyr Ser Thr Asp Pro
            180                 185                 190

Tyr Ile Met Asp Ser Trp Val Thr Gly Leu Pro Pro Ile Leu Tyr Ser
        195                 200                 205

Ala Ser Val Ile Ala Met Ser Leu Val Leu Val Leu Lys Leu Val Ala
    210                 215                 220

Ala Val Arg Thr Arg Arg Tyr Leu Gly Leu Lys Gln Phe Ser Ser Tyr
225                 230                 235                 240

His Ile Leu Leu Ile Met Phe Thr Gln Thr Leu Phe Val Pro Thr Ile
                245                 250                 255

Leu Thr Ile Leu Ala Tyr Ala Phe Tyr Gly Tyr Asn Asp Ile Leu Ile
            260                 265                 270

His Ile Ser Thr Thr Ile Thr Val Val Leu Leu Pro Phe Thr Ser Ile
        275                 280                 285

Trp Ala Ser Ile Ala Asn Asn Ser Arg Ser Leu Met Ser Ala Ala Ser
    290                 295                 300

Leu Tyr Phe Ser Gly Ser Asn Ser Ser Leu Ser Glu Leu Ser Ser Pro
305                 310                 315                 320

Ser Pro Ser Asp Asn Asp Thr Leu Asn Glu Asn Val Phe Ala Phe Phe
                325                 330                 335

Pro Asp Lys Leu Gln Lys Met Asn Ser Ser Glu Ala Val Ser Ala Val
            340                 345                 350

Asp Lys Val Val Val His Asp His Phe Asp Thr Ile Ser Gln Lys Ser
        355                 360                 365

Ile Pro His Asp Ile Leu Glu Ile Leu Gln Gly Asn Glu Gly Gly Gln
    370                 375                 380

Met Lys Glu His Ile Ser Val Tyr Ser Asp Asp Ser Phe Ser Lys Thr
385                 390                 395                 400

Thr Pro Pro Ile Val Gly Gly Asn Leu Leu Ile Thr Asn Thr Asp Ile
                405                 410                 415

Gly Met Lys
```

<210> SEQ ID NO 93
<211> LENGTH: 1257
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 93

```
atggactcct acttgttgaa ccatccaggt gacatctctt tgaacttcgc cttgccattg      60

tccgatgaag tctacactat taccttcaac gacttagact ctcaatcttc tttttccatt     120

caatacttgg tcatccactc ttgtgccatt accgtctgtt tgaccttgtt ggttttgttg     180

aacttgttca tcagaaacaa gaagactcca gtcttcgttt tgaaccaagt catcttgttc     240
```

-continued

```
ttcgctatcg tcagatcttc tttgttcatc ggttttatga agtctccatt gtccaccatc    300

accgcctctt tcaccggtat catttctgat gaccaaaaac acttctacaa ggtctccgtc    360

gctgctaacg ccgctttgat cattttggtc atgttgattc aagtttcttt cacttaccaa    420

atctacatta ttttcagatc cccagaagtt agaaagttcg gtgtcttcat gacctccgcc    480

ttgggtgtct tgatggctgt taccttcggt ttttacgtta actccgctgt cgcttctacc    540

aagcaatacc aacacatctt ctactctacc gacccataca tcatggactc ttgggtcact    600

ggtttgccac caatcttgta ctctgcttcc gtcatcgcta tgtctttggt cttggttttg    660

aagttggtcg ctgctgtcag aaccagaaga tacttgggtt tgaagcaatt ctcctcctac    720

cacatcttgt tgattatgtt cacccaaacc ttgttcgttc caaccatctt gaccatctta    780

gcttacgctt tctacggtta caacgatatc ttgatccata tttctaccac catcaccgtt    840

gtcttgttgc cattcacctc catttgggct tctatcgcca acaactctag atccttgatg    900

tctgccgctt ccttgtactt ctccggttcc aactcctctt tgtctgaatt gtcttctcca    960

tctccatctg ataacgacac tttgaacgaa aacgtcttcg cctttttcc agacaagttg    1020

caaaagatga actcttctga agccgtttct gctgtcgaca aggtcgttgt tcacgaccac   1080

tttgatacca tctcccaaaa gtctatccca cacgacatct tggaaatttt gcaaggtaac   1140

gaaggtggtc aaatgaagga acacatctct gtctactctg atgactcttt ctccaagact   1200

actccaccaa ttgtcggtgg taacttgttg atcaccaaca ccgacatcgg tatgaag      1257
```

<210> SEQ ID NO 94
<211> LENGTH: 369
<212> TYPE: PRT
<213> ORGANISM: Neosartorya fischeri

<400> SEQUENCE: 94

```
Met Asn Ser Thr Phe Asp Pro Trp Thr Gln Asn Ile Thr Leu Thr Gln
1               5                   10                  15

Ser Asp Gly Thr Thr Val Ile Ser Ser Leu Ala Leu Ala Asp Asp Tyr
            20                  25                  30

Leu His Tyr Met Ile Arg Leu Gly Ile Asn Tyr Gly Ala Gln Leu Gly
        35                  40                  45

Ala Cys Ala Val Leu Leu Leu Val Leu Leu Leu Leu Thr Arg Pro Glu
    50                  55                  60

Lys Arg Val Ser Ser Val Phe Val Leu Asn Val Ala Ala Leu Leu Ala
65                  70                  75                  80

Asn Ile Ile Arg Leu Gly Cys Gln Leu Ser Tyr Phe Ser Thr Gly Phe
                85                  90                  95

Ala Arg Met Tyr Ala Leu Leu Ala Gly Asp Phe Ser Arg Val Ser Arg
            100                 105                 110

Gly Ala Tyr Ala Gly Gln Val Met Ala Ser Val Phe Phe Thr Ile Val
        115                 120                 125

Phe Ile Cys Val Glu Ala Ser Leu Val Leu Gln Val Gln Val Val Cys
    130                 135                 140

Ser Asn Leu Arg Arg Gln Tyr Arg Ile Leu Leu Leu Gly Ala Ser Thr
145                 150                 155                 160

Leu Ala Ala Leu Val Pro Ile Gly Val Arg Leu Thr Tyr Ser Val Leu
                165                 170                 175

Asn Cys Met Val Ile Met His Ala Gly Thr Met Asp His Leu Asp Trp
            180                 185                 190
```

-continued

```
Leu Glu Ser Ala Thr Asn Ile Val Thr Thr Val Ser Ile Cys Phe Phe
        195                 200                 205

Cys Ala Val Phe Val Val Lys Leu Gly Leu Ala Ile Lys Met Arg Lys
    210                 215                 220

Arg Leu Gly Val Lys Gln Phe Gly Pro Met Arg Val Ile Phe Ile Met
225                 230                 235                 240

Gly Cys Gln Thr Met Thr Ile Pro Ala Ile Phe Ala Ile Cys Gln Tyr
                245                 250                 255

Phe Ser Arg Ile Pro Glu Phe Ser His Asn Val Leu Thr Leu Val Ile
            260                 265                 270

Ile Ser Leu Pro Leu Ser Ser Ile Trp Ala Gly Phe Ala Leu Val Gln
        275                 280                 285

Ala Asn Ser Thr Ala Arg Ser Thr Glu Ser Arg His His Leu Trp Asn
    290                 295                 300

Ile Leu Ser Ser Asp Gly Ala Thr Arg Asp Lys Pro Ser Gln Cys Val
305                 310                 315                 320

Ser Ser Pro Met Thr Ser Pro Thr Thr Thr Cys Tyr Ser Glu Gln Ser
                325                 330                 335

Thr Ser Lys Pro Gln Gln Asp Pro Glu Asn Gly Phe Gly Ile Ser Val
            340                 345                 350

Ala His Asp Ile Ser Ile His Ser Phe Arg Lys Asp Ala His Gly Asp
        355                 360                 365

Ile


<210> SEQ ID NO 95
<211> LENGTH: 1110
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 95

atgaactcca ccttcgaccc atggacccaa aacattactt tgactcaatc cgacggtacc      60

actgtcatct cctctttggc tttggccgat gactacttgc actacatgat tagattgggt     120

atcaactacg gtgcccaatt gggtgcttgt gctgttttgt tgttggtttt gttattgttg     180

actagaccag aaaagagagt ttcttctgtc ttcgttttga acgtcgctgc tttgttggct     240

aacatcatca gattgggttg tcaattgtcc tacttctcta ccggtttcgc tagaatgtac     300

gccttgttgg ccggtgactt ctccagagtc tctcgtggtg cttacgccgg tcaagttatg     360

gcctccgtct tcttcaccat tgtcttcatt tgtgttgaag cttctttggt tttgcaagtt     420

caagtcgtct gttctaactt gagaagacaa tacagaatct tgttattggg tgcttccact     480

ttggctgcct tggttccaat tggtgttcgt ttgacttact ccgttttaaa ctgtatggtt     540

attatgcacg ctggtactat ggaccacttg gattggttgg aatctgctac caacatcgtt     600

actaccgttt ctatttgttt cttctgtgct gttttcgttg tcaaattagg tttggctatc     660

aagatgagaa agcgtttggg tgtcaaacaa ttcggtccaa tgagagttat cttcatcatg     720

ggttgtcaaa ccatgaccat cccagctatt ttcgctattt gtcaatactt ctctagaatt     780

ccagaatttt ctcataacgt tttgactttg gttatcatct ctttgccatt gtcttctatc     840

tgggccggtt ttgctttggt ccaagccaac tctaccgcca gatctaccga atctagacat     900

catttgtgga acattttgtc ttccgatggt gctaccagag acaagccatc ccaatgtgtt     960

tcttctccaa tgacctctcc aaccactacc tgttactccg aacaatccac ctctaagcca    1020
```

caacaagacc cagaaaacgg ttttggtatt tctgttgccc acgatatttc catccactct 1080
ttcagaaagg acgcccacgg tgatatttag 1110

<210> SEQ ID NO 96
<211> LENGTH: 566
<212> TYPE: PRT
<213> ORGANISM: Neurospora crassa

<400> SEQUENCE: 96

Met Ala Ser Ser Ser Ser Pro Pro Ala Asp Ile Phe Ser Gly Ile Thr
1 5 10 15

Gln Ser Leu Asn Ser Thr His Ala Thr Leu Thr Leu Pro Ile Pro Pro
20 25 30

Ala Asp Arg Asp His Leu Glu Asn Gln Val Leu Phe Leu Phe Asp Asn
35 40 45

His Gly Gln Leu Leu Asn Val Thr Thr Thr Tyr Ile Asp Ala Phe Asn
50 55 60

Asn Met Leu Val Ser Thr Thr Ile Asn Tyr Ala Thr Gln Ile Gly Ala
65 70 75 80

Thr Phe Ile Met Leu Ala Ile Met Leu Leu Met Thr Pro Arg Arg Arg
85 90 95

Phe Lys Arg Leu Pro Thr Ile Ile Ser Leu Leu Ala Leu Cys Ile Asn
100 105 110

Leu Ile Arg Val Val Leu Leu Ala Leu Phe Phe Pro Ser His Trp Thr
115 120 125

Asp Phe Tyr Val Leu Tyr Ser Gly Asp Trp Gln Phe Val Pro Pro Gly
130 135 140

Asp Met Gln Ile Ser Val Ala Ala Thr Val Leu Ser Ile Pro Val Thr
145 150 155 160

Ala Leu Leu Leu Ser Ala Leu Met Val Gln Ala Trp Ser Met Met Gln
165 170 175

Leu Trp Thr Pro Leu Trp Arg Ala Leu Val Val Leu Val Ser Gly Leu
180 185 190

Leu Ser Leu Val Thr Val Ala Met Ser Phe Ala Asn Cys Ile Phe Gln
195 200 205

Ala Lys Asn Ile Leu Tyr Ala Asp Pro Leu Pro Ser Tyr Trp Val Arg
210 215 220

Lys Leu Tyr Leu Ala Leu Thr Thr Gly Ser Ile Ser Trp Phe Thr Phe
225 230 235 240

Leu Phe Met Ile Arg Leu Val Met His Met Trp Thr Asn Arg Ser Ile
245 250 255

Leu Pro Ser Met Lys Gly Leu Lys Ala Met Asp Val Leu Ile Ile Thr
260 265 270

Asn Ser Ile Leu Met Leu Ile Pro Val Leu Phe Ala Gly Leu Glu Phe
275 280 285

Leu Asp Ser Ala Ser Gly Phe Glu Ser Gly Ser Leu Thr Gln Thr Ser
290 295 300

Val Val Ile Val Leu Pro Leu Gly Thr Leu Val Ala Gln Arg Ile Ala
305 310 315 320

Thr Arg Gly Tyr Met Pro Asp Ser Leu Glu Ala Ser Ser Gly Pro Asn
325 330 335

Gly Ser Leu Pro Leu Ser Asn Leu Ser Phe Ala Gly Gly Gly Gly Gly
340 345 350

```
Gly Ser Gly Gly His Lys Asp Lys Glu Asn Gly Gly Gly Ile Ile Pro
        355                 360                 365

Pro Thr Thr Asn Asn Thr Ala Ala Thr Asn Phe Ser Ser Ser Ile Ala
    370                 375                 380

Cys Ser Gly Ile Ser Cys Leu Pro Lys Val Lys Arg Met Thr Ala Ser
385                 390                 395                 400

Ser Ala Ser Ser Ser Gln Arg Pro Leu Leu Thr Met Thr Asn Ser Thr
                405                 410                 415

Ile Ala Ser Asn Asp Ser Ser Gly Phe Pro Ser Pro Gly Ile His Asn
            420                 425                 430

Thr Thr Thr Thr Thr Thr Gln Tyr Gln Tyr Ser Met Gly Met Asn Met
        435                 440                 445

Pro Asn Phe Pro Pro Val Pro Phe Pro Gly Tyr Gln Ser Arg Thr Thr
    450                 455                 460

Gly Val Thr Ser His Ile Val Ser Asp Gly Arg His His Gln Gly Met
465                 470                 475                 480

Asn Arg His Pro Ser Val Asp His Phe Asp Arg Glu Leu Ala Arg Ile
                485                 490                 495

Asp Asp Glu Asp Asp Asp Gly Tyr Pro Phe Ala Ser Ser Glu Lys Ala
            500                 505                 510

Val Met His Gly Asp Asp Asp Asp Asp Val Glu Arg Gly Arg Arg Arg
        515                 520                 525

Ala Leu Pro Pro Ser Leu Gly Gly Val Arg Val Glu Arg Thr Ile Glu
    530                 535                 540

Thr Arg Ser Glu Glu Arg Met Pro Ser Pro Asp Pro Leu Gly Val Thr
545                 550                 555                 560

Lys Pro Arg Ser Phe Glu
                565
```

<210> SEQ ID NO 97
<211> LENGTH: 1701
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 97

```
atggcgtcct cttcctcacc acctgcagac attttctcag ggatcacgca atcactaaat     60

agtacacacg cgacgcttac actaccgatt ccgccagcgg acagggatca tctggaaaat    120

caagtattat ttttgtttga caatcacggt cagttactta atgtaactac aacttacatt    180

gacgctttta acaatatgct ggtctctact actataaact atgcaacgca aattggagct    240

acttttataa tgctagccat tatgttatta atgactccca gaaggaggtt caaacgttta    300

ccaacaatta ttagcttgtt agccttatgt attaatttga tcagggtggt tttgctggcc    360

ctgtttttc cttctcactg gacagacttc tacgtgttgt attccggtga ctggcagttt     420

gtacctccag ggatatgca aatatctgtt gctgctacgg ttttgtctat cccagtgacg     480

gcattattat tgagcgcatt gatggttcaa gcctggtcaa tgatgcaatt atggacacca    540

ctgtggaggg cactagtggt actagtgtcc gggctattgt cactggtaac tgtggcaatg    600

agtttcgcga attgcatttt ccaagcgaaa aatattttgt atgccgaccc tttaccctcc    660

tactgggtca gaaaattgta cttagcatta acgactgggt ctataagttg gttcacattc    720

ctttttatga taagattggt tatgcatatg tggacaaaca gatctatatt accaagcatg    780
```

-continued

```
aagggtttga aggctatgga tgtattgatt attacgaatt ctatattgat gttaatccca    840

gtgttgtttg caggcttgga atttctggat agtgcctctg gatttgagtc cgggtctttg    900

actcaaacct ctgtagtgat tgtcctgcct ttgggtactt tagtagcaca aagaatagct    960

acgaggggtt acatgcccga tagtctggag gcttctagcg gaccaaatgg ttcattgccg   1020

ttatctaatt taagtttcgc tggagggggc ggtggtggtt ctgggggaca taaagataaa   1080

gaaaacggtg gcggtattat accgcctact acgaacaata ctgctgctac taatttttct   1140

tcatcaatcg cgtgttctgg tatatcttgt ttaccaaaag tcaaaagaat gaccgcgagt   1200

tcagcctcaa gtagccagag accgttgttg acaatgacta actcaaccat agcgagtaat   1260

gacagttcag gtttcccttc tcctggcata cataatacca ctactacgac aacacaatac   1320

caatattcca tgggaatgaa catgccgaac tttcctccag tcccgttccc aggttaccag   1380

tcacgtacta ccggtgttac ttcccatatt gtgtccgacg gtagacatca ccagggtatg   1440

aacaggcacc catctgttga ccattttgat agggaacttg ctaggattga tgatgaagat   1500

gacgatggtt accctttcgc atcaagtgaa aaggccgtta tgcacggaga cgatgacgac   1560

gatgtggaaa ggggacgtcg tagagctcta ccaccatcct taggtggagt tagagttgaa   1620

aggacgatcg agaccaggag cgaggaacgt atgccatctc cggacccatt gggtgttacg   1680

aagcctagat cattcgagta g                                             1701


<210> SEQ ID NO 98
<211> LENGTH: 397
<212> TYPE: PRT
<213> ORGANISM: Pseudogymnoascus destructans

<400> SEQUENCE: 98

Met Ser Thr Ala Asn Val His Leu Pro Ala Asp Phe Asp Pro Thr Arg
1               5                   10                  15

Gln Asn Ile Thr Ile Tyr Thr Pro Asp Gly Thr Pro Val Val Ala Thr
            20                  25                  30

Leu Pro Met Ile Asn Leu Phe Asn Arg Gln Asn Asn Glu Ile Cys Val
        35                  40                  45

Val Tyr Gly Cys Gln Leu Gly Ala Ser Leu Ile Met Phe Leu Val Val
    50                  55                  60

Leu Leu Thr Thr Arg Val Ser Lys Arg Lys Ser Pro Ile Phe Val Leu
65                  70                  75                  80

Asn Val Leu Ser Leu Ile Ile Ser Cys Leu Arg Ser Leu Leu Gln Ile
                85                  90                  95

Leu Tyr Tyr Ile Gly Pro Trp Thr Glu Ile Tyr Arg Tyr Leu Ser Phe
            100                 105                 110

Asp Tyr Ser Thr Val Pro Ala Ser Ala Tyr Ala Asn Ser Val Ala Ala
        115                 120                 125

Thr Leu Leu Thr Leu Phe Leu Leu Ile Thr Ile Glu Ala Ser Leu Val
    130                 135                 140

Leu Gln Thr Asn Val Val Cys Lys Ser Met Ser Ser His Ile Arg Trp
145                 150                 155                 160

Pro Val Thr Ala Leu Ser Met Val Val Ser Leu Leu Ala Ile Ser Phe
                165                 170                 175

Arg Phe Gly Leu Thr Ile Arg Asn Ile Glu Gly Ile Leu Gly Ala Thr
            180                 185                 190

Val Lys Ser Asp Ser Leu Met Phe Ser Gly Ala Ser Leu Ile Ser Glu
        195                 200                 205
```

-continued

```
Thr Ala Ser Ile Trp Phe Phe Cys Thr Ile Phe Val Ile Lys Leu Gly
    210                 215                 220

Trp Thr Leu Tyr Gln Arg Lys Lys Met Gly Leu Lys Gln Trp Gly Pro
225                 230                 235                 240

Met Gln Ile Ile Thr Ile Met Ala Gly Cys Thr Met Leu Ile Pro Ser
                245                 250                 255

Leu Phe Thr Val Leu Glu Phe Phe Pro Glu Glu Thr Phe Tyr Glu Ala
            260                 265                 270

Gly Thr Leu Ala Ile Cys Leu Val Ala Ile Leu Leu Pro Leu Ser Ser
        275                 280                 285

Val Trp Ala Ala Ala Ala Ile Asp Gly Asp Glu Pro Val Arg Pro His
    290                 295                 300

Gly Ser Thr Pro Lys Phe Ala Ser Phe Asn Met Gly Ser Asp Tyr Lys
305                 310                 315                 320

Ser Ser Ser Ala His Leu Pro Arg Ser Ile Arg Lys Ala Ser Val Pro
                325                 330                 335

Ala Glu His Leu Ser Arg Thr Ser Glu Glu Glu Leu Gly Asp Asp Gly
            340                 345                 350

Thr Leu Asn Arg Gly Gly Ala Tyr Gly Met Asp Arg Met Ser Gly Ser
        355                 360                 365

Ile Ser Pro Arg Gly Val Arg Ile Glu Arg Thr Tyr Glu Val His Thr
    370                 375                 380

Ala Gly Arg Gly Gly Ser Ile Glu Arg Glu Asp Ile Phe
385                 390                 395
```

<210> SEQ ID NO 99
<211> LENGTH: 1194
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 99

```
atgtccactg ccaacgttca tttaccagct gatttcgatc caactagaca aaacatcact     60

atctataccc cagacggtac cccagttgtt gctaccttgc caatgatcaa tttgtttaac    120

agacaaaaca acgaaatctg tgttgtttac ggttgtcaat tgggtgcctc tttaattatg    180

ttcttggttg ttttgttgac caccagagtt tccaagagaa aatctccaat cttcgtcttg    240

aacgttttgt ctttgattat ttcttgttta agatccttgt tgcaaatttt atactatatt    300

ggtccatgga ccgagatcta cagatacttg tctttcgatt actctactgt cccagcttcc    360

gcttacgcta attctgttgc tgccacttta ttaaccttat tcttattgat taccattgaa    420

gcttctttag ttttacaaac taacgttgtc tgcaagtcta tgtcttctca cattcgttgg    480

ccagttactg ctttgtccat ggttgtctct ttattggcta tttcttttag attcggtttg    540

accatccgta acatcgaagg tatcttaggt gctactgtca aatccgactc cttaatgttc    600

tctggtgcct ctttgatctc tgaaactgct tctatctggt tcttctgcac tattttcgtt    660

attaaattgg gttggacctt gtaccaaaga aagaagatgg gtttgaagca atggggtcca    720

atgcaaatta tcactatcat ggctggttgc accatgttga tcccatcctt gttcactgtt    780

ttggaattct tccctgaaga aactttctac gaggccggta ctttggctat ctgtttggtt    840

gctattttgt tgccattatc ttccgtctgg gctgccgctg ctattgatgg tgatgaacca    900

gtccgtccac atggttctac cccaaaattc gcttctttca acatgggttc cgactacaaa    960
```

```
tcttcttctg ctcacttgcc aagatctatt agaaaggcct ccgtcccagc tgaacattta   1020

tctagaactt ctgaagaaga gttaggtgac gacggtactt tgaacagagg tggtgcctac   1080

ggtatggaca gaatgtccgg ttctatctcc cctagaggtg tcagaattga aagaacttac   1140

gaagttcata ccgctggtag aggtggttct atcgagagag aggacatctt ctag         1194


<210> SEQ ID NO 100
<211> LENGTH: 296
<212> TYPE: PRT
<213> ORGANISM: Hypocrea jecorina

<400> SEQUENCE: 100

Met Ser Ser Phe Asp Pro Tyr Thr Gln Asn Ile Thr Ile Leu Val Ser
1               5                   10                  15

Pro Ser Ser Pro Pro Ile Ser Ile Pro Ile Pro Val Ile Asp Ala Phe
            20                  25                  30

Asn Asp Glu Thr Ala Ser Ile Ile Thr Asn Tyr Ala Ala Gln Leu Gly
        35                  40                  45

Ala Ala Leu Ala Met Leu Leu Val Leu Leu Ala Ala Thr Pro Thr Ala
    50                  55                  60

Arg Leu Leu Arg Ala Asp Gly Pro Ser Leu Leu His Ala Leu Ala Leu
65                  70                  75                  80

Leu Val Cys Val Val Arg Thr Val Leu Leu Ile Tyr Phe Phe Leu Thr
                85                  90                  95

Pro Phe Ser His Phe Tyr Gln Val Trp Thr Gly Asp Phe Ser Gln Val
            100                 105                 110

Pro Ala Trp Asn Tyr Arg Ala Ser Ile Ala Gly Thr Val Leu Ser Thr
        115                 120                 125

Leu Leu Thr Val Val Thr Asp Ala Ala Leu Val Asn Gln Ala Trp Thr
    130                 135                 140

Met Val Ser Leu Phe Ala Pro Arg Thr Lys Arg Ala Val Cys Val Leu
145                 150                 155                 160

Ser Leu Leu Ile Thr Leu Leu Ala Ile Ser Phe Arg Val Ala Tyr Thr
                165                 170                 175

Val Ile Gln Cys Glu Gly Ile Ala Glu Leu Ala Ala Pro Arg Gln Tyr
            180                 185                 190

Ala Trp Leu Ile Arg Ala Thr Leu Ile Phe Asn Ile Cys Ser Ile Ala
        195                 200                 205

Trp Phe Cys Ala Leu Phe Asn Ser Lys Leu Val Ala His Leu Val Thr
    210                 215                 220

Asn Arg Gly Val Leu Pro Ser Arg Arg Ala Met Ser Pro Met Glu Val
225                 230                 235                 240

Leu Ile Met Ala Asn Gly Ile Leu Met Ile Val Pro Val Val Phe Ala
                245                 250                 255

Ile Leu Glu Trp His His Phe Ile Asn Phe Glu Ala Gly Ser Leu Thr
            260                 265                 270

Pro Thr Ser Ile Ala Ile Ile Leu Pro Leu Ser Ser Leu Ala Ala Gln
        275                 280                 285

Arg Ile Ala Asn Thr Ser Ser Ser
    290                 295


<210> SEQ ID NO 101
<211> LENGTH: 891
<212> TYPE: DNA
<213> ORGANISM: Artificial Sequence
<220> FEATURE:
```

<223> OTHER INFORMATION: Description of Artificial Sequence: Synthetic
polynucleotide

<400> SEQUENCE: 101
atgtcttcct tcgacccata cactcaaaac attactattt tggtttctcc atcctctcca 60
ccaatttcca ttccaatccc agttatcgac gctttcaacg acgaaaccgc ttctatcatt 120
actaactacg ccgctcaatt aggtgctgct ttggccatgt tattagtttt gttggccgct 180
actccaaccg ctagattgtt aagagctgat ggtccatcct tgttgcacgc tttggccttg 240
ttagtctgtg tcgtcagaac tgtcttattg atctacttct tcttgacccc attctctcac 300
ttctaccaag tctggaccgg tgacttctct caagttccag cttggaacta cagagcttct 360
attgctggta ccgttttgtc tactttgttg accgttgtta ccgacgctgc tttggttaac 420
caagcttgga ctatggtttc tttattcgct ccaagaacta agagagccgt ttgtgttttg 480
tccttgttaa tcaccttgtt ggccatttct ttcagagtcg cttacaccgt cattcaatgt 540
gaaggtatcg ctgaattggc tgctccaaga caatacgctt ggttgatcag agccactttg 600
atctttaaca tctgttccat tgcctggttc tgtgctttgt tcaactctaa gttggttgct 660
cacttggtta ccaacagagg tgtcttgcca tcccgtagag ccatgtcccc aatggaagtt 720
ttgattatgg ccaacggtat cttgatgatt gttccagttg ttttcgctat cttggaatgg 780
caccacttca ttaacttcga agctggttct ttaaccccaa cctccatcgc cattatcttg 840
ccattgtcct ctttggccgc ccaaagaatc gccaacactt cttcctctta g 891

<210> SEQ ID NO 102
<211> LENGTH: 367
<212> TYPE: PRT
<213> ORGANISM: Tuber melanosporum

<400> SEQUENCE: 102

Met Glu Gln Ile Pro Val Tyr Glu Arg Pro Gly Phe Asn Pro His Lys
1 5 10 15

Gln Asn Ile Thr Leu Phe Lys His Asp Gly Ser Thr Val Thr Val Gly
20 25 30

Leu His Glu Leu Asp Ala Met Phe Thr His Ser Ile Arg Val Ala Val
35 40 45

Val Phe Ala Ser Gln Ile Gly Ala Cys Ala Leu Leu Ser Val Ile Val
50 55 60

Ala Met Val Thr Lys Arg Glu Lys Arg Arg Ala Leu Phe Phe Leu His
65 70 75 80

Ile Ile Ser Leu Leu Leu Val Val Val Arg Ser Val Leu Gln Ile Leu
85 90 95

Tyr Phe Val Gly Pro Trp Ala Glu Thr Tyr Asn Tyr Val Ala Tyr Tyr
100 105 110

Tyr Glu Asp Ile Pro Leu Ser Asp Lys Leu Ile Ser Ile Trp Ala Gly
115 120 125

Ile Ile Gln Leu Ile Leu Asn Ile Cys Ile Leu Leu Ser Leu Ile Leu
130 135 140

Gln Val Arg Val Val Tyr Ala Thr Ser Pro Lys Leu Asn Thr Ile Met
145 150 155 160

Thr Leu Val Ser Cys Val Ile Ala Ser Ile Ser Val Gly Phe Phe Phe
165 170 175

Thr Val Ile Val Gln Ile Ser Glu Ala Ile Leu Asn Gly Val Gly Tyr
180 185 190

-continued

```
Asp Gly Trp Val Tyr Lys Val His Arg Gly Val Phe Ala Gly Ala Ile
        195                 200                 205

Ala Phe Phe Ser Phe Ile Phe Ile Phe Lys Leu Ala Phe Ala Ile Arg
    210                 215                 220

Arg Arg Lys Ala Leu Gly Leu Gln Arg Phe Gly Pro Leu Gln Val Ile
225                 230                 235                 240

Phe Ile Met Gly Cys Gln Thr Met Ile Val Pro Ala Ile Phe Ala Thr
                245                 250                 255

Leu Glu Asn Gly Val Gly Phe Glu Gly Met Ser Ser Leu Thr Ala Thr
            260                 265                 270

Leu Ala Val Ile Ser Leu Pro Leu Ser Ser Met Trp Ala Ala Ala Gln
        275                 280                 285

Thr Asp Gly Pro Ser Pro Gln Ser Thr Pro Arg Asp Gly Tyr Arg Arg
    290                 295                 300

Phe Ser Thr Arg Arg Ser Ala Leu Asn Arg Ser Asp Pro Ser Gly Gly
305                 310                 315                 320

Arg Ser Val Asp Met Asn Thr Leu Asp Ser Thr Gly Asn Asp Ser Leu
                325                 330                 335

Ala Leu His Val Asp Lys Thr Phe Thr Val Glu Ser Ser Pro Ser Ser
            340                 345                 350

Gln Ser Gln Ala Gly Pro His Lys Glu Arg Gly Phe Glu Phe Ala
        355                 360                 365
```

<210> SEQ ID NO 103
<211> LENGTH: 1104
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 103

```
atggagcaaa tcccagtcta cgagcgtcca ggtttcaacc cacacaagca aaacattacc     60

ttgttcaagc atgatggttc tactgttact gtcggtttgc atgagttgga cgccatgttc    120

actcattcca tcagagttgc tgtcgtcttc gcctctcaaa ttggtgcttg tgctttgttg    180

tctgttatcg ttgctatggt caccaagaga gaaaagagac gtgctttgtt cttcttgcac    240

attatttcct tgttgttggt cgttgttcgt tccgtcttgc aaatcttgta cttcgtcggt    300

ccatgggctg aaacttataa ttacgtcgcc tactactatg aagacattcc tttgtctgac    360

aaattgattt ccatttgggc tggtattatc caattgattt tgaatatctg tattttgtta    420

tctttgatct tgcaagttcg tgtcgtttac gccacctctc caaaattgaa cactattatg    480

actttagtct cttgtgttat cgcttctatt tctgtcggtt tcttctttac tgtcatcgtt    540

caaatttctg aggctatttt aaacggtgtt ggttacgacg gttgggttta caaagtccat    600

agaggtgtct tcgctggtgc tatcgccttc ttctctttca tcttcatctt taagttggcc    660

ttcgctatca gaagaagaaa ggctttgggt ttgcaaagat tcggtccatt gcaagttatc    720

ttcatcatgg gttgtcaaac tatgattgtt ccagctatct ttgctacttt ggaaaacggt    780

gttggtttcg aaggtatgtc ctctttgact gctaccttgg ctgtcatttc cttaccattg    840

tcttctatgt gggccgccgc tcaaaccgac ggtccatctc cacaatccac tccaagagac    900

ggttatagaa gattctctac tcgtagatct gccttgaaca gatctgaccc atctggtggt    960

agatctgttg acatgaacac cttggactct accggtaacg attccttagc tttgcacgtt   1020

gataagactt ttactgttga atcttcccca tcctcccaat ctcaagctgg tccacacaag   1080
```

gaaagaggtt tcgaattcgc ctag 1104

<210> SEQ ID NO 104
<211> LENGTH: 527
<212> TYPE: PRT
<213> ORGANISM: Dactylellina haptotyla

<400> SEQUENCE: 104

Met Asp His Asn Thr Gln His Phe Asn Arg Pro Glu Tyr Ile Glu Ile
1 5 10 15

Pro Val Pro Pro Ser Lys Gly Phe Asn Pro His Thr Asn Pro Ala Phe
20 25 30

Phe Ile Tyr Pro Asp Gly Ser Asn Met Thr Phe Trp Phe Gly Gln Ile
35 40 45

Asp Asp Phe Arg Arg Asp Gln Leu Phe Thr Asn Thr Ile Phe Ser Ile
50 55 60

Gln Ile Gly Ala Ala Leu Val Ile Leu Cys Val Met Phe Cys Val Thr
65 70 75 80

His Ala Asp Lys Arg Lys Thr Ile Val Tyr Leu Leu Asn Val Ser Asn
85 90 95

Leu Phe Val Val Ile Ile Arg Gly Val Phe Phe Val His Tyr Phe Met
100 105 110

Gly Gly Leu Ala Arg Thr Tyr Thr Thr Phe Thr Trp Asp Thr Ser Asp
115 120 125

Val Gln Gln Ser Glu Lys Ala Thr Ser Ile Val Ser Ser Ile Cys Ser
130 135 140

Leu Ile Leu Met Ile Gly Thr Gln Ile Ser Leu Leu Leu Gln Val Arg
145 150 155 160

Ile Cys Tyr Ala Leu Asn Pro Arg Ser Lys Thr Ala Ile Leu Val Thr
165 170 175

Cys Gly Ser Ile Ser Gly Ile Ala Thr Thr Ala Tyr Leu Leu Leu Gly
180 185 190

Ala Tyr Thr Ile Gln Leu Arg Glu Lys Pro Pro Asp Met Lys Phe Met
195 200 205

Lys Trp Ala Lys Pro Val Val Asn Ala Leu Val Ala Leu Ser Ile Val
210 215 220

Ser Phe Ser Gly Ile Phe Ser Trp Arg Met Phe Gln Ser Val Arg Asn
225 230 235 240

Arg Arg Arg Met Gly Phe Thr Gly Ile Gly Ser Leu Glu Ser Leu Leu
245 250 255

Ala Ser Gly Phe Gln Cys Leu Val Phe Pro Gly Leu Val Thr Thr Ala
260 265 270

Leu Thr Val Ala Gly Ser Thr Trp Tyr Ile Ala Val Asn Leu Thr Thr
275 280 285

Pro Ser Asp Leu Thr Ala Ile Tyr Asn Cys Ser Ala Phe Phe Ala Tyr
290 295 300

Ala Phe Ser Ile Pro Leu Leu Lys Glu Arg Ala Gln Val Glu Lys Thr
305 310 315 320

Ile Ser Val Val Ile Ala Ile Ala Gly Val Leu Val Val Ala Tyr Gly
325 330 335

Asp Gly Ala Asp Asp Gly Ser Thr Ser Asn Gly Glu Lys Ala Arg Leu
340 345 350

Gly Gly Asn Val Leu Ile Gly Ile Gly Ser Val Leu Tyr Gly Leu Tyr
355 360 365

```
Glu Val Leu Tyr Lys Lys Leu Leu Cys Pro Pro Ser Gly Ala Ser Pro
    370                 375                 380

Gly Arg Ser Val Val Phe Ser Asn Thr Val Cys Ala Cys Ile Gly Ala
385                 390                 395                 400

Phe Thr Leu Leu Phe Leu Trp Ile Pro Leu Pro Leu Leu His Trp Ser
                405                 410                 415

Gly Trp Glu Ile Phe Glu Leu Pro Thr Gly Lys Thr Ala Lys Leu Leu
            420                 425                 430

Gly Ile Ser Ile Ala Ala Asn Ala Thr Phe Ser Gly Ser Phe Leu Ile
        435                 440                 445

Leu Ile Ser Leu Thr Gly Pro Val Leu Ser Ser Val Ala Ala Leu Leu
    450                 455                 460

Thr Ile Phe Leu Val Ala Ile Thr Asp Arg Ile Leu Phe Gly Arg Glu
465                 470                 475                 480

Leu Thr Ser Ala Ala Ile Leu Gly Gly Leu Leu Ile Ile Ala Ala Phe
                485                 490                 495

Ala Leu Leu Ser Trp Ala Thr Trp Lys Glu Met Ile Glu Glu Asn Glu
            500                 505                 510

Lys Asp Thr Ile Asp Ser Ile Ser Asp Val Gly Asp His Asp Asp
        515                 520                 525


<210> SEQ ID NO 105
<211> LENGTH: 1584
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 105

atggaccaca acacccaaca cttcaacaga cctgaataca ttgaaatccc agttccacca      60

tctaagggtt tcaacccaca caccaaccct gctttcttca tctacccaga cggttctaat     120

atgacctttt ggttcggtca aatcgacgat ttcagacgtg accaattatt cactaacacc     180

atcttttcca ttcaaattgg tgccgctttg gtcatcttat gtgtcatgtt ttgtgttacc     240

cacgctgata agcgtaaaac cattgtctac ttgttaaacg tttccaactt gttcgttgtt     300

atcattagag gtgttttctt tgttcattac ttcatgggtg gtttggccag aacctatacc     360

actttcacct gggatacttc tgatgttcaa caatctgaga aggctacttc cattgtctcc     420

tctatttgtt ctttgatttt gatgatcggt actcaaatct ccttattgtt gcaagtcaga     480

atctgttacg ctttgaaccc aagatccaag accgctatct tggttacttg tggttctatt     540

tccggtattg ctaccactgc ttatttattg ttgggtgctt acactattca attgagagaa     600

aagccaccag acatgaagtt catgaagtgg gctaagccag ttgttaacgc tttggttgcc     660

ttgtccattg tctccttttc tggtattttc tcttggagaa tgttccaatc tgtcagaaac     720

agaagaagaa tgggtttcac tggtatcggt tccttggaat ctttgttggc ttctggtttc     780

caatgtttag tcttccctgg tttggttact accgctttga ccgtcgccgg ttccacttgg     840

tatatcgctg ttaacttaac tactccatct gacttgaccg ctatttacaa ctgttccgct     900

tttttcgctt atgctttctc cattccattg ttaaaggaaa gagctcaagt tgaaaagacc     960

atttctgttg tcattgctat cgctggtgtc ttagtcgttg cttacggtga cggtgctgac    1020

gacggttcca cctctaacgg tgaaaaggct agattgggtg gtaacgtctt gatcggtatc    1080

ggttctgtct tgtatggttt atacgaagtc ttgtataaga agttattatg tccaccatct    1140
```

```
ggtgcttccc caggtagatc tgttgttttc tctaataccg tttgtgcttg catcggtgct   1200

ttcactttgt tattcttgtg gatcccattg ccattgttgc actggtccgg ttgggaaatt   1260

tttgaattgc caaccggtaa gactgctaag ttattgggta tttccattgc cgctaacgcc   1320

accttctctg gttctttctt gatcttaatt tctttgactg gtccagtttt gtcctctgtt   1380

gccgccttgt tgaccatttt cttggttgct attactgaca gaattttatt cggtagagaa   1440

ttgacttctg ctgccatttt gggtggtttg ttgatcatcg ctgccttcgc tttgttatct   1500

tgggctactt ggaaggaaat gattgaagag aacgagaagg atactatcga ttccatctct   1560

gacgttggtg accacgatga ctag                                          1584
```

```
<210> SEQ ID NO 106
<211> LENGTH: 468
<212> TYPE: PRT
<213> ORGANISM: Sporothrix scheckii

<400> SEQUENCE: 106

Met Lys Pro Ala Ala Gly Pro Ala Ser Ser Pro Phe Asp Pro Phe Asn
1               5                   10                  15

Gln Thr Phe Tyr Leu Thr Gly Pro Asp Asn Thr Thr Val Pro Val Ser
            20                  25                  30

Val Pro Gln Val Asp Tyr Ile Trp His Tyr Ile Ile Gly Thr Ser Ile
        35                  40                  45

Asn Tyr Gly Ser Gln Ile Gly Ala Cys Leu Leu Met Leu Leu Val Met
    50                  55                  60

Leu Thr Leu Thr Ser Lys Ser Arg Phe Ser Arg Ala Ala Thr Leu Ile
65                  70                  75                  80

Asn Val Ala Ser Leu Leu Ile Gly Val Ile Arg Cys Val Leu Leu Ala
                85                  90                  95

Val Tyr Phe Thr Ser Ser Leu Thr Glu Leu Tyr Ala Leu Phe Val Gly
            100                 105                 110

Asp Tyr Ser Gln Val Arg Arg Ser Asp Leu Cys Val Ser Ala Val Ala
        115                 120                 125

Thr Phe Phe Ser Leu Pro Gln Leu Val Leu Ile Glu Ala Ala Leu Phe
    130                 135                 140

Leu Gln Ala Tyr Ser Met Ile Lys Met Trp Pro Ser Leu Trp Arg Ala
145                 150                 155                 160

Val Val Leu Ala Met Ser Val Val Val Ala Val Cys Ala Ile Gly Phe
                165                 170                 175

Lys Phe Ala Ser Val Val Met Arg Met Arg Ser Thr Leu Thr Leu Asp
            180                 185                 190

Asp Ser Leu Asp Phe Trp Leu Val Glu Val Asp Leu Ala Phe Thr Ala
        195                 200                 205

Thr Thr Ile Phe Trp Phe Cys Phe Ile Tyr Ile Ile Arg Leu Val Ile
    210                 215                 220

His Met Trp Glu Tyr Arg Ser Ile Leu Pro Pro Met Gly Ser Val Ser
225                 230                 235                 240

Ala Met Glu Val Leu Val Met Thr Asn Gly Ala Leu Met Leu Val Pro
                245                 250                 255

Val Ile Phe Ala Ala Ile Glu Ile Asn Gly Leu Ser Ser Phe Glu Ser
            260                 265                 270

Gly Ser Leu Val His Thr Ser Val Ile Val Leu Leu Pro Leu Gly Ser
        275                 280                 285
```

Leu Ile Ala Gln Ala Met Thr Arg Pro Asp Gly Tyr Val Gln Arg Thr
    290                 295                 300

Asn Thr Ser Gly Ala Ser Gly Ala Ser Gly Ala His Pro Gly Arg Asn
305                 310                 315                 320

Gly Ser Gly His Gly Gly His Gly Gly Ala Tyr Ser Arg Ala Met Thr
                325                 330                 335

Asn Thr Leu Asn Thr Leu Asp Thr Leu Asp Thr Val Asp Ser Lys Thr
            340                 345                 350

Ser Ile Met His His His His His His His Arg Asn His Ser Asn Gly
        355                 360                 365

Met Ser Lys Thr Lys Ala Asn Ser Gly Thr Trp Ser His Ala Ser Asp
    370                 375                 380

Ala Asn Ser Thr Asn Ala Met Ile Ser Gly Gly Ile Ala Thr Gln Val
385                 390                 395                 400

Arg Ile Gln Ala Asn Gln Ser Thr Leu Gly Asn Thr Gly Met Ser Gly
                405                 410                 415

Gly Ser Gly Ala Pro Asn Ser His Thr Arg Asn Asn Ser Leu Ala Ala
            420                 425                 430

Met Glu Pro Val Glu Lys Gln Leu His Asp Ile Asp Ala Thr Pro Leu
        435                 440                 445

Ser Ala Ser Asp Cys Arg Val Trp Val Asp Arg Glu Val Glu Val Arg
    450                 455                 460

Arg Asp Met Val
465

<210> SEQ ID NO 107
<211> LENGTH: 1407
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 107
atgaaacccg ccgctggacc tgcatctagt ccattcgacc catttaacca aacgttttac 60
ctgaccggtc cagataatac cactgtacca gtctcagtcc cacaagttga ctatatctgg 120
cattatatta ttggaacatc catcaactat ggttctcaga tcggagcctg tttacttatg 180
cttcttgtga tgttgacatt gacttcaaag tcaagatttt ctcgtgcggc cactctgatt 240
aacgtagcaa gcttattgat tggagtaatt cgttgtgttc ttttagctgt ctactttact 300
tcttctctaa ctgaattgta tgctctgttc gttggcgatt acagccaggt ccgtaggtct 360
gatctttgtg tctctgctgt ggcaaccttc tttagtctac cacaattagt tctaatagaa 420
gctgctttgt ttctacaggc ttatagtatg atcaaaatgt ggccatccct gtggagagca 480
gtggttttag ctatgtcagt ggtggtggct gtgtgtgcaa tcggttttaa gttcgcgtcc 540
gttgttatgc gtatgaggtc aacattaaca ttggacgatt ctttggattt ctggctagtg 600
gaagtcgatc tggcttttac agcaactact attttttggt tttgtttcat ctacattata 660
aggttggtta ttcatatgtg ggaatataga agcattttac caccaatggg gtctgtttct 720
gctatggagg ttcttgttat gaccaatgga gcgttgatgt tagttccagt gattttcgcc 780
gcaatagaaa tcaatggttt atcaagcttt gaatcagggt cactggttca tacatcagtg 840
attgtattat tacctttagg tagcttgata gcgcaagcaa tgacacgtcc agatgggtat 900
gtccaaagaa cgaatacatc tggagcatca ggcgcaagtg gtgcacatcc tggtagaaat 960

```
ggatccggac acggtggtca tggtggtgcg tactcaagag ccatgactaa taccctaaat   1020

acattggata cattggatac cgtagacagt aagacatcca taatgcatca tcatcatcac   1080

catcatagaa accactcaaa tggcatgagt aagacgaagg caaatagtgg aacatggagc   1140

catgcgtcag atgctaactc caccaatgct atgatcagcg gtggtatcgc aactcaagtt   1200

aggattcaag ctaatcagtc aaccttagga aatacgggga tgtccggggg ctctggagcc   1260

cctaattctc atactcgtaa taactcattg gctgctatgg aaccagtgga gaagcaactg   1320

catgatatcg atgccacacc tttaagcgca tctgattgca gggtctgggt tgatcgtgag   1380

gtcgaggtca gaagggacat ggtctag                                        1407


<210> SEQ ID NO 108
<211> LENGTH: 369
<212> TYPE: PRT
<213> ORGANISM: Yarrowia lipolytica

<400> SEQUENCE: 108

Met Gln Leu Pro Pro Arg Pro Asp Phe Asp Ile Ala Thr Leu Val Ala
1               5                   10                  15

Ser Ile Thr Val Pro Glu Thr Glu Leu Val Leu Gly Gln Met Pro Leu
            20                  25                  30

Gly Ala Leu Glu Gln Leu Tyr Gln Asn Arg Leu Arg Leu Ala Ile Leu
        35                  40                  45

Phe Gly Val Arg Val Gly Ala Ala Val Leu Thr Leu Ile Ala Met His
    50                  55                  60

Leu Ile Ser Lys Lys Asn Arg Thr Lys Ile Leu Phe Leu Ala Asn Gln
65                  70                  75                  80

Met Ser Leu Ile Met Leu Ile Ile His Ala Ala Leu Tyr Phe Arg Phe
                85                  90                  95

Leu Leu Gly Pro Phe Ala Ser Met Leu Met Met Val Ala Tyr Ile Val
            100                 105                 110

Asp Pro Arg Ser Asn Val Ser Asn Asp Ile Ser Val Ser Val Ala Thr
        115                 120                 125

Asn Val Phe Met Met Leu Met Ile Met Ser Val Gln Leu Ser Leu Ala
    130                 135                 140

Val Gln Thr Arg Ser Val Phe His Ala Trp Leu Lys Ser Arg Ile Tyr
145                 150                 155                 160

Val Thr Val Gly Leu Ile Leu Leu Ser Leu Val Val Phe Val Phe Trp
                165                 170                 175

Thr Thr His Thr Ile Val Ser Cys Ile Val Leu Thr His Pro Thr Arg
            180                 185                 190

Asp Leu Pro Ser Met Gly Trp Thr Arg Leu Ala Ser Asp Val Ser Phe
        195                 200                 205

Ala Cys Ser Ile Ser Phe Ala Ser Leu Val Leu Leu Ala Lys Leu Val
    210                 215                 220

Thr Ala Ile Arg Val Arg Lys Thr Leu Gly Lys Lys Pro Leu Gly Tyr
225                 230                 235                 240

Thr Lys Val Leu Val Ile Met Ser Thr Gln Ser Leu Val Val Pro Ser
                245                 250                 255

Ile Leu Ile Ile Val Asn Tyr Ala Leu Pro Glu Lys Asn Ser Trp Ile
            260                 265                 270

Leu Ser Gly Val Ala Tyr Leu Met Val Val Leu Ser Leu Pro Leu Ser
        275                 280                 285

Ser Ile Trp Ala Thr Ala Val His Asp Asp Glu Met Gln Ser Asn Tyr
```

-continued

```
    290                 295                 300

Leu Leu Ser Ala Leu Lys Asp Gly His Val Gln Pro Ser Glu Ser Lys
305                 310                 315                 320

Leu Lys Thr Val Phe Leu Asn Arg Leu Arg Pro Phe Ser Thr Thr Thr
                325                 330                 335

Asn Arg Asp Asp Glu Ser Ser Val Asp Ser Pro Ala Met Pro Ser Pro
            340                 345                 350

Glu Ser Asp Val Thr Phe Leu Asn Thr Gly Phe Glu Cys Asp Glu Lys
        355                 360                 365

Met


<210> SEQ ID NO 109
<211> LENGTH: 1110
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 109

atgcaattgc caccacgtcc agacttcgac attgccactt tggttgcctc tatcactgtt     60

ccagaaactg aattggtctt gggtcaaatg ccattgggtg ctttagaaca attgtaccaa    120

aacagattgc gtttggctat tttgttcggt gtcagagtcg gtgctgctgt tttgaccttg    180

attgctatgc acttaatctc caagaagaac agaaccaaga tcttgttctt ggctaaccaa    240

atgtctttga tcatgttgat catccatgct gctttgtact tcagattctt gttgggtcca    300

ttcgcctcca tgttgatgat ggttgcttac atcgttgatc caagatctaa cgtctctaac    360

gatatctctg tttctgttgc caccaacgtt ttcatgatgt tgatgattat gtccgtccaa    420

ttgtctttgg ctgttcaaac ccgttctgtt ttccacgctt ggttgaagtc tcgtatttac    480

gttaccgttg gtttaatctt gttgtccttg gtcgtcttcg tcttctggac cacccacact    540

atcgtttctt gtatcgtttt aacccatcca actagagact tgccatctat gggttggact    600

agattagctt ctgacgtttc cttcgcttgt tctatctctt tcgcttcttt ggtcttgttg    660

gctaagttgg tcaccgccat cagagttaga aagaccttgg gtaagaagcc attgggttac    720

accaaggttt tggtcatcat gtccactcaa tctttagtcg ttccatctat cttgattatc    780

gttaactacg ctttgccaga aaaaaactct tggatcttgt ctggtgtcgc ttacttgatg    840

gttgttttgt ccttaccatt gtcctccatt tgggctaccg ccgtccatga cgacgaaatg    900

caatccaact acttgttgtc tgccttgaaa gatggtcacg ttcaaccatc cgaatctaag    960

ttgaagactg ttttcttgaa cagattgaga ccattctcta ctaccactaa cagagacgat   1020

gaatcctctg ttgattcccc agccatgcca tctccagaat ctgatgttac cttcttgaac   1080

actggtttcg aatgtgacga aaagatgtag                                    1110


<210> SEQ ID NO 110
<211> LENGTH: 471
<212> TYPE: PRT
<213> ORGANISM: Torulaspora delbrueckii

<400> SEQUENCE: 110

Met Ser Asp Ser Ala Gln Asn Leu Ser Asp Leu Ala Phe Asn Ser Ser
1               5                   10                  15

Tyr Asn Pro Leu Asp Ser Phe Ile Thr Phe Thr Ser Ile Tyr Gly Asp
            20                  25                  30
```

-continued

```
Asn Thr Ala Val Lys Phe Ser Val Leu Gln Asp Met Val Asp Val Asn
        35                  40                  45

Thr Asn Glu Ala Ile Val Tyr Gly Thr Arg Cys Gly Ala Ser Val Leu
    50                  55                  60

Thr Gln Ile Ile Met Trp Met Ile Ser Lys Asn Arg Arg Thr Pro Val
65                  70                  75                  80

Phe Ile Ile Asn Gln Val Ser Leu Thr Leu Ile Leu Ile His Ser Ala
                85                  90                  95

Leu Tyr Phe Lys Tyr Leu Leu Ser Gly Phe Gly Ser Val Val Tyr Gly
            100                 105                 110

Leu Thr Ala Phe Pro Gln Leu Ile Lys Pro Gly Asp Leu Arg Ala Phe
        115                 120                 125

Ala Ala Ala Asn Ile Val Met Val Leu Leu Val Ala Ser Ile Glu Ala
    130                 135                 140

Ser Leu Ile Phe Gln Val Lys Val Ile Phe Thr Gly Asp Asn Met Lys
145                 150                 155                 160

Arg Val Gly Leu Ile Leu Thr Ile Ile Cys Thr Cys Met Gly Leu Ala
                165                 170                 175

Thr Val Thr Met Tyr Phe Ile Thr Ala Val Lys Ser Ile Val Ser Leu
            180                 185                 190

Tyr Arg Asp Met Ser Gly Ser Ser Thr Val Leu Tyr Asn Val Ser Leu
        195                 200                 205

Ile Met Leu Ala Ser Ser Ile His Phe Met Ala Leu Ile Leu Val Val
    210                 215                 220

Lys Leu Phe Leu Ala Val Arg Ser Arg Arg Phe Leu Gly Leu Lys Gln
225                 230                 235                 240

Phe Asp Ser Phe His Ile Leu Leu Ile Ile Ser Cys Gln Thr Leu Leu
                245                 250                 255

Val Pro Ser Leu Leu Phe Ile Ile Ala Tyr Ser Phe Pro Ser Ser Lys
            260                 265                 270

Asn Ile Glu Ser Leu Lys Ala Ile Ala Val Leu Thr Val Val Leu Ser
        275                 280                 285

Leu Pro Leu Ser Ser Met Trp Ala Thr Ala Ala Asn Asn Phe Thr Asn
    290                 295                 300

Ser Ser Ser Ser Gly Ser Asp Ser Ala Pro Thr Asn Gly Gly Phe Tyr
305                 310                 315                 320

Gly Arg Gly Ser Ser Asn Leu Tyr Pro Glu Lys Thr Asp Asn Arg Ser
                325                 330                 335

Pro Lys Gly Ala Arg Asn Ala Leu Tyr Glu Leu Arg Ser Lys Asn Asn
            340                 345                 350

Ala Glu Gly Gln Ala Asp Ile Tyr Thr Val Thr Asp Ile Glu Asn Asp
        355                 360                 365

Ile Phe Asn Asp Leu Ser Lys Pro Val Glu Gln Asn Ile Phe Ser Asp
    370                 375                 380

Val Gln Ile Ile Asp Ser His Ser Leu His Lys Ala Cys Ser Lys Glu
385                 390                 395                 400

Asp Pro Val Met Thr Leu Tyr Thr Pro Asn Thr Ala Ile Glu Gly Glu
                405                 410                 415

Glu Arg Lys Leu Trp Thr Ser Asp Cys Ser Cys Ser Thr Asn Gly Ser
            420                 425                 430

Thr Pro Val Lys Lys Lys Ser Thr Gly Glu Tyr Ala Asn Leu Pro Pro
        435                 440                 445

His Leu Leu Arg Tyr Asp Glu Asn Tyr Asp Glu Glu Ala Gly Gly Arg
```

450 455 460

Arg Lys Ala Ser Leu Lys Trp
465 470

<210> SEQ ID NO 111
<211> LENGTH: 1416
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 111
atgtctgact ccgcccaaaa cttgtccgat ttggccttca actcttctta taacccattg 60
gactccttta ttacctttac ctctatctac ggtgataaca ctgctgttaa gttctccgtt 120
ttacaagaca tggttgacgt taatactaat gaagccatcg tttacggtac ccgttgtggt 180
gcttctgtct tgacccaaat tatcatgtgg atgatttcta aaaacagaag aaccccagtc 240
tttattatta accaagtttc tttgactttg attttaattc actctgcctt gtacttcaag 300
tacttgttgt ctggtttcgg ttccgttgtc tacggtttga ctgctttccc acaattgatt 360
aagccaggtg atttgagagc tttcgctgct gctaacatcg ttatggtctt gttggtcgct 420
tctattgaag cttccttaat cttccaagtc aaagttatct tcaccggtga taacatgaag 480
agagtcggtt taatcttgac tattatttgt acttgtatgg gtttagctac tgttaccatg 540
tactttatta ctgccgtcaa gtctattgtc tctttgtacc gtgacatgtc tggttcctcc 600
accgttttat ataacgtttc tttaattatg ttggcttcct ccatccactt tatggctttg 660
atcttggttg tcaaattgtt cttggctgtt agatctagaa gattcttggg tttgaaacaa 720
ttcgattctt tccacatttt gttgatcatc tcttgtcaaa ctttgttggt tccatcttta 780
ttattcatta ttgcttactc ttttccatct tctaagaaca ttgaatcttt gaaggctatc 840
gctgttttga ccgtcgtttt gtctttgcca ttgtcttcta tgtgggctac tgctgctaat 900
aacttcacta actcttcctc ctccggttcc gactccgctc caaccaatgg tggtttctac 960
ggtagaggtt cttccaactt gtatcctgaa aagactgata acagatcccc aaagggtgcc 1020
agaaacgctt tatacgaatt aagatctaag aacaatgctg agggtcaagc tgatatttac 1080
accgttaccg atattgaaaa cgatattttc aacgatttgt ccaagccagt tgagcaaaac 1140
attttctctg atgttcaaat tattgattct cattctttgc ataaggcttg ttctaaagaa 1200
gacccagtca tgactttgta cactccaaac actgctattg aaggtgagga gagaaaattg 1260
tggacttctg actgttcctg ttccactaac ggttccaccc cagttaagaa gaagtccacc 1320
ggtgaatacg ccaatttacc accacactta ttaagatatg atgaaaacta cgatgaagaa 1380
gctggtggta gacgtaaggc ctccttgaaa tggtag 1416

<210> SEQ ID NO 112
<211> LENGTH: 354
<212> TYPE: PRT
<213> ORGANISM: Komagataella pastoris

<400> SEQUENCE: 112

Met Glu Glu Tyr Ser Asp Ser Phe Asp Pro Ser Gln Gln Leu Leu Asn
1 5 10 15

Phe Thr Ser Leu Tyr Gly Glu Thr Asp Ala Thr Phe Ala Glu Leu Asp
20 25 30

Asp Tyr His Phe Tyr Val Val Lys Tyr Ala Ile Val Tyr Gly Ala Arg

```
        35                  40                  45

Ile Gly Val Gly Met Phe Cys Thr Leu Met Leu Phe Val Val Ser Lys
    50                  55                  60

Ser Trp Lys Thr Pro Ile Phe Val Leu Asn Gln Ser Ser Leu Ile Leu
65                  70                  75                  80

Leu Ile Ile His Ser Gly Phe Tyr Ile His Tyr Leu Thr Asn Gln Phe
                85                  90                  95

Ser Ser Leu Thr Tyr Met Phe Thr Arg Ile Pro Asn Glu Thr His Ala
            100                 105                 110

Gly Val Asp Leu Arg Ile Asn Val Val Thr Asn Thr Leu Tyr Ala Leu
        115                 120                 125

Leu Ile Leu Ser Ile Glu Ile Ser Leu Ile Tyr Gln Val Phe Val Ile
    130                 135                 140

Phe Lys Gly Val Tyr Glu Asn Ser Leu Arg Trp Ile Val Thr Ile Phe
145                 150                 155                 160

Thr Ala Leu Phe Ala Ala Ala Val Val Ala Ile Asn Phe Tyr Val Thr
                165                 170                 175

Thr Leu Gln Ser Val Ser Met Tyr Asn Ser Asn Val Asp Phe Pro Arg
            180                 185                 190

Trp Ala Ser Asn Val Pro Leu Ile Leu Phe Ala Ser Ser Val Asn Trp
        195                 200                 205

Ala Cys Leu Leu Leu Ser Leu Lys Leu Phe Phe Ala Ile Lys Val Arg
    210                 215                 220

Arg Ser Leu Gly Leu Arg Gln Phe Asp Thr Phe His Ile Leu Ala Ile
225                 230                 235                 240

Met Phe Ser Gln Thr Leu Ile Ile Pro Ser Ile Leu Ile Val Leu Gly
                245                 250                 255

Tyr Thr Gly Thr Arg Asp Arg Asp Ser Leu Ala Ser Leu Gly Phe Leu
            260                 265                 270

Leu Ile Val Val Ser Leu Pro Phe Ser Ser Met Trp Ala Ala Thr Ala
        275                 280                 285

Asn Asn Ser Asn Ile Pro Thr Ser Thr Gly Ser Phe Ala Trp Lys Asn
    290                 295                 300

Arg Tyr Ser Pro Ser Thr Tyr Ser Asp Asp Thr Thr Ala Val Ser Lys
305                 310                 315                 320

Ser Phe Thr Ile Met Thr Ala Lys Asp Glu Cys Phe Thr Thr Asp Thr
                325                 330                 335

Glu Gly Ser Pro Arg Phe Ile Lys Gly Asp Arg Thr Ser Glu Asp Leu
            340                 345                 350

His Phe


<210> SEQ ID NO 113
<211> LENGTH: 1065
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 113

atggaagaat actccgactc cttcgaccca tcccaacaat tgttgaactt cacttcctta     60

tacggtgaaa ccgatgctac tttcgctgaa ttggacgact accacttcta cgtcgttaag    120

tacgccatcg tttacggtgc cagaattggt gtcggtatgt tttgtacttt gatgttgttc    180

gttgtttcca agtcttggaa gactccaatc ttcgtcttga accaatcttc tttgattttg    240
```

```
ttgattattc actccggttt ctacatccac tacttgacca accaattctc ttccttgacc    300

tacatgttca ctagaatccc aaacgaaacc catgctggtg tcgatttgcg tattaacgtc    360

gttaccaaca ccttgtacgc tttgttgatc ttatctattg aaatttcctt aatttaccaa    420

gtcttcgtta tcttcaaagg tgtctacgaa aactctttaa gatggattgt tactattttc    480

accgctttat tcgccgccgc cgtcgttgct attaacttct acgtcactac tttgcaatct    540

gtctctatgt acaactctaa cgttgacttt ccaagatggg cttctaacgt cccattgatc    600

ttgttcgctt cttctgtcaa ctgggcttgt ttgttgttgt ccttgaagtt gttcttcgct    660

atcaaggtta gaagatcttt gggtttgaga caattcgaca cttttcacat cttggccatc    720

atgttctctc aaactttgat tatcccatcc attttgattg tcttgggtta cactggtacc    780

agagacagag actccttggc ttctttgggt ttcttgttga tcgttgtttc tttgccattt    840

tcctctatgt gggctgccac tgctaacaac tccaacatcc caacctctac cggttctttc    900

gcctggaaga acagatactc cccatctact tactccgacg ataccactgc tgtttccaag    960

tccttcacta ttatgaccgc taaggatgaa tgtttcacca ctgataccga aggttctcca   1020

agattcatca agggtgacag aacctccgaa gatttgcact tctag                   1065
```

```
<210> SEQ ID NO 114
<211> LENGTH: 14
<212> TYPE: PRT
<213> ORGANISM: Vibrio cholerae

<400> SEQUENCE: 114

Ala Asp Gly Tyr Gly Leu Ala Gly Phe Pro Pro Glu His Arg
1               5                   10


<210> SEQ ID NO 115
<211> LENGTH: 8
<212> TYPE: PRT
<213> ORGANISM: Vibrio cholerae

<400> SEQUENCE: 115

Ala Asp Ser Arg Pro Pro Asp Glu
1               5


<210> SEQ ID NO 116
<211> LENGTH: 10
<212> TYPE: PRT
<213> ORGANISM: Vibrio cholerae

<400> SEQUENCE: 116

Ala Asp Ser Arg Pro Pro Asp Glu Ile Lys
1               5                   10


<210> SEQ ID NO 117
<211> LENGTH: 12
<212> TYPE: PRT
<213> ORGANISM: Vibrio cholerae

<400> SEQUENCE: 117

Ala Asp Ser Arg Pro Pro Asp Glu Ile Lys Gln Ser
1               5                   10


<210> SEQ ID NO 118
<211> LENGTH: 18
<212> TYPE: PRT
<213> ORGANISM: Vibrio cholerae
```

<400> SEQUENCE: 118

Ala Asp Ser Arg Pro Pro Asp Glu Ile Lys Gln Ser Gly Gly Leu Met
1 5 10 15

Pro Arg

<210> SEQ ID NO 119
<211> LENGTH: 8
<212> TYPE: PRT
<213> ORGANISM: Vibrio cholerae

<400> SEQUENCE: 119

Ala Gly Phe Pro Pro Glu His Arg
1 5

<210> SEQ ID NO 120
<211> LENGTH: 15
<212> TYPE: PRT
<213> ORGANISM: Vibrio cholerae

<400> SEQUENCE: 120

Ala Leu Gly Gly Ile Pro Tyr Ser Gln Ile Tyr Gly Trp Tyr Arg
1 5 10 15

<210> SEQ ID NO 121
<211> LENGTH: 17
<212> TYPE: PRT
<213> ORGANISM: Vibrio cholerae

<400> SEQUENCE: 121

Ala Pro Ala Ala Asp Gly Tyr Gly Leu Ala Gly Phe Pro Pro Glu His
1 5 10 15

Arg

<210> SEQ ID NO 122
<211> LENGTH: 41
<212> TYPE: PRT
<213> ORGANISM: Vibrio cholerae

<400> SEQUENCE: 122

Ala Thr Ala Pro Asn Met Phe Asn Val Asn Asp Val Leu Gly Ala Tyr
1 5 10 15

Ser Pro His Pro Asp Glu Gln Glu Val Ser Ala Leu Gly Gly Ile Pro
20 25 30

Tyr Ser Gln Ile Tyr Gly Trp Tyr Arg
35 40

<210> SEQ ID NO 123
<211> LENGTH: 27
<212> TYPE: PRT
<213> ORGANISM: Vibrio cholerae

<400> SEQUENCE: 123

Ala Tyr Ser Pro His Pro Asp Glu Gln Glu Val Ser Ala Leu Gly Gly
1 5 10 15

Ile Pro Tyr Ser Gln Ile Tyr Gly Trp Tyr Arg
20 25

<210> SEQ ID NO 124
<211> LENGTH: 19
<212> TYPE: PRT
<213> ORGANISM: Vibrio cholerae

<400> SEQUENCE: 124

Asp Ile Ala Pro Ala Ala Asp Gly Tyr Gly Leu Ala Gly Phe Pro Pro
1 5 10 15

Glu His Arg

<210> SEQ ID NO 125
<211> LENGTH: 26
<212> TYPE: PRT
<213> ORGANISM: Vibrio cholerae

<400> SEQUENCE: 125

Asp Arg Tyr Tyr Ser Asn Leu Asp Ile Ala Pro Ala Ala Asp Gly Tyr
1 5 10 15

Gly Leu Ala Gly Phe Pro Pro Glu His Arg
20 25

<210> SEQ ID NO 126
<211> LENGTH: 9
<212> TYPE: PRT
<213> ORGANISM: Vibrio cholerae

<400> SEQUENCE: 126

Asp Ser Arg Pro Pro Asp Glu Ile Lys
1 5

<210> SEQ ID NO 127
<211> LENGTH: 31
<212> TYPE: PRT
<213> ORGANISM: Vibrio cholerae

<400> SEQUENCE: 127

Asp Val Leu Gly Ala Tyr Ser Pro His Pro Asp Glu Gln Glu Val Ser
1 5 10 15

Ala Leu Gly Gly Ile Pro Tyr Ser Gln Ile Tyr Gly Trp Tyr Arg
20 25 30

<210> SEQ ID NO 128
<211> LENGTH: 10
<212> TYPE: PRT
<213> ORGANISM: Vibrio cholerae

<400> SEQUENCE: 128

Phe Gly Val Leu Asp Glu Gln Leu His Arg
1 5 10

<210> SEQ ID NO 129
<211> LENGTH: 26
<212> TYPE: PRT
<213> ORGANISM: Vibrio cholerae

<400> SEQUENCE: 129

Phe Leu Asp Glu Tyr Gln Ser Lys Val Lys Arg Gln Ile Phe Ser Gly
1 5 10 15

Tyr Gln Ser Asp Ile Asp Thr His Asn Arg
20 25

<210> SEQ ID NO 130
<211> LENGTH: 31
<212> TYPE: PRT
<213> ORGANISM: Vibrio cholerae

<400> SEQUENCE: 130

```
Phe Leu Asp Glu Tyr Gln Ser Lys Val Lys Arg Gln Ile Phe Ser Gly
1               5                   10                  15

Tyr Gln Ser Asp Ile Asp Thr His Asn Arg Ile Lys Asp Glu Leu
            20                  25                  30


<210> SEQ ID NO 131
<211> LENGTH: 35
<212> TYPE: PRT
<213> ORGANISM: Vibrio cholerae

<400> SEQUENCE: 131

Phe Asn Val Asn Asp Val Leu Gly Ala Tyr Ser Pro His Pro Asp Glu
1               5                   10                  15

Gln Glu Val Ser Ala Leu Gly Gly Ile Pro Tyr Ser Gln Ile Tyr Gly
            20                  25                  30

Trp Tyr Arg
        35


<210> SEQ ID NO 132
<211> LENGTH: 28
<212> TYPE: PRT
<213> ORGANISM: Vibrio cholerae

<400> SEQUENCE: 132

Gly Ala Tyr Ser Pro His Pro Asp Glu Gln Glu Val Ser Ala Leu Gly
1               5                   10                  15

Gly Ile Pro Tyr Ser Gln Ile Tyr Gly Trp Tyr Arg
            20                  25


<210> SEQ ID NO 133
<211> LENGTH: 13
<212> TYPE: PRT
<213> ORGANISM: Vibrio cholerae

<400> SEQUENCE: 133

Gly Gly Ile Pro Tyr Ser Gln Ile Tyr Gly Trp Tyr Arg
1               5                   10


<210> SEQ ID NO 134
<211> LENGTH: 8
<212> TYPE: PRT
<213> ORGANISM: Vibrio cholerae

<400> SEQUENCE: 134

Gly Gln Ser Glu Tyr Phe Asp Arg
1               5


<210> SEQ ID NO 135
<211> LENGTH: 21
<212> TYPE: PRT
<213> ORGANISM: Vibrio cholerae

<400> SEQUENCE: 135

Gly Gln Ser Glu Tyr Phe Asp Arg Gly Thr Gln Met Asn Ile Asn Leu
1               5                   10                  15

Tyr Asp His Ala Arg
            20


<210> SEQ ID NO 136
<211> LENGTH: 13
<212> TYPE: PRT
<213> ORGANISM: Vibrio cholerae
```

<400> SEQUENCE: 136

Gly Thr Gln Met Asn Ile Asn Leu Tyr Asp His Ala Arg
1 5 10

<210> SEQ ID NO 137
<211> LENGTH: 8
<212> TYPE: PRT
<213> ORGANISM: Vibrio cholerae

<400> SEQUENCE: 137

Gly Thr Gln Thr Gly Phe Val Arg
1 5

<210> SEQ ID NO 138
<211> LENGTH: 21
<212> TYPE: PRT
<213> ORGANISM: Vibrio cholerae

<400> SEQUENCE: 138

Gly Thr Gln Thr Gly Phe Val Arg His Asp Asp Gly Tyr Val Ser Thr
1 5 10 15

Ser Ile Ser Leu Arg
20

<210> SEQ ID NO 139
<211> LENGTH: 11
<212> TYPE: PRT
<213> ORGANISM: Vibrio cholerae

<400> SEQUENCE: 139

Gly Tyr Gln Ser Asp Ile Asp Thr His Asn Arg
1 5 10

<210> SEQ ID NO 140
<211> LENGTH: 29
<212> TYPE: PRT
<213> ORGANISM: Vibrio cholerae

<400> SEQUENCE: 140

Gly Tyr Arg Asp Arg Tyr Tyr Ser Asn Leu Asp Ile Ala Pro Ala Ala
1 5 10 15

Asp Gly Tyr Gly Leu Ala Gly Phe Pro Pro Glu His Arg
20 25

<210> SEQ ID NO 141
<211> LENGTH: 9
<212> TYPE: PRT
<213> ORGANISM: Vibrio cholerae

<400> SEQUENCE: 141

His Asp Asp Gly Tyr Val Ser Thr Ser
1 5

<210> SEQ ID NO 142
<211> LENGTH: 13
<212> TYPE: PRT
<213> ORGANISM: Vibrio cholerae

<400> SEQUENCE: 142

His Asp Asp Gly Tyr Val Ser Thr Ser Ile Ser Leu Arg
1 5 10

<210> SEQ ID NO 143

<211> LENGTH: 11
<212> TYPE: PRT
<213> ORGANISM: Vibrio cholerae

<400> SEQUENCE: 143

His Phe Gly Val Leu Asp Glu Gln Leu His Arg
1 5 10

<210> SEQ ID NO 144
<211> LENGTH: 9
<212> TYPE: PRT
<213> ORGANISM: Vibrio cholerae

<400> SEQUENCE: 144

Lys Gln Ser Gly Gly Leu Met Pro Arg
1 5

<210> SEQ ID NO 145
<211> LENGTH: 20
<212> TYPE: PRT
<213> ORGANISM: Vibrio cholerae

<400> SEQUENCE: 145

Leu Asp Ile Ala Pro Ala Ala Asp Gly Tyr Gly Leu Ala Gly Phe Pro
1 5 10 15

Pro Glu His Arg
20

<210> SEQ ID NO 146
<211> LENGTH: 34
<212> TYPE: PRT
<213> ORGANISM: Vibrio cholerae

<400> SEQUENCE: 146

Asn Val Asn Asp Val Leu Gly Ala Tyr Ser Pro His Pro Asp Glu Gln
1 5 10 15

Glu Val Ser Ala Leu Gly Gly Ile Pro Tyr Ser Gln Ile Tyr Gly Trp
20 25 30

Tyr Arg

<210> SEQ ID NO 147
<211> LENGTH: 19
<212> TYPE: PRT
<213> ORGANISM: Vibrio cholerae

<400> SEQUENCE: 147

Gln Glu Val Ser Ala Leu Gly Gly Ile Pro Tyr Ser Gln Ile Tyr Gly
1 5 10 15

Trp Tyr Arg

<210> SEQ ID NO 148
<211> LENGTH: 13
<212> TYPE: PRT
<213> ORGANISM: Vibrio cholerae

<400> SEQUENCE: 148

Gln Ile Phe Ser Gly Tyr Gln Ser Asp Ile Asp Thr His
1 5 10

<210> SEQ ID NO 149
<211> LENGTH: 14
<212> TYPE: PRT
<213> ORGANISM: Vibrio cholerae

<400> SEQUENCE: 149

Gln Ile Phe Ser Gly Tyr Gln Ser Asp Ile Asp Thr His Asn
1               5                   10

<210> SEQ ID NO 150
<211> LENGTH: 15
<212> TYPE: PRT
<213> ORGANISM: Vibrio cholerae

<400> SEQUENCE: 150

Gln Ile Phe Ser Gly Tyr Gln Ser Asp Ile Asp Thr His Asn Arg
1               5                   10                  15

<210> SEQ ID NO 151
<211> LENGTH: 9
<212> TYPE: PRT
<213> ORGANISM: Vibrio cholerae

<400> SEQUENCE: 151

Gln Ser Asp Ile Asp Thr His Asn Arg
1               5

<210> SEQ ID NO 152
<211> LENGTH: 8
<212> TYPE: PRT
<213> ORGANISM: Vibrio cholerae

<400> SEQUENCE: 152

Gln Ser Gly Gly Leu Met Pro Arg
1               5

<210> SEQ ID NO 153
<211> LENGTH: 14
<212> TYPE: PRT
<213> ORGANISM: Vibrio cholerae

<400> SEQUENCE: 153

Arg His Asp Asp Gly Tyr Val Ser Thr Ser Ile Ser Leu Arg
1               5                   10

<210> SEQ ID NO 154
<211> LENGTH: 16
<212> TYPE: PRT
<213> ORGANISM: Vibrio cholerae

<400> SEQUENCE: 154

Arg Gln Ile Phe Ser Gly Tyr Gln Ser Asp Ile Asp Thr His Asn Arg
1               5                   10                  15

<210> SEQ ID NO 155
<211> LENGTH: 13
<212> TYPE: PRT
<213> ORGANISM: Vibrio cholerae

<400> SEQUENCE: 155

Ser Ala His Leu Val Gly Gln Thr Ile Leu Ser Gly His
1               5                   10

<210> SEQ ID NO 156
<211> LENGTH: 16
<212> TYPE: PRT
<213> ORGANISM: Vibrio cholerae

<400> SEQUENCE: 156

Ser Ala His Leu Val Gly Gln Thr Ile Leu Ser Gly His Ser Thr Tyr
1 5 10 15

<210> SEQ ID NO 157
<211> LENGTH: 17
<212> TYPE: PRT
<213> ORGANISM: Vibrio cholerae

<400> SEQUENCE: 157

Ser Ala His Leu Val Gly Gln Thr Ile Leu Ser Gly His Ser Thr Tyr
1 5 10 15

Tyr

<210> SEQ ID NO 158
<211> LENGTH: 28
<212> TYPE: PRT
<213> ORGANISM: Vibrio cholerae

<400> SEQUENCE: 158

Ser Ala His Leu Val Gly Gln Thr Ile Leu Ser Gly His Ser Thr Tyr
1 5 10 15

Tyr Ile Tyr Val Ile Ala Thr Ala Pro Asn Met Phe
20 25

<210> SEQ ID NO 159
<211> LENGTH: 8
<212> TYPE: PRT
<213> ORGANISM: Vibrio cholerae

<400> SEQUENCE: 159

Ser Asp Ile Asp Thr His Asn Arg
1 5

<210> SEQ ID NO 160
<211> LENGTH: 12
<212> TYPE: PRT
<213> ORGANISM: Vibrio cholerae

<400> SEQUENCE: 160

Ser Gly Tyr Gln Ser Asp Ile Asp Thr His Asn Arg
1 5 10

<210> SEQ ID NO 161
<211> LENGTH: 22
<212> TYPE: PRT
<213> ORGANISM: Vibrio cholerae

<400> SEQUENCE: 161

Ser Asn Leu Asp Ile Ala Pro Ala Ala Asp Gly Tyr Gly Leu Ala Gly
1 5 10 15

Phe Pro Pro Glu His Arg
20

<210> SEQ ID NO 162
<211> LENGTH: 8
<212> TYPE: PRT
<213> ORGANISM: Vibrio cholerae

<400> SEQUENCE: 162

Ser Gln Ile Tyr Gly Trp Tyr Arg
1 5

<210> SEQ ID NO 163
<211> LENGTH: 16
<212> TYPE: PRT
<213> ORGANISM: Vibrio cholerae

<400> SEQUENCE: 163

Ser Arg Pro Pro Asp Glu Ile Lys Gln Ser Gly Gly Leu Met Pro Arg
1 5 10 15

<210> SEQ ID NO 164
<211> LENGTH: 40
<212> TYPE: PRT
<213> ORGANISM: Vibrio cholerae

<400> SEQUENCE: 164

Thr Ala Pro Asn Met Phe Asn Val Asn Asp Val Leu Gly Ala Tyr Ser
1 5 10 15

Pro His Pro Asp Glu Gln Glu Val Ser Ala Leu Gly Gly Ile Pro Tyr
20 25 30

Ser Gln Ile Tyr Gly Trp Tyr Arg
35 40

<210> SEQ ID NO 165
<211> LENGTH: 43
<212> TYPE: PRT
<213> ORGANISM: Vibrio cholerae

<400> SEQUENCE: 165

Val Ile Ala Thr Ala Pro Asn Met Phe Asn Val Asn Asp Val Leu Gly
1 5 10 15

Ala Tyr Ser Pro His Pro Asp Glu Gln Glu Val Ser Ala Leu Gly Gly
20 25 30

Ile Pro Tyr Ser Gln Ile Tyr Gly Trp Tyr Arg
35 40

<210> SEQ ID NO 166
<211> LENGTH: 23
<212> TYPE: PRT
<213> ORGANISM: Vibrio cholerae

<400> SEQUENCE: 166

Val Lys Arg Gln Ile Phe Ser Gly Tyr Gln Ser Asp Ile Asp Thr His
1 5 10 15

Asn Arg Ile Lys Asp Glu Leu
20

<210> SEQ ID NO 167
<211> LENGTH: 8
<212> TYPE: PRT
<213> ORGANISM: Vibrio cholerae

<400> SEQUENCE: 167

Val Leu Asp Glu Gln Leu His Arg
1 5

<210> SEQ ID NO 168
<211> LENGTH: 10
<212> TYPE: PRT
<213> ORGANISM: Vibrio cholerae

<400> SEQUENCE: 168

Tyr Gln Ser Asp Ile Asp Thr His Asn Arg
1 5 10

<210> SEQ ID NO 169
<211> LENGTH: 23
<212> TYPE: PRT
<213> ORGANISM: Vibrio cholerae

<400> SEQUENCE: 169

Tyr Ser Asn Leu Asp Ile Ala Pro Ala Ala Asp Gly Tyr Gly Leu Ala
1 5 10 15

Gly Phe Pro Pro Glu His Arg
20

<210> SEQ ID NO 170
<211> LENGTH: 26
<212> TYPE: PRT
<213> ORGANISM: Vibrio cholerae

<400> SEQUENCE: 170

Tyr Ser Pro His Pro Asp Glu Gln Glu Val Ser Ala Leu Gly Gly Ile
1 5 10 15

Pro Tyr Ser Gln Ile Tyr Gly Trp Tyr Arg
20 25

<210> SEQ ID NO 171
<211> LENGTH: 9
<212> TYPE: PRT
<213> ORGANISM: Vibrio cholerae

<400> SEQUENCE: 171

Tyr Ser Gln Ile Tyr Gly Trp Tyr Arg
1 5

<210> SEQ ID NO 172
<211> LENGTH: 17
<212> TYPE: PRT
<213> ORGANISM: Vibrio cholerae

<400> SEQUENCE: 172

Tyr Tyr Ser Asn Leu Asp Ile Ala Pro Ala Ala Asp Gly Tyr Gly Leu
1 5 10 15

Ala

<210> SEQ ID NO 173
<211> LENGTH: 24
<212> TYPE: PRT
<213> ORGANISM: Vibrio cholerae

<400> SEQUENCE: 173

Tyr Tyr Ser Asn Leu Asp Ile Ala Pro Ala Ala Asp Gly Tyr Gly Leu
1 5 10 15

Ala Gly Phe Pro Pro Glu His Arg
20

<210> SEQ ID NO 174
<211> LENGTH: 9
<212> TYPE: PRT
<213> ORGANISM: Vibrio cholerae

<400> SEQUENCE: 174

Ala Ile Ala Ala Ile Ser Met Ala Asn
1 5

<210> SEQ ID NO 175
<211> LENGTH: 8
<212> TYPE: PRT
<213> ORGANISM: Vibrio cholerae

<400> SEQUENCE: 175

Glu Met Ala Ile Ile Thr Phe Lys
1               5

<210> SEQ ID NO 176
<211> LENGTH: 10
<212> TYPE: PRT
<213> ORGANISM: Vibrio cholerae

<400> SEQUENCE: 176

Phe Ser Tyr Thr Glu Ser Leu Ala Gly Lys
1               5                   10

<210> SEQ ID NO 177
<211> LENGTH: 11
<212> TYPE: PRT
<213> ORGANISM: Vibrio cholerae

<400> SEQUENCE: 177

Ile Phe Ser Tyr Thr Glu Ser Leu Ala Gly Lys
1               5                   10

<210> SEQ ID NO 178
<211> LENGTH: 14
<212> TYPE: PRT
<213> ORGANISM: Vibrio cholerae

<400> SEQUENCE: 178

Asn Asp Lys Ile Phe Ser Tyr Thr Glu Ser Leu Ala Gly Lys
1               5                   10

<210> SEQ ID NO 179
<211> LENGTH: 14
<212> TYPE: PRT
<213> ORGANISM: Vibrio cholerae

<400> SEQUENCE: 179

Asn Gly Ala Thr Phe Gln Val Glu Val Pro Gly Ser Gln His
1               5                   10

<210> SEQ ID NO 180
<211> LENGTH: 19
<212> TYPE: PRT
<213> ORGANISM: Vibrio cholerae

<400> SEQUENCE: 180

Asn Gly Ala Thr Phe Gln Val Glu Val Pro Gly Ser Gln His Ile Asp
1               5                   10                  15

Ser Gln Lys

<210> SEQ ID NO 181
<211> LENGTH: 20
<212> TYPE: PRT
<213> ORGANISM: Vibrio cholerae

<400> SEQUENCE: 181

Asn Gly Ala Thr Phe Gln Val Glu Val Pro Gly Ser Gln His Ile Asp
1               5                   10                  15

Ser Gln Lys Lys

20

<210> SEQ ID NO 182
<211> LENGTH: 10
<212> TYPE: PRT
<213> ORGANISM: Vibrio cholerae

<400> SEQUENCE: 182

Ser Tyr Thr Glu Ser Leu Ala Gly Lys Arg
1 5 10

<210> SEQ ID NO 183
<211> LENGTH: 12
<212> TYPE: PRT
<213> ORGANISM: Vibrio cholerae

<400> SEQUENCE: 183

Thr Pro His Ala Ile Ala Ala Ile Ser Met Ala Asn
1 5 10

<210> SEQ ID NO 184
<211> LENGTH: 8
<212> TYPE: PRT
<213> ORGANISM: Vibrio cholerae

<400> SEQUENCE: 184

Tyr Thr Glu Ser Leu Ala Gly Lys
1 5

<210> SEQ ID NO 185
<211> LENGTH: 13
<212> TYPE: PRT
<213> ORGANISM: Saccharomyces cerevisiae

<400> SEQUENCE: 185

Trp His Trp Leu Gln Leu Lys Pro Gly Gln Pro Met Tyr
1 5 10

<210> SEQ ID NO 186
<211> LENGTH: 13
<212> TYPE: PRT
<213> ORGANISM: Candida albicans

<400> SEQUENCE: 186

Gly Phe Arg Leu Thr Asn Phe Gly Tyr Phe Glu Pro Gly
1 5 10

<210> SEQ ID NO 187
<211> LENGTH: 469
<212> TYPE: PRT
<213> ORGANISM: Candida albicans

<400> SEQUENCE: 187

Met Asn Ile Asn Ser Thr Phe Ile Pro Asp Lys Pro Gly Asp Ile Ile
1 5 10 15

Ile Ser Tyr Ser Ile Pro Gly Leu Asp Gln Pro Ile Gln Ile Pro Phe
20 25 30

His Ser Leu Asp Ser Phe Gln Thr Asp Gln Ala Lys Ile Ala Leu Val
35 40 45

Met Gly Ile Thr Ile Gly Ser Cys Ser Met Thr Leu Ile Phe Leu Ile
50 55 60

Ser Ile Met Tyr Lys Thr Asn Lys Leu Thr Asn Leu Lys Leu Lys Leu
65 70 75 80

```
Lys Leu Lys Tyr Ile Leu Gln Trp Ile Asn Gln Lys Ile Phe Thr Lys
                85                  90                  95

Lys Arg Asn Asp Asn Lys Gln Gln Gln Gln Gln Gln Gln Gln Gln Ile
            100                 105                 110

Glu Ser Ser Ser Tyr Asn Asn Thr Thr Thr Thr Leu Gly Gly Tyr Lys
        115                 120                 125

Leu Phe Leu Phe Tyr Leu Asn Ser Leu Ile Leu Leu Ile Gly Ile Ile
    130                 135                 140

Arg Ser Gly Cys Tyr Leu Asn Tyr Asn Leu Gly Pro Leu Asn Ser Leu
145                 150                 155                 160

Ser Phe Val Phe Thr Gly Trp Tyr Asp Gly Ser Ser Phe Ile Ser Ser
                165                 170                 175

Asp Val Thr Asn Gly Phe Lys Cys Ile Leu Tyr Ala Leu Val Glu Ile
            180                 185                 190

Ser Leu Gly Phe Gln Val Tyr Val Met Phe Lys Thr Ser Asn Leu Lys
        195                 200                 205

Ile Trp Gly Ile Met Ala Ser Leu Leu Ser Ile Gly Leu Gly Leu Ile
    210                 215                 220

Val Val Ala Phe Gln Ile Asn Leu Thr Ile Leu Ser His Ile Arg Phe
225                 230                 235                 240

Ser Arg Ala Ile Ser Thr Asn Arg Ser Glu Glu Glu Ser Ser Ser Ser
                245                 250                 255

Leu Ser Ser Asp Ser Val Gly Tyr Val Ile Asn Ser Ile Trp Met Asp
            260                 265                 270

Leu Pro Thr Ile Leu Phe Ser Ile Ser Ile Asn Ile Met Thr Ile Leu
        275                 280                 285

Leu Ile Gly Lys Leu Ile Ile Ala Ile Arg Thr Arg Arg Tyr Leu Gly
    290                 295                 300

Leu Lys Gln Phe Asp Ser Phe His Ile Leu Leu Ile Gly Phe Ser Gln
305                 310                 315                 320

Thr Leu Ile Ile Pro Ser Ile Ile Leu Val Val His Tyr Phe Tyr Leu
                325                 330                 335

Ser Gln Asn Lys Asp Ser Leu Leu Gln Gln Ile Ser Leu Leu Leu Ile
            340                 345                 350

Ile Leu Met Leu Pro Leu Ser Ser Leu Trp Ala Gln Thr Ala Asn Asn
        355                 360                 365

Thr His Asn Ile Asn Ser Ser Pro Ser Leu Ser Phe Ile Ser Arg His
    370                 375                 380

His Leu Ser Asp Ser Ser Arg Ser Gly Gly Ser Asn Thr Ile Val Ser
385                 390                 395                 400

Asn Gly Gly Ser Asn Gly Gly Gly Gly Gly Gly Gly Asn Phe Pro Val
                405                 410                 415

Ser Gly Ile Asp Ala Gln Leu Pro Pro Asp Ile Glu Lys Ile Leu His
            420                 425                 430

Glu Asp Asn Asn Tyr Lys Leu Leu Asn Ser Asn Asn Glu Ser Val Asn
        435                 440                 445

Asp Gly Asp Ile Ile Ile Asn Asp Glu Gly Met Ile Thr Lys Gln Ile
    450                 455                 460

Thr Ile Lys Arg Val
465
```

<210> SEQ ID NO 188
<211> LENGTH: 1410

<212> TYPE: DNA
<213> ORGANISM: Candida albicans

<400> SEQUENCE: 188
atgaatatca attcaacttt catacctgat aaaccaggcg atataattat tagttattca 60
attccaggat tagatcaacc aattcaaatt cctttccatt cattagattc atttcaaacc 120
gatcaagcta aaatagcttt agtcatgggg ataactattg ggagttgttc aatgacatta 180 attttttga tttctataat gtataaaact aataaattaa caaatttaaa attaaaatta 240
aaattaaaat atatcttgca atggataaat caaaaaatct tcaccaaaaa aaggaatgac 300
aacaaacaac aacaacaaca acaacaacaa caaattgaat catcatcata taacaatact 360
actactacgc tggggggtta taaattattt ttattttatc ttaattcatt gattttatta 420
attggtatta ttcgatcagg ttgttattta aattataatt taggtccatt aaattcactt 480
agttttgtat ttactggttg gtatgatgga tcatcattta tatcatccga tgtaactaat 540
ggatttaaat gtattttata tgctttagtg gaaatttcat taggtttcca agtttatgtg 600
atgttcaaaa cttcaaattt aaaaatttgg gggataatgg catcattatt atcaattggt 660
ttaggattga ttgttgttgc ctttcaaatc aatttaacaa ttttatctca tattcgattt 720
tcccgggcta tatcaactaa cagaagtgaa gaagaatcat catcatcatt atcatctgat 780
tcggttgggt atgtgattaa ttcaatatgg atggatttac caacaatatt attttccatt 840
agtattaata taatgacaat attattgatt ggtaaactta taattgctat tagaacaaga 900
cgttatttag gattgaaaca atttgatagt ttccatattt tattaattgg tttcagtcaa 960
acattaatta ttccttcaat tattttggtg gttcattatt tttatttatc acaaaataaa 1020
gattctttat tacaacaaat tagtctttta ttgattattt taatgttacc attaagttct 1080
ttatgggctc aaactgctaa taatactcat aatattaatt catctccaag tttatcattc 1140
atatctcgtc atcatctgtc tgatagtagt cgtagtggtg gttccaatac aattgttagt 1200
aatggtggta gtaatggtgg tggtggtggt ggtgggaatt tccctgtttc aggtattgat 1260
gcacaattac cacctgatat tgaaaaaatc ttacatgaag ataataatta taaattactt 1320
aatagtaata atgaaagtgt aaatgatgga gatattatca ttaatgatga aggtatgatt 1380
actaaacaaa tcaccatcaa aagagtgtag 1410

<210> SEQ ID NO 189
<211> LENGTH: 13
<212> TYPE: PRT
<213> ORGANISM: Candida glabrata

<400> SEQUENCE: 189

Trp His Trp Val Arg Leu Arg Lys Gly Gln Gly Leu Phe
1 5 10

<210> SEQ ID NO 190
<211> LENGTH: 417
<212> TYPE: PRT
<213> ORGANISM: Candida glabrata

<400> SEQUENCE: 190

Met Glu Met Gly Tyr Asp Pro Arg Met Tyr Asn Pro Arg Asn Glu Tyr
1 5 10 15

Leu Asn Phe Thr Ser Val Tyr Asp Val Asn Asp Thr Ile Arg Phe Ser
20 25 30

Thr Leu Asp Ala Ile Val Lys Gly Leu Leu Arg Ile Ala Ile Val His

```
        35                  40                  45

Gly Val Arg Leu Gly Ala Ile Phe Met Thr Leu Ile Ile Met Phe Ile
    50                  55                  60

Ser Ser Asn Thr Trp Lys Lys Pro Ile Phe Ile Ile Asn Met Val Ser
65                  70                  75                  80

Leu Met Leu Val Met Ile His Ser Ala Leu Ser Phe His Tyr Leu Leu
                85                  90                  95

Ser Asn Tyr Ser Ser Ile Ser Tyr Ile Leu Thr Gly Phe Pro Gln Leu
            100                 105                 110

Ile Thr Ser Asn Asn Lys Arg Ile Gln Asp Ala Ala Ser Ile Val Gln
        115                 120                 125

Val Leu Leu Val Ala Ala Ile Glu Ala Ser Leu Val Phe Gln Ile His
    130                 135                 140

Val Met Phe Thr Ile Glu Asn Ile Lys Leu Ile Arg Glu Ile Val Leu
145                 150                 155                 160

Ser Ile Ser Ile Ala Met Gly Leu Ala Thr Val Ala Thr Tyr Leu Ala
                165                 170                 175

Ala Ala Ile Lys Leu Ile Arg Gly Leu His Asp Glu Val Met Pro Gln
            180                 185                 190

Thr His Leu Ile Phe Asn Leu Ser Ile Ile Leu Leu Ala Ser Ser Ile
        195                 200                 205

Asn Phe Met Thr Phe Ile Leu Val Ile Lys Leu Phe Phe Ala Ile Arg
    210                 215                 220

Ser Arg Arg Tyr Leu Gly Leu Arg Gln Phe Asp Ala Phe His Ile Leu
225                 230                 235                 240

Leu Ile Met Phe Cys Gln Ser Leu Leu Ile Pro Ser Val Leu Tyr Ile
                245                 250                 255

Ile Val Tyr Ala Val Asp Ser Arg Ser Asn Gln Asp Tyr Leu Ile Pro
            260                 265                 270

Ile Ala Asn Leu Phe Val Val Leu Ser Leu Pro Leu Ser Ser Ile Trp
        275                 280                 285

Ala Asn Thr Ser Asn Asn Ser Ser Arg Ser Pro Lys Tyr Trp Lys Asn
    290                 295                 300

Ser Gln Thr Asn Lys Ser Asn Gly Ser Phe Val Ser Ser Ile Ser Val
305                 310                 315                 320

Asn Ser Asp Ser Gln Asn Pro Leu Tyr Lys Lys Ile Val Arg Phe Thr
                325                 330                 335

Ser Lys Gly Asp Thr Thr Arg Ser Ile Val Ser Asp Ser Thr Leu Ala
            340                 345                 350

Glu Val Gly Lys Tyr Ser Met Gln Asp Val Ser Asn Ser Asn Phe Glu
        355                 360                 365

Cys Arg Asp Leu Asp Phe Glu Lys Val Lys His Thr Cys Glu Asn Phe
    370                 375                 380

Gly Arg Ile Ser Glu Thr Tyr Ser Glu Leu Ser Thr Leu Asp Thr Thr
385                 390                 395                 400

Ala Leu Asn Glu Thr Arg Leu Phe Trp Lys Gln Gln Ser Gln Cys Asp
                405                 410                 415

Lys
```

<210> SEQ ID NO 191
<211> LENGTH: 1254
<212> TYPE: DNA
<213> ORGANISM: Candida glabrata

<400> SEQUENCE: 191

```
atggagatgg gctacgatcc aagaatgtat aatccaagaa atgaatactt gaatttcacg     60
tcggtatatg atgtaaatga cacaatcaga ttttcgactc tggacgccat tgtaaaagga    120
ttgcttagaa ttgccattgt tcatggagtt agattgggag caatattcat gacgttaata    180
ataatgttta tctcatcaaa tacatggaaa aaacccatat ttataattaa catggtgtcg    240
ttgatgttag ttatgattca ttccgcactt agcttccatt accttttatc gaattattct    300
tcaatttctt atatactgac agggtttcct cagttgatta caagcaataa taaacgaatt    360
caagatgcag cgagtatagt ccaagtttta ttggttgctg cgatagaagc atcattggta    420
tttcagattc atgttatgtt tacgattgaa aacattaagc ttattagaga aatagtactc    480
tctatatcga tagcaatggg attggcaaca gtggctacat atcttgctgc agcaataaag    540
ctgataagag gactgcatga tgaggtaatg ccacaaacac atcttatttt caatttatct    600
ataatattgc ttgcatcctc cataaatttt atgacattta tattggtcat taaacttttc    660
ttcgctatta gatctagaag atatctcggt cttcgtcaat tcgatgcttt tcatatttta    720
ttaatcatgt tctgccagtc attattgata ccctcagtat tatatattat agtttacgcg    780
gttgatagca gatctaatca ggattatctg attccaattg ccaatttatt tgttgtttta    840
tctttgccat tatcctctat ctgggctaac acatcaaata actcatccag atctccaaaa    900
tattggaaaa actctcaaac gaataagagc aatgggtctt ttgtctcttc aatatctgtc    960
aatagtgact cacaaaaccc tttgtacaaa aagattgtac gttttacatc aaaaggcgac   1020
actacccgta gtattgtaag tgattcaaca ttagcagagg tgggaaaata ctctatgcaa   1080
gacgttagca attcaaactt tgaatgtcga gaccttgatt ttgagaaggt aaaacatact   1140
tgcgaaaatt ttggcagaat atctgaaaca tatagtgagt taagtacttt agataccact   1200
gccctcaatg agactcggtt gttttggaaa caacaaagtc agtgtgacaa atag         1254
```

<210> SEQ ID NO 192
<211> LENGTH: 9
<212> TYPE: PRT
<213> ORGANISM: Paracoccidioides brasiliensis

<400> SEQUENCE: 192

```
Trp Cys Thr Arg Pro Gly Gln Gly Cys
1               5
```

<210> SEQ ID NO 193
<211> LENGTH: 356
<212> TYPE: PRT
<213> ORGANISM: Paracoccidioides brasiliensis

<400> SEQUENCE: 193

```
Met Ala Pro Ser Phe Asp Pro Phe Asn Gln Ser Val Val Phe His Lys
1               5                   10                  15

Ala Asp Gly Thr Pro Phe Asn Val Ser Ile His Glu Leu Asp Asp Phe
            20                  25                  30

Val Gln Tyr Asn Thr Lys Val Cys Ile Asn Tyr Ser Ser Gln Leu Gly
        35                  40                  45

Ala Ser Val Ile Ala Gly Leu Met Leu Ala Met Leu Thr His Ser Glu
    50                  55                  60

Lys Arg Arg Leu Pro Val Phe Phe Leu Asn Thr Phe Ala Leu Ala Met
65                  70                  75                  80

Asn Phe Ala Arg Leu Leu Cys Met Thr Ile Tyr Phe Thr Thr Gly Phe
```

```
                85                  90                  95

Asn Lys Ser Tyr Ala Tyr Phe Gly Gln Asp Tyr Ser Gln Val Pro Gly
            100                 105                 110

Ser Ala Tyr Ala Ala Ser Val Leu Gly Val Val Phe Thr Thr Leu Leu
        115                 120                 125

Val Ile Ser Met Glu Met Ser Leu Leu Ile Gln Thr Arg Val Val Cys
    130                 135                 140

Thr Thr Leu Pro Asp Ile Gln Arg Tyr Leu Leu Met Ala Val Ser Ser
145                 150                 155                 160

Ala Ile Ser Leu Met Ala Ile Gly Phe Arg Leu Gly Leu Met Val Glu
                165                 170                 175

Asn Cys Ile Ala Ile Val Gln Ala Ser Asn Phe Ala Pro Phe Ile Trp
            180                 185                 190

Leu Gln Ser Ala Ser Asn Ile Thr Ile Thr Ile Ser Thr Cys Phe Phe
        195                 200                 205

Ser Ala Val Phe Val Thr Lys Leu Ala Tyr Ala Leu Val Thr Arg Ile
    210                 215                 220

Arg Leu Gly Leu Thr Arg Phe Gly Ala Met Gln Val Met Phe Ile Met
225                 230                 235                 240

Ser Cys Gln Thr Met Val Ile Pro Ala Ile Phe Ser Ile Leu Gln Tyr
                245                 250                 255

Pro Leu Pro Lys Tyr Glu Met Asn Ser Asn Leu Phe Thr Leu Val Ala
            260                 265                 270

Ile Phe Leu Pro Leu Ser Ser Leu Trp Ala Ser Val Ala Thr Arg Ser
        275                 280                 285

Ser Phe Glu Thr Ser Ser Ser Gly Arg His Gln Tyr Leu Trp Pro Ser
    290                 295                 300

Glu Gln Ser Asn Asn Val Thr Asn Ser Glu Ile Lys Tyr Gln Val Ser
305                 310                 315                 320

Phe Ser Gln Asn His Thr Thr Leu Arg Ser Gly Gly Ser Val Ala Thr
                325                 330                 335

Thr Leu Ser Pro Asp Arg Leu Asp Pro Val Tyr Cys Glu Val Glu Ala
            340                 345                 350

Gly Thr Lys Ala
        355


<210> SEQ ID NO 194
<211> LENGTH: 1071
<212> TYPE: DNA
<213> ORGANISM: Paracoccidioides brasiliensis

<400> SEQUENCE: 194

atggcaccct cattcgaccc cttcaaccaa agcgtggtct tccacaaggc cgacggaact      60

ccattcaacg tctcaatcca tgaactagac gacttcgtgc agtacaacac caaagtctgc     120

atcaactact cttcccagct cggagcatct gtcattgcag gactcatgct tgccatgctg     180

acacactcag aaaagcgtcg tctgccagtt ttcttcctaa acacattcgc actggccatg     240

aactttgccc gcctgctctg catgaccatc tacttcacca cgggcttcaa caagtcctat     300

gcctactttg gtcaggatta ctcccaggtg cctgggagcg cctacgcagc ctctgtcttg     360

ggcgttgtct tcaccactct cctggtaatc agcatggaaa tgtccctcct gatccaaaca     420

agggttgtct gcacgaccct tccggatatc caacgttatc tactcatggc agtttcctcc     480

gcgatttccc tgatggccat cgggttccgc cttggcttaa tggttgagaa ctgcattgcc     540
```

-continued

```
attgtgcagg cgtcgaattt cgccccttttt atctggcttc aaagcgcctc gaacatcacc    600

attacgatca gcacatgttt cttcagtgcc gtctttgtta cgaaattggc atatgcactc    660

gtcactcgta tacgactagg cttgacgagg tttggtgcta tgcaggttat gttcatcatg    720

tcctgccaga ctatggtgat tccagccatc ttctcaattc tccaataccc actccccaag    780

tacgaaatga actccaacct ctttacgctg gtggccattt tcctccctct ttcctcgcta    840

tgggcttcag ttgctacgag atccagtttc gagacgtctt cttccggccg ccatcagtat    900

ctttggccaa gcgaacagag caataacgtc accaattcgg aaattaagta tcaggtcagc    960

ttctctcaga accacactac gttgcggtct ggagggtctg tggccacgac actctccccg   1020

gaccggctcg acccggttta ttgtgaagtt gaagctggca caaaggccta g            1071


<210> SEQ ID NO 195
<211> LENGTH: 10
<212> TYPE: PRT
<213> ORGANISM: Fusarium graminearum

<400> SEQUENCE: 195

Trp Cys Trp Trp Lys Gly Gln Pro Cys Trp
1               5                   10


<210> SEQ ID NO 196
<211> LENGTH: 386
<212> TYPE: PRT
<213> ORGANISM: Fusarium graminearum

<400> SEQUENCE: 196

Met Ser Lys Glu Val Phe Asp Pro Phe Thr Gln Asn Val Thr Phe Phe
1               5                   10                  15

Ala Pro Asp Gly Lys Thr Glu Ile Ser Ile Pro Val Ala Ala Ile Asp
            20                  25                  30

Gln Val Arg Arg Met Met Val Asn Thr Thr Ile Asn Tyr Ala Thr Gln
        35                  40                  45

Leu Gly Ala Cys Leu Ile Met Leu Val Val Leu Leu Val Met Val Pro
    50                  55                  60

Lys Glu Lys Phe Arg Arg Pro Phe Met Ile Leu Gln Ile Thr Ser Leu
65                  70                  75                  80

Val Ile Ser Cys Cys Arg Met Leu Leu Leu Ser Ile Phe His Ser Ser
                85                  90                  95

Gln Phe Leu Asp Phe Tyr Val Phe Trp Gly Asp Asp His Ser Arg Ile
            100                 105                 110

Pro Arg Ser Ala Tyr Ala Pro Ser Val Ala Gly Asn Thr Met Ser Leu
        115                 120                 125

Cys Leu Val Ile Ser Val Glu Thr Met Leu Met Ser Gln Ala Trp Thr
    130                 135                 140

Met Val Arg Leu Trp Pro Asn Val Trp Lys Tyr Ile Ile Ala Gly Val
145                 150                 155                 160

Ser Leu Ile Val Ser Ile Met Ala Ile Ser Val Arg Leu Ala Tyr Thr
                165                 170                 175

Ile Ile Gln Asn Asn Ala Val Leu Lys Leu Glu Pro Ala Phe His Met
            180                 185                 190

Phe Trp Leu Ile Lys Trp Thr Val Ile Met Asn Val Ala Ser Ile Ser
        195                 200                 205

Trp Trp Cys Ala Ile Phe Asn Ile Lys Leu Val Trp His Leu Ile Ser
    210                 215                 220
```

```
Asn Arg Gly Ile Leu Pro Ser Tyr Lys Thr Phe Thr Pro Met Glu Val
225                 230                 235                 240

Leu Ile Met Thr Asn Gly Ile Leu Met Ile Ile Pro Val Ile Phe Ala
                245                 250                 255

Ser Leu Glu Trp Ala His Phe Val Asn Phe Glu Ser Ala Ser Leu Thr
            260                 265                 270

Leu Thr Ser Val Ala Val Ile Leu Pro Leu Gly Thr Leu Ala Ala Gln
        275                 280                 285

Arg Ile Ala Ser Ser Ala Pro Ser Ser Ala Asn Ser Thr Gly Ala Ser
    290                 295                 300

Ser Gly Ile Arg Tyr Gly Val Ser Gly Pro Ser Ser Phe Thr Gly Phe
305                 310                 315                 320

Lys Ala Pro Ser Phe Ser Thr Gly Thr Thr Asp Arg Pro His Val Ser
                325                 330                 335

Ile Tyr Ala Arg Cys Glu Ala Gly Thr Ser Ser Arg Glu His Ile Asn
            340                 345                 350

Pro Gln Gly Val Glu Leu Ala Lys Leu Asp Pro Glu Thr Asp His His
        355                 360                 365

Val Arg Val Asp Arg Ala Phe Leu Gln Arg Glu Glu Arg Ile Arg Ala
    370                 375                 380

Pro Leu
385
```

<210> SEQ ID NO 197
<211> LENGTH: 1161
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 197

```
atgtctaagg aagttttcga cccattcact caaaacgtta ctttcttcgc tccagacggt     60
aagactgaaa tctctatccc agttgctgct atcgaccaag ttagaagaat gatggttaac    120
actactatca actacgctac tcaattgggt gcttgtttga tcatgttggt tgttttgttg    180
gttatggttc caaaggaaaa gttcagaaga ccattcatga tcttgcaaat cacttctttg    240
gttatctctt gttgtagaat gttgttgttg tctatcttcc actcttctca attcttggac    300
ttctacgttt tctggggtga cgaccactct agaatcccaa gatctgctta cgctccatct    360
gttgctggta acactatgtc tttgtgtttg gttatctctg ttgaaactat gttgatgtct    420
caagcttgga ctatggttag attgtggcca aacgtttgga agtacatcat cgctggtgtt    480
tctttgatcg tttctatcat ggctatctct gttagattgg cttacactat catccaaaac    540
aacgctgttt tgaagttgga accagctttc cacatgttct ggttgatcaa gtggactgtt    600
atcatgaacg ttgcttctat ctcttggtgg tgtgctatct tcaacatcaa gttggtttgg    660
cacttgatct ctaacagagg tatcttgcca tcttacaaga ctttcactcc aatggaagtt    720
ttgatcatga ctaacggtat cttgatgatc atcccagtta tcttcgcttc tttggaatgg    780
gctcacttcg ttaacttcga atctgcttct ttgactttga cttctgttgc tgttatcttg    840
ccattgggta ctttggctgc tcaaagaatc gcttcttctg ctccatcttc tgctaactct    900
actggtgctt cttctggtat cagatacggt gtttctggtc catcttcttt cactggtttc    960
aaggctccat ctttctctac tggtactact gacagaccac acgtttctat ctacgctaga   1020
tgtgaagctg gtacttcttc tagagaacac atcaacccac aaggtgttga attggctaag   1080
```

ttggacccag aaactgacca ccacgttaga gttgacagag ctttcttgca aagagaagaa 1140
agaatcagag ctccattgta g 1161

<210> SEQ ID NO 198
<211> LENGTH: 11
<212> TYPE: PRT
<213> ORGANISM: Magnaporthe oryzea

<400> SEQUENCE: 198

Gln Trp Cys Pro Arg Arg Gly Gln Pro Cys Trp
1 5 10

<210> SEQ ID NO 199
<211> LENGTH: 415
<212> TYPE: PRT
<213> ORGANISM: Magnaporthe oryzea

<400> SEQUENCE: 199

Met Asp Gln Thr Leu Ser Ala Thr Gly Thr Ala Thr Ser Pro Pro Gly
1 5 10 15

Pro Ala Leu Thr Val Asp Pro Arg Phe Gln Thr Ile Thr Met Leu Thr
20 25 30

Pro Ala Leu Met Gly Gln Gly Phe Glu Glu Val Gln Thr Thr Pro Ala
35 40 45

Glu Ile Asn Asp Val Tyr Phe Leu Ala Phe Asn Thr Ala Ile Gly Tyr
50 55 60

Ser Thr Gln Ile Gly Ala Cys Phe Ile Met Leu Leu Val Leu Leu Thr
65 70 75 80

Met Thr Ala Lys Ala Arg Phe Ala Arg Ile Pro Thr Ile Ile Asn Thr
85 90 95

Ala Ala Leu Val Val Ser Ile Ile Arg Cys Thr Leu Leu Val Ile Phe
100 105 110

Phe Thr Ser Thr Met Met Glu Phe Tyr Thr Ile Phe Ser Asp Asp Phe
115 120 125

Ser Phe Val His Pro Asn Asp Ile Arg Arg Ser Val Ala Ala Thr Val
130 135 140

Phe Ala Pro Leu Gln Leu Ala Leu Val Glu Ala Ala Leu Met Val Gln
145 150 155 160

Ala Trp Ala Met Val Glu Leu Trp Pro Arg Ala Trp Lys Val Ser Gly
165 170 175

Ile Ala Phe Ser Leu Ile Leu Ala Thr Val Thr Val Ala Phe Lys Cys
180 185 190

Ala Ser Ala Ala Val Thr Val Lys Ser Ala Leu Glu Pro Leu Asp Pro
195 200 205

Arg Pro Tyr Leu Trp Ile Arg Gln Thr Asp Leu Ala Phe Thr Thr Ala
210 215 220

Met Val Thr Trp Phe Cys Phe Leu Phe Asn Val Arg Leu Ile Met His
225 230 235 240

Met Trp Gln Asn Arg Ser Ile Leu Pro Thr Val Lys Gly Leu Ser Pro
245 250 255

Met Glu Val Leu Val Met Ala Asn Gly Leu Leu Met Val Phe Pro Val
260 265 270

Leu Phe Ala Gly Leu Tyr Tyr Gly Asn Phe Gly Gln Phe Glu Ser Ala
275 280 285

Ser Leu Thr Ile Thr Ser Val Val Leu Val Leu Pro Leu Gly Thr Leu

-continued

```
    290                 295                 300

Val Ala Gln Arg Leu Ala Val Asn Asn Thr Val Ala Gly Ser Ser Ala
305                 310                 315                 320

Asn Thr Asp Met Asp Asp Lys Leu Ala Phe Leu Gly Asn Ala Thr Thr
                325                 330                 335

Val Thr Ser Ser Ala Ala Gly Phe Ala Gly Ser Ser Ala Ser Ala Thr
            340                 345                 350

Arg Ser Arg Leu Ala Ser Pro Arg Gln Asn Ser Gln Leu Ser Thr Ser
        355                 360                 365

Val Ser Ala Gly Lys Pro Arg Ala Asp Pro Ile Asp Leu Glu Leu Gln
    370                 375                 380

Arg Ile Asp Asp Glu Asp Asp Asp Phe Ser Arg Ser Gly Ser Ala Gly
385                 390                 395                 400

Gly Val Arg Val Glu Arg Ser Ile Glu Arg Arg Glu Glu Arg Leu
                405                 410                 415


<210> SEQ ID NO 200
<211> LENGTH: 1248
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 200

atggaccaaa ctttgtctgc tactggtact gctacttctc caccaggtcc agctttgact     60

gttgacccaa gattccaaac tatcactatg ttgactccag ctttgatggg tcaaggtttc    120

gaagaagttc aaactactcc agctgaaatc aacgacgttt acttcttggc tttcaacact    180

gctatcggtt actctactca aatcggtgct tgtttcatca tgttgttggt tttgttgact    240

atgactgcta aggctagatt cgctagaatc ccaactatca tcaacactgc tgctttggtt    300

gtttctatca tcagatgtac tttgttggtt atcttcttca cttctactat gatggaattc    360

tacactatct tctctgacga cttctctttc gttcacccaa acgacatcag aagatctgtt    420

gctgctactg ttttcgctcc attgcaattg gctttggttg aagctgcttt gatggttcaa    480

gcttgggcta tggttgaatt gtggccaaga gcttggaagg tttctggtat cgctttctct    540

ttgatcttgg ctactgttac tgttgctttc aagtgtgctt ctgctgctgt tactgttaag    600

tctgctttgg aaccattgga cccaagacca tacttgtgga tcagacaaac tgacttggct    660

ttcactactg ctatggttac ttggttctgt ttcttgttca acgttagatt gatcatgcac    720

atgtggcaaa acagatctat cttgccaact gttaagggtt tgtctccaat ggaagttttg    780

gttatggcta acggtttgtt gatggttttc ccagttttgt tcgctggttt gtactacggt    840

aacttcggtc aattcgaatc tgcttctttg actatcactt ctgttgtttt ggttttgcca    900

ttgggtactt tggttgctca aagattggct gttaacaaca ctgttgctgg ttcttctgct    960

aacactgaca tggacgacaa gttggctttc ttgggtaacg ctactactgt tacttcttct   1020

gctgctggtt tcgctggttc ttctgcttct gctactagat ctagattggc ttctccaaga   1080

caaaactctc aattgtctac ttctgtttct gctggtaagc caagagctga cccaatcgac   1140

ttggaattgc aaagaatcga cgacgaagac gacgacttct ctagatctgg ttctgctggt   1200

ggtgttagag ttgaaagatc tatcgaaaga agagaagaaa gattgtag                1248


<210> SEQ ID NO 201
<211> LENGTH: 9
```

<212> TYPE: PRT
<213> ORGANISM: Botrytis cinerea

<400> SEQUENCE: 201

```
Trp Cys Gly Arg Pro Gly Gln Pro Cys
1               5
```

<210> SEQ ID NO 202
<211> LENGTH: 398
<212> TYPE: PRT
<213> ORGANISM: Botrytis cinerea

<400> SEQUENCE: 202

```
Met Ala Ser Asn Ser Ser Asn Phe Asp Pro Leu Thr Gln Ser Ile Thr
1               5                   10                  15

Ile Leu Met Ala Asp Gly Ile Thr Thr Val Ser Phe Thr Pro Leu Asp
            20                  25                  30

Ile Asp Phe Phe Tyr Tyr Tyr Asn Val Ala Cys Cys Ile Asn Tyr Gly
        35                  40                  45

Ala Gln Ala Gly Ala Cys Leu Leu Met Phe Phe Val Val Val Val Leu
    50                  55                  60

Thr Lys Ala Val Lys Arg Lys Thr Leu Leu Phe Val Leu Asn Val Leu
65                  70                  75                  80

Ser Leu Ile Phe Gly Phe Leu Arg Ala Met Leu Tyr Ala Ile Tyr Phe
                85                  90                  95

Leu Gln Gly Phe Asn Asp Phe Tyr Ala Ala Phe Thr Phe Asp Phe Ser
            100                 105                 110

Arg Val Pro Arg Ser Ser Tyr Ala Ser Ser Val Ala Gly Ser Val Ile
        115                 120                 125

Pro Leu Cys Met Thr Ile Thr Val Asn Met Ser Leu Tyr Leu Gln Ala
    130                 135                 140

Tyr Thr Val Cys Lys Asn Leu Asp Asp Ile Lys Arg Ile Ile Leu Thr
145                 150                 155                 160

Thr Leu Ser Ala Ile Val Ala Leu Leu Ala Ile Gly Phe Arg Phe Ala
                165                 170                 175

Ala Thr Val Val Asn Ser Val Ala Ile Leu Ala Thr Ser Ala Ser Ser
            180                 185                 190

Val Pro Met Gln Trp Leu Val Lys Gly Thr Leu Val Thr Glu Thr Ile
        195                 200                 205

Ser Ile Trp Phe Phe Ser Leu Ile Phe Thr Gly Lys Leu Val Trp Thr
    210                 215                 220

Leu Tyr Asn Arg Arg Arg Asn Gly Trp Arg Gln Trp Ser Ala Val Arg
225                 230                 235                 240

Ile Leu Ala Ala Met Gly Gly Cys Thr Met Val Ile Pro Ser Ile Phe
                245                 250                 255

Ala Ile Leu Glu Tyr Val Thr Pro Val Ser Phe Pro Glu Ala Gly Ser
            260                 265                 270

Ile Ala Leu Thr Ser Val Ala Leu Leu Leu Pro Ile Ser Ser Leu Trp
        275                 280                 285

Ala Gly Met Val Thr Asp Glu Glu Thr Ser Ala Ile Asp Val Ser Asn
    290                 295                 300

Leu Thr Gly Ser Arg Thr Met Leu Gly Ser Gln Ser Gly Asn Phe Ser
305                 310                 315                 320

Arg Lys Thr His Ala Ser Asp Ile Thr Ala Gln Ser Ser His Leu Asp
                325                 330                 335
```

-continued

```
Phe Ser Ser Arg Lys Gly Ser Asn Ala Thr Met Met Arg Lys Gly Ser
            340                 345                 350

Asn Ala Met Asp Gln Val Thr Thr Ile Asp Cys Val Val Glu Asp Asn
        355                 360                 365

Gln Ala Asn Arg Gly Leu Arg Asp Ser Thr Glu Met Asp Leu Glu Ala
    370                 375                 380

Met Gly Val Arg Val Asn Lys Ser Tyr Gly Val Gln Lys Ala
385                 390                 395


<210> SEQ ID NO 203
<211> LENGTH: 1197
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 203

atggcttcta actcttctaa cttcgaccca ttgactcaat ctatcactat cttgatggct     60

gacggtatca ctactgtttc tttcactcca ttggacatcg acttcttcta ctactacaac    120

gttgcttgtt gtatcaacta cggtgctcaa gctggtgctt gtttgttgat gttcttcgtt    180

gttgttgttt tgactaaggc tgttaagaga aagactttgt tgttcgtttt gaacgttttg    240

tctttgatct tcggtttctt gagagctatg ttgtacgcta tctacttctt gcaaggtttc    300

aacgacttct acgctgcttt cactttcgac ttctctagag ttccaagatc ttcttacgct    360

tcttctgttg ctggttctgt tatcccattg tgtatgacta tcactgttaa catgtctttg    420

tacttgcaag cttacactgt ttgtaagaac ttggacgaca tcaagagaat catcttgact    480

actttgtctg ctatcgttgc tttgttggct atcggtttca gattcgctgc tactgttgtt    540

aactctgttg ctatcttggc tacttctgct tcttctgttc caatgcaatg gttggttaag    600

ggtactttgg ttactgaaac tatctctatc tggttcttct ctttgatctt cactggtaag    660

ttggtttgga ctttgtacaa cagaagaaga aacggttgga gacaatggtc tgctgttaga    720

atcttggctg ctatgggtgg ttgtactatg gttatcccat ctatcttcgc tatcttggaa    780

tacgttactc cagtttcttt cccagaagct ggttctatcg ctttgacttc tgttgctttg    840

ttgttgccaa tctcttcttt gtgggctggt atggttactg acgaagaaac ttctgctatc    900

gacgtttcta acttgactgg ttctagaact atgttgggtt ctcaatctgg taacttctct    960

agaaagactc acgcttctga catcactgct caatcttctc acttggactt ctcttctaga   1020

aagggttcta acgctactat gatgagaaag ggttctaacg ctatggacca agttactact   1080

atcgactgtg ttgttgaaga caaccaagct aacagaggtt tgagagactc tactgaaatg   1140

gacttggaag ctatgggtgt tagagttaac aagtcttacg gtgttcaaaa ggcttag      1197


<210> SEQ ID NO 204
<211> LENGTH: 10
<212> TYPE: PRT
<213> ORGANISM: Aspergillus nidulans

<400> SEQUENCE: 204

Trp Cys Arg Phe Arg Gly Gln Val Cys Gly
1               5                   10


<210> SEQ ID NO 205
<211> LENGTH: 9
<212> TYPE: PRT
<213> ORGANISM: Aspergillus oryzae
```

<400> SEQUENCE: 205

Trp Cys Ala Leu Pro Gly Gln Gly Cys
1 5

<210> SEQ ID NO 206
<211> LENGTH: 10
<212> TYPE: PRT
<213> ORGANISM: Beauvaria bassiana

<400> SEQUENCE: 206

Trp Cys Met Arg Pro Gly Gln Pro Cys Trp
1 5 10

<210> SEQ ID NO 207
<211> LENGTH: 14
<212> TYPE: PRT
<213> ORGANISM: Candida lustianiae

<400> SEQUENCE: 207

Lys Trp Lys Trp Ile Lys Phe Arg Asn Thr Asp Val Ile Gly
1 5 10

<210> SEQ ID NO 208
<211> LENGTH: 13
<212> TYPE: PRT
<213> ORGANISM: Candida tenuis

<400> SEQUENCE: 208

Phe Ser Trp Asn Tyr Arg Leu Lys Trp Gln Pro Ile Ser
1 5 10

<210> SEQ ID NO 209
<211> LENGTH: 9
<212> TYPE: PRT
<213> ORGANISM: Neosartorya fischeri

<400> SEQUENCE: 209

Trp Cys His Leu Pro Gly Gln Gly Cys
1 5

<210> SEQ ID NO 210
<211> LENGTH: 11
<212> TYPE: PRT
<213> ORGANISM: Neurospora crassa

<400> SEQUENCE: 210

Gln Trp Cys Arg Ile His Gly Gln Ser Cys Trp
1 5 10

<210> SEQ ID NO 211
<211> LENGTH: 10
<212> TYPE: PRT
<213> ORGANISM: Pseudogymnoascus destructans

<400> SEQUENCE: 211

Phe Cys Trp Arg Pro Gly Gln Pro Cys Gly
1 5 10

<210> SEQ ID NO 212
<211> LENGTH: 10
<212> TYPE: PRT
<213> ORGANISM: Hypocrea jecorina

<400> SEQUENCE: 212

```
Trp Cys Tyr Arg Ile Gly Glu Pro Cys Trp
1               5                   10


<210> SEQ ID NO 213
<211> LENGTH: 10
<212> TYPE: PRT
<213> ORGANISM: Tuber melanosporum

<400> SEQUENCE: 213

Trp Thr Pro Arg Pro Gly Arg Gly Ala Tyr
1               5                   10


<210> SEQ ID NO 214
<211> LENGTH: 8
<212> TYPE: PRT
<213> ORGANISM: Dactylellina haptotyla

<400> SEQUENCE: 214

Trp Cys Val Tyr Asn Ser Cys Pro
1               5


<210> SEQ ID NO 215
<211> LENGTH: 10
<212> TYPE: PRT
<213> ORGANISM: Sporothrix scheckii

<400> SEQUENCE: 215

Tyr Cys Pro Leu Lys Gly Gln Ser Cys Trp
1               5                   10


<210> SEQ ID NO 216
<211> LENGTH: 14
<212> TYPE: PRT
<213> ORGANISM: Yarrowia lipolytica

<400> SEQUENCE: 216

Trp Arg Trp Phe Trp Leu Pro Gly Tyr Gly Glu Pro Asn Trp
1               5                   10


<210> SEQ ID NO 217
<211> LENGTH: 11
<212> TYPE: PRT
<213> ORGANISM: Torulaspora delbrueckii

<400> SEQUENCE: 217

Gly Trp Met Arg Leu Arg Leu Gly Gln Pro Leu
1               5                   10


<210> SEQ ID NO 218
<211> LENGTH: 13
<212> TYPE: PRT
<213> ORGANISM: Komagataella pastoris

<400> SEQUENCE: 218

Phe Arg Trp Arg Asn Asn Glu Lys Asn Gln Pro Phe Gly
1               5                   10


<210> SEQ ID NO 219
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
```

-continued

<400> SEQUENCE: 219

Trp His Trp Leu Glu Leu Pro Gly Ser Gln Pro Met Tyr
1 5 10

<210> SEQ ID NO 220
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 220

Val Glu Val Pro Gly Ser Gln His Ile Asp Ser Lys Lys Ala
1 5 10

<210> SEQ ID NO 221
<211> LENGTH: 301
<212> TYPE: PRT
<213> ORGANISM: Saccharomyces cerevisiae

<400> SEQUENCE: 221

Met Ser Asp Ala Ala Pro Ser Leu Ser Asn Leu Phe Tyr Asp Pro Thr
1 5 10 15

Tyr Asn Pro Gly Gln Ser Thr Ile Asn Tyr Thr Ser Ile Tyr Gly Asn
20 25 30

Gly Ser Thr Ile Thr Phe Asp Glu Leu Gln Gly Leu Val Asn Ser Thr
35 40 45

Val Thr Gln Ala Ile Met Phe Gly Val Arg Cys Gly Ala Ala Ala Leu
50 55 60

Thr Leu Ile Val Met Trp Met Thr Ser Arg Ser Arg Lys Thr Pro Ile
65 70 75 80

Phe Ile Ile Asn Gln Val Ser Leu Phe Leu Ile Ile Leu His Ser Ala
85 90 95

Leu Tyr Phe Lys Tyr Leu Leu Ser Asn Tyr Ser Ser Val Thr Tyr Ala
100 105 110

Leu Thr Gly Phe Pro Gln Phe Ile Ser Arg Gly Asp Val His Val Tyr
115 120 125

Gly Ala Thr Asn Ile Ile Gln Val Leu Leu Val Ala Ser Ile Glu Thr
130 135 140

Ser Leu Val Phe Gln Ile Lys Val Ile Phe Thr Gly Asp Asn Phe Lys
145 150 155 160

Arg Ile Gly Leu Met Leu Thr Ser Ile Ser Phe Thr Leu Gly Ile Ala
165 170 175

Thr Val Thr Met Tyr Phe Val Ser Ala Val Lys Gly Met Ile Val Thr
180 185 190

Tyr Asn Asp Val Ser Ala Thr Gln Asp Lys Tyr Phe Asn Ala Ser Thr
195 200 205

Ile Leu Leu Ala Ser Ser Ile Asn Phe Met Ser Phe Val Leu Val Val
210 215 220

Lys Leu Ile Leu Ala Ile Arg Ser Arg Arg Phe Leu Gly Leu Lys Gln
225 230 235 240

Phe Asp Ser Phe His Ile Leu Leu Ile Met Ser Cys Gln Ser Leu Leu
245 250 255

Val Pro Ser Ile Ile Phe Ile Leu Ala Tyr Ser Leu Lys Pro Asn Gln
260 265 270

Gly Thr Asp Val Leu Thr Thr Val Ala Thr Leu Leu Ala Val Leu Ser 275 280 285

Leu Pro Leu Ser Ser Met Trp Ala Thr Ala Ala Asn Asn
290 295 300

<210> SEQ ID NO 222
<211> LENGTH: 357
<212> TYPE: PRT
<213> ORGANISM: Histoplasma capsulatum

<400> SEQUENCE: 222

Met Ser Ser Ser Phe Pro Asp Pro Phe Asp Gln Asn Val Val Phe His
1 5 10 15

Lys Ala Asp Gly Thr Pro Phe Asn Val Ser Ile His Asp Leu Asp Glu
20 25 30

Phe Val Gln Tyr Gly Ile Arg Val Cys Ile Asn Tyr Ala Ala Gln Leu
35 40 45

Gly Ala Thr Val Ile Ala Ile Val Met Leu Ala Leu Leu Thr Gln Ser
50 55 60

Asp Lys Arg Arg Thr Pro Val Phe Phe Leu Asn Thr Ser Ala Leu Thr
65 70 75 80

Met Asn Phe Ala Arg Leu Leu Cys Met Thr Ile Tyr Phe Thr Thr Gly
85 90 95

Phe Asn Ser Thr Tyr Ala Phe Phe Ser Leu Asp Tyr Ser Arg Val Pro
100 105 110

Gly Ser Ala Tyr Ala Asp Ser Ile Leu Gly Ile Ala Phe Ala Thr Ile
115 120 125

Leu Val Ile Cys Met Glu Met Ser Leu Val Ile Gln Thr Gln Val Val
130 135 140

Cys Ala Thr Leu Ser Glu Ile Gln Arg Arg Leu Leu Leu Val Val Ser
145 150 155 160

Ile Leu Ile Ala Leu Leu Ala Ile Gly Phe Arg Met Gly Leu Met Val
165 170 175

Glu Asn Cys Ile Ala Ile Met Asn Ala Ser Asn Phe Arg Pro Phe Ile
180 185 190

Trp Leu Gln Ser Ala Ser Asn Ile Ala Ile Thr Ile Ser Thr Cys Phe
195 200 205

Phe Ser Ala Val Phe Val Thr Lys Leu Gly Tyr Ala Leu Val Thr Arg
210 215 220

Arg Arg Leu Gly Met Thr Arg Phe Gly Ala Met Gln Val Met Phe Ile
225 230 235 240

Ser Phe Gln Thr Met Val Ile Pro Ala Ile Phe Ser Ile Ile Gln Tyr
245 250 255

Pro Ile Pro Leu Tyr Glu Met Asn Ser Asn Val Phe Thr Leu Val Ala
260 265 270

Ile Phe Leu Pro Leu Ser Ser Leu Trp Ala Ala Ala Ala Thr Lys His
275 280 285

Ser Phe Glu Thr Leu Thr Ser Gly Pro His Gln Tyr Leu Trp Ser Ser
290 295 300

Glu Arg Ser Asn Ser Thr Ser Ser Ala Thr Gly His Gln Gly Ser Leu
305 310 315 320

Cys Gln Asn Gln Ser Thr Ile Arg Ser Gly Gly Ser Val Ala Thr Ser
325 330 335

-continued

```
Leu Ser Pro Asp Gln Leu Asp Arg Leu Tyr Thr Gly Leu Asp Phe Asp
        340                 345                 350

Ala Cys Ala Lys Ala
        355
```